United States Patent
Casimiro et al.

(10) Patent No.: US 12,358,998 B2
(45) Date of Patent: Jul. 15, 2025

(54) ANTI-CD6 ANTIBODY-GROWTH FACTOR COMPLEX FOR TREATING AUTOIMMUNE DISEASES

(71) Applicant: CITY OF HOPE, Duarte, CA (US)

(72) Inventors: Jose Enrique Montero Casimiro, Duarte, CA (US); Bart Otto Roep, Duarte, CA (US); John Charles Williams, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 1087 days.

(21) Appl. No.: 17/256,553

(22) PCT Filed: Jul. 1, 2019

(86) PCT No.: PCT/US2019/040211
§ 371 (c)(1),
(2) Date: Dec. 28, 2020

(87) PCT Pub. No.: WO2020/006576
PCT Pub. Date: Jan. 2, 2020

(65) Prior Publication Data
US 2022/0073637 A1 Mar. 10, 2022

Related U.S. Application Data

(60) Provisional application No. 62/692,509, filed on Jun. 29, 2018.

(51) Int. Cl.
| | |
|---|---|
| C07K 16/28 | (2006.01) |
| A61K 38/18 | (2006.01) |
| A61K 39/395 | (2006.01) |
| A61K 47/68 | (2017.01) |
| A61P 3/10 | (2006.01) |
| A61P 37/06 | (2006.01) |
| C07K 14/485 | (2006.01) |
| C07K 14/495 | (2006.01) |
| C07K 14/705 | (2006.01) |
| C07K 16/46 | (2006.01) |

(52) U.S. Cl.
CPC ...... *C07K 16/2896* (2013.01); *A61K 38/1808* (2013.01); *A61K 38/1841* (2013.01); *A61K 39/3955* (2013.01); *A61K 47/6811* (2017.08); *A61P 3/10* (2018.01); *A61P 37/06* (2018.01); *C07K 14/485* (2013.01); *C07K 14/495* (2013.01); *C07K 14/70596* (2013.01); *C07K 16/46* (2013.01); *C07K 2317/24* (2013.01); *C07K 2317/55* (2013.01); *C07K 2317/622* (2013.01); *C07K 2317/64* (2013.01); *C07K 2317/92* (2013.01); *C07K 2319/00* (2013.01); *C07K 2319/33* (2013.01); *C07K 2319/50* (2013.01); *C07K 2319/75* (2013.01)

(58) Field of Classification Search
CPC ............ C07K 14/485; C07K 16/2896; C07K 2319/00; C07K 14/495; C07K 14/70596; C07K 2319/33; A61K 38/1808; A61K 38/1841; A61K 39/3955; A61K 47/6811; A61P 3/10; A61P 37/06
See application file for complete search history.

(56) References Cited

U.S. PATENT DOCUMENTS

| | | |
|---|---|---|
| 2003/0104014 A1 | 6/2003 | Casimiro et al. |
| 2006/0195945 A1 | 8/2006 | Lee et al. |
| 2015/0023959 A1 | 1/2015 | Chhabra et al. |
| 2016/0075785 A1 | 3/2016 | Ast et al. |
| 2016/0213760 A1 | 7/2016 | Tripathy et al. |

FOREIGN PATENT DOCUMENTS

WO   WO-2018/119001 A1   6/2018

OTHER PUBLICATIONS

Nataraj et al, "Growth Factors", Chapter G, pp. 1-13, of Encyclopedia of Molecular Pharmacology, 2021, S. Offermans, W. Rosenthal (eds.)).*
Lee et al, 2008. J. Cell. Mol. Med. 12(5A): 1593-1604.*
Li et al, 2018. Diabetes. 67: 1847-1857.*
Consuegra-Fernandez et al, Autoimmunity Reviews, 17: 493-503.*
Benjamini et al, 1991. Immunology: A Short Course, 2nd edition, p. 40 only.*
Ferrara et al (2015. mAbs. 7(1): 32-41).*
Toyoda et al, 1995. Journal of Biological Chemistry. 270(13): 7495-7500.*
Riese et al, 2014. Semin Cell Dev Biol. 28: 49-56.*
Zeng et al, 2014. Semin Cell Dev Biol. 28: 2-11, 28: 49-56.*
Consuegra-Fernandez et al, 2018. Autoimmunity Reviews, 17(5): 493-503. (Correction to reference X listed on PTO-892 mailed on Feb. 15, 2024. Corrected to add date and issue).*
International Search Report mailed on Nov. 13, 2019, for PCT Application No. PCT/US2019/040211, filed Jul. 1, 2019, 6 pages.
Pinkse, G.G.M. et al. (Dec. 20, 2005, e-published Dec. 9, 2005). "Autoreactive CD8 T cells associated with beta cell destruction in type 1 diabetes," *PNAS USA* 102(51):18425-18430.
Thrailkill, K.M. et al. (Sep. 2007, e-published Jun. 11, 2007). "Matrix metalloproteinase-2 dysregulation in type 1 diabetes," *Diabetes Care* 30(9):2321-2326.

(Continued)

*Primary Examiner* — Zachary C Howard
(74) *Attorney, Agent, or Firm* — Mintz, Levin, Cohn, Ferris, Glovsky and Popeo, P.C.

(57) ABSTRACT

Provided herein are, inter alia, anti-CD6 antibody-growth factor complexes including an anti-CD6 antibody portion bound to a growth factor protein (e.g., EGF) through a linker, which may be cleavable by a protease (e.g., diabetic microenvironment specific protease). The compositions provided herein are, inter alia, useful for the treatment of autoimmune diseases (e.g., type I diabetes).

20 Claims, 64 Drawing Sheets
Specification includes a Sequence Listing.

(56) References Cited

OTHER PUBLICATIONS

Unger, W.W., et al. "Islet-Specific CTL Cloned from a Type 1 Diabetes Patient Cause Beta-Cell Destruction after Engraftment into HLA-A2 Transgenic NOD/SCID/IL2RG Null Mice," *PLoS One*, 2012. 7(11): p. e49213.
Written Opinion mailed on Nov. 13, 2019, for PCT Application No. PCT/US2019/040211, filed Jul. 1, 2019, 13 pages.

\* cited by examiner

|  | Somatostatin+ | Somatostatin- | Total |
|---|---|---|---|
| HER2-S+ | 4 | 51 | 55 |
| HER2-S- | 12 | 254 | 266 |
| Total | 16 | 305 | 321 |

MMP2/9 Substrate

Initial purification

Titer: 11.37 mg/L
Comparative productivity within order

Titer: 9.06 mg/L
Comparative productivity within order

Titer: 7.54 mg/L
Comparative productivity within order

Titer: 10.53 mg/L
Comparative productivity within order

Titer: 10.96 mg/L
Comparative productivity within order

Titer: 9.55 mg/L
Comparative productivity within order

ANTI-CD6 ANTIBODY-GROWTH FACTOR COMPLEX FOR TREATING AUTOIMMUNE DISEASES

CROSS-REFERENCES TO RELATED APPLICATIONS

This application is a national phase entry of PCT/US2019/040211, filed Jul. 1, 2019, which claims the benefit of U.S. Provisional Application No. 62/692,509, filed Jun. 29, 2018, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-670NO1US_Sequence_Listing_ST25.txt, created May 4, 2021, 147,456 bytes, machine format IBM-PC, MS Windows operating system, is hereby incorporated by reference.

BACKGROUND

Type 1 diabetes mellitus (T1D) precipitates from the autoimmune attack of pancreatic beta cells, resulting in a loss of functional beta cell mass. Functional beta cell mass is impacted positively by processes that increase the number and size of beta cells and negatively by those that deplete the numbers of cells (i.e., apoptosis, necrosis, and other modes of cell death). In addition, beta cell secretory function/capacity is a substantial determinant of functional beta cell mass.

In T1D patients, the proliferative/regenerative potential of adult and human islets is low. Thus, it is important to prevent or delay the autoimmune attack and resultant destruction of beta cells, and to establish methods to promote beta cell mass expansion, increase beta cell survival, and/or enhance the function of existing/remaining beta cells and engage cellular repair mechanisms to restore functional beta cell mass. However, therapeutic strategies aiming to simultaneously target the pancreatic islet-infiltrating lymphocytes and protect and replenish the functional beta cell mass are limited. Provided herein are solutions to these and other problems in the art.

BRIEF SUMMARY OF THE INVENTION

In an aspect, an anti-CD6 antibody-growth factor complex is provided. The complex includes (i) an anti-CD6 antibody or fragment thereof; and (ii) a growth factor protein or fragment thereof, wherein the growth factor protein is bound to the anti-CD6 antibody through a chemical linker.

In another aspect, an isolated nucleic acid encoding a complex provided herein including embodiments thereof is provided.

In another aspect, an expression vector including the nucleic acid provided herein including embodiments thereof is provided.

In another aspect, a cell including the expression vector provided herein including embodiments thereof is provided.

In another aspect, a method of treating an autoimmune disease in a subject in need thereof is provided. The method includes administering to a subject a therapeutically effective amount of a complex provided herein including embodiments thereof is provided, thereby treating an autoimmune disease in the subject.

In another aspect, a pharmaceutical composition including a therapeutically effective amount of a complex provided herein including embodiments thereof and a pharmaceutically acceptable excipient is provided.

In an aspect, an anti-CD6 antibody-growth factor complex is provided. The complex includes (i) a CD6 Fab or fragment thereof and (ii) an EGF protein or fragment thereof, wherein the EGF protein is bound to the CD6 Fab through a diabetic microenvironment specific protease site.

In an aspect, an antibody is provided. The antibody includes (1) a central hole enclosed by a heavy chain variable (VH) region, a light chain variable (VL) region, a heavy chain constant (CH1) region and a light chain constant (CL) region of the antibody between a first cavity and a second cavity; and (2) a non-CDR peptide binding region including: (a) a first cavity lined by a first set of amino acid residues of the VH, VL, CHI, and CL regions of the antibody (b) a second cavity lined by a second set of amino acid residues of the VH, VL, CHI, and CL regions of the antibody; and a hole region enclosing the hole between the first cavity and the second cavity, the hole region lined by a third set of amino acid residues of the VH, VL, CHI, and CL regions of the antibody, wherein the antibody is an anti-CD6 antibody.

In an aspect, a method of treating an autoimmune disease in a subject in need thereof is provided. The method includes administering to the subject an antibody provided herein including embodiments thereof.

In another aspect, a method of treating an autoimmune disease in a subject in need thereof is provided. The method includes administering to a subject a therapeutically effective amount of a complex provided herein including embodiments thereof.

BRIEF DESCRIPTION OF THE DRAWINGS

FIG. 8A. Site directed mutagenesis used to convert to 175C in the anti-CD6 antibody. FIG. 8B. Two independent expression trials. Yield was approximately 50 mg/L.

In FIG. 17A, C, and E the anti-CD6 antibody-growth factor complex is a meditope-enabled anti-CD6. In FIG. 17B, D, and F the anti-CD6 antibody-growth factor complex is a bionic anti-CD6/EGF antibody conjugate. Anti-CD6 meditope-enabled antibody recognition on the y-axis of human PBMC (FIG. 17A, 17C) and isolated Tregs from a healthy donor (FIG. 17E) with anti-CD3 (FIG. 17A) or anti-CD6 (FIG. 17C, 17E) on the x-axis is shown. Bionic anti-CD6/EGF antibody conjugate (complex) recognition on the y-axis of human PBMC (FIG. 17B, 17D) and isolated Tregs from a healthy donor (FIG. 17F) with anti-CD3 (FIG. 17B) or anti-CD6 (FIG. 17D, 17F) on the x-axis is shown.

FIG. 28A FPLC trace of an exemplary anti-CD6 antibody-growth factor complex provided herein is shown. FIG. 29B SDS PAGE gel of two fractions collected from the FPLC purification are shown. The uncleaved and cleaved bionic anti-CD6/EGF antibody conjugate bands are indicated by arrows.

Concentrations of purified cleaved bionic anti-CD6/EGF antibody conjugate ranging from 50 nM to 0.39 nM were flown over the chip at 25° C. On-rate constant $k_{on}$ is $2.3\times10^6$ 1/(Ms), the off-rate constant $k_{off}$ is 0.0017 (1/s), and the Kp was determined to be $7.62\times10^{-10}$ M.

Figure 34:
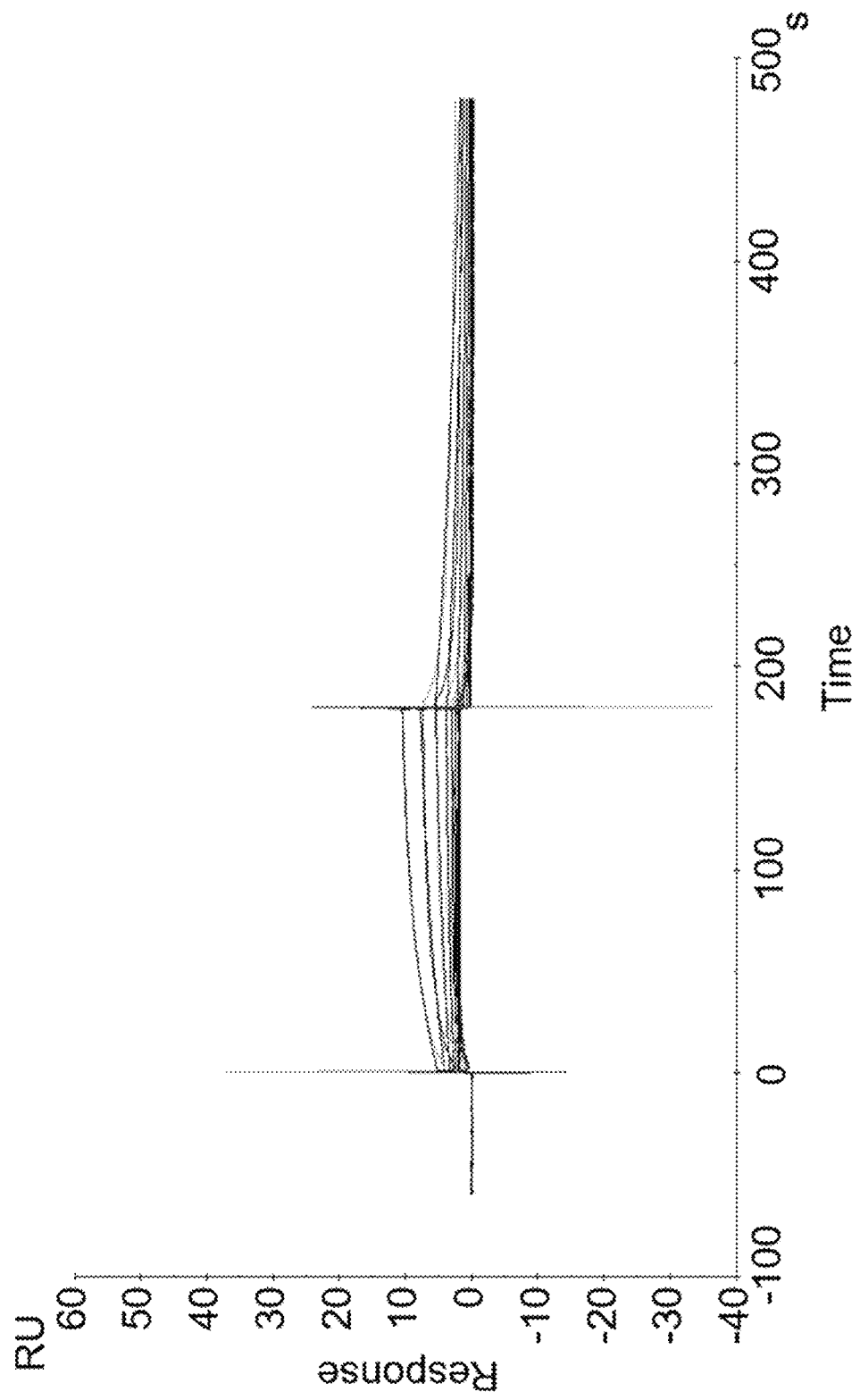

FIG. 34. SPR of an exemplary anti-CD6 antibody-growth factor complex provided herein. SPR with MMP2 cleaved D104N mutant bionic anti-CD6/EGF antibody conjugate with CD6 Ecto is shown. CD6 Ecto was immobilized to a Biacore CM5 chip using NHS chemistry. Concentrations of purified cleaved bionic D104N anti-CD6/EGF antibody conjugate ranging from 4 µM to 0.016 µm were flown over the chip at 25° C. On-rate constant $k_{on}$ is $4.7\times10^3$ 1/(Ms), the off-rate constant $k_{off}$ is 0.0038 (1/s), and the $K_D$ is determined to be $8.0\times10^{-7}$ M.

Figure 35:
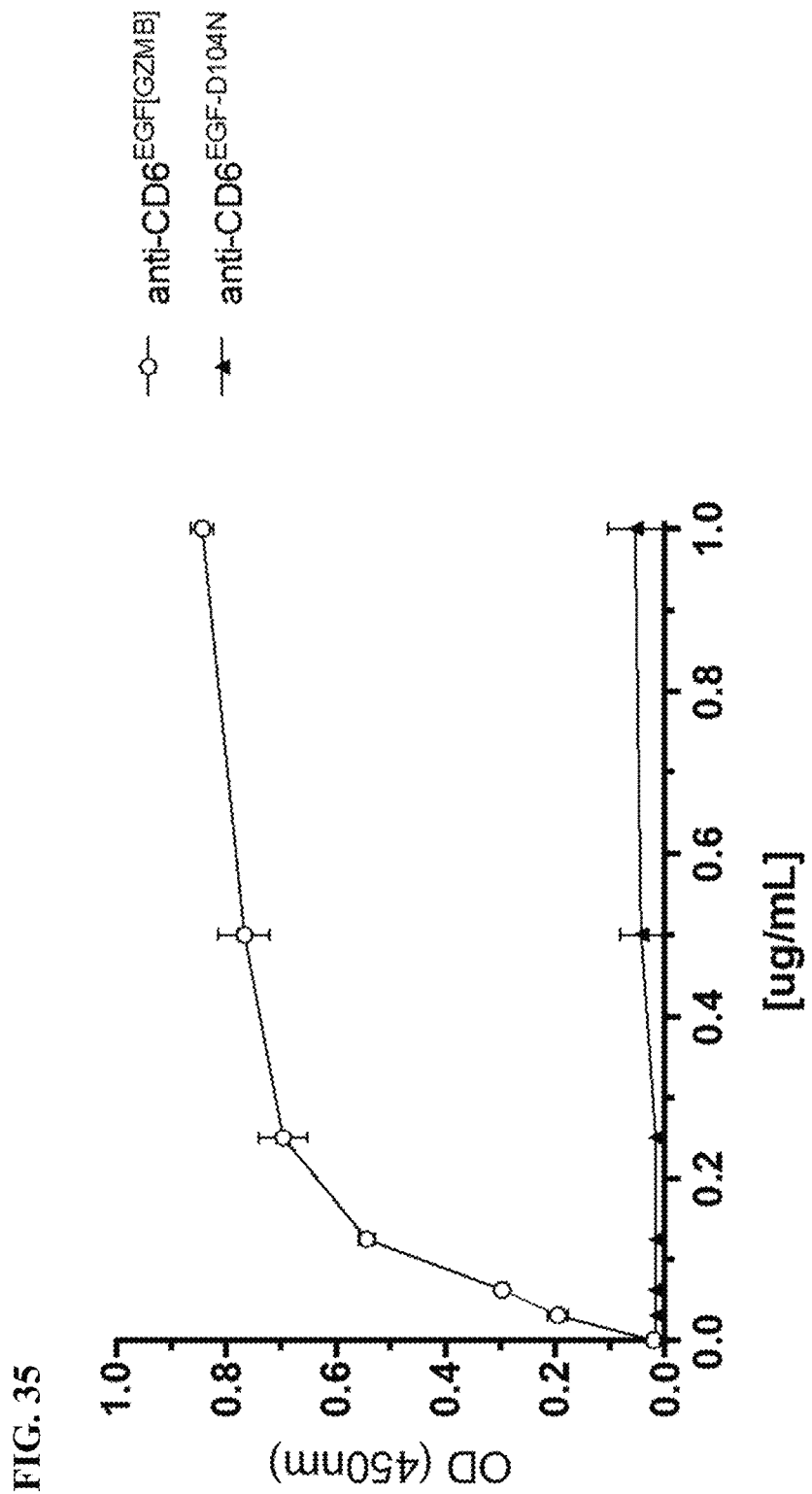

FIG. 35. Human CD6 binding of exemplary anti-CD6/EGF antibody-growth factor complexes provided herein. ELISA of bionic anti-CD6/EGF antibody conjugate of SEQ ID NO: 38 and D104N mutant bionic anti-CD6/EGF antibody conjugate binding to CD6 is shown. The dilution of the antibodies was carried out with respect to the concentration obtained by $OD_{280}$. The enzymatic site is non-cleaved for both mAbs.

Figure 36A:
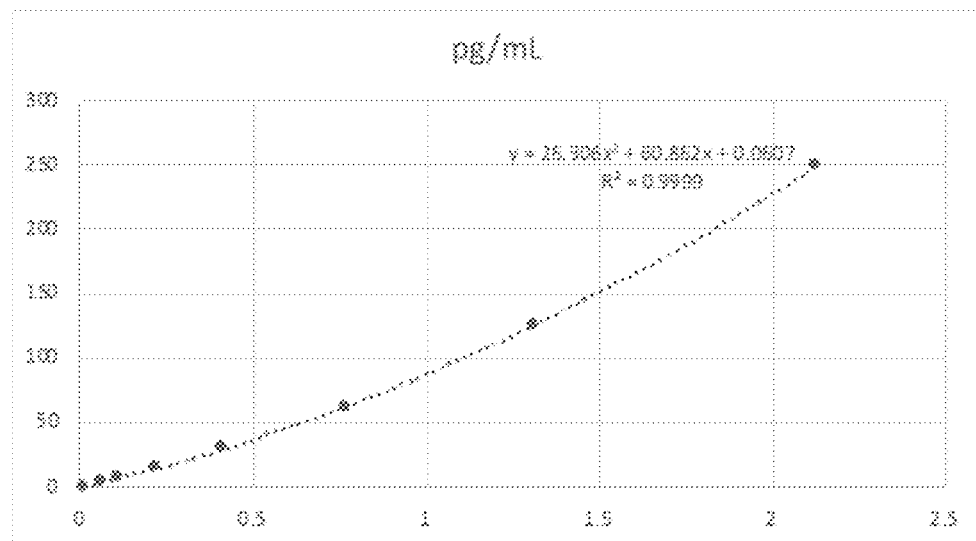
Figure 36B:
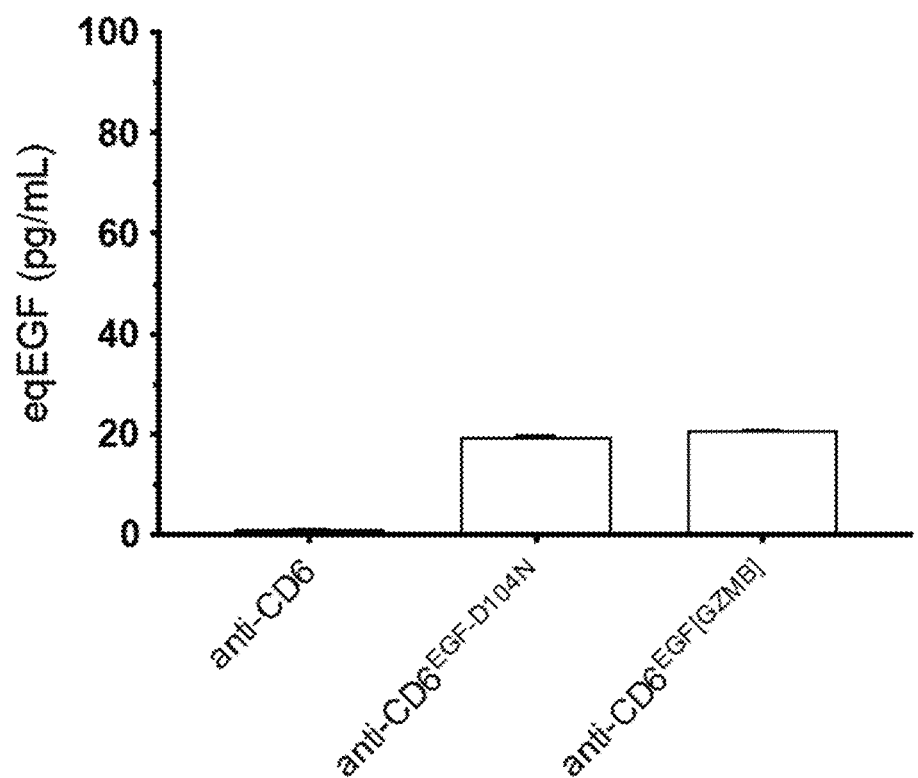

FIG. 36A-36B. EGF content from in vitro human islet cells. Standard curve of EGF concentrations as determined by ELISA using a Human EGF Quantikine ELISA Kit (R&D) is shown (FIG. 36A). EGF in human islet cells from bionic anti-CD6/EGF antibody conjugate of SEQ ID NO:38 (anti-CD6$^{EGF\ [GZMB]}$) and D104N mutant bionic anti-CD6/EGF antibody conjugate (anti-CD6$^{EGF-D104N}$) is shown (FIG. 36B). The granzyme site is non-cleaved for both complexes.

Figure 37:
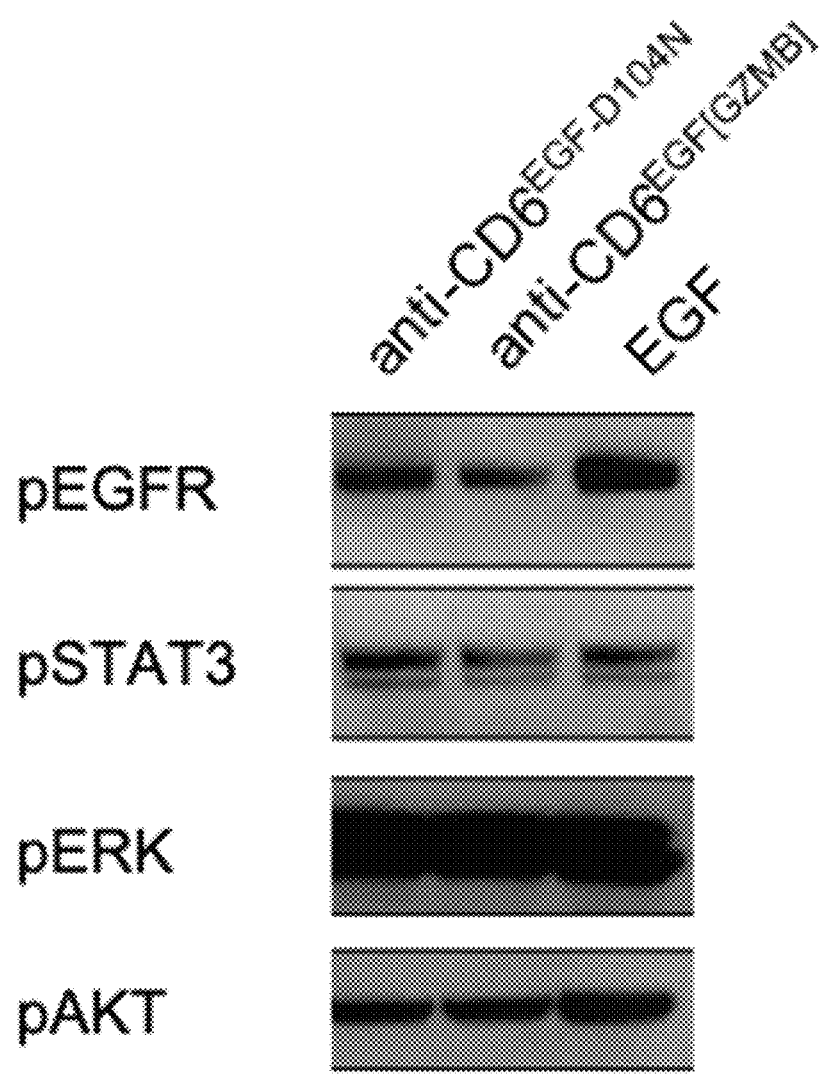

FIG. 37. EGF functionality of exemplary anti-CD6/EGF antibody-growth factor complexes provided herein. A Western blot with proteins as indicated in 1.1B4 cells stimulated with recombinant human EGF (EGF), D104N mutant bionic anti-CD6/EGF antibody conjugate (anti-CD6$^{EGF-D104N}$), or bionic anti-CD6/EGF antibody conjugate of SEQ ID NO:38 (anti-CD6$^{EGF[GZMB]}$) is shown. The granzyme site is non-cleaved for both complexes and the complexes were adjusted to 125 µg/mL of equivalent EGF (eqEGF).

Figure 38A:
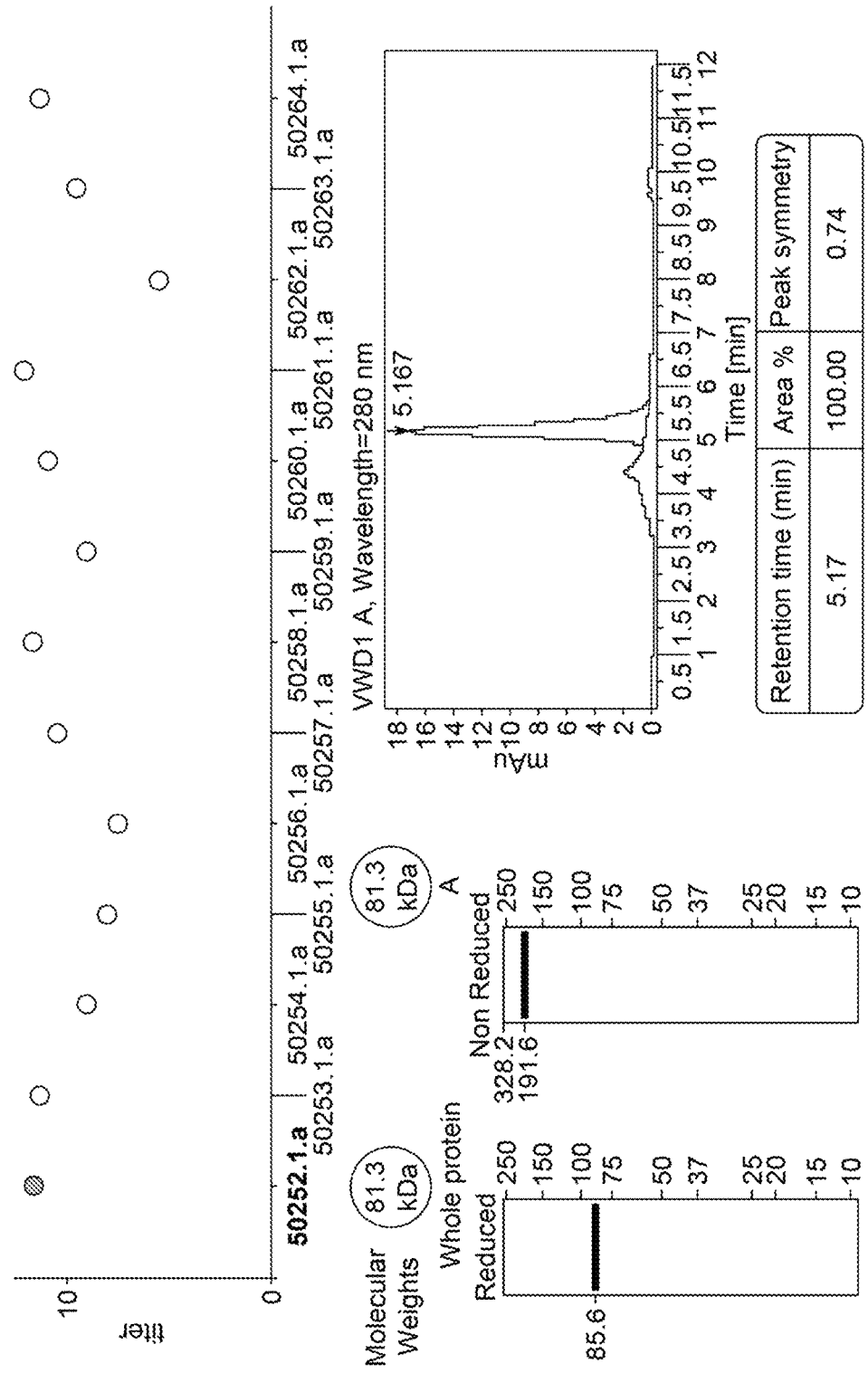
Figure 38B:
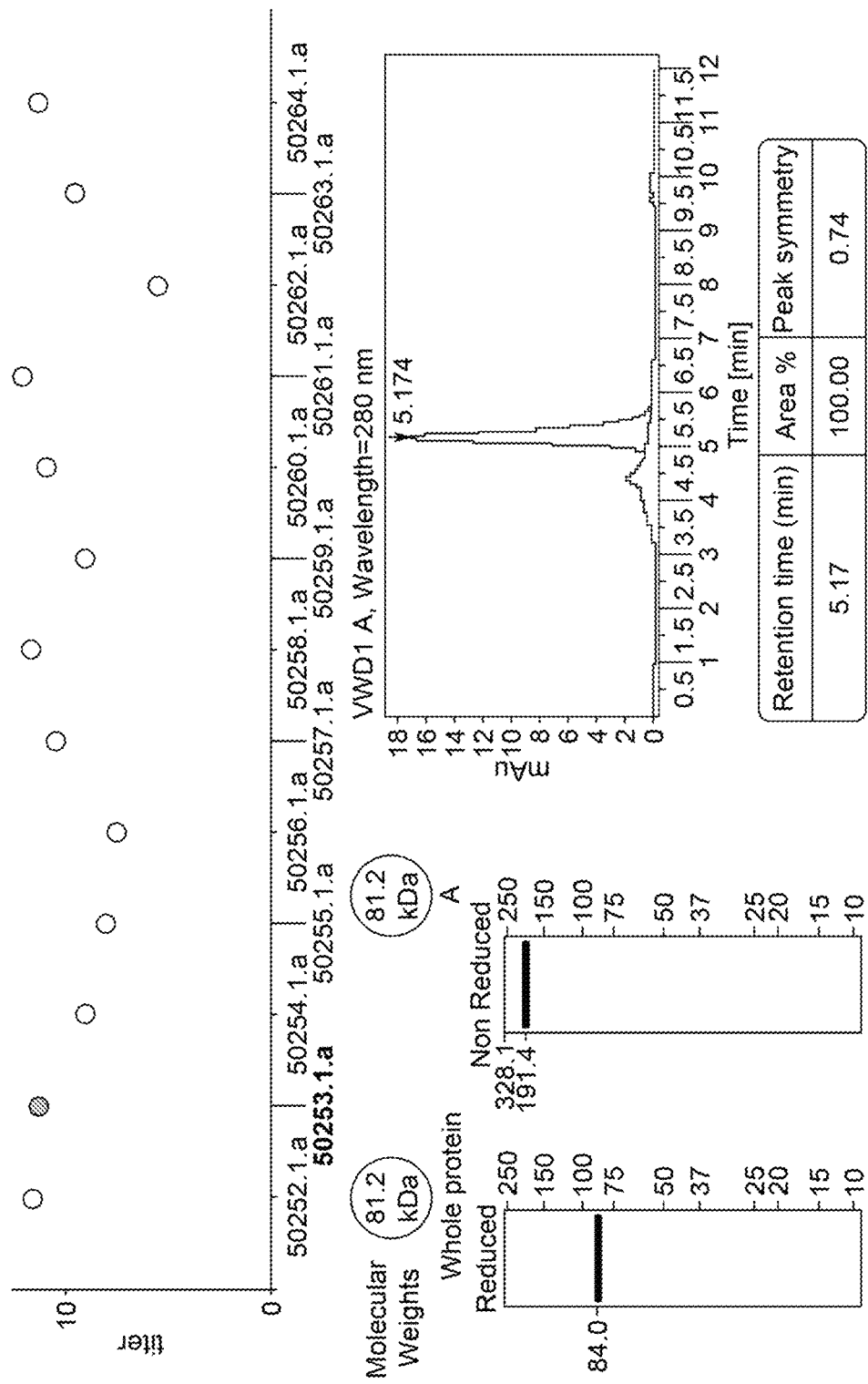
Figure 38C:
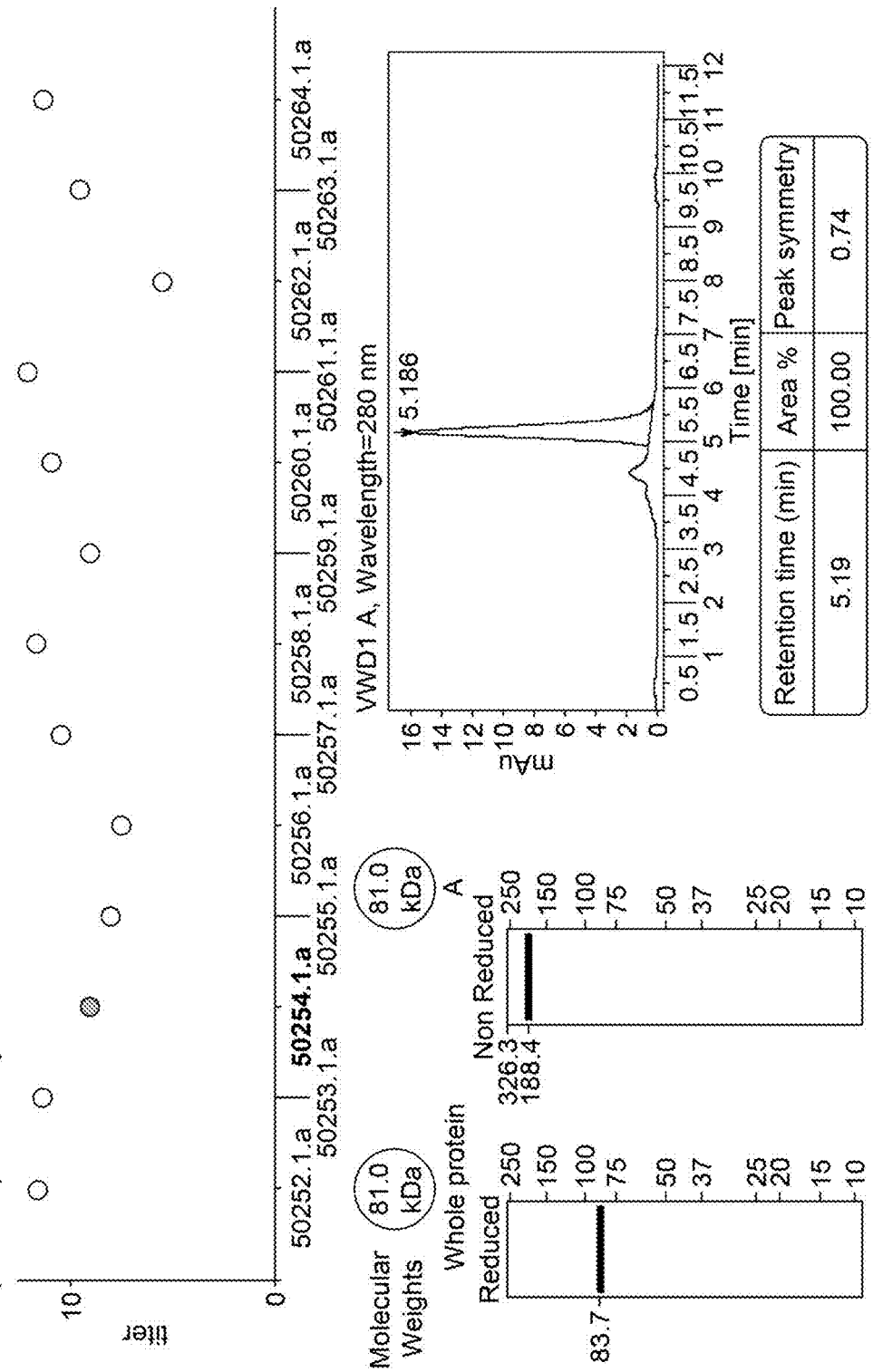
Figure 38D:
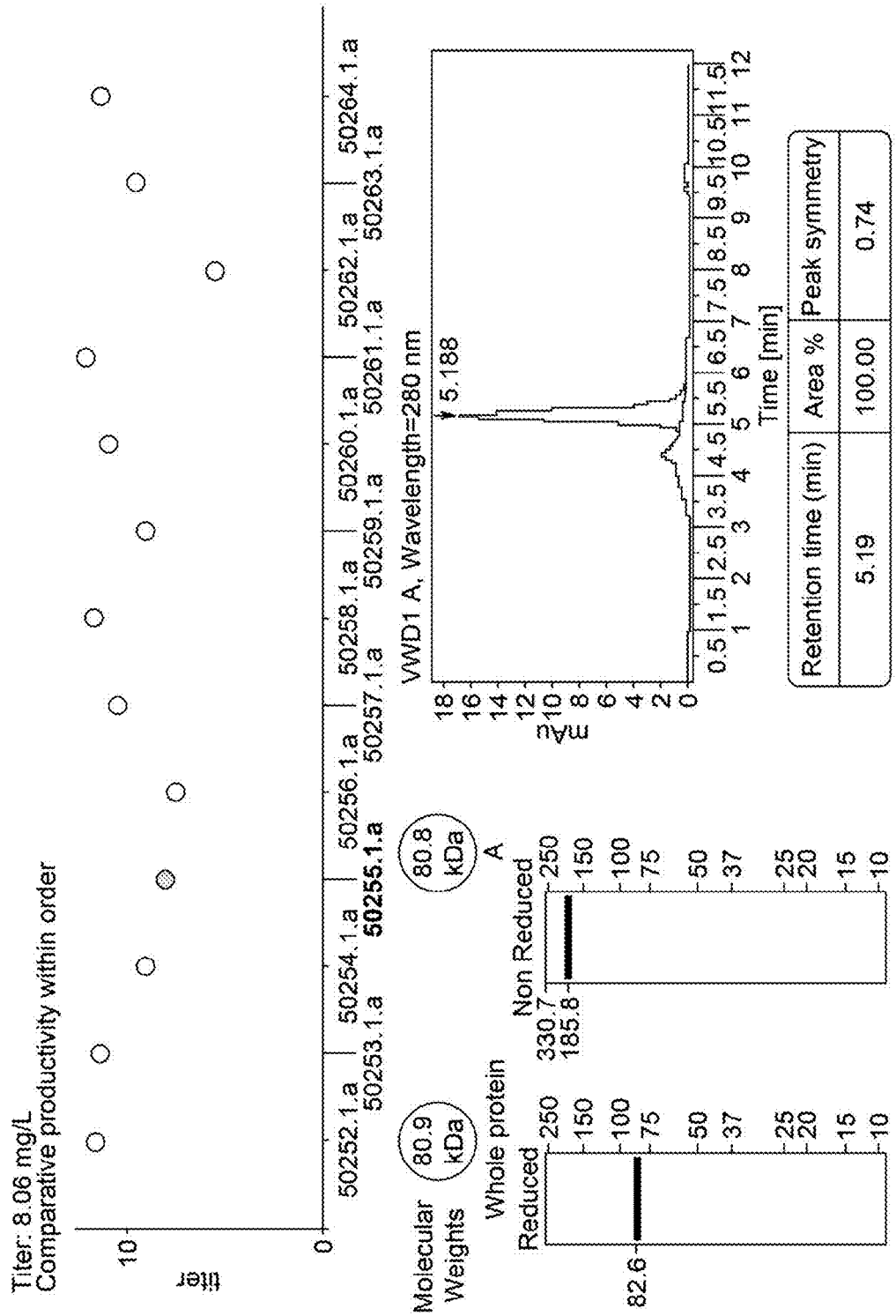
Figure 38E:
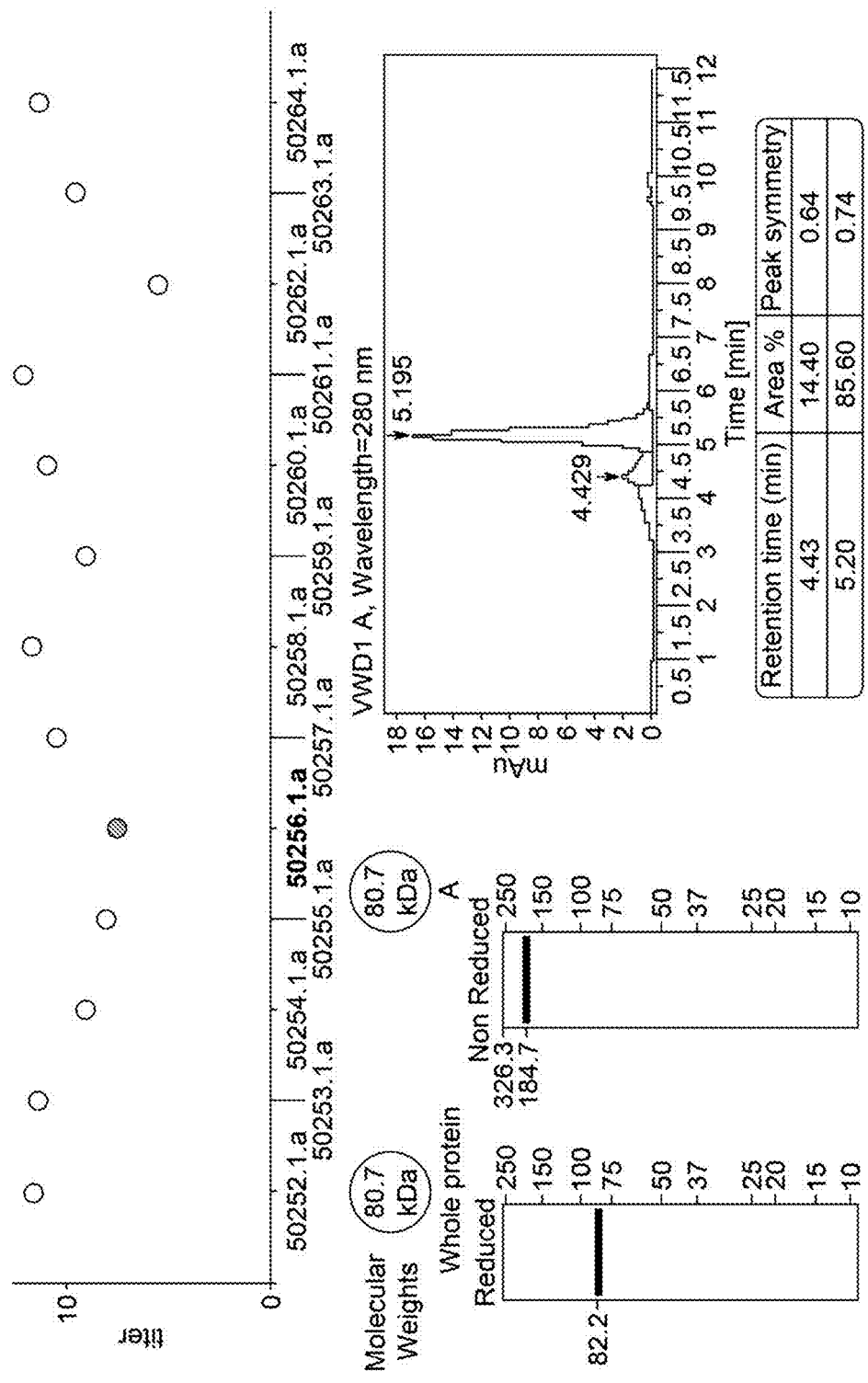
Figure 38F:
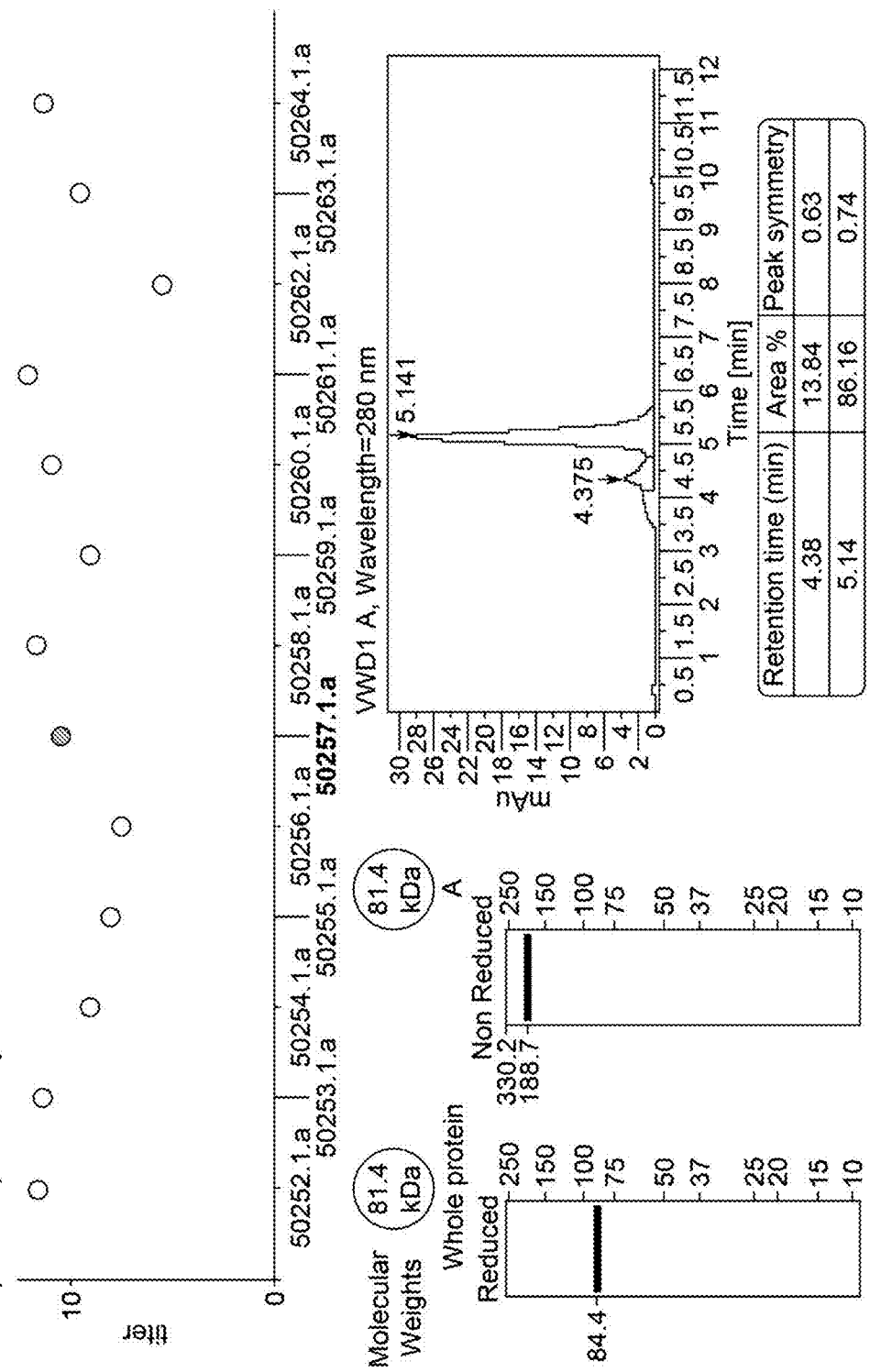
Figure 38G:
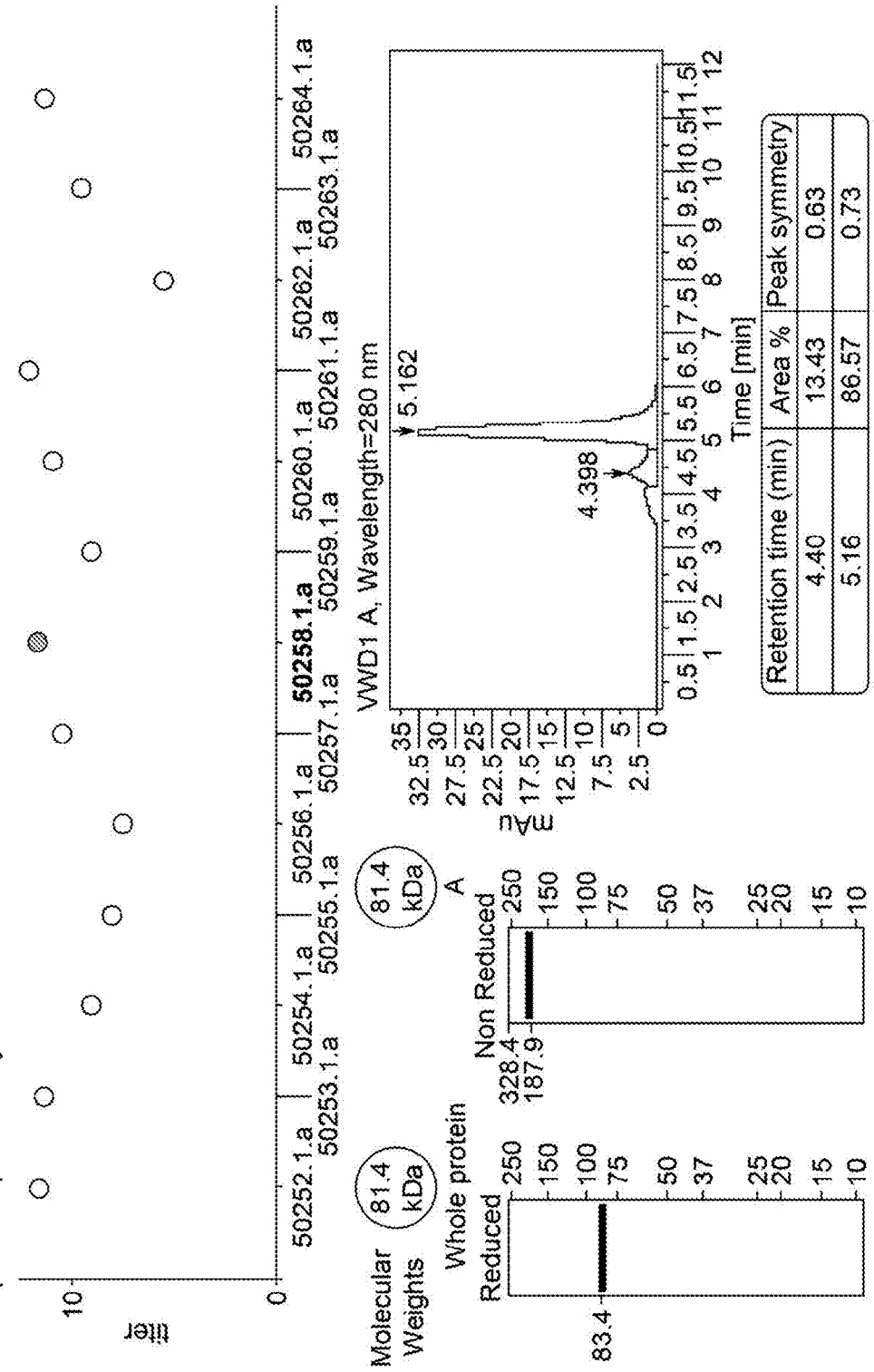
Figure 38H:
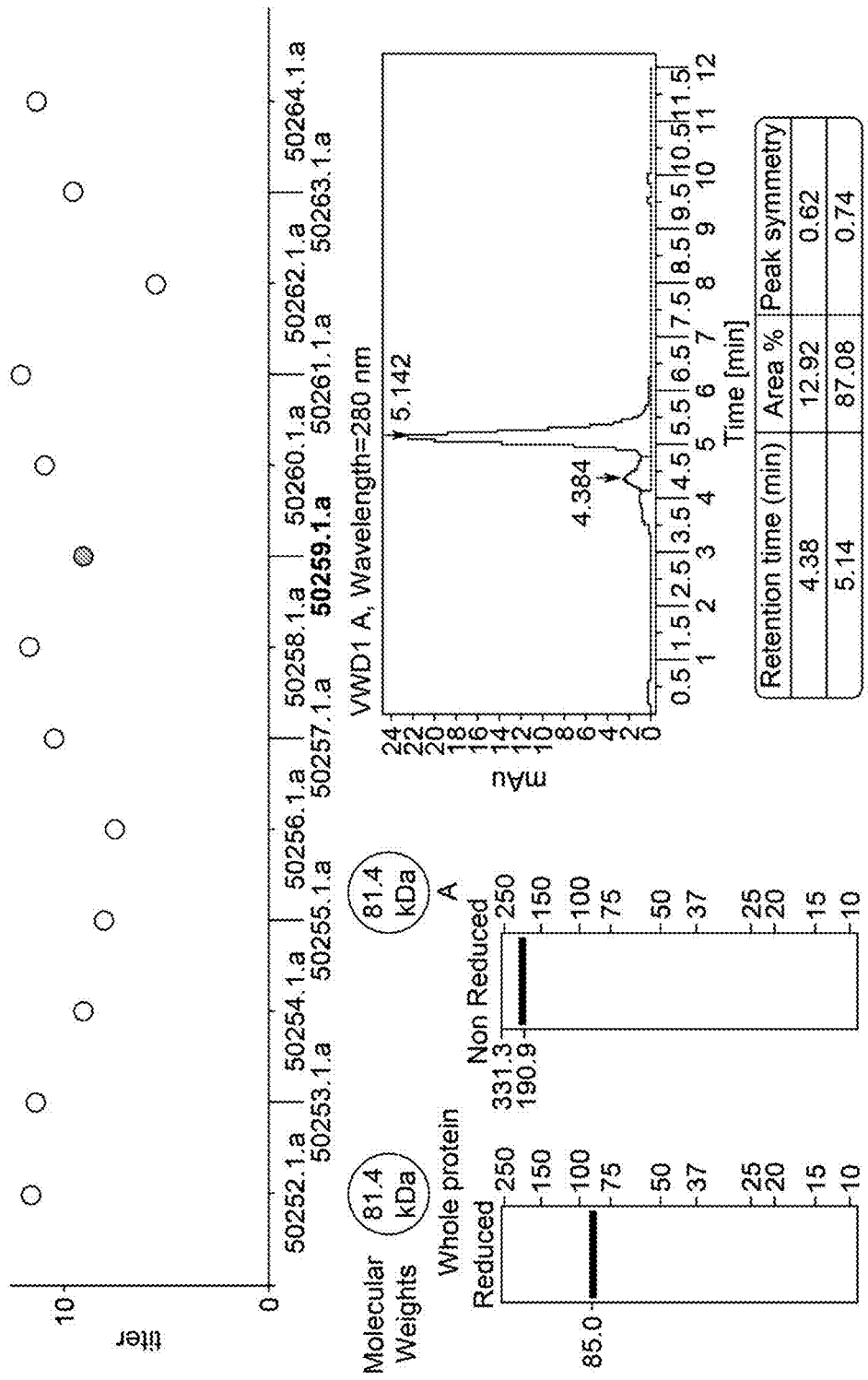
Figure 38I:
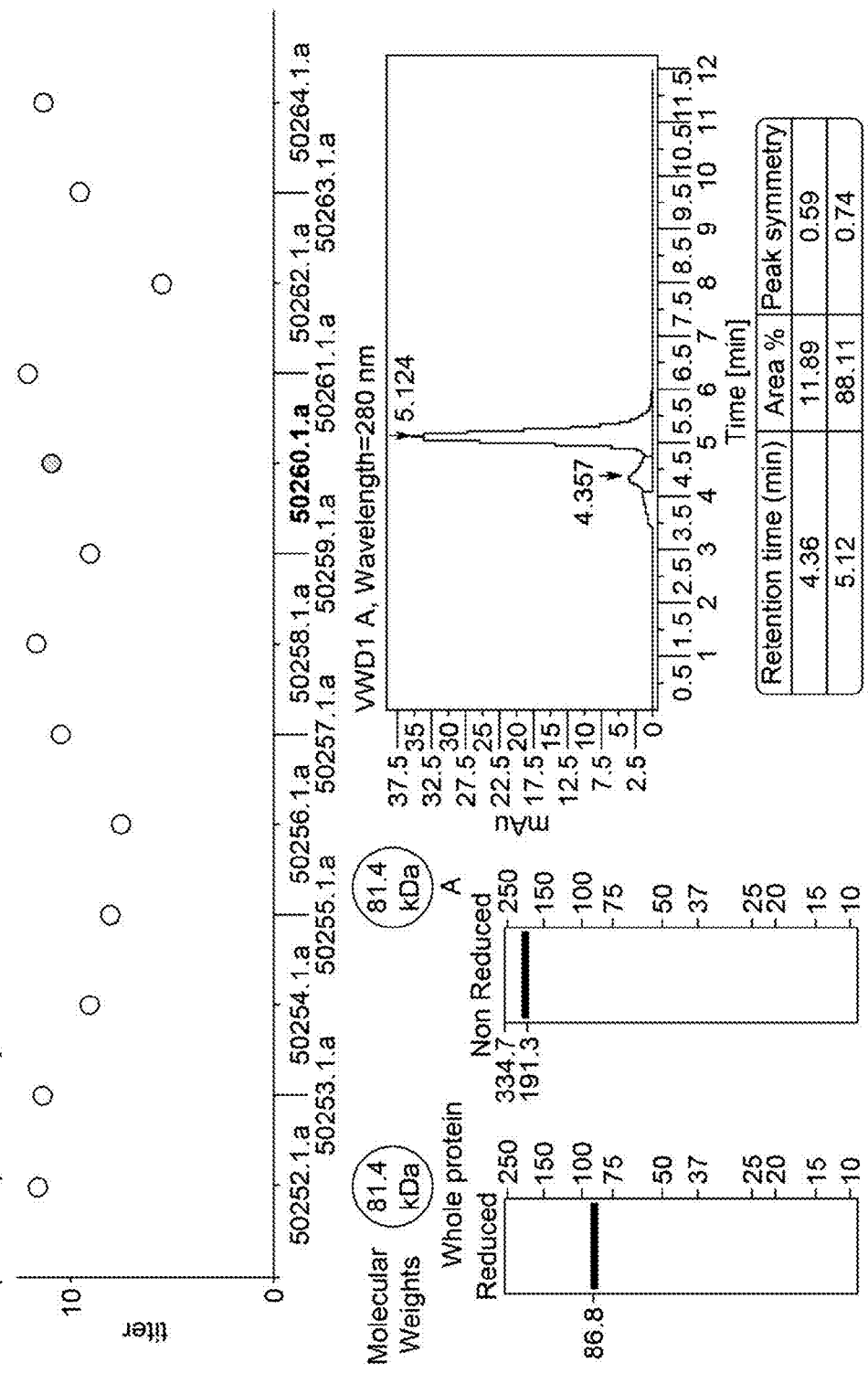
Figure 38J:
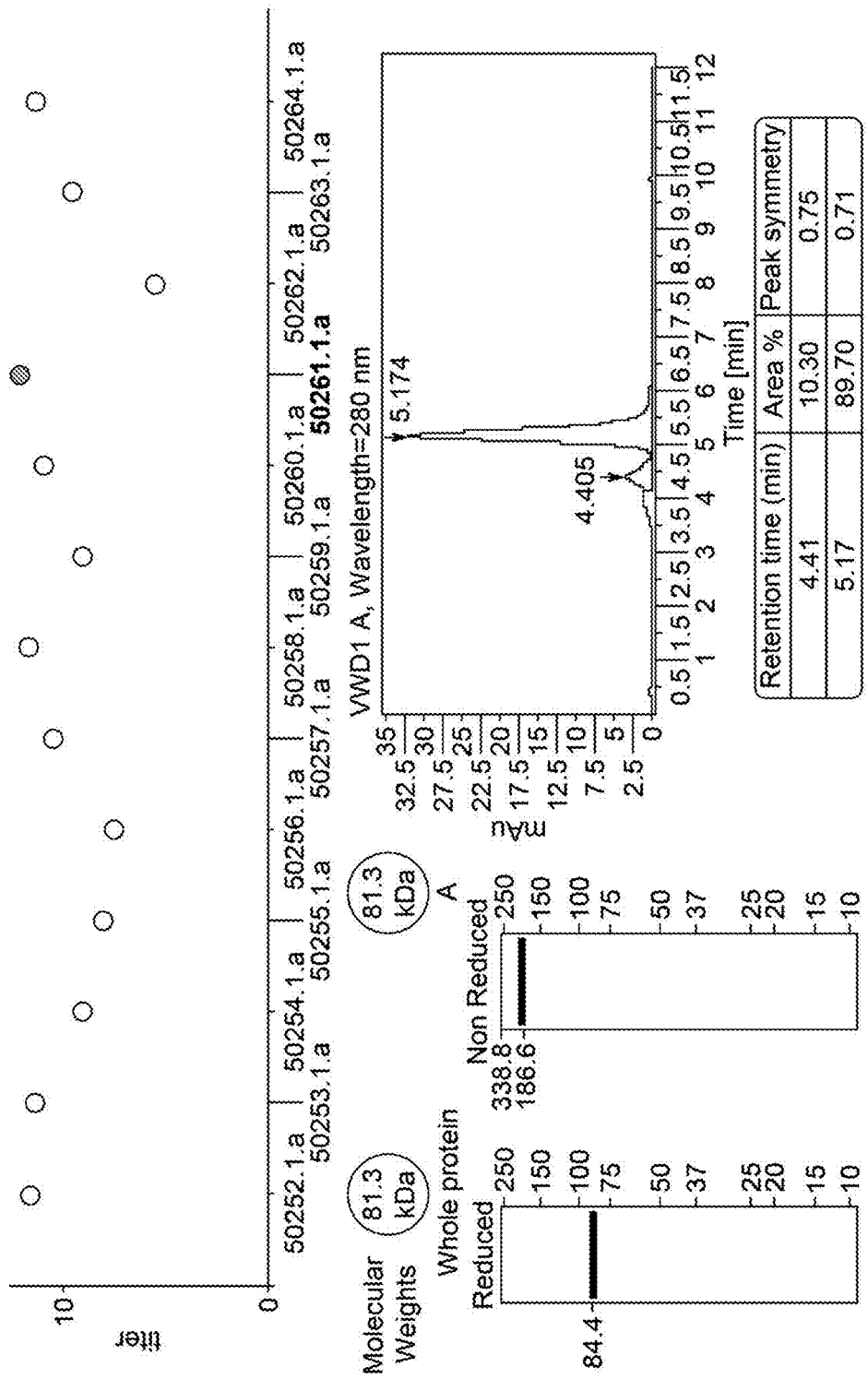
Figure 38K:
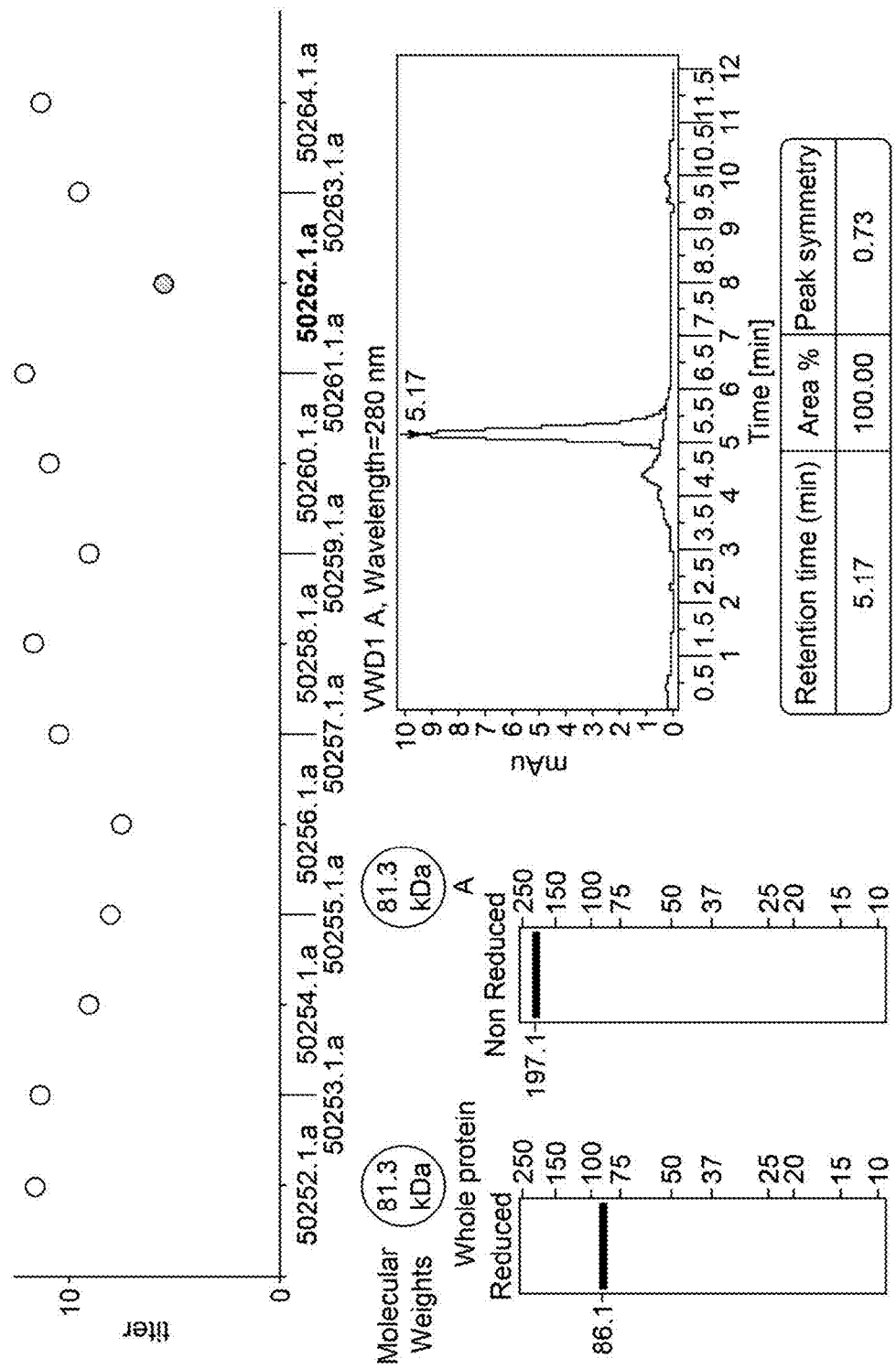
Figure 38L:
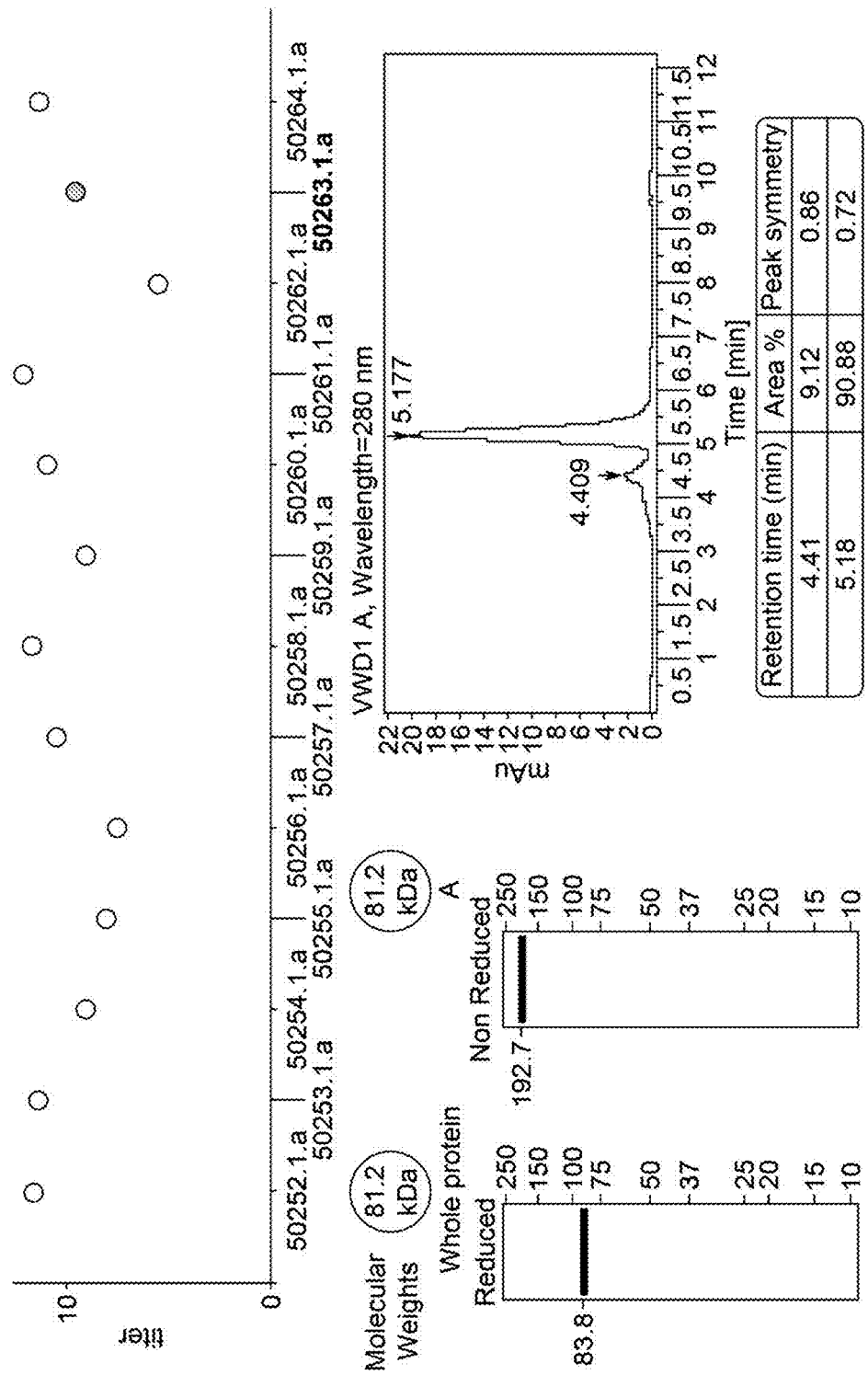
Figure 38M:
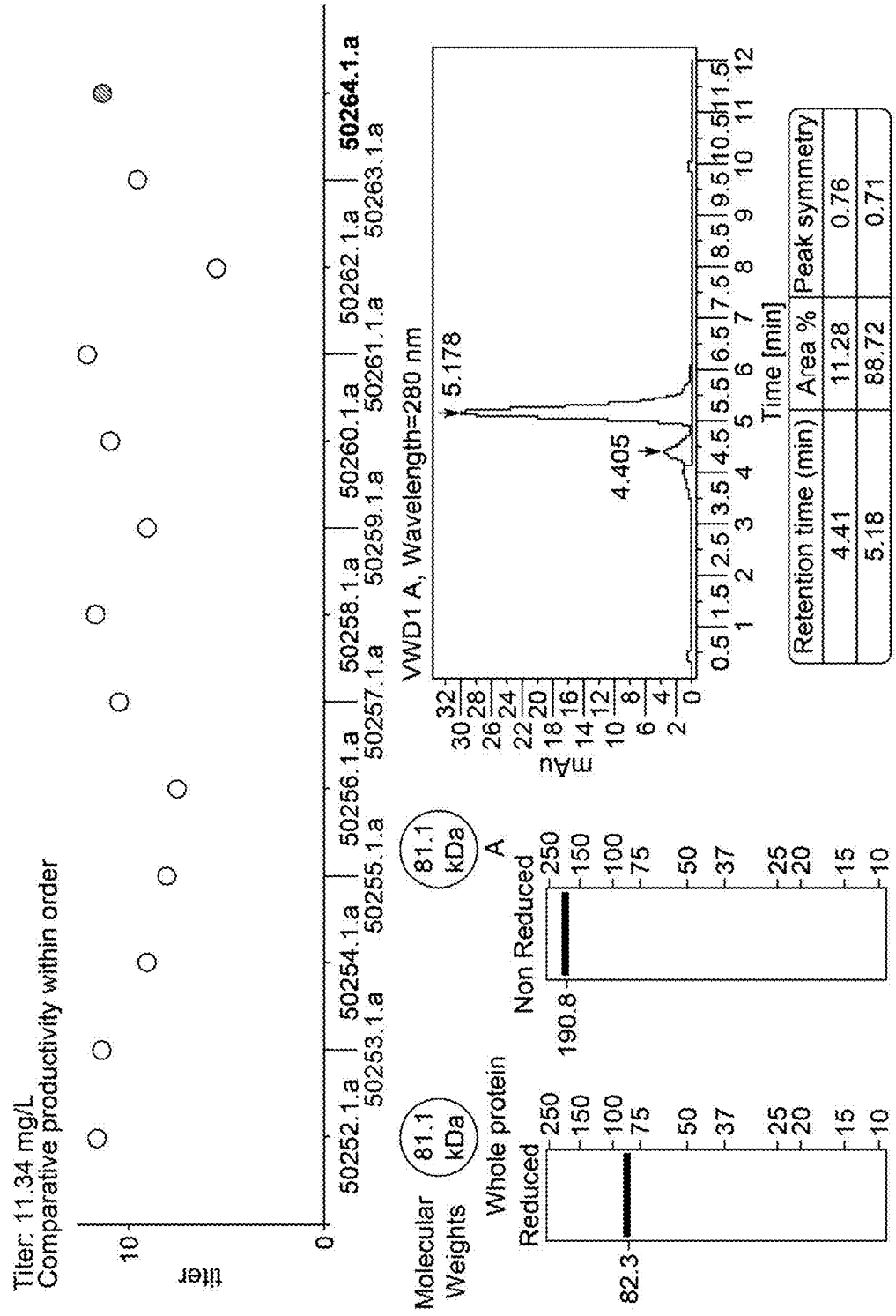

FIG. 38A-38M Expression data of exemplary anti-CD6/EGF antibody-growth factor complexes with varying linker length and compostion provided herein. Titer (upper panel), reduced and non-reduced sample on an SDS PAGE gel (lower left panel), and size exclusion chromatography characterization (lower right panel) of the complex of SEQ ID NO:38 (FIG. 38A), SEQ ID NO: 42 (FIG. 38B), SEQ ID NO: 44 (FIG. 38C), SEQ ID NO: 46 (FIG. 38D), SEQ ID NO:48 (FIG. 38E), SEQ ID NO:50 (FIG. 38F), SEQ ID NO:52 (FIG. 38G), SEQ ID NO: 54 (FIG. 38H), SEQ ID NO:56 (FIG. 38I), SEQ ID NO:58 (FIG. 38J), SEQ ID NO:60 (FIG. 38K), SEQ ID NO:62 (FIG. 38L), SEQ ID NO:64 (FIG. 38M) are shown.

Figure 39A:
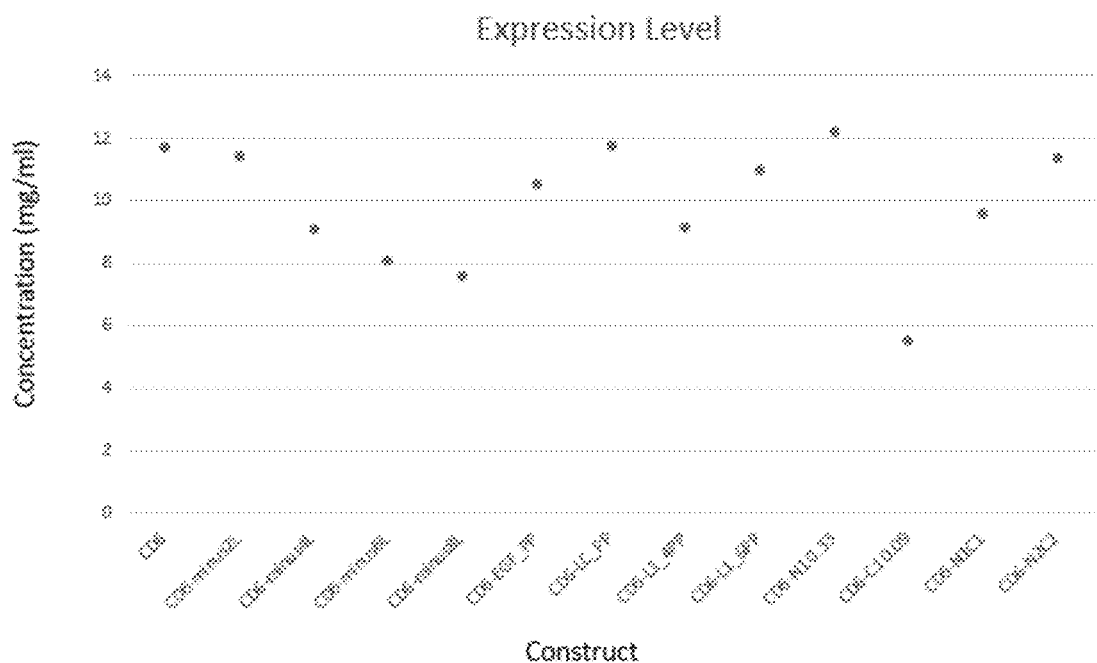
Figure 39B:
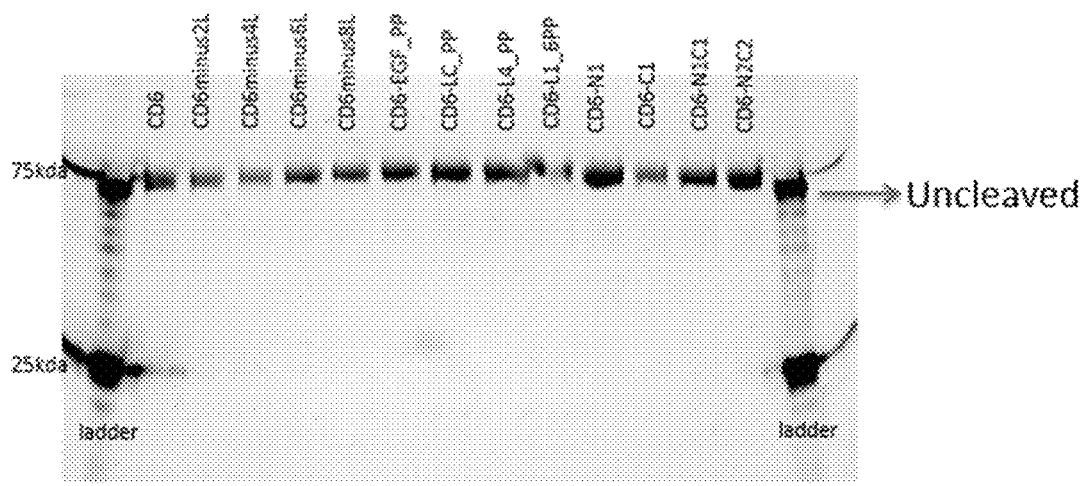
Figure 39C:
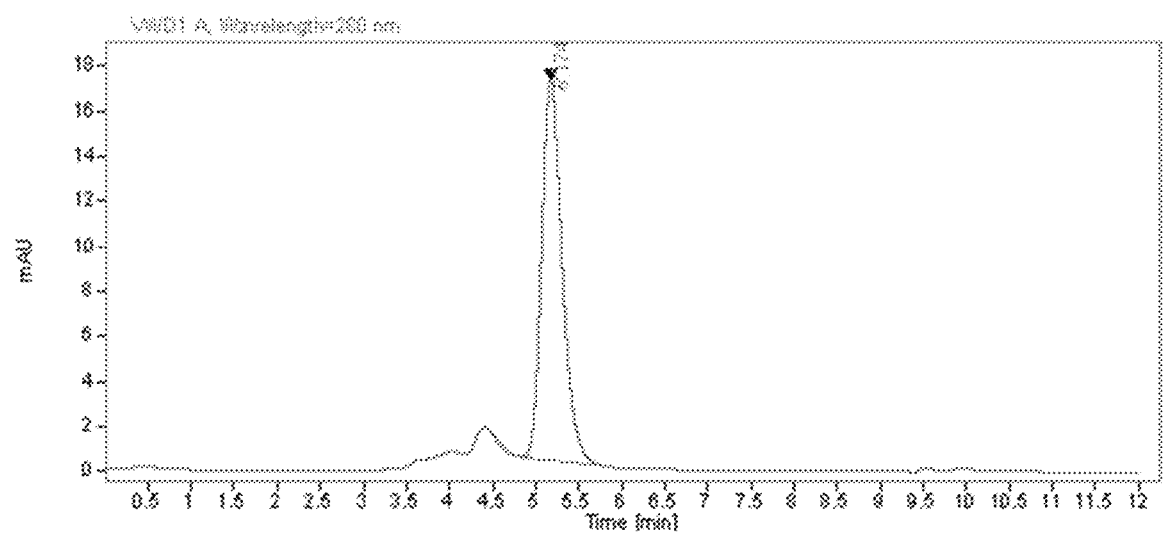

FIG. 39A-39C. Exemplary anti-CD6/EGF antibody-growth factor complexes with varying linker lengths as provided herein show good expression levels (FIG. 39A), are expressed as a single chain as shown by SDS PAGE gel (FIG. 39B), and are predominantly monomeric as demonstrated by a representative chromatogram using size exclusion chromatography (FIG. 39C). Complexes were expressed in HEK cells (suspended-10 mL), purified from the media using MabSelect Sure affinity column and size exclusion chromatography, and formulated in PBS (phosphate buffer saline).

Figure 40:
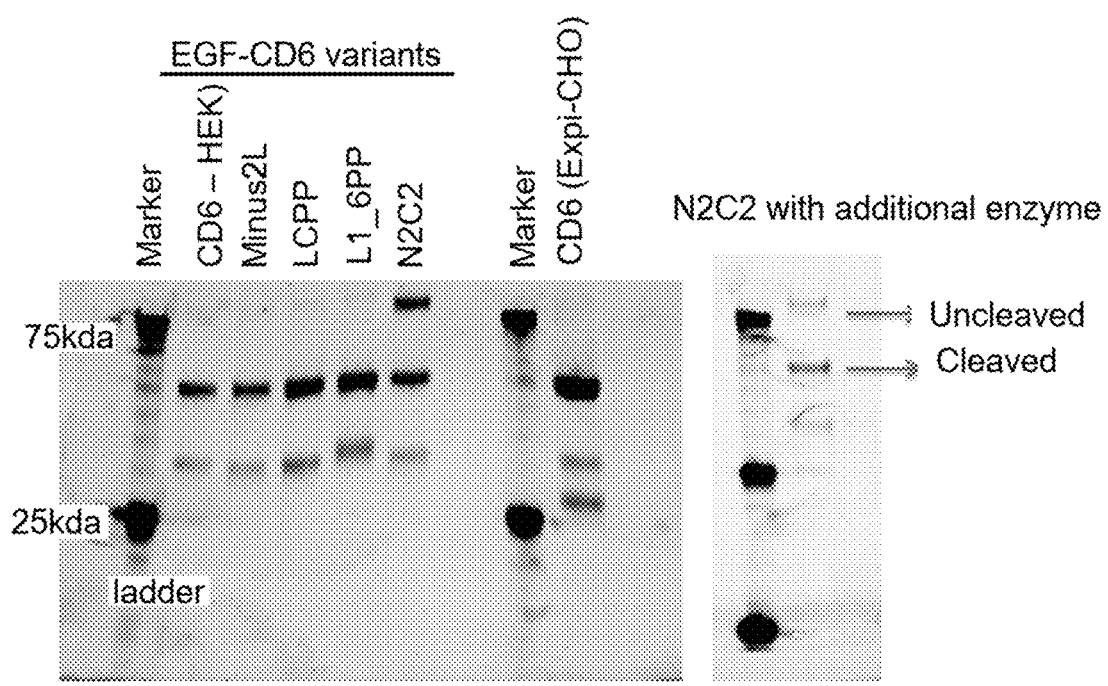
Figure 41:
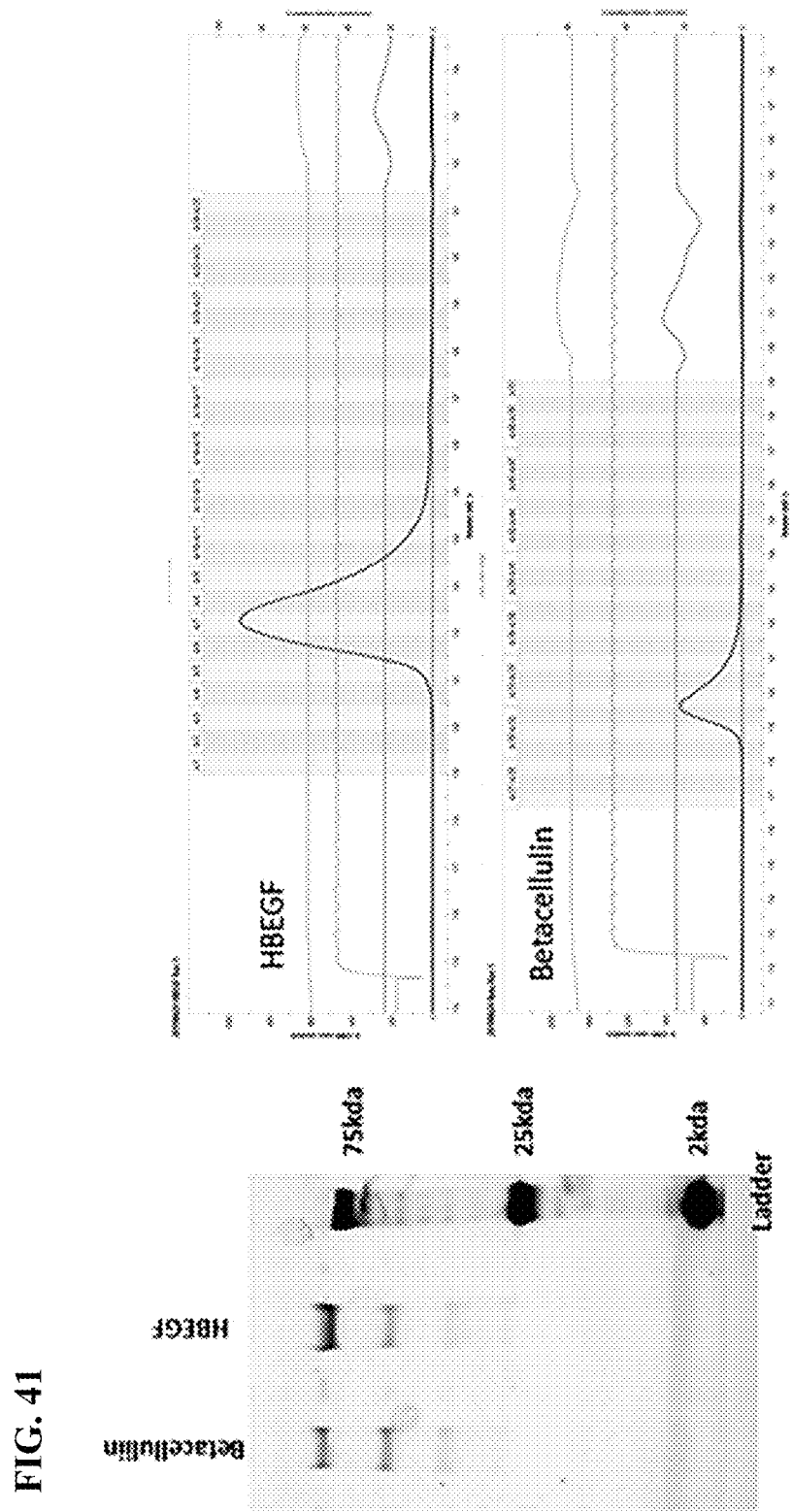
Figure 42:
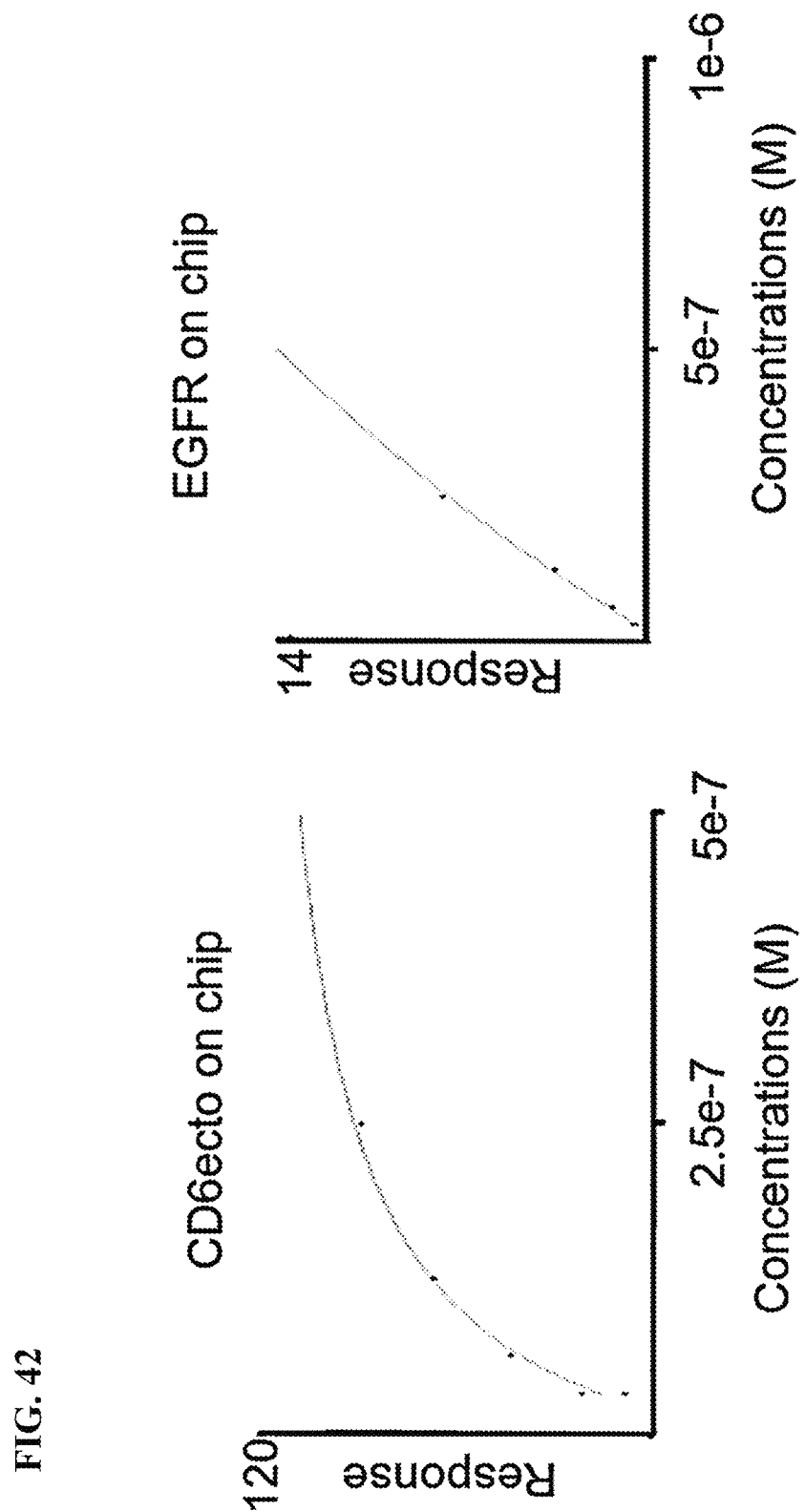

FIG. 40. Representative SDS-PAGE characterizing the cleavage of exemplary anti-CD6/EGF antibody-growth factor complexes with varying linker lengths as provided herein. 100 ng of granzyme B was added to 500 nM (32 ug) of each EGF-CD6 bionic products and the initial granzyme EGF-CD6 bionic expressed in ExpiCHO cells. All complexes were cleaved efficiently except the N2C2 variant. An addition of an extra granzyme B aliquot (100 ng) and exposure overnight was required to observe substantial cleavage.

FIG. 41. Exemplary growth factor proteins betacellulin (SEQ ID NO:68) and HBEGF (SEQ ID NO:69), members of the EGF family, bind to EGFR in a similar manner as EGF and activate downstream signaling pathways. The DNA sequence encoding EGF in the exemplary anti-CD6/EGF antibody-growth factor complexes provided herein was replaced by DNA encoding betacellulin or HBEGF, the complexes were expressed in ExpiCHO and purified using a proteinA/G affinity column followed by a size exclusion chromatography column. The yield for each complex is ~40 mg/L. The left panel shows each purified product characterized by SDS-PAGE. The right panel shows the chromatogram of HBEFG or Betacellulin, as indicated, using size exclusion chromatography.

FIG. 42. Representative binding data determined by SPR with the CD6-minus2L anti-CD6/EGF antibody-growth factor complex of SEQ ID NO:42. Both panels are based on equilibrium binding. The left panel shows binding of the CD6minus2L anti-CD6/EGF antibody-growth factor complex to the ecto CD6 domain. The right panel shows the binding of the CD6minus2L anti-CD6/EGF antibody-growth factor complex to the ecto EGFR domain. The data indicate that the complexes are capable of binding to their intended target.

DETAILED DESCRIPTION

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom (e.g. O, N, P, Si or S) and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH—CH—O—CH$_3$, —Si(CH$_3$) 3, —CH$_2$—CH═N—OCH$_3$, —CH═C H—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si (CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$- and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5 (4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R")=NR", —S(O) R', —S(O)$_2$R', —S(O)$_2$N(R)('R"—NRSO$_2$R'), —CN, and —NO$_2$ in a number ranging from zero to (2m'+1), where m' is the total number of carbon atoms in such radical. R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O) $CH_3$, —C(O) $CF_3$, —C(O) $CH_2OCH_3$, and the like).

Similar to the substituents described for the alkyl radical, substituents for the aryl and heteroaryl groups are varied and are selected from, for example:—OR', —NR'R", —SR', -halogen, —SiR'R"R''', —OC(O)R', —C(O) R', —$CO_2$R', —CONR'R", —OC(O)NR'R", —NR"C(O)R', —NR'—C(O)NR"R''', NR"C(O)$_2$R', NRC (NR'R")=NR", S (O) R', —S(O)$_2$R', —S(O)$_2$N(R') (R", —NRSO$_2$R'), —CN, —$NO_2$, —R', —$N_3$, —CH(Ph)$_2$, fluoro ($C_1$-$C_4$)alkoxy, and fluoro ($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{3A}$-substituted or unsubstituted alkyl, a plurality of $R^{3A}$ substituents may be attached to the alkyl moiety wherein each $R^{3A}$ substituent is optionally different. Where an R-substituted moiety is substituted with a plurality of R substituents, each of the R-substituents may be differentiated herein using a prime symbol (') such as R', R", etc. For example, where a moiety is $R^{3A}$-substituted or unsubstituted alkyl, and the moiety is substituted with a plurality of $R^{3A}$ substituents, the plurality of $R^{3A}$ substituents may be differentiated as $R^{3A'}$, $R^{3A''}$, $R^{3A'''}$, etc. In some embodiments, the plurality of $R^{3A}$ substituents is 3. In some embodiments, the plurality of $R^{3A}$ substituents is 2.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')—, where variables s and are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur(S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O) H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O) H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O) H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O) H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

As used herein, the term "conjugate" refers to the association between atoms or molecules. The association can be direct or indirect. For example, a conjugate between an antigen binding domain and a peptide compound can be direct, e.g., by covalent bond (e.g., a disulfide bond), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive moieties or functional groups used for conjugate chemistries (including "click chemistries" as known in the art) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold;
(h) amine or sulfhydryl groups, which can be, for example, acylated, alkylated or oxidized;
(i) alkenes, which can undergo, for example, cycloadditions, acylation, Michael addition, etc.;
(j) epoxides, which can react with, for example, amines and hydroxyl compounds;
(k) phosphoramidites and other standard functional groups useful in nucleic acid synthesis;
(l) metal silicon oxide bonding;
(m) metal bonding to reactive phosphorus groups (e.g. phosphines) to form, for example, phosphate diester bonds; and
(n) sulfones, for example, vinyl sulfone.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stockmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the antigen binding domain and the peptide compound described herein.

The terms "a" or "an," as used in herein means one or more. In addition, the phrase "substituted with a [n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The symbol "~~~" denotes the point of attachment of a chemical moiety to the remainder of a molecule or chemical formula.

Descriptions of compounds (e.g., peptide compounds, antibodies, antibody-peptide complexes, chemical compounds) of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine(S), Threonine (T); and 8) Cysteine (C), Methionine (M) (see, e.g., Creighton, Proteins (1984)).

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" refers to a peptide attached to the remainder of a molecule (e.g. $R^1$, $R^2$, or $-L^{3A}-L^{3B}-R^3$ of the peptide compound of formula (I) or (II)). A peptidyl moiety may be substituted with a chemical linker that serves to attach the peptidyl moiety to $R^1$, $R^2$, or $-L^{3A}-L^{3B}-R^3$ of the peptide compound of formula (I) or formula (II). The peptidyl moiety may also be substituted with additional chemical moieties (e.g., additional R substituents). In embodiments, the peptidyl moiety forms part of the peptide compound of formula (I). In embodiments, the peptidyl moiety forms part of the peptide compound of formula (II). The term "meditope" as used herein refers to a peptidyl moiety included in the peptide compound as described herein. Thus, in embodiments, a meditope is a peptidyl moiety.

The peptidyl moiety (e.g., meditope) may be a linear or a cyclic peptide moiety. Various methods for cyclization of a peptide moiety may be used, e.g., to address in vivo stability and to enable chemoselective control for subsequent conjugation chemistry. In some embodiments, the cyclization strategy is a lactam cyclization strategy, including head-to-tail (head-tail) lactam cyclization (between the terminal residues of the acyclic peptide) and/or lactam linkage between other residues. Lactam formation may also be affected by incorporating residues such as glycine, β-Ala, and/or 7-aminoheptanoic acid, and the like, into the acyclic peptide cyclization precursors to produce different lactam ring sizes and modes of connectivity. Additional cyclization strategies such as "click" chemistry and olefin metathesis also can be used. Such methods of peptide and peptidomimetic cyclization are well known in the art. In embodiments, the peptidyl moiety (e.g., meditope) is a linear peptidyl moiety (e.g., linear meditope). In embodiments, the peptidyl moiety (e.g., meditope) is a cyclic peptidyl moiety (e.g., cyclic meditope).

The term "peptide compound" refers to a compound including a peptidyl portion. In embodiments, the peptide compound includes a peptide or peptidyl moiety directly (covalently) or indirectly (non-covalently) attached to one or more chemical substituents (e.g., $R^1$, $R^2$, or $-L^{3A}-L^{3B}-R^3$). In embodiments, the peptide compound includes a peptide or peptidyl moiety covalently attached to one or more chemical substituents. In embodiments, the peptide compound includes a peptidyl moiety. In embodiments, the peptide compound is a compound of formula (I). In embodiments, the peptide compound is a compound of formula (II). In embodiments, the peptide compound forms part of the chemical linker provided herein (e.g., covalent linker or non-covalent linker). Thus, the complexes provided herein may include a non-covalent linker including a peptidyl moiety, wherein the peptidyl moiety is a meditope. In embodiments, the chemical linker is a non-covalent peptidyl linker including a meditope. In embodiments, the chemical linker is a covalent peptidyl linker including a meditope.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or antigen binding domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or antigen binding domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using a sequence comparison algorithms or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., at least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. In certain embodiments relating to two sequences of different lengths, the comparison window includes the entire length of the shorter of the two sequences. In some embodiments relating to two sequences of different lengths, the comparison window includes the entire length of the longer of the two sequences.

Methods of alignment of sequences for comparison are well known in the art. Optimal alignment of sequences for comparison can be conducted, e.g., by the local homology algorithm of Smith and Waterman (1970) *Adv. Appl. Math.* 2: 482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

Preferred examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (NCBI), as is known in the art. An exemplary BLAST algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In certain embodiments, the NCBI BLASTN or BLASTP program is used to align sequences. In certain embodiments, the BLASTN or BLASTP program uses the defaults used by NCBI. In certain embodiments, the BLASTN program (for nucleotide sequences) uses as defaults: a word size (W) of 28; an expectation threshold (E) or 10; max matches in a query range set to 0; match/mismatch scores of 1,-2; linear gap costs; the filter for low complexity regions used; and mask for lookup table only used. In certain embodiments, the BLASTP program (for amino acid sequences) uses as defaults a word size (W) of 3; an expectation threshold (E) of 10; max matches in a query range set to 0; the BLOSUM62 matrix (see Henikoff and Henikoff 1992) *Proc. Natl. Acad. Sci. USA* 89:10915); gap costs of existence: 11 and extension: 1; and conditional compositional score matrix adjustment.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P (N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. VH refers to the variable region of the heavy chain. VL refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain (VH or VL) typically has three CDRs identified as CDR1, CDR2 and CDR3. The CDRs of VH are also referred to herein as CDR $H_1$, CDR $H_2$ and CDR $H_3$, respectively, wherein CDR $H_1$ corresponds to CDR 1 of VH, CDR $H_2$ corresponds to CDR 2 of VH and CDR $H_3$ corresponds to CDR 3 of VH. Likewise, the CDRs of VL are referred to herein as CDR L1, CDR L2 and CDR L3, respectively, wherein CDR LI corresponds to CDR 1 of VL, CDR L2 corresponds to CDR 2 of VL and CDR L3 corresponds to CDR 3 of VL.

The CDRs of the variable region of the light chain are further referred to herein as LCDR1, LCDR2 and LCDR3, respectively, wherein LCDRI corresponds to CDR 1 of VL, LCDR 2 corresponds to CDR 2 of VL and LCDR 3 corresponds to CDR 3 of VL. Likewise, the CDRs of the variable region of the heavy chain are further referred to herein as HCDR1, HCDR2 and HCDR3, respectively, wherein HCDRI corresponds to CDR 1 of VH, HCDR 2 corresponds to CDR 2 of VH and HCDR 3 corresponds to CDR 3 of VH.

In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (available on the World Wide Web at the bioinfo.org.uk website). The present invention is not limited to FRs and CDRs as defined by the Kabat numbering system, but includes all numbering systems, including the canonical numbering system or of Chothia and Lesk J. Mol. Biol. 196:901-917, 1987; Chothia et al., Nature 342:877-883, 1989; and/or Al-Lazikani et al., J. Mol. Biol. 273:927-948, 1997; the numbering system of Honnegher and Plükthun J. Mol. Biol. 309:657-670, 2001; or the IMGT system discussed in Giudicelli et al., Nucleic Acids Res. 25:206-211 1997. In one example, the CDRs are defined according to the Kabat numbering system.

"Framework regions" (FRs) are those variable region residues other than the CDR residues. The FRs of VH are also referred to herein as FR H1, FR H2, FR H3 and FR H4, respectively, wherein FR H1 corresponds to FR 1 of VH, FR H2 corresponds to FR 2 of VH, FR H3 corresponds to FR 3 of VH and FR H4 corresponds to FR 4 of VH. Likewise, the FRs of the variable region of the heavy chain are further referred to herein as HFR1, HFR2, HFR3 and HFR4, respectively, wherein HFRI corresponds to FR 1 of VH, HFR 2 corresponds to FR 2 of VH, HFR 3 corresponds to FR 3 of VH and HFR 4 corresponds to FR 4 of VH.

Likewise, the FRs of VL are referred to herein as FR L1, FR L2, FR L3 and FR L4, respectively, wherein FR LI corresponds to FR 1 of VL, FR L2 corresponds to FR 2 of VL, FR L3 corresponds to FR 3 of VL and FR L4 corresponds to FR 4 of VL. Likewise, the FRs of the variable region of the light chain are further referred to herein as LFR1, LFR2, LFR3 and LFR4, respectively, wherein LFRI corresponds to FR 1 of VL, LFR 2 corresponds to FR 2 of VL, LFR 3 corresponds to FR 3 of VL and LFR 4 corresponds to FR 4 of VL.

The term "antigen" as provided herein refers to molecules capable of binding to the antibody binding site, wherein the binding site is not a non-CDR peptide binding region.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31 (3): 169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

An "affibody" as described herein is commonly well known in the art and refers to small, robust proteins engineered to bind to a large number of target proteins or peptides with high affinity, by imitating monoclonal antibodies. Affibodies are therefore a member of the family of antibody mimetics. In embodiments, an affibody is a molecule including of three alpha helices with about 58 amino acids and a molar mass of about 6 kDa. In embodiments, the anti-CD6 antibody is an affibody.

An "antibody variant" as provided herein refers to a polypeptide capable of binding to an antigen and including one or more structural domains of an antibody or fragment thereof.

Non-limiting examples of antibody variants include single-domain antibodies or nanobodies, affibodies (polypeptides smaller than monoclonal antibodies (e.g., about 6kDA) and capable of binding antigens with high affinity and imitating monoclonal antibodies, monospecific Fab2, bispecific Fab2, trispecific Fab3, monovalent IgGs, scFv, bispecific diabodies, trispecific triabodies, scFv-Fc, minibodies, IgNAR, V-NAR, hcIgG, VhH, or peptibodies. In embodiments, the anti-CD6 antibody is an antibody variant. A "nanobody" or "single domain antibody" as described herein is commonly well known in the art and refers to an antibody fragment consisting of a single monomeric variable antibody domain. Like a whole antibody, it is able to bind selectively to a specific antigen. In embodiments, the anti-CD6 antibody is a nanobody. A "peptibody" as provided herein refers to a peptide moiety attached (through a covalent or non-covalent linker) to the Fc domain of an antibody. In embodiments, the anti-CD6 antibody is a peptibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

A "single domain antibody" as provided herein refers to an antibody fragment including a single monomeric variable antibody domain. Like a whole antibody, a single domain antibody is able to bind selectively to a specific antigen. The molecular weight of a single domain antibody is 12-15 kDa, single domain antibody. In embodiments, a single domain antibody is a variable heavy chain domain. In embodiments, a single domain antibody is a variable light chain domain. Non-limiting examples of single domain antibodies include camelid-derived VHH fragments and VNAR (variable immunoglobulin new antigen receptor) fragments. In embodiments, the single-domain antibody is a peptide domain of about 110 amino acids. In embodiments, the single-domain antibody includes a variable heavy chain domain. In embodiments, the single-domain antibody includes a variable light chain domain. In embodiments, the anti-CD6 antibody is a single domain antibody.

A "therapeutic antibody" as provided herein refers to any antibody or functional fragment thereof that is used to treat cancer, autoimmune diseases, transplant rejection, cardiovascular disease or other diseases or conditions such as those described herein.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody.

A "therapeutic agent" or "therapeutic moiety" as referred to herein, is a composition (e.g., small molecule, peptide, nucleic acid, protein, fragment) useful in treating or preventing a disease.

The phrase "specifically (or selectively) binds to an antibody" or "specifically (or selectively) immunoreactive with," when referring to a protein or peptide refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

The term "anti-CD6 antibody" as used herein refers to an antibody capable of binding CD6 through the antibody's CDR sequences. Thus, the anti-CD6 antibody includes an antibody binding site composed of CDRs (e.g., LCDR1, LCDR2, LCDR3, HCDR1, HCDR2, HCDR3,) that specifically bind CD6.

"CD6," also known as TP120, as referred to herein includes any of the recombinant or naturally-occurring forms of cluster of differentiation 6 (CD6) protein or variants or homologs thereof that maintain CD6 activity (e.g. within at least 50%, 80%, 90%, 95%, 96%, 97%, 98%, 99% or 100% activity compared to CD6). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring CD6 protein. In embodiments, the CD6 protein is substantially identical to the protein identified by the UniProt reference number P30203 or a variant or homolog having substantial identity thereto. In embodiments, CD6 is a human CD6 protein. In embodiments, a variant or mutant CD6 protein includes no more than 5, 4, 3, 2, or 1 deletions compared to the naturally occurring CD6 protein. In embodiments, a variant or mutant CD6 protein includes no more than 5, 4, 3, 2, or 1 insertions compared to the naturally occurring CD6 protein. In embodiments, a variant or mutant CD6 protein does not include deletions compared to the naturally occurring CD6 protein. In embodiments, a variant or mutant CD6 protein does not include insertions compared to the naturally occurring CD6 protein. In embodiments, a variant or mutant CD6 protein includes substitutions that are conservative substitutions compared to the naturally occurring CD6 protein. In embodiments, CD6 is the protein identified by the NCBI sequence reference NP_006716.3, or an isoform or naturally occurring mutant or variant thereof. In various embodiments, CD6 is the protein as identified by the NCBI sequence reference NP_001241679.1, or an isoform or naturally occurring mutant or variant thereof. In certain embodiments, CD6 is the protein as identified by the NCBI sequence reference NP_001241680.1, or an isoform or naturally occurring mutant or variant thereof. Non-limiting examples of human CD6 amino acid sequences available under NCBI sequence references are as follows:

NP_006716.3
(SEQ ID NO: 7)
MWLFFGITGLLTAALSGHPSPAPPDQLNTSSAESELWEPGERLPVRLINGSSSCSGTVEV

RLEASWEPACGALWDSRAAEAVCRALGCGGAEAASQLAPPTPELPPPPAAGNTSVAAN

ATLAGAPALLCSGAEWRLCEVVEHACRSDGRRARVTCAENRALRLVDGGGACAGRVE

MLEHGEWGSVCDDTWDLEDAHVVCRQLGCGWAVQALPGLHFTPGRGPIHRDQVNCS

GAEAYLWDCPGLPGQHYCGHKEDAGAVCSEHQSWRLTGGADRCEGQVEVHFRGVWN

TVCDSEWYPSEAKVLCQSLGCGTAVERPKGLPHSLSGRMYYSCNGEELTLSNCSWRFN

NSNLCSQSLAARVLCSASRSLHNLSTPEVPASVQTVTIESSVTVKIENKESRELMLLIPSIV

LGILLLGSLIFIAFILLRIKGKYALPVMVNHQHLPTTIPAGSNSYQPVPITIPKEVFMLPIQV

QAPPPEDSDSGSDSDYEHYDFSAQPPVALTTFYNSQRHRVTDEEVQQSRFQMPPLEEGL

EELHASHIPTANPGHCITDPPSLGPQYHPRSNSESSTSSGEDYCNSPKSKLPPWNPQVFSS

ERSSFLEQPPNLELAGTQPAFSAGPPADDSSSTSSGEWYQNFQPPPQPPSEEQFGCPGSPS

PQPDSTDNDDYDDISAA

NP_001241679.1
(SEQ ID NO: 8)
MWLFFGITGLLTAALSGHPSPAPPDQLNTSSAESELWEPGERLPVRLINGSSSCSGTVEV

RLEASWEPACGALWDSRAAEAVCRALGCGGAEAASQLAPPTPELPPPPAAGNTSVAAN

ATLAGAPALLCSGAEWRLCEVVEHACRSDGRRARVTCAENRALRLVDGGGACAGRVE

MLEHGEWGSVCDDTWDLEDAHVVCRQLGCGWAVQALPGLHFTPGRGPIHRDQVNCS

GAEAYLWDCPGLPGQHYCGHKEDAGAVCSEHQSWRLTGGADRCEGQVEVHFRGVWN

TVCDSEWYPSEAKVLCQSLGCGTAVERPKGLPHSLSGRMYYSCNGEELTLSNCSWRFN

NSNLCSQSLAARVLCSASRSLHNLSTPEVPASVQTVTIESSVTVKIENKESRELMLLIPSIV

LGILLLGSLIFIAFILLRIKGKYVFMLPIQVQAPPPEDSDSGSDSDYEHYDFSAQPPVALTT

FYNSQRHRVTDEEVQQSRFQMPPLEEGLEELHASHIPTANPGHCITDPPSLGPQYHPRSN

SESSTSSGEDYCNSPKSKLPPWNPQVFSSERSSFLEQPPNLELAGTQPAFSGSPSPQPDSTD

NDDYDDISAA

NP_001241680.1
(SEQ ID NO: 9)
MWLFFGITGLLTAALSGHPSPAPPDQLNTSSAESELWEPGERLPVRLINGSSSCSGTVEV

RLEASWEPACGALWDSRAAEAVCRALGCGGAEAASQLAPPTPELPPPPAAGNTSVAAN

ATLAGAPALLCSGAEWRLCEVVEHACRSDGRRARVTCAENRALRLVDGGGACAGRVE

MLEHGEWGSVCDDTWDLEDAHVVCRQLGCGWAVQALPGLHFTPGRGPIHRDQVNCS

GAEAYLWDCPGLPGQHYCGHKEDAGAVCSEHQSWRLTGGADRCEGQVEVHFRGVWN

TVCDSEWYPSEAKVLCQSLGCGTAVERPKGLPHSLSGRMYYSCNGEELTLSNCSWRFN

NSNLCSQSLAARVLCSASRSLHNLSTPEVPASVQTVTIESSVTVKIENKESRELMLLIPSIV

LGILLLGSLIFIAFILLRIKGKYALPVMVNHQHLPTTIPAGSNSYQPVPITIPKEDSQRHRVT

DEEVQQSRFQMPPLEEGLEELHASHIPTANPGHCITDPPSLGPQYHPRSNSESSTSSGEDY

CNSPKSKLPPWNPQVFSSERSSFLEQPPNLELAGTQPAFSGSPSPQPDSTDNDDYDDISAA

"CD166," also known as ALCAM, as referred to herein includes any of the recombinant or naturally-occurring forms of cluster of differentiation 166 (CD166) protein or variants or homologs thereof that maintain CD166 activity (e.g. within at least 50%, 80%, 90%, 95%, 96%, 97%, 98%, 99% or 100% activity compared to CD166). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring CD166 protein. In embodiments, the CD166 protein is substantially identical to the protein identified by the UniProt reference number Q13740 or a variant or homolog having substantial identity thereto. In embodiments, CD166 is a human CD166 protein. In embodiments, a variant or mutant CD166 protein includes no more than 5, 4, 3, 2, or 1 deletions compared to the naturally occurring CD166 protein. In embodiments, a variant or mutant CD166 protein includes no more than 5, 4, 3, 2, or 1 insertions compared to the naturally occurring CD166 protein. In embodiments, a variant or mutant CD166 protein does not include deletions compared to the naturally occurring CD166 protein. In embodiments, a variant or mutant CD166 protein does not include insertions compared to the naturally occurring CD166 protein. In embodiments, a variant or mutant CD166 protein includes substitutions that are conservative substitutions compared to the naturally occurring CD166 protein. In embodiments, CD166 is the protein identified by the NCBI sequence reference NP_001230209.1, or an isoform or naturally occurring mutant or variant thereof. In various embodiments, CD166 is the protein as identified by the NCBI sequence reference NP_001230210.1, or an isoform or naturally occurring mutant or variant thereof. In embodiments, CD166 is the protein as identified by the NCBI sequence reference NP_001230212.1, or an isoform or naturally occurring mutant or variant thereof. In embodiments, CD166 is the protein as identified by the NCBI sequence reference NP_001618.2, or an isoform or naturally occurring mutant or variant thereof.

"Her2" as referred to herein includes any of the recombinant or naturally-occurring forms of the human epidermal growth factor receptor 2 protein, also known as receptor tyrosine-protein kinase erbB-2, or variants or homologs thereof that maintain Her2 activity (e.g. within at least 50%, 80%, 90%, 95%, 96%, 97%, 98%, 99% or 100% activity compared to Her2). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring Her2 protein. In embodiments, the Her2 protein is substantially identical to the protein identified by the UniProt reference number P04626 or a variant or homolog having substantial identity thereto.

"CD318," also known as CDCP1, as referred to herein includes any of the recombinant or naturally-occurring forms of cluster of differentiation 318 (CD318) protein or variants or homologs thereof that maintain CD318 activity (e.g. within at least 50%, 80%, 90%, 95%, 96%, 97%, 98%, 99% or 100% activity compared to CD318). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring CD318 protein. In embodiments, the CD318 protein is substantially identical to the protein identified by the UniProt reference number Q9H5V8 or a variant or homolog having substantial identity thereto. In embodiments, CD318 is a human CD318 protein. In embodiments, a variant or mutant CD318 protein includes no more than 5, 4, 3, 2, or 1 deletions compared to the naturally occurring CD318 protein. In embodiments, a variant or mutant CD318 protein includes no more than 5, 4, 3, 2, or 1 insertions compared to the naturally occurring CD318 protein. In embodiments, a variant or mutant CD318 protein does not include deletions compared to the naturally occurring CD318 protein. In embodiments, a variant or mutant CD318 protein does not include insertions compared to the naturally occurring CD318 protein. In embodiments, a variant or mutant CD318 protein includes substitutions that are conservative substitutions compared to the naturally occurring CD318 protein. In embodiments, CD318 is the protein identified by the NCBI sequence reference NP 073753.3, or an isoform or naturally occurring mutant or variant thereof. In various embodiments, CD318 is the protein as identified by the NCBI sequence reference NP_073753.3, or an isoform or naturally occurring mutant or variant thereof.

The term "EGF" as referred to herein includes any of the recombinant or naturally-occurring forms of epidermal growth factor (EGF) protein or variants or homologs thereof that maintain EGF activity (e.g. within at least 50%, 80%, 90%, 95%, 96%, 97%, 98%, 99% or 100% activity compared to EGF). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring EGF protein. In embodiments, the EGF protein is substantially identical to the protein identified by the UniProt reference number P01133 or a variant or homolog having substantial identity thereto. In embodiments, the EGF protein is substantially identical (e.g., at least 85%, 90%, 95%, 96%, 97%, 98%, 99% or 100% identical) to the amino acid sequence of

```
                                          SEQ ID NO: 4
(NSDSECPLSHDGYCLHDGVCMYIEALDKYACNCVVGYIGERCQYRDLKW
WELR.
```

In embodiments, the EGF protein is substantially identical (e.g., at least 85%, 90%, 95%, 96%, 97%, 98%, 99% or 100% identical) to the amino acid sequence of SEQ ID NO:12. In embodiments, EGF is a human EGF protein. In embodiments, EGF is the protein identified by the NCBI sequence reference NP_001171601.1, or an isoform or naturally occurring mutant or variant thereof. In various embodiments, EGF is the protein as identified by the NCBI sequence reference NP_001171602.1, or an isoform or naturally occurring mutant or variant thereof. In various embodiments, EGF is the protein as identified by the NCBI sequence reference NP 001954.2, or an isoform or naturally occurring mutant or variant thereof. In certain embodiments, EGF is the protein as identified by the NCBI sequence reference NP_001343950.1, or an isoform or naturally occurring mutant or variant thereof. In embodiments, a variant or mutant EGF protein or fragment includes no more than 5, 4, 3, 2, or 1 deletions compared to the naturally occurring EGF protein. In embodiments, a variant or mutant EGF protein or fragment includes no more than 5, 4, 3, 2, or 1 insertions compared to the naturally occurring EGF protein. In embodiments, a variant or mutant EGF protein or fragment does not include deletions compared to the naturally occurring EGF protein. In embodiments, a variant or mutant EGF protein or fragment does not include insertions compared to the naturally occurring EGF protein. In embodiments, a variant or mutant EGF protein or fragment includes substitutions that are conservative substitutions compared to the naturally occurring EGF protein.

The term "gastrin" as referred to herein includes any of the recombinant or naturally-occurring forms of gastrin protein or variants or homologs thereof that maintain gastrin activity (e.g. within at least 50%, 80%, 90%, 95%, 96%, 97%, 98%, 99% or 100% activity compared to gastrin). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring gastrin protein. In embodiments, the gastrin protein is substantially identical to the protein identified by the UniProt reference number P01350 or a variant or homolog having substantial identity thereto. In embodiments, gastrin is a human gastrin protein. In embodiments, gastrin is the protein identified by the NCBI sequence reference NP_000796.1, or an isoform or naturally occurring mutant or variant thereof. In embodiments, a variant or mutant gastrin protein or fragment includes no more than 5, 4, 3, 2, or 1 deletions compared to the naturally occurring gastrin protein. In embodiments, a variant or mutant gastrin protein or fragment includes no more than 5, 4, 3, 2, or 1 insertions compared to the naturally occurring gastrin protein. In embodiments, a variant or mutant gastrin protein or fragment does not include deletions compared to the naturally occurring gastrin protein. In embodiments, a variant or mutant gastrin protein or fragment does not include insertions compared to the naturally occurring gastrin protein. In embodiments, a variant or mutant gastrin protein or fragment includes substitutions that are conservative substitutions compared to the naturally occurring gastrin protein.

The term "GLP-1" or "GLP1" as referred to herein includes any of the recombinant or naturally-occurring forms of Glucagon-precursor-like peptide-1 (GLP-1) protein or variants or homologs thereof that maintain GLP-1 activity (e.g. within at least 50%, 80%, 90%, 95%, 96%, 97%, 98%, 99% or 100% activity compared to GLP-1). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring GLP-1 protein. In embodiments, the GLP-1 protein is substantially identical to the protein identified by the UniProt reference number P01275 or a variant or homolog having substantial identity thereto. In embodiments, GLP-1 is a human GLP-1 protein. In embodiments, GLP-1 is the protein identified by the NCBI sequence reference NP_002053.3, or an isoform or naturally occurring mutant or variant thereof. In embodiments, GLP-1 is the protein identified by the NCBI sequence reference NP_002053.3, or an isoform or naturally occurring mutant or variant thereof. In embodiments, a variant or mutant GLP-1 protein or fragment includes no more than 5, 4, 3, 2, or 1 deletions compared to the naturally occurring GLP-1 protein. In embodiments, a variant or mutant GLP-1 protein or fragment includes no more than 5, 4, 3, 2, or 1 insertions compared to the naturally occurring GLP-1 protein. In embodiments, a variant or mutant GLP-1 protein or fragment does not include deletions compared to the naturally occurring GLP-1 protein. In embodiments, a variant or mutant GLP-1 protein or fragment does not include insertions compared to the naturally occurring GLP-1 protein. In embodiments, a variant or mutant GLP-1 protein or fragment includes substitutions that are conservative substitutions compared to the naturally occurring GLP-1 protein.

The term "betacellulin" or "BTC" as referred to herein includes any of the recombinant or naturally-occurring forms of betacellulin protein or variants or homologs thereof that maintain betacellulin activity (e.g. within at least 50%, 80%, 90%, 95%, 96%, 97%, 98%, 99% or 100% activity compared to betacellulin). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring betacellulin protein. In embodiments, the betacellulin protein is substantially identical to the protein identified by the UniProt reference number P35070 or a variant or homolog having substantial identity thereto. In embodiments, betacellulin is a human betacellulin protein. In embodiments, betacellulin is the protein identified by the NCBI sequence reference NP_001720.1, or an isoform or naturally occurring mutant or variant thereof. In embodiments, a variant or mutant betacellulin protein or fragment includes no more than 5, 4, 3, 2, or 1 deletions compared to the naturally occurring betacellulin protein. In embodiments, a variant or mutant betacellulin protein or fragment includes no more than 5, 4, 3, 2, or 1 insertions compared to the naturally occurring betacellulin protein. In embodiments, a variant or mutant betacellulin protein or fragment does not include deletions compared to the naturally occurring betacellulin protein. In embodiments, a variant or mutant betacellulin protein or fragment does not include insertions compared to the naturally occurring betacellulin protein. In embodiments, a variant or mutant betacellulin protein or fragment includes substitutions that are conservative substitutions compared to the naturally occurring betacellulin protein.

The term "heparin-binding EGF-like growth factor" or "HBEGF" as referred to herein includes any of the recombinant or naturally-occurring forms of heparin-binding EGF-like growth factor (HBEGF) protein or variants or homologs thereof that maintain HBEGF activity (e.g. within at least 50%, 80%, 90%, 95%, 96%, 97%, 98%, 99% or 100% activity compared to HBEGF). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring HBEGF protein. In embodiments, the HBEGF protein is substantially identical to the protein identified by the UniProt reference number Q99075 or a variant or homolog having substantial identity thereto. In embodiments, HBEGF is a human HBEGF protein. In embodiments, HBEGF is the protein identified by the NCBI sequence reference NP_001936.1, or an isoform or naturally occurring mutant or variant thereof. In embodiments, a variant or mutant HBEGF protein or fragment includes no more than 5, 4, 3, 2, or 1 deletions compared to the naturally occurring HBEGF protein. In embodiments, a variant or mutant HBEGF protein or fragment includes no more than 5, 4, 3, 2, or 1 insertions compared to the naturally occurring HBEGF protein. In embodiments, a variant or mutant HBEGF protein or fragment does not include deletions compared to the naturally occurring HBEGF protein. In embodiments, a variant or mutant HBEGF protein or fragment does not include insertions compared to the naturally occurring HBEGF protein. In embodiments, a variant or mutant HBEGF protein or fragment includes substitutions that are conservative substitutions compared to the naturally occurring HBEGF protein.

The term "Transforming growth factor alpha", "TGF-α", or "TGF alpha" as referred to herein includes any of the recombinant or naturally-occurring forms of Transforming growth factor alpha (TGF-α) protein or variants or homologs thereof that maintain TGF-α activity (e.g. within at least 50%, 80%, 90%, 95%, 96%, 97%, 98%, 99% or 100% activity compared to TGF-α). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring TGF-α protein. In embodiments, the TGF-α protein is substantially identical to the protein identified by the UniProt reference number P01135 or a variant or homolog having substantial identity thereto. In embodiments, TGF-α is a human TGF-α protein. In embodiments, TGF-α is the protein identified by the NCBI sequence reference NP_003227.1, or an isoform or naturally occurring mutant or variant thereof. In embodiments, a variant or mutant TGF-α protein or fragment includes no more than 5, 4, 3, 2, or 1 deletions compared to the naturally occurring GLP-1 protein. In embodiments, a variant or mutant TGF-α protein or fragment includes no more than 5, 4, 3, 2, or 1 insertions compared to the naturally occurring TGF-α protein. In embodiments, a variant or mutant TGF-α protein or fragment does not include deletions compared to the naturally occurring TGF-α protein. In embodiments, a variant or mutant TGF-α protein or fragment does not include insertions compared to the naturally occurring TGF-α protein. In embodiments, a variant or mutant TGF-α protein or fragment includes substitutions that are conservative substitutions compared to the naturally occurring TGF-α protein.

The term "amphiregulin" or "AREG" as referred to herein includes any of the recombinant or naturally-occurring forms of amphiregulin (AREG) protein or variants or homologs thereof that maintain amphiregulin activity (e.g. within at least 50%, 80%, 90%, 95%, 96%, 97%, 98%, 99% or 100% activity compared to amphiregulin). In some aspects, the variants or homologs have at least 90%, 95%, 96%, 97%, 98%, 99% or 100% amino acid sequence identity across the whole sequence or a portion of the sequence (e.g,. a 50, 100, 150 or 200 continuous amino acid portion) compared to a naturally occurring amphiregulin protein. In embodiments, the amphiregulin protein is substantially identical to the protein identified by the UniProt reference number P15514 or a variant or homolog having substantial identity thereto. In embodiments, amphiregulin is a human amphiregulin protein. In embodiments, amphiregulin is the protein identified by the NCBI sequence reference NP_001648.1, or an isoform or naturally occurring mutant or variant thereof. In embodiments, a variant or mutant amphiregulin protein or fragment includes no more than 5, 4, 3, 2, or 1 deletions compared to the naturally occurring amphiregulin protein. In embodiments, a variant or mutant amphiregulin protein or fragment includes no more than 5, 4, 3, 2, or 1 insertions compared to the naturally occurring amphiregulin protein. In embodiments, a variant or mutant amphiregulin protein or fragment does not include deletions compared to the naturally occurring amphiregulin protein. In embodiments, a variant or mutant amphiregulin protein or fragment does not include insertions compared to the naturally occurring amphiregulin protein. In embodiments, a variant or mutant amphiregulin protein or fragment includes substitutions that are conservative substitutions compared to the naturally occurring amphiregulin protein.

The term "epigen" or "epithelial mitogen" as referred to herein includes any of the recombinant or naturally-occurring forms of epigen protein or variants or homologs thereof that maintain epigen activity (e.g. within at least 50%, 80%, 90%, 95%, 96%, 97%, 98%, 99% or 100% activity compared to epigen). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring epigen protein. In embodiments, the epigen protein is substantially identical to the protein identified by the UniProt reference number Q6UW88 or a variant or homolog having substantial identity thereto. In embodiments, epigen is a human epigen protein. In embodiments, epigen is the protein identified by the NCBI sequence reference NP_001257918, or an isoform or naturally occurring mutant or variant thereof. In embodiments, epigen is the protein identified by the NCBI sequence reference NP_001257920.1, or an isoform or naturally occurring mutant or variant thereof. In embodiments, a variant or mutant epigen protein or fragment includes no more than 5, 4, 3, 2, or 1 deletions compared to the naturally occurring epigen protein. In embodiments, a variant or mutant epigen protein or fragment includes no more than 5, 4, 3, 2, or 1 insertions compared to the naturally occurring epigen protein. In embodiments, a variant or mutant epigen protein or fragment does not include deletions compared to the naturally occurring epigen protein. In embodiments, a variant or mutant epigen protein or fragment does not include insertions compared to the naturally occurring epigen protein. In embodiments, a variant or mutant epigen protein or fragment includes substitutions that are conservative substitutions compared to the naturally occurring epigen protein.

The term "epiregulin" or "EPR" as referred to herein includes any of the recombinant or naturally-occurring forms of epiregulin (EPR) protein or variants or homologs thereof that maintain EPR activity (e.g. within at least 50%, 80%, 90%, 95%, 96%, 97%, 98%, 99% or 100% activity compared to EPR). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring EPR protein. In embodiments, the EPR protein is substantially identical to the protein identified by the UniProt reference number O14944 or a variant or homolog having substantial identity thereto. In embodiments, EPR is a human EPR protein. In embodiments, EPR is the protein identified by the NCBI sequence reference NP_001423.1, or an isoform or naturally occurring mutant or variant thereof. In embodiments, a variant or mutant EPR protein or fragment includes no more than 5, 4, 3, 2, or 1 deletions compared to the naturally occurring EPR protein. In embodiments, a variant or mutant EPR protein or fragment includes no more than 5, 4, 3, 2, or 1 insertions compared to the naturally occurring EPR protein. In embodiments, a variant or mutant EPR protein or fragment does not include deletions compared to the naturally occurring EPR protein. In embodiments, a variant or mutant EPR protein or fragment does not include insertions compared to the naturally occurring EPR protein. In embodiments, a variant or mutant EPR protein or fragment includes substitutions that are conservative substitutions compared to the naturally occurring EPR protein.

The term "fragment," as used herein, means a portion of a polypeptide or polynucleotide that is less than the entire polypeptide or polynucleotide. As used herein, a "fragment" or "functional fragment" of a protein, e.g., EGF, GLP-1, gastrin, is a fragment of the polypeptide that is shorter than the full-length, immature, or mature polypeptide and has at least 25% (e.g., at least 30%, 40%, 50%, 60%, 70%, 80%, 90%, 95%, 98%, 99%, or even 100% or more) of the activity of full-length mature reference protein. Fragments of interest can be made by recombinant, synthetic, or proteolytic digestive methods. In embodiments, EGF fragments described herein have total lengths of about 50, about 45, about 40, about 35, about 30, about 25, about 20, about 15, or about 10 amino acids in length (including all intermediate lengths). In embodiments, the EGF fragment includes an amino acid of SEQ ID NO:5 (DGYCLHDGVCMYIEALDKYAC). In embodiments, the EGF fragment is an amino acid of SEQ ID NO:5. In embodiments, the EGF fragment includes an amino acid of SEQ ID NO:6 (DGYCLHDGVSMYIEALDKYAC (quasi-cyclic peptide (Cys4-Cys21) with a Cys-to-Ser substitution at position 10)). In embodiments, gastrin fragments described herein have total lengths of about 50, about 45, about 40, about 35, about 30, about 25, about 20, about 15, or about 10 amino acids in length (including all intermediate lengths). In embodiments, the EGF fragment is an amino acid of SEQ ID NO:6. In embodiments, the fragment is a gastrin fragment. In embodiments, the fragment is a GLP-1 fragment. In embodiments, gastrin fragments described herein have total lengths of about 50, about 45, about 40, about 35, about 30, about 25, about 20, about 15, or about 10 amino acids in length (including all intermediate lengths). In embodiments, GLP-1 fragments described herein have total lengths of about 50, about 45, about 40, about 35, about 30, about 25, about 20, about 15, or about 10 amino acids in length (including all intermediate lengths). In embodiments, the fragment is a betacellulin fragment. In embodiments, betacellulin fragments described herein have total lengths of about 55, about 50, about 45, about 40, about 35, about 30, about 25, about 20, about 15, or about 10 amino acids in length (including all intermediate lengths). In embodiments, the fragment is an HBEGF fragment. In embodiments, HBEGF fragments described herein have total lengths of about 55, about 50, about 45, about 40, about 35, about 30, about 25, about 20, about 15, or about 10 amino acids in length (including all intermediate lengths).

A "ligand" refers to an agent, e.g., a polypeptide or other molecule, capable of binding to a receptor. In embodiments, a ligand is a ligand capable of binding to an epidermal growth factor receptor (EGFR). In embodiments, the ligand is epidermal growth factor (EGF). In embodiments, the ligand is gastrin. In embodiments, the ligand is GLP-1. In embodiments, the ligand is CD6. In embodiments, the ligand is ALCAM. In embodiments, the ligand is CD318. In embodiments, the ligand is a fragment.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, an antibody and an antigen or a ligand and a receptor. In embodiments, contacting includes, for example, allowing an antibody (e.g., anti-CD6 antibody) to bind an antigen (e.g., CD6). In embodiments, contacting includes allowing a peptide (e.g., EGF) to bind to a receptor (e.g., EGFR).

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

As defined herein, the term "inhibition", "inhibit", "inhibiting" and the like in reference to a protein-inhibitor (e.g., antagonist) interaction means negatively affecting (e.g. decreasing) the activity or function of the protein relative to the activity or function of the protein in the absence of the inhibitor. In embodiments inhibition refers to reduction of a disease or symptoms of disease. Thus, in embodiments, inhibition includes, at least in part, partially or totally blocking stimulation, decreasing, preventing, or delaying activation, or inactivating, desensitizing, or down-regulating signal transduction or enzymatic activity or the amount of a protein. The amount of inhibition may be 10%, 20%, 30%, 40%, 50%, 60%, 70%, 80%, 90%, 100% or less in comparison to a control in the absence of the antagonist. In embodiments, the inhibition is 1.5-fold, 2-fold, 3-fold, 4-fold, 5-fold, 10-fold, or more than the expression or activity in the absence of the antagonist.

As defined herein, the term "activation", "activate", "activating" and the like in reference to a protein-activator (e.g., agonist) interaction means positively affecting (e.g. increasing) the activity or function of the relative to the activity or function of the protein in the absence of the activator. Thus, in embodiments, activation may include, at least in part, partially or totally increasing stimulation, increasing or enabling activation, or activating, sensitizing, or up-regulating signal transduction or enzymatic activity or the amount of a protein decreased in a disease. The amount of activation may be 10%, 20%, 30%, 40%, 50%, 60%, 70%, 80%, 90%, 100% or more in comparison to a control in the absence of the agonist. In embodiments, the activation is 1.5-fold, 2-fold, 3-fold, 4-fold, 5-fold, 10-fold, or more than the expression or activity in the absence of the agonist.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated activity (e.g. by using a method as described herein), results in reduction of the disease or one or more disease symptoms.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living member of the animal kingdom suffering from or that may suffer from the indicated disorder. In embodiments, the subject is a member of a species that includes individuals who naturally suffer from the disease. In embodiments, a subject is a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is an autoimmune disease (e.g. Type I Diabetes).

An "autoimmune disease" as used herein refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, and allergic asthma.

As used herein, an "inflammatory disease" refers to a disease or disorder associated with abnormal or altered inflammation. Inflammation is a biological response initiated by the immune system as part of the healing process in response to a pathogen, damaged cells or tissues or irritants. Chronic inflammation can lead to a variety of diseases. Inflammatory diseases include, but are not limited to, atherosclerosis, allergies, asthma, rheumatoid arthritis, transplant rejection, celiac disease, chronic prostatitis, inflammatory bowel diseases, pelvic inflammatory diseases, and inflammatory myopathies.

As used herein, the term "graft-versus-host disease" or "GvHD" refers to a disease or disorder associated with the receipt of transplanted tissue originated from a source (e.g., individual) having a genetic background different from the recipient. GvHD may be associated with stem cell transplants such as those that occur with bone marrow transplants, blood transfusions or other forms of transplanted tissues such as solid organ transplants. During GvHD white blood cells of the donor's immune system which remain within the donated tissue (the graft) may recognize the recipient (the host) as foreign (non-self) and subsequently attack the recipient's body's cells resulting in GvHD.

The term "associated" or "associated with" in the context of a substance or substance activity or function associated with a disease (e.g., Type I Diabetes) means that the disease (e.g. Type I Diabetes) is caused by (in whole or in part), or a symptom of the disease is caused by (in whole or in part) the substance or substance activity or function.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, "treating" refers to treatment of an autoimmune disease.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of*

*Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

Formulations suitable for oral administration can consist of (a) liquid solutions, such as an effective amount of the antibodies provided herein suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

"Co-administer" it is meant that a composition described herein is administered at the same time, just prior to, or just after the administration of one or more additional therapies.

The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

Antibodies and Complexes

Provided herein are, inter alia, antibodies and anti-CD6 antibody-growth factor complexes useful for the treatment of autoimmune diseases (e.g., Type 1 Diabetes (T1D), Multiple Sclerosis). The antibodies described herein, including embodiments thereof, are modified such that the antibody not only targets a specific antigen (e.g., CD6), but can simultaneously deliver a therapeutic agent (e.g., growth factor protein or fragment thereof) to a target cell or site (e.g., inflammatory site). The complexes (e.g., anti-CD6 antibody-growth factor complexes) provided herein, including embodiments thereof, include an anti-CD6 antibody or fragment thereof and a growth factor protein or fragment thereof, wherein the growth factor protein is bound to the anti-CD6 antibody through a chemical linker. Similarily to the antibodies provided herein, the complexes are capable to target a specific antigen (e.g., CD6) and deliver a therapeutic agent (e.g., the growth factor protein) to a target cell or site (e.g., inflammatory site). The complexes provided herein are described in detail under section headings below (e.g., antibody growth factor complexes).

The modified antibodies provided herein may be antibodies covalently or non-covalently bound to a peptide compound. The peptide compound provided herein may include a peptidyl moiety also referred to herein as "meditope." Any of the meditopes and meditope-antibody complexes described in WO 2018/106842 A1, which is incorporated herein in its entirety and for all purposes, may be used for the compositions or methods provided herein. The modified antibodies as described herein, including embodiments thereof, may be referred to herein, for example in the Examples, as meditope-enabled (me) antibodies. In embodiments, the meditope-enabled antibody is a monoclonal antibody (memAb). In embodiments, the meditope-enabled antibody is a humanized antibody. In embodiments, the Fab region of an antibody may be meditope enabled. In embodiments, the meditope-enabled antibody is a Fab. The term "meditope" as used herein refers to a peptidyl moiety included in the peptide compound as described herein. Thus, in embodiments, a meditope is a peptidyl moiety.

Meditope-enabled antibodies allow for the binding (e.g., covalent, non-covalent) of peptidyl moieties to a region in the Fab portion of the antibody without negatively influencing antibody binding site behavior. The peptidyl moieties (also referred to herein as meditopes) may be functionalized. For example, the peptidyl moieties may be conjugated to therapeutic agents (e.g., peptides (e.g., EGF, gastrin, GLP-1) or fragments (e.g., EGF fragment, gastrin fragment, GLP-1 fragment)) using, for example, suitable reactive groups and click chemistry. A functionalized peptidyl moiety may be referred to herein as a peptide compound. The ability of the antibody to bind (covalently, non-covalently) a peptide compound endows the meditope-enabled antibody with the functionality to simultaneously target its specific antigen via its antibody binding site and deliver a therapeutic agent (e.g., peptide, fragment).

The antibodies contemplated herein are anti-CD6 antibodies capable of binding (e.g., covalently, non-covalently) a peptidyl moiety in its Fab region, where the peptidyl moiety is further conjugated to one or multiple ligands or fragments of the Epidermal Growth Factor Receptor (e.g., EGF), gastrin or gastrin fragments, or GLP-1 or GLP-1 fragments. When systemically administered, the meditope-enabled anti-CD6 antibody targets the human inflammatory environment and simultaneously delivers an Epidermal Growth Factor or other ligand or fragment (e.g., gastrin, GLP-1), thereby inducing long-term specific immunomodulation of infiltrating CD6+ lymphocytes, and concurrently preserving and restoring the target cells from the autoimmune attack in the affected organ (e.g., functional beta cell mass in the case of Type 1 Diabetes).

Thus, in an aspect is provided an antibody, including: (1) a central hole enclosed by the heavy chain variable (VH) region, the light chain variable (VL) region, the heavy chain constant (CH1) region and the light chain constant (CL) region of the antibody between a first cavity and a second cavity; and (2) a non-CDR peptide binding region including: the first cavity lined by a first set of amino acid residues of the VH, VL, CHI, and CL regions of the antibody; the second cavity lined by a second set of amino acid residues of the VH, VL, CHI, and CL regions of the antibody; and a hole region enclosing the hole between the first cavity and the second cavity, the hole region lined by a third set of amino acid residues of the VH, VL, CHI, and CL regions of the antibody; wherein the antibody is an anti-CD6 antibody.

The "heavy chain variable (VH) region" as provided herein is a domain which includes the variable region of a heavy chain of an antibody or a fragment thereof. Likewise, the "light chain variable (VL) region" as provided herein is a domain including the variable region of a light chain of an antibody or a fragment thereof. In embodiments, the heavy chain variable (VH) region is the variable region of the heavy chain of an antibody. In embodiments, the heavy chain variable (VH) region is the variable region of the heavy chain of an antibody fragment. In embodiments, the heavy chain variable (VH) region is the variable region of the heavy chain of a Fab. In embodiments, the light chain variable (VL) region is the variable region of the light chain of an antibody. In embodiments, the light chain variable (VL) region is the variable region of the light chain of an antibody fragment. In embodiments, the light chain variable (VL) region is the variable region of the light chain of a Fab.

An "antigen binding domain" as provided herein is a region of an antibody that binds to an antigen (epitope). As described above, the antigen binding domain is generally composed of one constant and one variable domain of each of the heavy and the light chain (VL, VH, CL and CH1, respectively). The paratope or antigen-binding site is formed on the N-terminus of the antigen binding domain. The two variable domains of an antigen binding domain typically bind the epitope on an antigen. In embodiments, the antigen binding domain forms part of an antibody. In embodiments, the antigen binding domain forms part of a therapeutic antibody. In embodiments, the antigen binding domain forms part of a Fab. In embodiments, the antigen binding domain is a Fab.

In embodiments, the antigen binding domain includes a heavy chain constant region (CH) and a light chain constant region (CL). In embodiments, the heavy chain constant region (CH) is the constant region of the heavy chain of an antibody or fragment thereof. In embodiments, the light chain constant region (CL) is the constant region of the light chain of an antibody or fragment thereof. In embodiments, the heavy chain constant region (CH) is the constant region of a Fab. In embodiments, the light chain constant region (CL) is the constant region of the light chain of a Fab. In embodiments, the heavy chain constant region (CH) is the constant region of a F(ab)'2 dimer. In embodiments, the light chain constant region (CL) is the constant region of the light chain of a F(ab)'2 dimer. In embodiments, the antigen binding domain includes an Fc domain. In embodiments, the antigen binding domain is a humanized antigen binding domain. In embodiments, the antigen binding domain is a humanized mouse antigen binding domain.

In embodiments, the antigen binding domain is a meditope-enabled itolizumab domain. In embodiments, the antigen binding domain is a meditope-enabled antigen binding domain that binds selectively to CD6. In embodiments, the antigen binding domain is a meditope-enabled antigen binding domain including the CDRs of itolizumab. In embodiments, the antigen binding domain is a meditope-enabled antigen binding domain including the CDR1, CDR2, and CDR3 as set forth by SEQ ID NO:18, SEQ ID NO: 19 and SEQ ID NO:20, respectively. In embodiments, the antigen binding domain is a meditope-enabled antigen binding domain including a HCDRI of SEQ ID NO:18, a HCDR2 of SEQ ID NO: 19, or a HCDR3 of SEQ ID NO:20. In embodiments, the antigen binding domain is a meditope-enabled antigen binding domain including a HCDR1 of SEQ ID NO: 18, a HCDR2 of SEQ ID NO: 19, and a HCDR3 of SEQ ID NO: 20. In embodiments, HCDR1 includes the sequence of SEQ ID NO:18. In embodiments, HCDR2 includes the sequence of SEQ ID NO:19. In embodiments, HCDR3 includes the sequence of SEQ ID NO:20.

The "central hole" as provided herein refers, with respect to the three-dimensional structure of an antigen binding domain (e.g., Fab), to a hole within the antigen binding domain (e.g., Fab) and is located between a first and a second cavity. The central hole, as well as the first and second cavity of the antigen binding domain, is lined by portions of the heavy and light chain variable and constant regions. The central hole, the first cavity and the second cavity are thus lined by amino acid residues of the VH, VL, CHI, and CL regions, respectively. The amino acid residues of the VH, VL, CHI, and CL region enclosing the central hole form a hole region. The amino acid residues lining the first cavity are referred to herein as "first set of amino acid residues." The amino acid residues lining the second cavity are referred to herein as "second set of amino acid residues." And, the amino acid residues lining the hole region are referred to herein as "third set of amino acid residues." The amino acid residues included in the first, second and third sets of amino acid residues (i.e., the amino acid residues of the first cavity, the second cavity and the hole region) are amino acid residues of the VH, VL, CH1, and CL regions and do not form part of the CDRs. In embodiments, the amino acid residues included in the first cavity, the second cavity or the hole region are capable of forming a disulfide linkage with the peptide compound provided herein including embodiments thereof. In embodiments, the amino acid residues included in the first cavity, the second cavity or the hole region are capable of forming non-covalent interactions with the peptide compound provided herein including embodiments thereof. Thus, the first cavity, the second cavity and the hole region provided herein form part of a non-CDR peptide binding region. The "non-CDR peptide binding region" is a region of the antigen binding domain, which is capable of binding to the peptide compound provided herein including embodiments thereof. The non-CDR peptide binding region provided herein is a region within the antigen binding domain that does not include CDR residues of the heavy chains and CDR residues of the light chains. In embodiments, the non-CDR peptide binding region includes FR residues of the heavy chains and FR residues of the light chains. In embodiments, the non-CDR peptide binding region includes framework region amino acid residues. The first cavity of the non-CDR peptide binding region provided herein may also be referred to as a "meditope binding site." In embodiments, the meditope binding site includes the hole region.

In embodiments, amino acids of the first set of amino acid residues (amino acid residues of the first cavity) interact with the peptide compound provided herein including embodiments thereof. In embodiments, amino acids of the second set of amino acid residues (amino acid residues of the second cavity) interact with the peptide compound provided herein including embodiments thereof. In embodiments, amino acids of the third set of amino acid residues (amino acid residues of the hole region) interact with the peptide compound provided herein including embodiments thereof. In embodiments, amino acids of the first and the second set of amino acid residues (amino acid residues of the first and the second cavity) interact with the peptide compound provided herein including embodiments thereof. In embodiments, amino acids of the first and the third set of amino acid residues (amino acid residues of the first cavity and the hole region) interact with the peptide compound provided herein including embodiments thereof. In embodiments, amino acids of the second and the third set of amino acid residues (amino acid residues of the second cavity and the hole region) interact with the peptide compound provided herein including embodiments thereof. In embodiments, amino acids of the first, second and the third set of amino acid residues (amino acid residues of the first and second cavity and the hole region) interact with the peptide compound provided herein including embodiments thereof.

In embodiments, the peptide compound that binds to the non-CDR peptide binding region does not impact (e.g. measurably impact) the binding of the antigen binding domain to the antigen (e.g., CD6). In other words, in embodiments, occupancy of this site does not affect antigen binding. In embodiments, the non-CDR peptide binding region interacts with the peptidyl moiety (e.g., a meditope) of the peptide compound provided herein including embodiments thereof. The amino acid residues capable of interacting with the peptide compound including a peptidyl moiety (e.g., a meditope) may form part of the first cavity, the second cavity, the hole region or any combination thereof. The non-CDR peptide binding region may be engineered into any appropriate anti-CD6 antibody, thereby forming an antibody domain (antigen binding domain) with the non-CDR peptide binding region. An antigen binding domain including a non-CDR peptide binding region is also referred to herein as a meditope-enabled antibody, meditope-enabled domain or meditope-enabled antibody region (e.g., meditope-enabled anti-CD6 antibody).

In embodiments, the non-CDR peptide binding region includes residues 8, 9, 10, 38, 39, 40, 41 42, 43, 44, 45, 82, 83, 84, 85, 86, 87, 99, 100, 101, 102, 103, 104, 105, 142, 162, 163, 164, 165, 166, 167, 168, and 173 of the light chain and 6, 9, 38, 39, 40, 41, 42, 43, 44, 45, 84, 86, 87, 88, 89, 90, 91, 103, 104, 105, 106, 107, 108, 111, 110, 147, 150, 151, 152, 173, 174, 175, 176, 177, 185, 186, and 187 of the heavy chain of the antibody, according to Kabat numbering. In embodiments, the non-CDR peptide binding region includes constant region residues.

In embodiments, the non-CDR peptide binding region includes residues 40, 41, 83, and 85 of the light chain of a meditope-enabled antibody, according to Kabat numbering, and/or residues 39, 89, 105, and 108 of the heavy chain of the meditope-enabled antibody, according to Kabat numbering.

In embodiments, one or more residues are replaced to create a meditope-enabled anti-CD6 antibody. In embodiments, these residues are selected from light chain framework residues 10, 39-43, 83, 85, 100 and 104, according to Kabat numbering (see Kabat E. A., et al. (1991) Sequences of Proteins of Immunological Interest, Fifth Edition. NIH Publication No. 91-3242, incorporated herein by reference in its entirety), and/or heavy chain framework residue numbers 40, 89 and 105, according to Kabat numbering. In general, unless otherwise specified, amino acid positions in the heavy or light chain of an antibody refer to Kabat numbering. In embodiments, residues in the anti-CD6 antibody corresponding to light chain residues 9, 10, 39, 40, 41, 42, 43, 83, 85, 100, and/or 104, and/or heavy chain residues 40, 89, and/or 105, are replaced, for example, with amino acids present at those positions within cetuximab. Cetuximab has a naturally occurring meditope binding site (e.g., non-CDR peptide binding region), therefore, aligning other antibodies to the cetuximab sequence may be useful for identifying positions in a non-meditope-enabled antibody (i.e., anti-CD6 antibody) sequence that may be modified to form a meditope binding site. Descriptions of such methods can be found in Donaldson et al., PNAS 2013 and U.S. Pat. No. 9,669,108 B2, which are incorporated herein by reference in their entirety and for all purposes.

In embodiments, the one or more residues replaced are light chain framework residues including, but not limited to, 40, 41, 83 and 85, according to Kabat numbering. In embodiments, light chain residue 40 is replaced with threonine; light chain residue 41 is replaced with asparagine, light chain residue 83 is replaced with isoleucine or valine, and/or light chain residue 85 is replaced with aspartate. In one embodiment, light chain framework Pro40 is replaced with Thr (P40T) or Ser (P40S), light chain framework Gly41 is replaced with Asn (G41N), light chain framework residue Phe83 is replaced with Ile (F83I) or Val (F83V) and light chain framework residue Thr85 is replaced with Asp (T85D) or Asn (T85N).

In embodiments, the VL region has a valine or isoleucine at position 9, an isoleucine or leucine at position 10, an arginine at position 39, a threonine at position 40, an asparagine at position 41, a glycine at position 42, a serine at position 43, an isoleucine at position 83, an aspartate at position 85, and an alanine at position 100; and the VH region has a serine at position 40 and an isoleucine at position 89, according to Kabat numbering.

In embodiments, the VL region does not contain a proline at position 40, a glycine at position 41, or a threonine at position 85, according to Kabat numbering, and/or the VH region does not contain an asparagine or alanine at position 40 or a valine at position 89, according to Kabat numbering. In embodiments, the VL region does not contain a serine at position 10, a proline at position 40, a glycine at position 41, a phenylalanine at position 83, or a threonine at position 85, according to Kabat numbering, and/or the VH region does not contain an asparagine or alanine at position 40 or a valine at position 89, according to Kabat numbering.

In embodiments, the meditope-enabled anti-CD6 antibody has a light chain having P8, V9 or 19, I10 or L10, Q38, $R^{39}$, T40, $N_{41}$, G42, S43, P44, $R^{45}$, D82, I83, A84, D85, Y86, Y87, G99, A100, G101, T102, K103, L104, E105, R142, S162, V163, T164, E165, Q166, D167, S168, and Y173, according to Kabat numbering, and/or a heavy chain having Q6, P9, R38, Q39, S40, P41, G42, K43, G44, L45, S84, D86, T87, A88, I89, Y90, Y91, W103, G104, Q105, G106, T107, L108, V109, T110, V111, Y147, E150, P151, V152, T173, F174, P175, A176, V177, Y185, S186, and L187, according to Kabat numbering.

In embodiments, the meditope-enabled antibodies are generated via CDR grafting, typically by modifying one or more complementarity determining regions (CDR) (e.g., one or more of CDR1, CDR2, CDR3) of the heavy and/or light chain of a meditope-enabled antibody to replace them with other CDRs, such as CDRs of existing or new antibodies. Non-limiting examples of meditope-enabled antibodies useful for CDR grafting include meditope-enabled trastuzumab and meditope-enabled M5A (anti-CEA) antibody. Additionally, CDRs may be grafted onto cetuximab, which has a naturally occurring non-CDR peptide binding site. CDR grafting is standard practice for producing humanized monoclonal antibodies, e.g., by grafting CDRs of an antibody generated in a non-human species, such as mouse, onto a human antibody framework. See U.S. Pat. Nos. 5,558,864 and 8,133,982; Kettleborough et al., "Humanization of a mouse monoclonal antibody by CDR-grafting: the importance of framework residues on loop conformation," Protein Eng., 4:773-783 (1991). Thus, in certain embodiments, the antigen specificity of a meditope-enabled antibody is altered by grafting the CDRs of preexisting or newly-generated antibodies of interest. In embodiments, the CDRs grafted onto meditope-enabled antibodies include CDRs capable of binding to CD6. In embodiments, the CDRs grafted onto meditope-enabled antibodies include the CDR sequences of itolizumab. In embodiments, the CDRs grafted onto meditope-enabled antibodies include the CDR1, CDR2, or CDR3 set forth by SEQ ID NOs: 18-20, respectively. The sequences set forth by SEQ ID NOs: 18, 19, and 20 correspond to CDR1, CDR2, and CDR3 of the heavy chain variable region, respectively (i.e. HCDR1, HCDR2, and HCDR3, respectively).

In embodiments, the meditope-enabled anti-CD6 antibody light chain includes the sequence of, or amino acid sequence encoded by SEQ ID NO:1. In embodiments, the meditope-enabled anti-CD6 antibody light chain is the sequence of, or amino acid sequence encoded by, SEQ ID NO:1. In embodiments, the meditope-enabled anti-CD6 antibody light chain has at least or about 50%, 60%, 70%, 80%, 85%, 90%, 91%, 92%, 93%, 94%, 95%, 96%, 97%, 98%, or 99% sequence identity with the sequence of, or amino acid sequence encoded by, SEQ ID NO:1.

In embodiments, the meditope-enabled anti-CD6 antibody heavy chain includes the sequence of, or amino acid sequence encoded by, SEQ ID NO:2. In embodiments, the meditope-enabled anti-CD6 antibody heavy chain is the sequence of, or amino acid sequence encoded by, SEQ ID NO:2. In embodiments, the meditope-enabled anti-CD6 antibody heavy chain has at least or about 50%, 60%, 70%, 80%, 85%, 90%, 91%, 92%, 93%, 94%, 95%, 96%, 97%, 98%, or 99% sequence identity with the sequence of, or amino acid sequence encoded by, SEQ ID NO: 2.

In embodiments, the meditope-enabled anti-CD6 antibody includes the sequence of, or amino acid sequence encoded by, SEQ ID NO:3. In embodiments, the meditope-enabled anti-CD6 antibody is the sequence of, or amino acid sequence encoded by, SEQ ID NO:3. In embodiments, the meditope-enabled anti-CD6 antibody has at least or about 50%, 60%, 70%, 80%, 85%, 90%, 91%, 92%, 93%, 94%, 95%, 96%, 97%, 98%, or 99% sequence identity with the sequence of, or amino acid sequence encoded by, SEQ ID NO:3.

In embodiments, the meditope-enabled anti-CD6 antibody includes the sequence of, or amino acid sequence encoded by, SEQ ID NO:13. In embodiments, the meditope-enabled anti-CD6 antibody is the sequence of, or amino acid sequence encoded by, SEQ ID NO:13. In embodiments, the meditope-enabled anti-CD6 antibody has at least or about 50%, 60%, 70%, 80%, 85%, 90%, 91%, 92%, 93%, 94%, 95%, 96%, 97%, 98%, or 99% sequence identity with the sequence of, or amino acid sequence encoded by, SEQ ID NO:13. In embodiments, the meditope-enabled anti-CD6 antibody includes an IgG Fc domain. In embodiments, the meditope-enabled anti-CD6 antibody includes an IgG1 Fc domain. In embodiments, the IgG Fc domain is a human IgG Fc domain. In embodiments, the IgG1 Fc domain is a human IgG1 Fc domain.

The anti-CD6 antibody-growth factor complexes provided herein may include a non-covalent linker and the non-covalent linker may include a peptide compound. The peptide compound may include a meditope (peptidyl moiety) non-covalently bound to the anti-CD6 antibody. Thus, in embodiments, the chemical linker includes a non-covalent linker. In embodiments, the non-covalent linker includes a peptide compound non-covalently bound to a non-CDR peptide binding region of the anti-CD6 antibody. In embodiments, the peptide compound is covalently bound to the growth factor protein. In embodiments, the peptide compound includes a meditope.

In embodiments, the antigen binding domain (e.g., antibody, antibody domain) includes a non-CDR peptide binding domain capable of forming a disulfide bond with the peptidyl moiety. This type of meditope-enabled antibody may be referred to herein as "cysteine-meditope-enabled antibody", "cysteine-meditope-enabled domain" or "cysteine-meditope-enabled antibody region." In embodiments, the meditope-enabled anti-CD6 antibody provided herein includes an antigen binding domain (e.g., Fab) covalently attached to a peptide compound through a disulfide linkage.

A "disulfide linkage", "disulfide bridge" or "disulfide bond" as provided herein refers to a covalent bond formed by reacting two thiol moieties. The first of the two reacting thiol moieties forms part of the antigen binding domain provided herein and the second thiol moiety forms part of the peptide compound provided herein. In embodiments, the covalent complex provided herein has the structure of RA-S—S-RB, wherein RA is an antigen binding domain and RB is a peptide compound. The disulfide linkage is formed between a cysteine of the antigen binding domain (first cysteine) and a thiol side chain amino acid (e.g., a cysteine or a substituted arginine) included in the peptide compound. Any of the first cysteines provided herein may form a disulfide linkage with any of the thiol side chain amino acids included in the peptide compound.

A "thiol side chain amino acid" as provided herein is an amino acid which includes a side chain with a sulfur atom, wherein the sulfur forms part of a disulfide linkage, and may also be referred to herein as a "sulfur-containing side chain amino acid." A thiol side chain amino acid as referred to herein includes a sulfur atom derived from a reacted-SH substituent (i.e., a thiol group or thiol substituent which is a group or substituent including a thiol). Thus, the thiol side chain amino acid provided herein may also be referred to as sulfur amino acid side chain. The sulfur atom of a thiol side chain amino acid is formed through reaction of a side chain thiol group with a thiol group of a second reactant (e.g., the side chain thiol group of the first cysteine). In embodiments, the sulfur atom forms part of the side chain of an amino acid (e.g., a cysteine side chain). In embodiments, the sulfur atom forms part of a substituted amino acid side chain (e.g., a substituted arginine side chain). Where the sulfur atom forms part of a substituted amino acid side chain, the amino acid side chain may be substituted with a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the substituted amino acid side chain is substituted with octyl-thiol. In embodiments, the octyl-thiol has the formula:

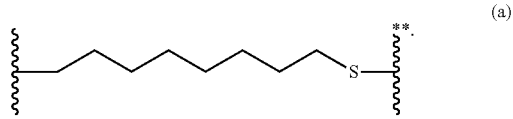

(a)

In formula (a) * denotes the attachment point with the amino acid side chain and ** denotes the point of attachment with a first cysteine.

In embodiments, the non-CDR peptide binding region provided herein includes a first cysteine, which forms a disulfide linkage with a thiol side chain amino acid included in the peptide compound provided herein, thereby covalently attaching the peptide compound to the antigen binding domain. In embodiments, the first cysteine forms part of the first set of amino acid residues (amino acid residues of the first cavity), the second set of amino acid residues (amino acid residues of the second cavity) or the third set of amino acid residues (amino acid residues of the hole region).

In embodiments, the first set of amino acid residues includes the first cysteine at a position corresponding to Kabat position 102 of the VL region. In embodiments, the first set of amino acid residues includes the first cysteine at a position corresponding to Kabat position 142 of the VL region. In embodiments, the first set of amino acid residues includes the first cysteine at a position corresponding to Kabat position 143 of the VL region.

In embodiments, the second set of amino acid residues includes the first cysteine at a position corresponding to Kabat position 208 of the VH region. In embodiments, the second set of amino acid residues includes the first cysteine at a position corresponding to Kabat position 158 of the VH region.

In embodiments, the third set of amino acid residues includes the first cysteine at a position corresponding to Kabat position 174 or 175 of the VH region. In embodiments, the third set of amino acid residues includes the first cysteine at a position corresponding to Kabat position 174. 175 of the VH region. In embodiments, the third set of amino acid residues includes the first cysteine at a position corresponding to Kabat position 175 of the VH region.

The anti-CD6 antibody-growth factor complexes provided herein may include a covalent linker and the covalent linker may include a peptide compound. The peptide compound may include a meditope (peptidyl moiety) covalently bound to the anti-CD6 antibody through a disulfide linkage. Thus, in embodiments, the covalent linker includes a peptide compound covalently bound to the anti-CD6 antibody through a disulfide linkage. In embodiments, the peptide compounds may be covalently bound to the growth factor protein. In embodiments, the anti-CD6 antibody includes a central hole enclosed by the heavy chain variable (VH) domain, the light chain variable (VL) domain, the heavy chain constant (CH1) domain and the light chain constant (CL) domain of the anti-CD6 antibody between a first cavity and a second cavity, a non-CDR peptide binding region including the first cavity lined by a first set of amino acid residues of the VH, VL, CH1, and CL domains of the anti-CD6 antibody, the second cavity lined by a second set of amino acid residues of the VH, VL, CHI, and CL domains of the anti-CD6 antibody, a hole region enclosing the hole between the first cavity and the second cavity, the hole region lined by a third set of amino acid residues of the VH, VL, CHI, and CL domains of the anti-CD6 antibody, wherein the non-CDR peptide binding region comprises a first cysteine, and wherein the peptide compound includes a thiol side chain amino acid covalently bound to the anti-CD6 antiody through a disulfide linkage between the first cysteine and the thiol side chain amino acid. In embodiments, the peptide compound includes a meditope. In embodiments, the second set of amino acid residues includes the first cysteine at a position corresponding to Kabat position 158 of the VH domain.

Peptide Compounds

The peptide compounds provided herein, and, more specifically, the peptidyl portion or peptidyl moiety (i.e., meditope) of the peptide compound, may form a disulfide bond with a cysteine-meditope-enabled anti-CD6 antibody. Alternatively, the peptide compounds provided herein, and, more specifically, the peptidyl portion (i.e., meditope) of the peptide compound, may form non-covalent associations (e.g., hydrogen bonds) with a meditope-enabled anti-CD6 antibody. In embodiments, the peptide compound includes reactive moieties that extend through the hole region, allowing a steric hindering group to be conjugated to the extended end. The placement of a steric hindering group on the peptidyl moiety following its association with the non-CDR peptide binding region and extension of a reactive moiety through the hole region results in the mechanical interlocking of the peptide compound with the meditope-enabled anti-CD6 antibody.

In embodiments, the peptide compound is designed starting with peptidyl moiety (i.e., meditope) cQFD (SEQ ID NO:22) or cQYN (SEQ ID NO:23). These peptidyl moieties may be further modified to endow the peptidyl moiety with specific functionality. Suitable modifications include, but are not limited to, any peptide modification known in the art, such as, but not limited to, modifications to the manner and/or position of peptide cyclization, modifications to one or more amino acid components of the cyclic peptide, or adding or deleting one or more amino acid from the cyclic peptide. In embodiments, cQFD is altered with one or more of the following modifications: a modification of Arg8, a modification of Phe3, a modification of Leu5, a modification of Leu10, change to the mode of peptide cyclization, and/or an incorporation of hydratable carbonyl functionality at one or more positions, and one or more amino acid deletions or additions. In embodiments, cQYN is modified to include one or more of the following: a modification of Arg8, a modification of Leu5, a modification of Leu10, change to the mode of peptide cyclization, and/or an incorporation of hydratable carbonyl functionality at one or more positions, and one or more deletions or additions. Certain amino acid positions within the meditope may be deleted or replaced with a different natural amino acid or an unnatural amino acid, or the meditope may be chemically conjugated with a therapeutic agent (e.g., peptide, fragment).

The peptide compounds provided herein may be linear or cyclic compounds (i.e., compounds including linear or cyclic peptidyl moieties) and may include a steric hindering chemical moiety or a therapeutic agent (e.g., peptide, fragment). In embodiments, the peptide compound is cyclized (e.g. cyclized through amino acid side chain moieties). In embodiments, the peptide compound is a linear peptide compound.

In embodiments, a peptide compound of formula:

$$R^1\text{-}X0\text{-}X1\text{-}X2\text{-}X3\text{-}X_4\text{-}X5\text{-}X6\text{-}X7\text{-}X8\text{-}X9\text{-}X10\text{-}X11\text{-}X12\text{-}R^2 \quad (I)$$

is provide. In formula (I), X0 is Ser or null. X1 is Ser, Cys, Gly, β-alanine, diaminopropionic acid, β-azidoalanine, or null. X2 is Gln or null. X3 is Phe, Tyr, β,β'-diphenyl-Ala, His, Asp, 2-bromo-L-phenylalanine, 3-bromo-L-phenylalanine, 4-bromo-L-phenylalanine, Asn, Gln, a modified Phe, a hydratable carbonyl-containing residue, or a boronic acid-containing residue. X4 is Asp or Asn. X5 is Leu, β,β'-diphenyl-Ala, Phe, Trp, Tyr, a non-natural analog of phenylalanine, tryptophan, or tyrosine, a hydratable carbonyl-containing residue, or a boronic acid-containing residue. X6 is the thiol side chain amino acid or serine. X7 is the thiol side chain amino acid, Thr, or Ser. X8 is the thiol side chain amino acid, Arg, Ala, or an amino acid comprising a side chain of the formula -$L^{3A}$-$L^{3B}$-$R^3$, wherein $L^{3A}$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene, $L^{3B}$ is a chemical linker and $R^3$ is a steric hindering chemical moiety. X9 is the thiol side chain amino acid, Arg or Ala. X10 is Leu, Gln, Glu, β,β'-diphenyl-Ala, Phe, Trp, Tyr; a non-natural analog of phenylalanine, tryptophan, or tyrosine, a hydratable carbonyl-containing residue, or a boronic acid-containing residue. X11 is the thiol side chain amino acid, Gln, Lys or Arg. X12 is Ser, Cys, Gly, 7-aminoheptanoic acid, β-alanine, diaminopropionic acid, propargylglycine, isoaspartic acid, or null. $R^1$ is null, -L 10A_$L^{10B}$-$R^{10}$ an amino acid peptide sequence optionally substituted with -L 10A-$L^{10B}$_$R^{10}$. $R^2$ is null, -L20A_$L^{20B}$ $R^{20}$, an amino acid peptide sequence optionally substituted with -L20A-$L^{20B}$-$R^{20}$ [$^{10}$A [10B [20A $L^{20B}$ are independently a bond, a peptidyl linker, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. $R^{10}$ and $R^{20}$ are independently a reactive moiety, a diagnostic moiety, a therapeutic moiety or a detectable moiety. X1 and X12 are optionally joined together to form a cyclic peptidyl moiety. $R^1$ and X11 are optionally joined together to form a cyclic peptidyl moiety.

A "protected amino acid residue" (e.g., a protected Cys or protected Arg) as provided herein refers to an amino acid which is covalently attached to a protecting or leaving group. The protecting or leaving group may be attached to the side chain of the amino acid. The terms "protecting group" or "leaving group" are used based on their general meaning well known in the chemical arts. Exemplary leaving groups include without limitation any of the amino acid protecting groups described in Isidro-Llobet et al. (Chem. Rev., 2009, 109 (6), pp 2455-2504) and Andreu et al. (Methods in Molecular Biology, Vol. 35, Chapter 7, Peptide Synthesis Protocols, 1994, Humana Press Inc.), which are hereby incorporated in their entirety and for all purposes. In embodiments, the protected Cys includes a thio-pyrimidine moiety. In embodiments, the protected Cys includes a thio-pyridine moiety. In embodiments, the thio-pyridine moiety is covalently attached (through a disulfide bond) to the side chain of the Cys.

Thus, in embodiments, the protected Cys is a thio-pyridine-substituted Cys. In embodiments, the thio-pyridine moiety has the formula:

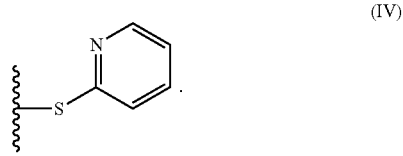 [SMILES: *Sc1ccccn1]

(IV)

In formula (IV), ~~~ denotes the point of attachment to the amino acid side chain.

In embodiments, the peptide compound has the structure

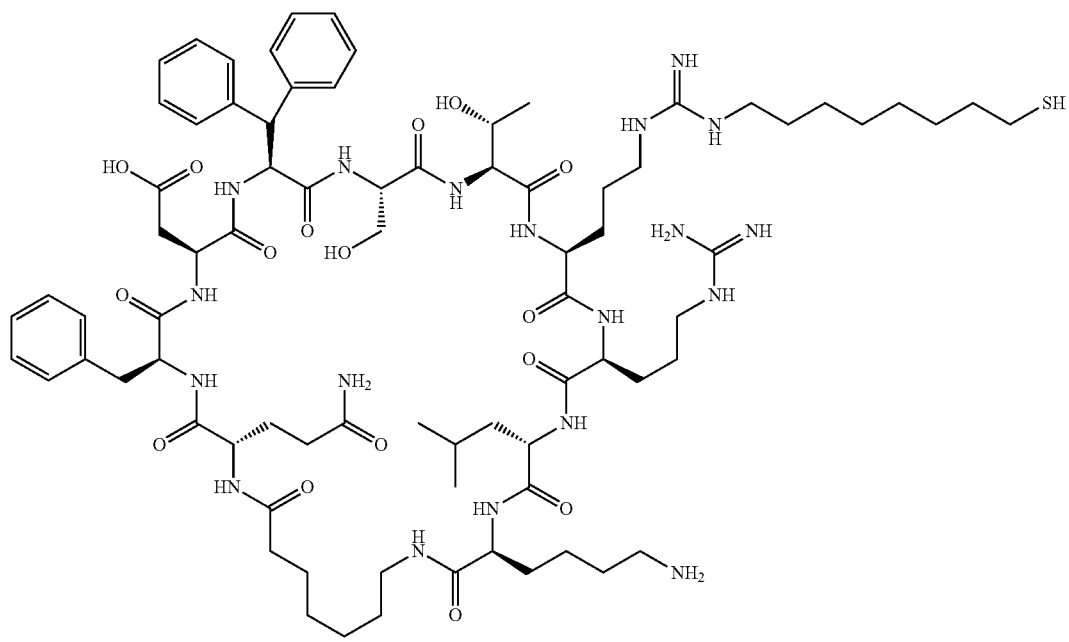

Chemical Formula: $C_{79}H_{123}N_{19}O_{16}S$
Exact Mass: 1625.9116
Molecular Weight: 1628.0046

In embodiments, the peptide compound has the formula:

$$R^1\text{-X0-X1-X2-X3-X}_4\text{-X5-X6-X7-X8-X9-X10-X11-X12-X13-X14-X15-R}^2 \quad (II).$$

In formula (II), X0 is Ser or null. X1 is Ser, Cys, Gly, β-alanine, diaminopropionic acid, β-azidoalanine, or null. X2 is Gln or null. X3 is Phe, Tyr, β,β'-diphenyl-Ala, His, Asp, 2-bromo-L-phenylalanine, 3-bromo-L-phenylalanine, 4-bromo-L-phenylalanine, Asn, Gln, a modified Phe, a hydratable carbonyl-containing residue, or a boronic acid-containing residue. X4 is Asp or Asn. X5 is Leu, β,β'-diphenyl-Ala, Phe, Trp, Tyr, a non-natural analog of phenylalanine, tryptophan, or tyrosine, a hydratable carbonyl-containing residue, or a boronic acid-containing residue. X6 is Ser. X7 is the thiol side chain amino acid, Thr, or Ser. X8 is Arg, Ala, or an amino acid comprising a side chain of the formula -$L^{3A}$-$L^{3B}$-$R^3$, wherein $L^{3A}$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene, $L^{3B}$ is a chemical linker and $R^3$ is a steric hindering chemical moiety. X9 is the thiol side chain amino acid, Arg or Ala. X10 is Leu, Gln, Glu, β,β'-diphenyl-Ala, Phe, Trp, Tyr; a non-natural analog of phenylalanine, tryptophan, or tyrosine, a hydratable carbonyl-containing residue, or a boronic acid-containing residue. X11 is the thiol side chain amino acid, Gln, Lys or Arg. X12 is Ser, Cys, Gly, 7-aminoheptanoic acid, β-alanine, diaminopropionic acid, propargylglycine, isoaspartic acid, or null. X13 is Gly or Ser. X14 and X15 are independently Gly, Ser, Ala or the thiol side chain amino acid. $R^1$ is null, -$L^{10A}$-[10B_$R^{10}$, an amino acid peptide sequence optionally substituted with -$L^{10A}$-$L^{10B}$-

$R^{10}R^2$ is null, -L20A-$L^{20B}$-$R^{20}$, an amino acid peptide sequence optionally substituted with -L20A_$L^{20B}$_R 20 $L^{10A}$, $L^{10B}$, $L^{20A}$, $L^{20B}$ are independently a bond, a peptidyl linker, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. $R^{10}$ and $R^{20}$ are independently a reactive moiety, a diagnostic moiety, a therapeutic moiety or a detectable moiety. X1 and X12 are optionally joined together to form a cyclic peptidyl moiety.

In embodiments, $R^1$ of formula (I) and (II) is substituted (e.g., substituted with a substituent group(s), a size-limited substituent or a lower substituent group(s)) or unsubstituted alkyl, substituted (e.g., substituted with a substituent group(s), a size-limited substituent or a lower substituent group(s)) or unsubstituted heteroalkyl, substituted (e.g., substituted with a substituent group(s), a size-limited substituent or a lower substituent group(s)) or unsubstituted cycloalkyl, substituted (e.g., substituted with a substituent group(s), a size-limited substituent or a lower substituent group(s)) or unsubstituted heterocycloalkyl, substituted (e.g., substituted with a substituent group(s), a size-limited substituent or a lower substituent group(s)) or unsubstituted aryl or substituted (e.g., substituted with a substituent group(s), a size-limited substituent or a lower substituent group(s)) or unsubstituted heteroaryl.

In embodiments, $R^1$ of formula (I) and (II) is substituted or unsubstituted (e.g., $C_1$-$C_{20}$, $C_1$-$C_{10}$, $C_1$-$C_5$)alkyl, substituted or unsubstituted (e.g., 2 to 20 membered, 2 to 10 membered, 2 to 5 membered) heteroalkyl, substituted or unsubstituted (e.g., $C_3$-$C_8$, $C_3$-$C_6$, $C_3$-$C_5$) cycloalkyl, substituted or unsubstituted (e.g., 3 to 8 membered, 3 to 6 membered, 3 to 5 membered) heterocycloalkyl, substituted or unsubstituted (e.g., $C_6$-$C_{10}$, $C_6$-$C_8$, $C_6$-$C_5$) aryl or substituted or unsubstituted (e.g., 5 to 10 membered, 5 to 8 membered, 5 to 6 membered,) heteroaryl.

In embodiments, $R^1$ of formula (I) and (II) is unsubstituted (e.g., $C_1$-$C_{20}$, $C_1$-$C_{10}$, $C_1$-$C_5$)alkyl, unsubstituted (e.g., 2 to 20 membered, 2 to 10 membered, 2 to 5 membered) heteroalkyl, unsubstituted (e.g., $C_3$-$C_8$, $C_3$-$C_6$, $C_3$-$C_5$) cycloalkyl, unsubstituted (e.g., 3 to 8 membered, 3 to 6 membered, 3 to 5 membered) heterocycloalkyl, unsubstituted (e.g., $C_6$-$C_{10}$, $C_6$-$C_8$, $C_6$-$C_5$) aryl or unsubstituted (e.g., 5 to 10 membered, 5 to 8 membered, 5 to 6 membered,) heteroaryl.

In embodiments, $R^2$ of formula (I) and (II) is substituted (e.g., substituted with a substituent group(s), a size-limited substituent or a lower substituent group(s)) or unsubstituted alkyl, substituted (e.g., substituted with a substituent group(s), a size-limited substituent or a lower substituent group(s)) or unsubstituted heteroalkyl, substituted (e.g., substituted with a substituent group(s), a size-limited substituent or a lower substituent group(s)) or unsubstituted cycloalkyl, substituted (e.g., substituted with a substituent group(s), a size-limited substituent or a lower substituent group(s)) or unsubstituted heterocycloalkyl, substituted (e.g., substituted with a substituent group(s), a size-limited substituent or a lower substituent group(s)) or unsubstituted aryl or substituted (e.g., substituted with a substituent group(s), a size-limited substituent or a lower substituent group(s)) or unsubstituted heteroaryl.

In embodiments, $R^2$ of formula (I) and (II) is substituted or unsubstituted (e.g., $C_1$-$C_{20}$, $C_1$-$C_{10}$, $C_1$-$C_5$)alkyl, substituted or unsubstituted (e.g., 2 to 20 membered, 2 to 10 membered, 2 to 5 membered) heteroalkyl, substituted or unsubstituted (e.g., $C_3$-$C_8$, $C_3$-$C_6$, $C_3$-$C_5$) cycloalkyl, substituted or unsubstituted (e.g., 3 to 8 membered, 3 to 6 membered, 3 to 5 membered) heterocycloalkyl, substituted or unsubstituted (e.g., $C_6$-$C_{10}$, $C_6$-$C_8$, $C_6$-$C_5$) aryl or substituted or unsubstituted (e.g., 5 to 10 membered, 5 to 8 membered, 5 to 6 membered,) heteroaryl.

In embodiments, $R^2$ of formula (I) and (II) is unsubstituted (e.g., $C_1$-$C_{20}$, $C_1$-$C_{10}$, $C_1$-$C_5$)alkyl, unsubstituted (e.g., 2 to 20 membered, 2 to 10 membered, 2 to 5 membered) heteroalkyl, unsubstituted (e.g., $C_3$-$C_8$, $C_3$-$C_6$, $C_3$-$C_5$) cycloalkyl, unsubstituted (e.g., 3 to 8 membered, 3 to 6 membered, 3 to 5 membered) heterocycloalkyl, unsubstituted (e.g., $C_6$-$C_{10}$, $C_6$-$C_8$, $C_6$-$C_5$) aryl or unsubstituted (e.g., 5 to 10 membered, 5 to 8 membered, 5 to 6 membered,) heteroaryl.

In embodiments, $R^3$ of formula (I) and (II) is substituted (e.g., substituted with a substituent group(s), a size-limited substituent or a lower substituent group(s)) or unsubstituted alkyl, substituted (e.g., substituted with a substituent group(s), a size-limited substituent or a lower substituent group(s)) or unsubstituted heteroalkyl, substituted (e.g., substituted with a substituent group(s), a size-limited substituent or a lower substituent group(s)) or unsubstituted cycloalkyl, substituted (e.g., substituted with a substituent group(s), a size-limited substituent or a lower substituent group(s)) or unsubstituted heterocycloalkyl, substituted (e.g., substituted with a substituent group(s), a size-limited substituent or a lower substituent group(s)) or unsubstituted aryl or substituted (e.g., substituted with a substituent group(s), a size-limited substituent or a lower substituent group(s)) or unsubstituted heteroaryl.

In embodiments, $R^3$ of formula (I) and (II) is substituted or unsubstituted (e.g., $C_1$-$C_{20}$, $C_1$-$C_{10}$, $C_1$-$C_5$)alkyl, substituted or unsubstituted (e.g., 2 to 20 membered, 2 to 10 membered, 2 to 5 membered) heteroalkyl, substituted or unsubstituted (e.g., $C_3$-$C_8$, $C_3$-$C_6$, $C_3$-$C_5$) cycloalkyl, substituted or unsubstituted (e.g., 3 to 8 membered, 3 to 6 membered, 3 to 5 membered) heterocycloalkyl, substituted or unsubstituted (e.g., $C_6$-$C_{10}$, $C_6$-$C_8$, $C_6$-$C_5$) aryl or substituted or unsubstituted (e.g., 5 to 10 membered, 5 to 8 membered, 5 to 6 membered,) heteroaryl.

In embodiments, $R^3$ of formula (I) and (II) is unsubstituted (e.g., $C_1$-$C_{20}$, $C_1$-$C_{10}$, $C_1$-$C_5$)alkyl, unsubstituted (e.g., 2 to 20 membered, 2 to 10 membered, 2 to 5 membered) heteroalkyl, unsubstituted (e.g., $C_3$-$C_8$, $C_3$-$C_6$, $C_3$-$C_5$) cycloalkyl, unsubstituted (e.g., 3 to 8 membered, 3 to 6 membered, 3 to 5 membered) heterocycloalkyl, unsubstituted (e.g., $C_6$-$C_{10}$, $C_6$-$C_8$, $C_6$-$C_5$) aryl or unsubstituted (e.g., 5 to 10 membered, 5 to 8 membered, 5 to 6 membered,) heteroaryl.

In embodiments, $R^{10}$ of formula (I) and (II) is substituted (e.g., substituted with a substituent group(s), a size-limited substituent or a lower substituent group(s)) or unsubstituted alkyl, substituted (e.g., substituted with a substituent group(s), a size-limited substituent or a lower substituent group(s)) or unsubstituted heteroalkyl, substituted (e.g., substituted with a substituent group(s), a size-limited substituent or a lower substituent group(s)) or unsubstituted cycloalkyl, substituted (e.g., substituted with a substituent group(s), a size-limited substituent or a lower substituent group(s)) or unsubstituted heterocycloalkyl, substituted (e.g., substituted with a substituent group(s), a size-limited substituent or a lower substituent group(s)) or unsubstituted aryl or substituted (e.g., substituted with a substituent group(s), a size-limited substituent or a lower substituent group(s)) or unsubstituted heteroaryl.

In embodiments, $R^{10}$ of formula (I) and (II) is substituted or unsubstituted (e.g., $C_1$-$C_{20}$, $C_1$-$C_{10}$, $C_1$-$C_5$) alkyl, substituted or unsubstituted (e.g., 2 to 20 membered, 2 to 10 membered, 2 to 5 membered) heteroalkyl, substituted or unsubstituted (e.g., $C_3$-$C_8$, $C_3$-$C_6$, $C_3$-$C_5$) cycloalkyl, substituted or unsubstituted (e.g., 3 to 8 membered, 3 to 6 membered, 3 to 5 membered) heterocycloalkyl, substituted or unsubstituted (e.g., $C_6$-$C_{10}$, $C_6$-$C_8$, $C_6$-$C_5$) aryl or substituted or unsubstituted (e.g., 5 to 10 membered, 5 to 8 membered, 5 to 6 membered,) heteroaryl.

In embodiments, $R^{10}$ of formula (I) and (II) is unsubstituted (e.g., $C_1$-$C_{20}$, $C_1$-$C_{10}$, $C_1$-$C_5$) alkyl, unsubstituted (e.g., 2 to 20 membered, 2 to 10 membered, 2 to 5 membered) heteroalkyl, unsubstituted (e.g., $C_3$-$C_8$, $C_3$-$C_6$, $C_3$-$C_5$) cycloalkyl, unsubstituted (e.g., 3 to 8 membered, 3 to 6 membered, 3 to 5 membered) heterocycloalkyl, unsubstituted (e.g., $C_6$-$C_{10}$, $C_6$-$C_8$, $C_6$-$C_8$) aryl or unsubstituted (e.g., 5 to 10 membered, 5 to 8 membered, 5 to 6 membered,) heteroaryl.

In embodiments, $R^{20}$ of formula (I) and (II) is substituted (e.g., substituted with a substituent group(s), a size-limited substituent or a lower substituent group(s)) or unsubstituted alkyl, substituted (e.g., substituted with a substituent group(s), a size-limited substituent or a lower substituent group(s)) or unsubstituted heteroalkyl, substituted (e.g., substituted with a substituent group(s), a size-limited substituent or a lower substituent group(s)) or unsubstituted cycloalkyl, substituted (e.g., substituted with a substituent group(s), a size-limited substituent or a lower substituent group(s)) or unsubstituted heterocycloalkyl, substituted (e.g., substituted with a substituent group(s), a size-limited substituent or a lower substituent group(s)) or unsubstituted aryl or substituted (e.g., substituted with a substituent group(s), a size-limited substituent or a lower substituent group(s)) or unsubstituted heteroaryl.

In embodiments, $R^{20}$ of formula (I) and (II) is substituted or unsubstituted (e.g., $C_1$-$C_{20}$, $C_1$-$C_{10}$, $C_1$-$C_5$) alkyl, substituted or unsubstituted (e.g., 2 to 20 membered, 2 to 10 membered, 2 to 5 membered) heteroalkyl, substituted or unsubstituted (e.g., $C_3$-$C_8$, $C_3$-$C_6$, $C_3$-$C_5$) cycloalkyl, substituted or unsubstituted (e.g., 3 to 8 membered, 3 to 6 membered, 3 to 5 membered) heterocycloalkyl, substituted or unsubstituted (e.g., $C_6$-$C_{10}$, $C_6$-$C_8$, $C_6$-$C_5$) aryl or substituted or unsubstituted (e.g., 5 to 10 membered, 5 to 8 membered, 5 to 6 membered,) heteroaryl.

In embodiments, $R^{20}$ of formula (I) and (II) is unsubstituted (e.g., $C_1$-$C_{20}$, $C_1$-$C_{10}$, $C_1$-$C_5$) alkyl, unsubstituted (e.g., 2 to 20 membered, 2 to 10 membered, 2 to 5 membered) heteroalkyl, unsubstituted (e.g., $C_3$-$C_8$, $C_3$-$C_6$, $C_3$-$C_5$) cycloalkyl, unsubstituted (e.g., 3 to 8 membered, 3 to 6 membered, 3 to 5 membered) heterocycloalkyl, unsubstituted (e.g., $C_6$-$C_{10}$, $C_6$-$C_8$, $C_6$-$C_8$) aryl or unsubstituted (e.g., 5 to 10 membered, 5 to 8 membered, 5 to 6 membered,) heteroaryl.

$L^{3A}$ of formula (I) and (II) may be —O—, —S—, —S(O)$_2$—, —C(O)—, —C(O)O—, —C(O)NH—, —S(O)$_2$NH—, —NH—, —N=CH—, —NHC(O)NH—, substituted (e.g., substituted with a substituent group(s), a size-limited substituent or a lower substituent group(s)) or unsubstituted alkylene, substituted (e.g., substituted with a substituent group(s), a size-limited substituent or a lower substituent group(s)) or unsubstituted heteroalkylene, substituted (e.g., substituted with a substituent group(s), a size-limited substituent or a lower substituent group(s)) or unsubstituted cycloalkylene, substituted (e.g., substituted with a substituent group(s), a size-limited substituent or a lower substituent group(s)) or unsubstituted heterocycloalkylene, substituted (e.g., substituted with a substituent group(s), a size-limited substituent or a lower substituent group(s)) or unsubstituted arylene or substituted (e.g., substituted with a substituent group(s), a size-limited substituent or a lower substituent group(s)) or unsubstituted heteroarylene.

$L^{3A}$ of formula (I) and (II) may be —O—, —S—, —C(O)—, —C(O)O—, —C(O)NH—, —S(O)$_2$NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered,) heteroarylene.

$L^{3A}$ of formula (I) and (II) may be —O—, —S—, —C(O)—, —C(O)O—, —C(O)NH—, —S(O)$_2$NH—, —NH—, —NHC(O)NH—, unsubstituted (e.g., $C_1$-$C_{20}$, $C_1$-$C_{10}$, $C_1$-$C_5$) alkylene, unsubstituted (e.g., 2 to 20 membered, 2 to 10 membered, 2 to 5 membered) heteroalkylene, unsubstituted (e.g., $C_3$-$C_8$, $C_3$-$C_6$, $C_3$-$C_5$) cycloalkylene, unsubstituted (e.g., 3 to 8 membered, 3 to 6 membered, 3 to 5 membered) heterocycloalkylene, unsubstituted (e.g., $C_6$-$C_{10}$, $C_6$-$C_8$, $C_6$-$C_5$) arylene unsubstituted (e.g., 5 to 10 membered, 5 to 8 membered, 5 to 6 membered,) heteroarylene.

$L^{3B}$ of formula (I) and (II) is a chemical linker. The chemical linker provided herein may be a covalent or noncovalent linker. The chemical linker provided herein may include a chemically reactive functional group to react with a second chemically reactive functional group, thereby forming a covalent linker. A chemical linker as referred to herein may include the resulting linker formed by reacting two reactive groups (moieties), e.g., a covalent reactive group as described herein (e.g., alkyne, thiol, azide, maleimide). In embodiments, the chemical linker is a 1,3 triazole linker (i.e., a linker comprising a 1,3-triazolene linker moiety, e.g., in combination with alkyl (substituted or unsubstituted), amide, ester, sulfonamide and the like, including combinations thereof). The linkers provided herein may be covalently attached to the non-CDR peptide binding region or the steric hindering chemical moiety ($R^3$) applying methods well known in the art and compatible with the composition of the complex provided herein. The linker provided herein may include the conjugated product of reactive groups, at the point of attachment to e.g., the non-CDR peptide binding region or the steric hindering chemical moiety. Thus, the linker provided herein may be polyvalent and/or may be formed by conjugate chemistry techniques. Non-limiting examples of linkers useful for the compositions and methods provided herein are linkers that include alkyl groups (including substituted alkyl groups and alkyl groups containing heteroatom moieties and short alkyl groups), ester groups, amide groups, amine groups, epoxy groups and/or ethylene glycol or derivatives thereof. The linkers provided herein may include a sulfone group, forming sulfonamide, an ester group and/or an ether group (e.g., triethyl ether).

The chemical linker as provided herein (e.g. $L^{3B}$), may be —O—, —S—, —C(O)—, —C(O)O—, —C(O)NH—, —S(O)$_2$NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered,) heteroarylene.

The chemical linker as provided herein (e.g. $L^{3B}$), may be —O—, —S—, —C(O)—, —C(O)O—, —C(O)NH—, —S(O)$_2$NH—, —NH—, —NHC(O)NH—, unsubstituted (e.g., $C_1$-$C_{20}$, $C_1$-$C_{10}$, $C_1$-$C_5$) alkylene, unsubstituted (e.g., 2 to 20 membered, 2 to 10 membered, 2 to 5 membered) heteroalkylene, unsubstituted (e.g., $C_3$-$C_8$, $C_3$-$C_6$, $C_3$-$C_5$) cycloalkylene, unsubstituted (e.g., 3 to 8 membered, 3 to 6 membered, 3 to 5 membered) heterocycloalkylene, unsubstituted (e.g., $C_6$-$C_{10}$, $C_6$-$C_8$, $C_6$-$C_5$) arylene or unsubstituted (e.g., 5 to 10 membered, 5 to 8 membered, 5 to 6 membered,) heteroarylene.

In embodiments, the chemical linker ($L^{3B}$) is a covalent linker. [10A, $L^{10B}$, $L^{20A}$, and/or $L^{20B}$ of formula (I) and (II) may independently be a bond, a peptidyl linker, —O—, —S—, —C(O)—, —C(O)O—, —C(O)NH—, —S(O)$_2$NH—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

In embodiments, $L^{10A}$, $L^{10B}$, $L^{20A}$, and/or $L^{20B}$ are independently a bond, a peptidyl linker, —O—, —S—, —C(O)—, —C(O)O—, —C(O)NH—, —S(O)$_2$NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_8$) arylene or substituted or unsubstituted (e.g., 5 to 10 membered, 5 to 8 membered, 5 to 6 membered,) heteroarylene.

In embodiments, L 10A, $L^{10B}$, $L^{20A}$, and/or $L^{20B}$ are independently a bond, a peptidyl linker, —O—, —S—, —C(O)—, —C(O)O—, —C(O)NH—, —S(O)$_2$NH—, —NH—, —NHC(O)NH—, unsubstituted (e.g., $C_1$-$C_{20}$, $C_1$-$C_{10}$, $C_1$-$C_5$) alkylene, unsubstituted (e.g., 2 to 20 membered, 2 to 10 membered, 2 to 5 membered) heteroalkylene, unsubstituted (e.g., $C_3$-$C_8$, $C_3$-$C_6$, $C_3$-$C_5$) cycloalkylene, unsubstituted (e.g., 3 to 8 membered, 3 to 6 membered, 3 to 5 membered) heterocycloalkylene, unsubstituted (e.g., $C_6$-$C_{10}$, $C_6$-$C_8$, $C_6$-$C_5$) arylene or unsubstituted (e.g., 5 to 10 membered, 5 to 8 membered, 5 to 6 membered,) heteroarylene.

$L^{10A}$ of formula (I) and (II) may be a bond, a peptidyl linker, —O—, —S—, —C(O)—, —C(O)O—, —C(O)NH—, —S(O)$_2$NH—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

In embodiments, $L^{10A}$ is a bond, a peptidyl linker, —O—, —S—, —C(O)—, —C(O)O—, —C(O)NH—, —S(O)$_2$NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered,) heteroarylene.

In embodiments, $L^{10A}$ is a bond, a peptidyl linker, —O—, —S—, —C(O)—, —C(O)O—, —C(O)NH—, -S (O)2NH—, —NH—, —NHC(O)NH—, unsubstituted (e.g., $C_1$-$C_{20}$, $C_1$-$C_{10}$, $C_1$-$C_5$) alkylene, unsubstituted (e.g., 2 to 20 membered, 2 to 10 membered, 2 to 5 membered) heteroalkylene, unsubstituted (e.g., $C_3$-$C_8$, $C_3$-$C_6$, $C_3$-$C_5$) cycloalkylene, unsubstituted (e.g., 3 to 8 membered, 3 to 6 membered, 3 to 5 membered) heterocycloalkylene, unsubstituted (e.g., $C_6$-$C_{10}$, $C_6$-$C_8$, $C_6$-$C_5$) arylene or unsubstituted (e.g., 5 to 10 membered, 5 to 8 membered, 5 to 6 membered,) heteroarylene.

$L^{10B}$ of formula (I) and (II) may be a bond, a peptidyl linker, —O—, —S—, —C(O)—, —C(O)O—, —C(O)NH—, —S(O)$_2$NH—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

In embodiments, $L^{10B}$ is a bond, a peptidyl linker, —O—, —S—, —C(O)—, —C(O)O—, —C(O)NH—, -S (O)2NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered,) heteroarylene.

In embodiments, $L^{10B}$ is a bond, a peptidyl linker, —O—, —S—, —C(O)—, —C(O)O—, —C(O)NH—, -S (O)2NH—, —NH—, —NHC(O)NH—, unsubstituted (e.g., $C_1$-$C_{20}$, $C_1$-$C_{10}$, $C_1$-$C_5$) alkylene, unsubstituted (e.g., 2 to 20 membered, 2 to 10 membered, 2 to 5 membered) heteroalkylene, unsubstituted (e.g., $C_3$-$C_8$, $C_3$-$C_6$, $C_3$-$C_5$) cycloalkylene, unsubstituted (e.g., 3 to 8 membered, 3 to 6 membered, 3 to 5 membered) heterocycloalkylene, unsubstituted (e.g., $C_6$-$C_{10}$, $C_6$-$C_8$, $C_6$-$C_5$) arylene or unsubstituted (e.g., 5 to 10 membered, 5 to 8 membered, 5 to 6 membered,) heteroarylene.

$L^{20A}$ of formula (I) and (II) may be a bond, a peptidyl linker, —O—, —S—, —C(O)—, —C(O)O—, —C(O)NH—, —S(O)$_2$NH—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

In embodiments, $L^{20A}$ is a bond, a peptidyl linker, —O—, —S—, —C(O)—, —C(O)O—, —C(O)NH—, -S (O)2NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered,) heteroarylene.

In embodiments, $L^{20A}$ is a bond, a peptidyl linker, —O—, —S—, —C(O)—, —C(O)O—, —C(O)NH—, -S (O) 2NH—, —NH—, —NHC(O)NH—, unsubstituted (e.g., $C_1$-$C_{20}$, $C_1$-$C_{10}$, $C_1$-$C_5$) alkylene, unsubstituted (e.g., 2 to 20 membered, 2 to 10 membered, 2 to 5 membered) heteroalkylene, unsubstituted (e.g., $C_3$-$C_8$, $C_3$-$C_6$, $C_3$-$C_5$) cycloalkylene, unsubstituted (e.g., 3 to 8 membered, 3 to 6 membered, 3 to 5 membered) heterocycloalkylene, unsubstituted (e.g., $C_6$-$C_{10}$, $C_6$-$C_8$, $C_6$-$C_5$) arylene or unsubstituted (e.g., 5 to 10 membered, 5 to 8 membered, 5 to 6 membered,) heteroarylene.

$L^{20B}$ of formula (I) and (II) may be a bond, a peptidyl linker, —O—, —S—, —C(O)—, —C(O)O—, —C(O)NH—, —S(O)$_2$NH—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

In embodiments, $L^{20B}$ is a bond, a peptidyl linker, —O—, —S—, —C(O)—, —C(O)O—, —C(O)NH—, —S(O)$_2$NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_8$) arylene or substituted or unsubstituted (e.g., 5 to 10 membered, 5 to 8 membered, 5 to 6 membered,) heteroarylene.

In embodiments, $L^{20B}$ is a bond, a peptidyl linker, —O—, —S—, —C(O)—, —C(O)O—, —C(O)NH—, —S(O)$_2$NH—, —NH—, —NHC(O)NH—, unsubstituted (e.g., $C_1$-$C_{20}$, $C_1$-$C_{10}$, $C_1$-$C_5$) alkylene, unsubstituted (e.g., 2 to 20 membered, 2 to 10 membered, 2 to 5 membered) heteroalkylene, unsubstituted (e.g., $C_3$-$C_8$, $C_3$-$C_6$, $C_3$-$C_5$) cycloalkylene, unsubstituted (e.g., 3 to 8 membered, 3 to 6 membered, 3 to 5 membered) heterocycloalkylene, unsubstituted (e.g., $C_6$-$C_{10}$, $C_6$-$C_8$, $C_6$-$C_5$) arylene or unsubstituted (e.g., 5 to 10 membered, 5 to 8 membered, 5 to 6 membered,) heteroarylene.

In embodiments, a peptidyl linker includes glycine and serine. In embodiments, the peptidyl linker includes 6, 12, or, 24 residues. In embodiments, the residues are glycine or serine. In embodiments, the residues are glycine and serine.

$R^3$ of formula (I) and (II) is a steric hindering chemical moiety. A "steric hindering chemical moiety" provided herein is a moiety which is sterically hindered to pass through the central hole forming part of the antigen binding domain. The steric hindrance occurs between the steric hindering chemical moiety and the amino acids lining the central hole, thereby facilitating the mechanical interlock. Thus, the steric hindering chemical moiety is sufficient in size, dimension or volume to create steric hindrance ("plug"), thereby significantly decreasing (e.g., inhibiting or preventing) the ability of the steric hindering chemical moiety to pass through the hole towards the side of the antigen binding domain which forms the first cavity. In embodiments, the longest diameter of the central hole (e.g., the longest distance across the central hole measured from amino acid residue to amino acid residue by crystal structure) in which the steric hindering chemical moiety could pass is shorter than the longest dimension (e.g., diameter) of the steric hindering chemical moiety (also referred to herein as $R^3$). In embodiments, the central hole (e.g., the longest diameter of the hole as measure in a crystal structure) is from about 3 to about 10 Å in size (e.g., in length, in diameter). In embodiments, the longest dimension of the steric hindering chemical moiety is more than about 3 to about 10 Å in size. For example, where the central hole is 8 Å in size (e.g., the longest diameter of the hole as measure in a crystal structure or diameter), the steric hindering chemical moiety is more than about 8 Å in size (i.e., the longest dimension is more than about 8 Å in size). Binding of the steric hindering chemical moiety to the remainder of the peptide compound is typically accomplished using click chemistry. In embodiments, a chemically reactive functional group (e.g., alkyne) is present on the steric hindering chemical moiety that is reacted with a conjugate (click) chemistry present on the chemical linker to be reacted. In embodiments, the steric hindering chemical moiety is a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the steric hindering chemical moiety is a substituted or unsubstituted diphenyl. The steric hindering chemical moiety may or may not bind or interact with the non-CDR peptide binding region. In embodiments, the steric hindering chemical moiety does not bind or interact with the non-CDR peptide binding region.

The peptide compounds of formula (I) and (II) provided herein may include a therapeutic agent or detectable moiety. Thus, in embodiments, $R^{10}$ and $R^{20}$ are independently a therapeutic agent or a detectable agent. The therapeutic agent or detectable agent (also referred to herein as $R^{10}$ and/or $R^{20}$) may be attached through a non-covalent or covalent linker (also referred to herein as $L^{10A}$, $L^{10B}$, $L^{20A}$, or $L^{20B}$) to the peptide compound provided herein including embodiments thereof.

In embodiments, the therapeutic agent is a peptide. In embodiments, the therapeutic agent is a fragment. In embodiments, the therapeutic agent is EGF. In embodiments, the therapeutic agent is EGF or a fragment thereof. In embodiments, therapeutic moiety includes an epidermal growth factor receptor (EGFR)-binding domain. In embodiments, the therapeutic moiety includes epidermal growth factor (EGF). In embodiments, the EGF is human EGF. In embodiments, the human EGF includes the amino acid sequence of SEQ ID NO:4. In embodiments, the human EGF includes the amino acid sequence of SEQ ID NO: 12. In embodiments, the human EGF can have an amino acid sequence that is about 90%, about 91%, about 92%, about 93%, about 94%, about 95%, about 96%, about 97%, about 98%, about 99% identity to SEQ ID NO: 12. In embodiments, the human EGF can have an amino acid sequence that is about 90%, about 91%, about 92%, about 93%, about 94%, about 95%, about 96%, about 97%, about 98%, about 99% identity to SEQ ID NO: 12.

In embodiments, the therapeutic moiety is gastrin. In embodiments, therapeutic moiety includes gastrin. In embodiments, the gastrin is human gastrin. In embodiments, the therapeutic moiety is GLP-1. In embodiments, therapeutic moiety includes GLP-1. In embodiments, the GLP-1 is human GLP-1.

In embodiments, the fragment is an EGF fragment. In embodiments, the fragment is a human EGF fragment. In embodiments, the EGF fragment includes the amino acid sequence of SEQ ID NO: 5 or SEQ ID NO: 6. In embodiments, the EGF fragment includes an amino acid sequence that is about 90%, about 91%, about 92%, about 93%, about 94%, about 95%, about 96%, about 97%, about 98%, about 99% identity to SEQ ID NO: 5 or SEQ ID NO: 6. In embodiments, the fragment is a gastrin fragment. In embodiments, the fragment is a human gastrin fragment. In embodiments, the fragment is a GLP-1 fragment. In embodiments, the fragment is a human GLP-1 fragment.

In embodiments, the therapeutic agent is a plurality of peptides or fragments as provided herein, including embodiments thereof. In embodiments, the plurality of peptides or fragments are connected via chemical linkers or peptidyl linkers as provided herein, including embodiments thereof.

In embodiments, the peptide compound is non-covalently bound to the non-CDR peptide binding region of a meditope-enabled anti-CD6 antibody. In embodiments, the peptide compound is mechanically interlocked with the meditope-enabled anti-CD6 antibody. In embodiments, the peptide compound is covalently bound to the non-CDR peptide binding region of a meditope-enabled anti-CD6 antibody. In embodiments, the peptide compound is covalently bound to the non-CDR peptide binding region of a meditope-enabled anti-CD6 antibody through a disulfide bond. In embodiments, the peptidyl portion (e.g., meditope) of the peptide compound forms a covalent bond with the non-CDR peptide binding region of a meditope-enabled anti-CD6 antibody. In embodiments, the peptidyl portion (e.g., meditope) of the peptide compound forms a disulfide bond with the non-CDR peptide binding region of a meditope-enabled anti-CD6 antibody.

Anti-Cd6 Antibody-Growth Factor Complexes

Also provided herein are antibody complexes capable of binding CD6, while simultaneously delivering a growth factor. These antibody complexes are useful for inducing long-term specific immunomodulation of infiltrating CD6+ lymphocytes, and concurrently preserving and restoring target cells from the autoimmune attack in the affected organ (e.g., human islets of the pancreas (e.g., functional beta cell mass) in the case of Type 1 Diabetes).

In an aspect is provided an anti-CD6 antibody-growth factor complex including: (i) an anti-CD6 antibody or fragment thereof; and (ii) a growth factor protein or fragment thereof, wherein the growth factor protein is bound to the anti-CD6 antibody through a chemical linker. In embodiments, the anti-CD6 antibody is a monoclonal antibody (mAb). In embodiments, the anti-CD6 antibody is a humanized antibody. In embodiments, the anti-CD6 antibody is a recombinant antibody. In embodiments, the anti-CD6 antibody is a recombinant humanized monoclonal antibody. In embodiments, the anti-CD6 antibody is an antibody fragment. In embodiments, the anti-CD6 antibody is a Fab. In embodiments, the anti-CD6 antibody is a meditope-enabled antibody monoclonal antibody (memAb). In embodiments, the anti-CD6 antibody is a meditope-enabled humanized antibody. In embodiments, the anti-CD6 antibody is a meditope-enabled recombinant antibody. In embodiments, the anti-CD6 antibody is a meditope-enabled recombinant humanized monoclonal antibody. In embodiments, the anti-CD6 antibody is a meditope-enabled fragment. In embodiments, the anti-CD6 antibody is a meditope-enabled Fab.

In embodiments, the anti-CD6 antibody includes: (1) a central hole enclosed by the heavy chain variable (VH) region, the light chain variable (VL) region, the heavy chain constant (CH1) region and the light chain constant (CL) region of the antibody between a first cavity and a second cavity; and (2) a non-CDR peptide binding region including: the first cavity lined by a first set of amino acid residues of the VH, VL, CHI, and CL regions of the antibody; the second cavity lined by a second set of amino acid residues of the VH, VL, CHI, and CL regions of the antibody; and a hole region enclosing the hole between the first cavity and the second cavity, the hole region lined by a third set of amino acid residues of the VH, VL, CHI, and CL regions of the antibody.

The term "growth factor" as referred to herein, refers to a substance (e.g., protein, peptide, fragment) capable of stimulating cell growth, proliferation, healing (e.g., restoration), maturation, and/or cellular differentiation. Numerous types of growth factors are known in the art. In embodiments, the growth factor is a protein. In embodiments, the growth factor is a fragment. In embodiments, the growth factor is EGF or a functional fragment or variant thereof.

A chemical linker as provided herein may include a plurality of chemical moieties, wherein each of the plurality of moieties is chemically different. In embodiments, the chemical linker is a non-covalent linker. Any suitable non-covalent linker is contemplated herein, including, but not limited to, non-covalent linkers resulting in electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions, and the like. In embodiments, the non-covalent linker includes a peptide non-covalently bound to a non-CDR peptide binding region of the anti-CD6 antibody. In embodiments, the peptide is covalently bound to the growth factor protein.

Alternatively, the chemical linker may be a covalent linker. Thus, in embodiments, the chemical linker is a covalent linker. In embodiments, the chemical linker is a bond.

In an aspect is provided an anti-CD6 antibody-growth factor conjugate including: (i) an anti-CD6 antibody or fragment thereof; and (ii) a growth factor protein or fragment thereof, wherein the growth factor protein is covalently bound to the anti-CD6 antibody through a covalent linker.

The growth factor protein may be bound to different regions of the anti-CD6 antibody (e.g., light chain or heavy chain N-terminus or C-terminus). In embodiments, the growth factor protein is bound to the N-terminus of the light chain of the anti-CD6 antibody. In embodiments, the growth factor protein is bound to the C-terminus of the light chain of the anti-CD6 antibody. In embodiments, the growth factor protein is bound to the N-terminus of the heavy chain of the anti-CD6 antibody. In embodiments, the growth factor protein is bound to the C-terminus of the heavy chain of the anti-CD6 antibody.

In embodiments, the covalent linker includes a peptide covalently bound to the anti-CD6 antibody through a disulfide bond. In embodiments, the peptide is covalently bound to the growth factor protein.

In embodiments, the anti-CD6 antibody includes the CDR sequences of itolizumab (e.g., HCDR1, HCDR2, HCDR3, LCDR1, LCDR2, LCDR3). In embodiments, the anti-CD6 antibody includes the CDR sequences set forth by SEQ ID NOs: 18-20.

In embodiments, the anti-CD6 antibody includes the variable light chain of itolizumab. In embodiments, the anti-CD6 antibody is the variable light chain of itolizumab. In embodiments, the anti-CD6 antibody includes the amino acid sequence encoded by the sequence set forth by SEQ ID NO:1. In embodiments, the anti-CD6 antibody is the amino acid sequence encoded by the sequence set forth by SEQ ID NO: 1. In embodiments, the anti-CD6 antibody includes the sequence set forth by SEQ ID NO:1. In embodiments, the anti-CD6 antibody is the sequence set forth by SEQ ID NO:1. In embodiments, the anti-CD6 antibody includes the sequence set forth by SEQ ID NO:10. In embodiments, the anti-CD6 antibody is the sequence set forth by SEQ ID NO:10.

In embodiments, the anti-CD6 antibody includes the variable heavy chain of itolizumab. In embodiments, the anti-CD6 antibody is the variable heavy chain of itolizumab. In embodiments, the anti-CD6 antibody includes the amino acid sequence encoded by the sequence set forth by SEQ ID NO:2. In embodiments, the anti-CD6 antibody is the amino acid sequence encoded by the sequence set forth by SEQ ID NO:2. In embodiments, the anti-CD6 antibody includes the sequence set forth by SEQ ID NO:2. In embodiments, the anti-CD6 antibody is the sequence set forth by SEQ ID NO:2. In embodiments, the anti-CD6 antibody includes the sequence set forth by SEQ ID NO:11. In embodiments, the anti-CD6 antibody is the sequence set forth by SEQ ID NO: 11.

In embodiments, the anti-CD6 antibody includes the sequence set forth by SEQ ID NO: 3. In embodiments, the anti-CD6 antibody is the sequence set forth by SEQ ID NO:3. In embodiments, the anti-CD6 antibody includes the amino acid sequence encoded by the sequence set forth by SEQ ID NO:3. In embodiments, the anti-CD6 antibody is the amino acid sequence encoded by the sequence set forth by SEQ ID NO:3. In embodiments, the anti-CD6 antibody includes the sequence set forth by SEQ ID NO:13. In embodiments, the anti-CD6 antibody is the sequence set forth by SEQ ID NO:13. In embodiments, the anti-CD6 antibody includes the sequence encoded by the sequence set forth by SEQ ID NO:13. In embodiments, the anti-CD6 antibody is the sequence encoded by the sequence set forth by SEQ ID NO: 13.

In embodiments, the VL includes the following sequence or a variant thereof:

```
                                          (SEQ ID NO: 24)
IQMTQSPSSLSASVGDRVTITCKASRDIRSYLTWYQQKPGKAPKTLIYYA

TSLADGVPSRFSGSGSGQ.
```

In embodiments, the VL includes the following sequence or a variant thereof:
DIQMTQSPSSLSASVGDRVTITCKASRDIRSY (SEQ ID NO:25). In embodiments, the VL includes the following sequence or a variant thereof: LTWYQQKPGKAPKTLIYYAT-SLADGVPSRFSGSGSGQDYSLTISSLESDDTATYY-CLQH GESPFT (SEQ ID NO:26). In embodiments, the VL includes the following sequence or a variant thereof: FGSGTKLEIKRA (SEQ ID NO:27).

In embodiments, the VH includes the following sequence or a variant thereof:
EVOLVESGGGLVKPGGSLKLSCAASGFKFSRYAMS (SEQ ID NO:28). In embodiments, the VH includes the following sequence or a variant thereof:
WVRQAPGKRLEWVATISSGG (SEQ ID NO:29). In embodiments, the VH includes the following sequence or a variant thereof:
SYIYYPDSVKGRFTISRDNVKNTLYLQMSSLRSED-TAMYYCARRDYDLDYFDS (SEQ ID NO: 30). In embodiments, the VH includes the following sequence or a variant thereof:
WGQGTLVTVSS (SEQ ID NO:31).

In embodiments, the growth factor protein is epidermal growth factor (EGF) or a fragment thereof. In embodiments, the EGF is recombinant EGF. In embodiments, the EGF is human EGF. In embodiments, the EGF includes the amino acid sequence of SEQ ID NO:4. In embodiments, the EGF is the amino acid sequence of SEQ ID NO:4. In embodiments, the EGF includes the amino acid sequence of SEQ ID NO: 12. In embodiments, the EGF is the amino acid sequence of SEQ ID NO:12. In embodiments, the EGF fragment includes the amino acid sequence of SEQ ID NO:5 or 6. In embodiments, the EGF fragment includes the amino acid sequence of SEQ ID NO:5. In embodiments, the EGF fragment includes the amino acid sequence of SEQ ID NO:6. In embodiments, the EGF fragment is the amino acid sequence of SEQ ID NO:5. In embodiments, the EGF fragment is the amino acid sequence of SEQ ID NO:6.

In embodiments, the growth factor protein is glucagon-like peptide-1 (GLP-1) or a fragment thereof. In embodiments, a GLP-1 receptor antagonist may be used. In embodiments, the growth factor protein is gastrin or a fragment thereof.

Antibody-Growth Factor Complexes

Provided herein are, inter alia, anti-CD6 antibody-growth factor complexes having bifunctional capabilities useful for therapeutic and diagnostic purposes. The complexes provided herein are polypeptides including covalently or non-covalently bound to each other (i) an anti-CD6 antibody or fragment thereof able to target (bind) CD6-expressing cells (e.g., pancreatic cells) and (ii) a growth factor protein or fragment thereof (e.g., EGF) to, for example, protect pancreatic cells (e.g., beta cells) from a proinflammatory response. The complexes provided herein can be produced at very high yields and are therefore easy to manufacture. The complexes provided herein are, inter alia, therapeutically useful for the treatment of autoimmune diseases (e.g., type I diabetes, multiple sclerosis). The anti-CD6 antibodies or fragments thereof included in the complexes provided herein include, without limitation, domains of an antibody, antibody variant or fragments thereof (e.g., single chain antibodies, nanobodies, affybodies, Fabs), domains that bind to CD6.

As described above, the complexes provided herein may be single chain polypeptides that include an anti-CD6 antibody or fragment thereof covalently linked to a growth factor protein or fragment thereof. The anti-CD6 antibody complexes provided herein may include an anti-CD6 antibody or fragment thereof non-covalenlty bound to a peptide compound, e.g., a peptide compound including a peptidyl moiety such as a meditope described herein, wherein the meditope is covalently attached to a growth factor protein or fragment thereof (e.g., EGF). In other aspects, the anti-CD6 antibody complex includes an anti-CD6 antibody or fragment thereof covalently bound to a peptide compound (e.g., a peptide compound including a peptidyl moiety such as a meditope described herein), wherein the peptide compound includes a meditope bound to the antibody through a disulfide linkage and wherein the meditope includes a covalently attached growth factor protein or fragment thereof (e.g., EGF). In yet another aspect, the anti-CD6 antibody complex includes a growth factor protein or fragment thereof (e.g., EGF) covalently attached to the N-terminus or the C-terminus of the heavy chain of the anti-CD6 antibody or fragment thereof. In yet another aspect, the anti-CD6 antibody complex includes a growth factor protein or fragment thereof (e.g., EGF) covalently attached to the N-terminus or the C-terminus of the light chain of the anti-CD6 antibody or fragment thereof. In yet another aspect, the anti-CD6 antibody complex includes a growth factor protein or fragment thereof (e.g., EGF) covalently attached to the the C-terminus of the Fc domain of the anti-CD6 antibody or fragment thereof.

The anti-CD6 antibody-growth factor complexes provided herein are surprisingly stable and address the need in the art for high yield production of multi-specific therapeutics (e.g., bifunctional molecules useful for the treatment of type I diabetes). The anti-CD6 antibody-growth factor complexes provided herein are highly effective and specific, and exhibits minimal adverse effects. The anti-CD6 antibody-growth factor complexes provided herein including embodiments thereof may be single chain polypeptides including, for example, an anti-CD6 antibody light chain covalently bound to a growth factor protein or fragment thereof (e.g., EGF) through a first chemical linker and a second chemical linker covalently binding said growth factor protein to an anti-CD6 antibody heavy chain. The first chemical linker and the second chemical linker may be a cleavable linker or a non-cleavable linker. If the first chemical linker is a cleavable linker, the second chemical linker is a non-cleavable linker and vice versa.

Figure 9:
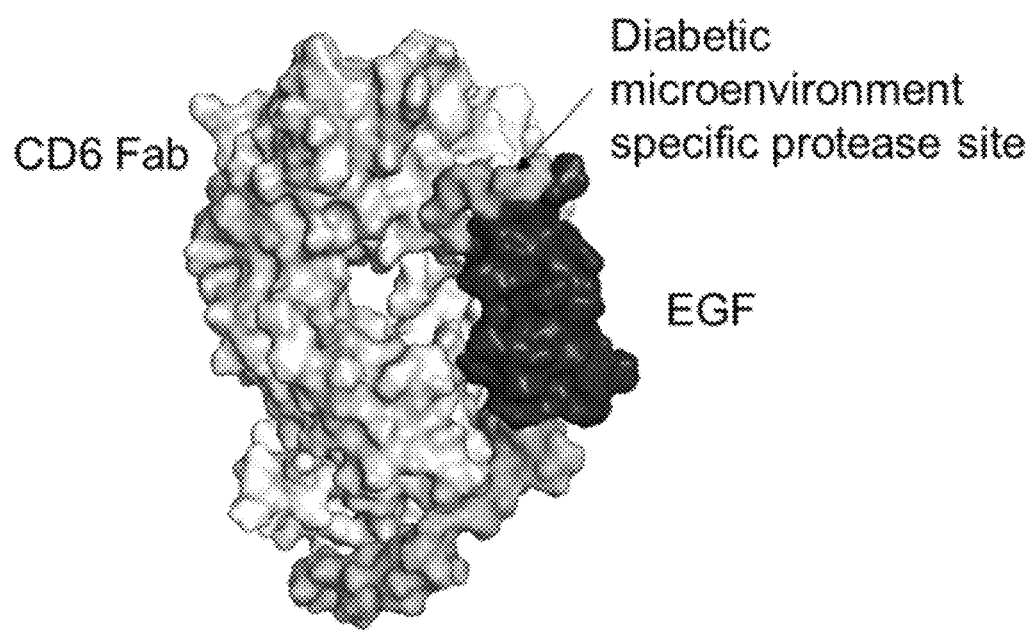
FIG. 9. Bionic EGF-CD6. To address PK/PD, exposing 'non-restricted' EGF from an antibody. As shown, the composition includes a diabetic microenvironment specific protease site. As such, the EGF may be released from a steric constraint upon cleavage of the site in the microenvironment.
Figure 10:
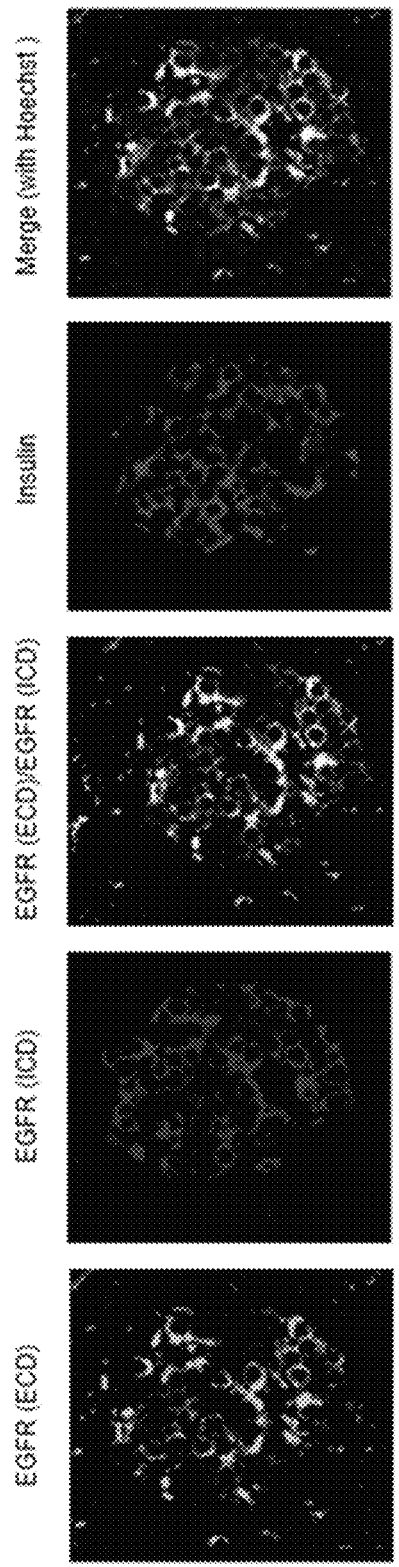
FIG. 10. EGFR extracellular domain (ECD), intracellular domain (ICD), and insulin expression in human islets. Representative images of paraffin-embedded pancreatic tissue sections from a healthy donor are shown. Tissue sections are stained for in the order from left to right: EGFR-ECD (first panel), EGFR-ICD (second panel), and insulin (fourth panel); double-staining of EGFR-ECD and EGFR-ICD (third panel) and EGFR-ECD/EGFR-ICD/Insulin co-detected with Hoechst stain (fifth panel).
Figure 11:
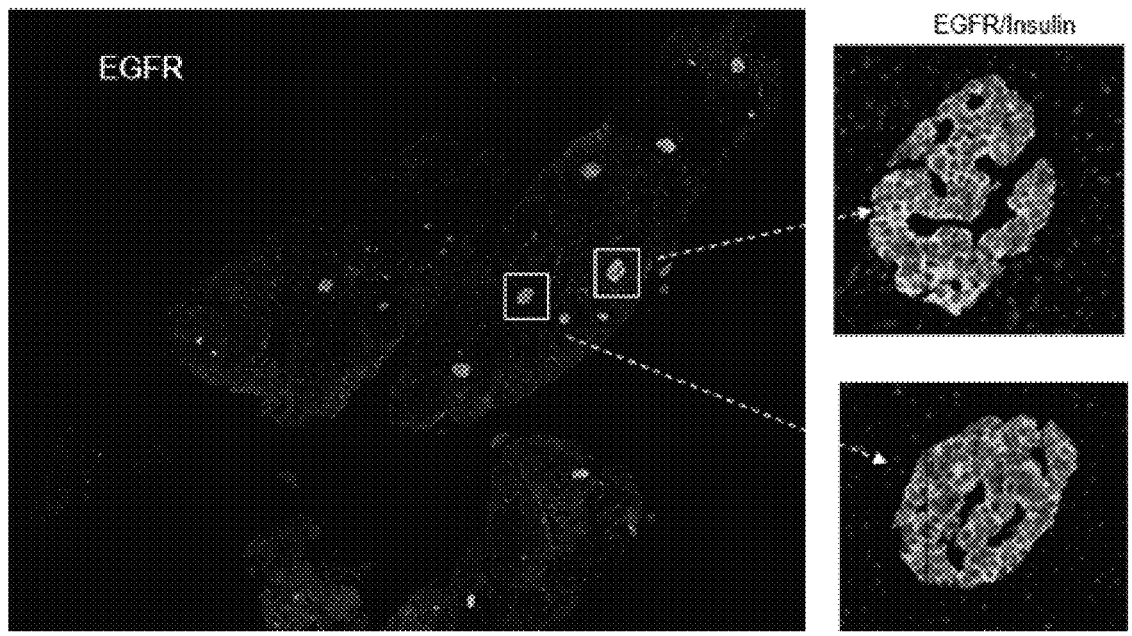
FIG. 11. EGFR heterogeneous distribution in human islets. Images of paraffin-embedded pancreatic tissue sections from a healthy donor stained for EGFR/Insulin are shown. Two panels on the right show magnified inserts of co-detected EGFR/Insulin.
Figure 12:
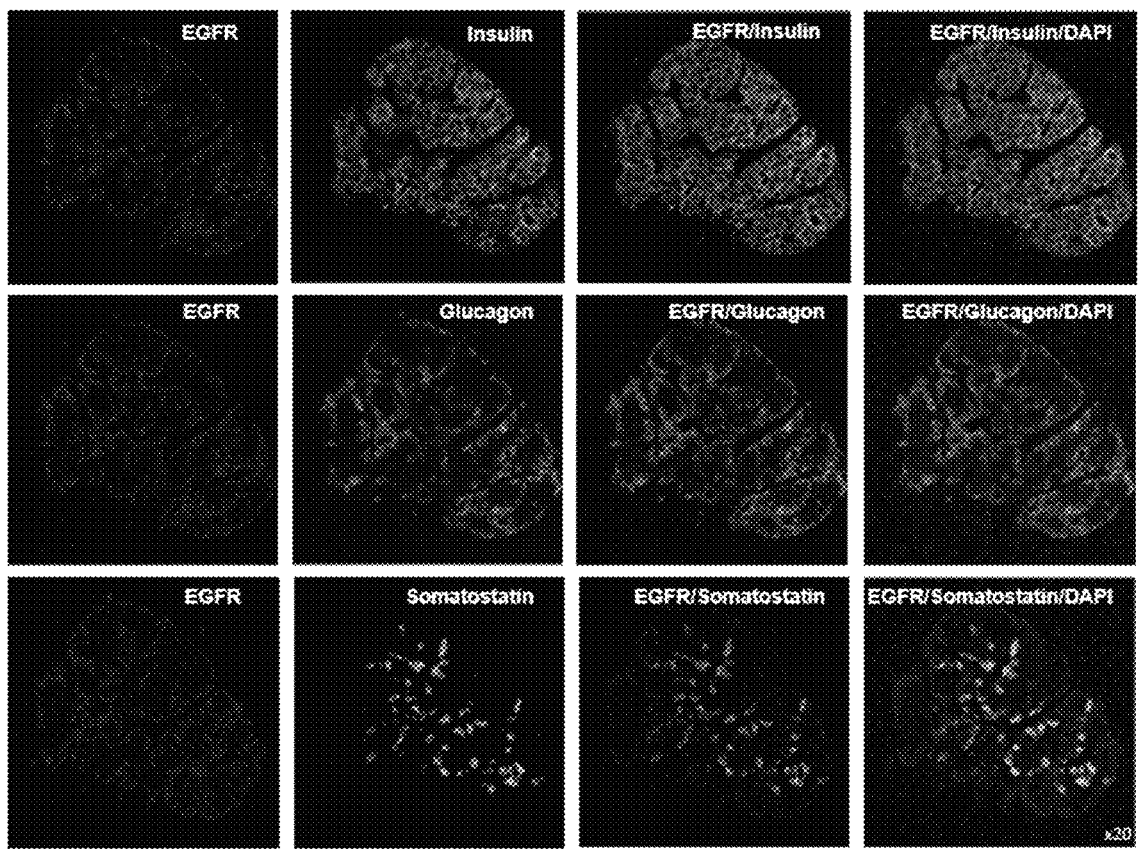
FIG. 12. Detection of EGFR, Insulin, Glucagon, and Somatostatin and co-expression of EGFR/Insulin, EGFR/Glucagon, and EGFR/Somatostatin in human islets. Representative images of pancreatic tissue sections from a healthy donor are shown.
Figure 24:
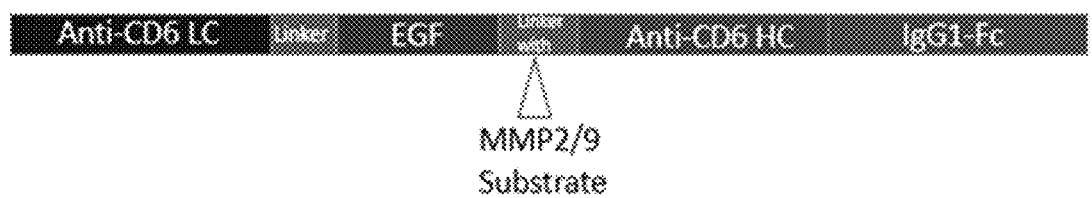
FIG. 24. Schematic representation of an exemplary anti-CD6 antibody-growth factor complex provided herein. A bionic anti-human CD6 meditope-enabled antibody is shown.
Figure 25A:
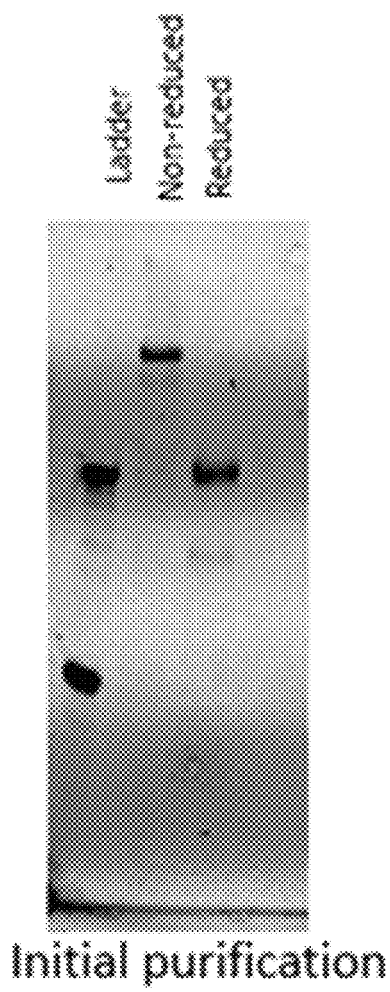
FIG. 25A-25B. SDS PAGE gels of an exemplary anti-CD6 antibody-growth factor complex provided herein. A bionic anti-CD6/EGF antibody conjugate of SEQ ID NO:32 was expressed in ExpiCHO cells and protein was harvested 7 days post transfection, using Protein G resin, and yielding 75 mg/L. Non-reduced and reduced bionic anti-CD6/EGF antibody conjugate samples are shown on a SDS PAGE gel (FIG. 25A). Bionic anti-CD6/EGF antibody conjugate was cleaved with MMP9, with the uncleaved (Uncut EGF) and cleaved product (Cut EGF) in non-reducing conditions (FIG. 25B, left) and in reducing conditions on a SDS PAGE gel (FIG. 25B, right).
Figure 25B:
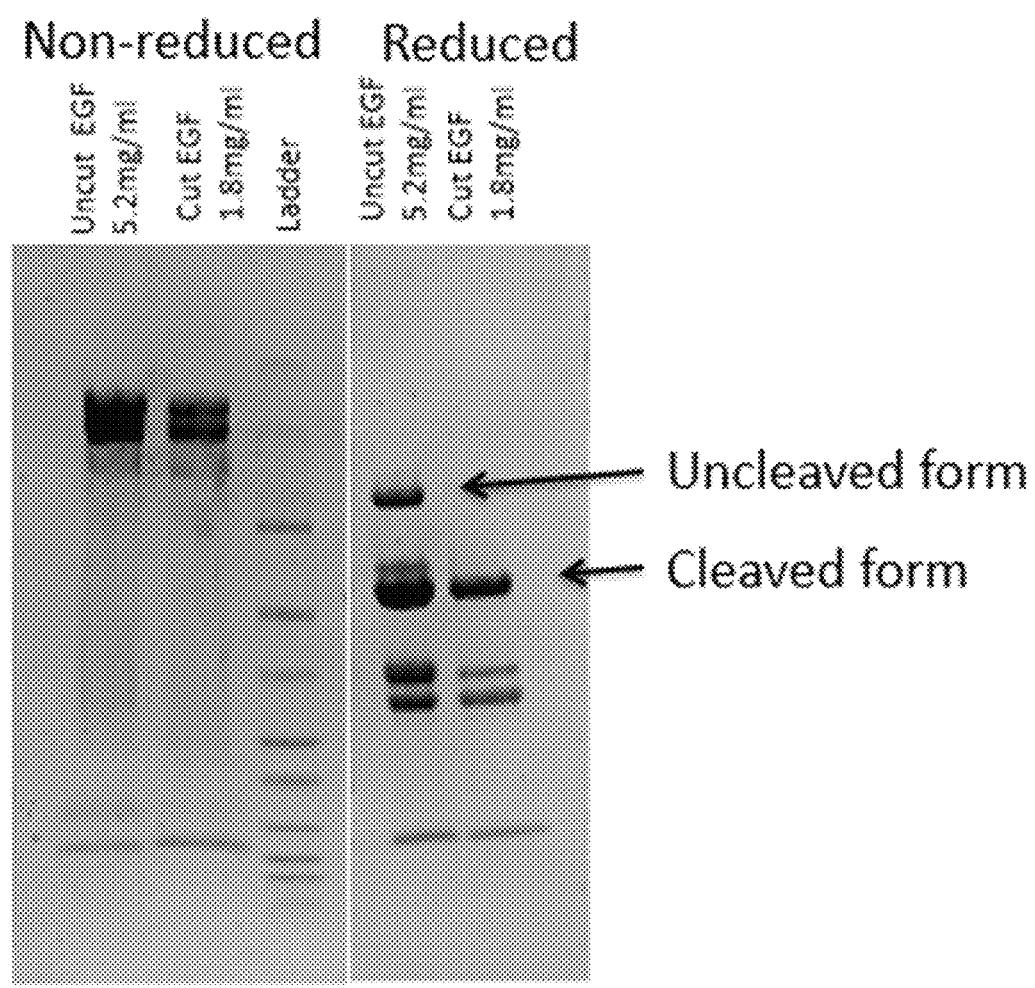
Figure 26:
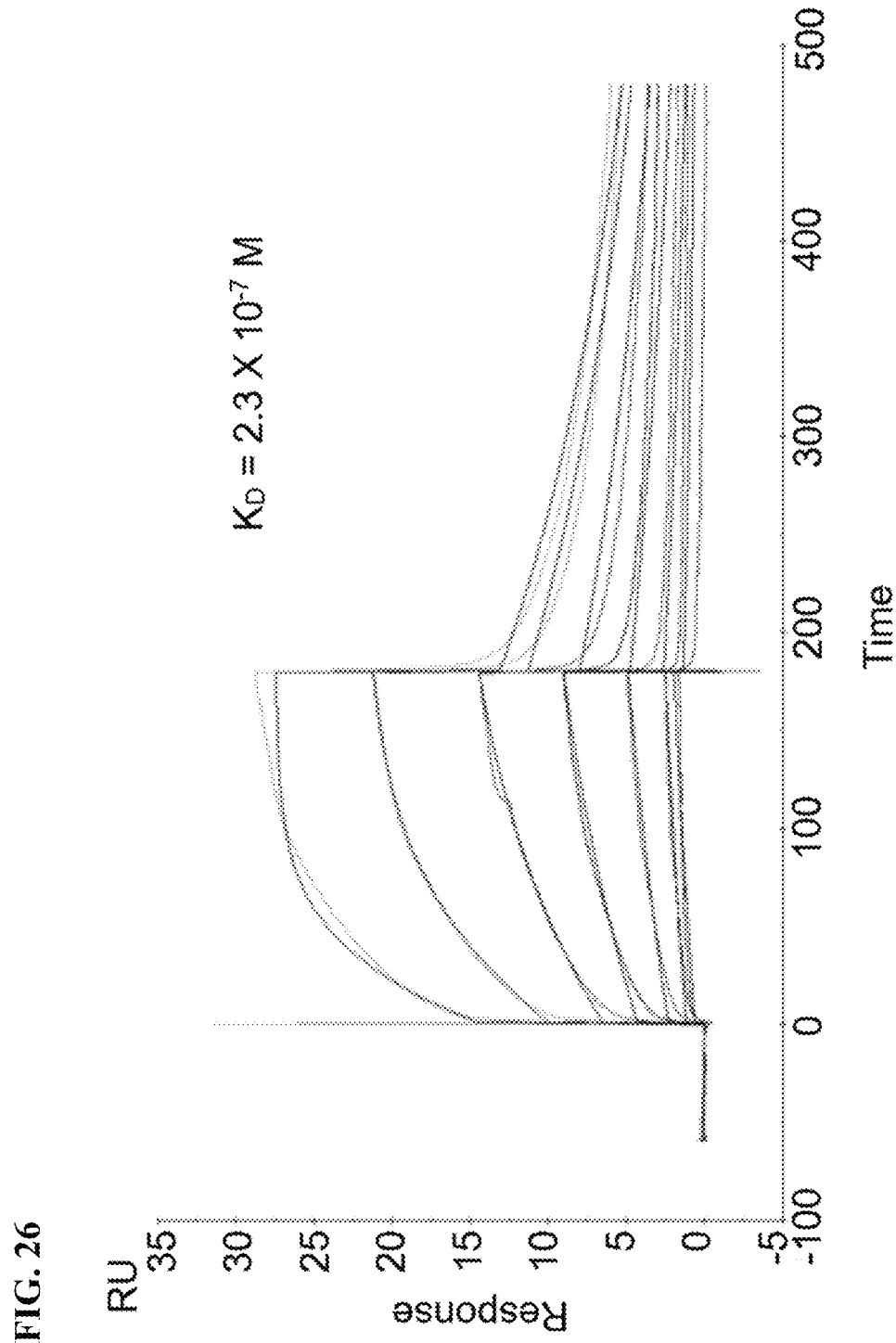
FIG. 26. Dissociation constant (Kp) of an exemplary anti-CD6 antibody-growth factor complex provided herein. Bionic anti-CD6/EGF antibody conjugate of SEQ ID NO:32 binding to EGFR is shown. EGFR was immobilized to a Biacore CM5 chip using NHS chemistry. Concentrations of previously cleaved and purified bionic anti-CD6/EGF antibody conjugate ranging from 0.0625 µM to 2 µM were flown over the chip at 25° C. The Kp was determined to be $2.3 \times 10^{-7}$ M.
Figure 27:
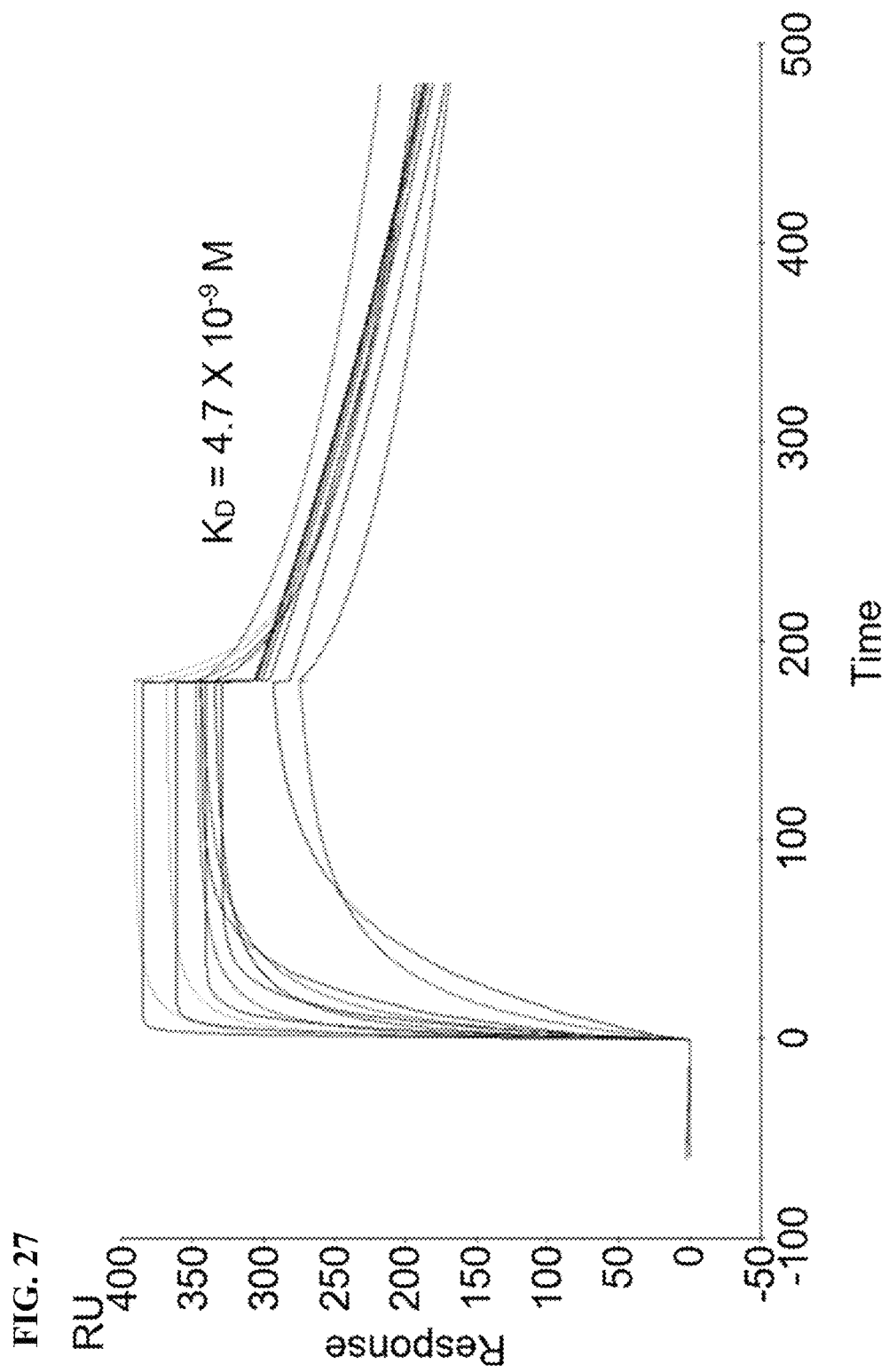
FIG. 27. Dissociation constant ($K_D$) of an exemplary anti-CD6 antibody-growth factor complex provided herein. Bionic anti-CD6/EGF antibody conjugate of SEQ ID NO:32 binding to CD6 Ecto (ectodomain) is shown. CD6 Ecto was immobilized to a Biacore CM5 chip using NHS chemistry. Concentrations of previously cleaved and purified bionic anti-CD6/EGF antibody conjugate ranging from 0.0625 µM to 2 µM were flown over the chip at 25° C. The $K_D$ was determined to be $4.7 \times 10^{-9}$ M.
Figure 28A:
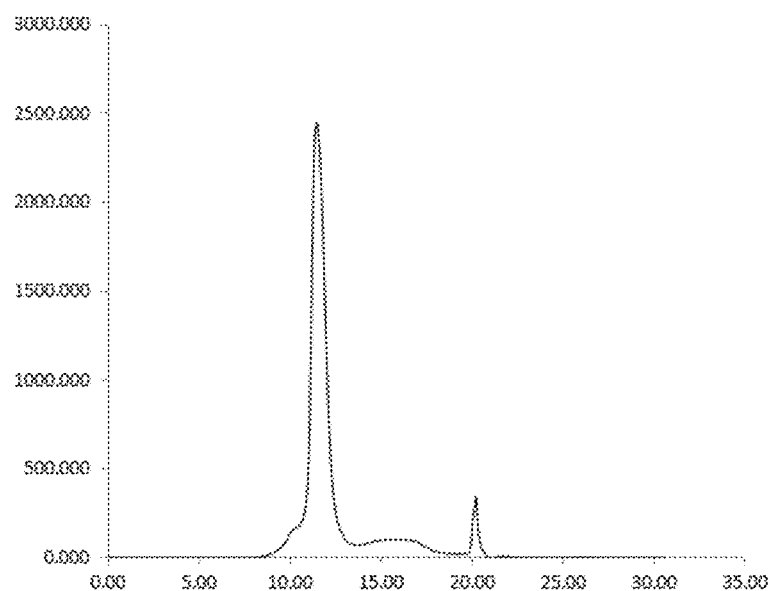
FIG. 28A-28B. Purification of an exemplary anti-CD6 antibody-growth factor complex provided herein. A bionic anti-CDG/EGF antibody conjugate of SEQ ID NO:38 with a granzyme site in a linker is characterized as shown.
Figure 28B:
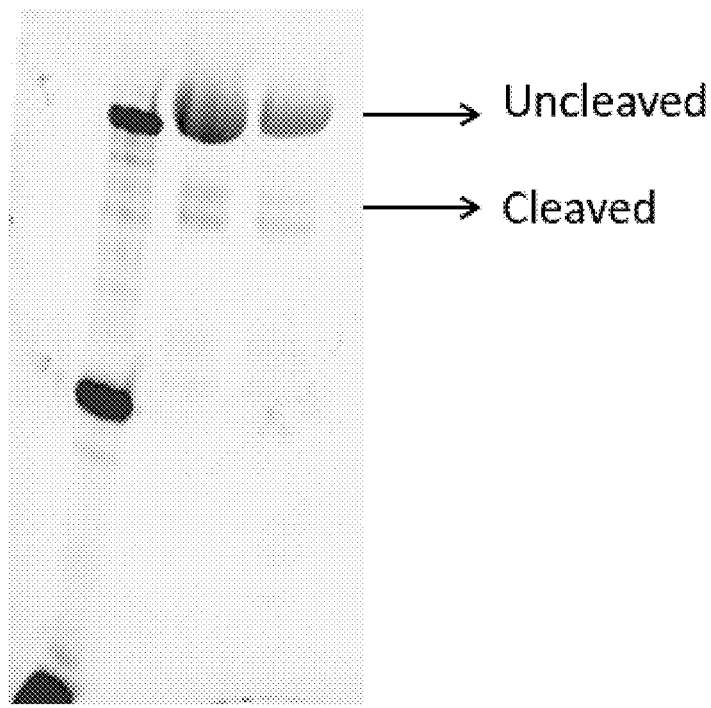

For example, through dimerization of the anti-CD6 heavy chain with the anti-CD6 light chain the complexes provided herin form molecular structures characteristic of the invention and referred to as "bionic molecules" or "switchblade molecules." Schematic representations of bionic and switchblade molecules are shown, for example, in FIG. 9 and FIG. 24. The anti-CD6 antibody-growth factor complexes provided herein that do not require cleavage of the chemical linker (e.g., first or second chemical linker) for the anti-CD6 antibody or the growth factor protein to bind their respective ligand, are referred to herein as "bionics" or "bionic molecules." Anti-CD6 antibody-growth factor complexes that include a cleavable linker (first or second chemical linker) and where the anti-CD6 antibody and/or the growth factor protein (e.g., EGF protein) are able to bind to their corresponding ligand/binding partner only upon cleavage of that cleavable linker (first or second chemical linker) are referred to herein as "switchblade" or "switchblade molecule." Switchblade molecules refer to anti-CD6 antibody-growth factor complexes that include a cleavable linker (e.g., a protease cleavable linker) connecting the anti-CD6 antibody with the growth factor protein (e.g., EGF protein), wherein the growth factor protein is occluded unless the linker is cleaved.

In an aspect, an anti-CD6 antibody-growth factor complex is provided. The complex includes (i) an anti-CD6 antibody or fragment thereof; and (ii) a growth factor protein or fragment thereof, wherein the growth factor protein is bound to the anti-CD6 antibody through a chemical linker.

The chemical linkers (e.g., first and/or second chemical linker) included in the anti-CD6 antibody-growth factor complexes provided herein may be cleavable and thereby conveying disease site specificity to the compositions provided herein. For example, the first and/or second chemical linker may be a cleavable linker including a cleavage site recognized by a pro-inflammatory protease (e.g., a diabetic microenvironment-specific protease). In the absence of a disease-specific protease the first and/or second chemical linker is not cleaved and the anti-CD6 antibody-growth factor complex is in a sterically occluded conformation, wherein the growth factor protein (e.g., EGF) does not bind its corresponding ligand. In the presence of a disease-specific protease (e.g., a pro-inflammatory protease, a diabetic microenvironment-specific protease) the first and/or second chemical linker is cleaved and the anti-CD6 antibody-growth factor complex forms a sterically open conformation, wherein the growth factor protein (e.g., EGF) is capable of binding its corresponding ligand. Thus, additional functionality (e.g., disease-specific activation such as type I diabetes-specific activation) can be included in the anti-CD6 antibody-growth factor complexes through steric hindrance, occlusion or masking of the growth factor protein (e.g., EGF).

An "anti-CD6 antibody or fragment thereof" as provided herein refers to an antibody domain capable of selectively binding to CD6 or a fragment thereof. Non-limiting examples of anti-CD6 antibody domains include single chain antibodies, antibody variants or fragments thereof, antibodies or fragments thereof, an antibody Fc region or fragments thereof. In embodiments, the the anti-CD6 antibody is a Fab. In embodiments, the the anti-CD6 antibody is a single domain antibody (sdAb).

In embodiments, the complex forms a single chain polypeptide. In embodiments, the anti-CD6 antibody includes a variable light chain domain. In embodiments, the anti-CD6 antibody includes a constant light chain domain. In embodiments, the anti-CD6 antibody includes an antibody light chain. In embodiments, the anti-CD6 antibody includes a variable heavy chain domain. In embodiments, the anti-CD6 antibody includes a constant heavy chain domain. In embodiments, the anti-CD6 antibody includes an antibody heavy chain.

A "variable light chain (VL) domain" as provided herein refers to the variable region of the light chain of an antibody (e.g., anti-CD6 antibody), an antibody variant or fragment thereof. Likewise, the "variable heavy chain (VH) domain" as provided herein refers to the variable region of the heavy chain of an antibody (e.g., anti-CD6 antibody), an antibody variant or fragment thereof. As described above, the variable light chain domain and the variable heavy chain domain together form the paratope, which binds an antigen (epitope). The paratope or antigen-binding site is formed at the N-terminus of an antibody, an antibody variant or fragment thereof. In embodiments, the variable light chain (VL) domain includes CDR L1, CDR L2, CDR L3 and FR L1, FR L2, FR L3 and FR L4 (framework regions) of an antibody light chain. In embodiments, the variable heavy chain (VH) domain includes CDR H1, CDR H2, CDR H3 and FR H1, FR H2, FR H3 and FR H4 (framework regions) of an antibody heavy chain.

The terms "CDR L1", "CDR L2" and "CDR L3" as provided herein refer to the complementarity determining regions (CDR) 1, 2, and 3 of the variable light (L) chain of an antibody or fragment thereof. In embodiments, the variable light chain provided herein includes in N-terminal to C-terminal direction a CDR LI, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody or fragment thereof. In embodiments, the variable light chain provided herein includes in N-terminal to C-terminal direction a CDR LI, a CDR L2 and a CDR L3.

"Framework regions" (FRs) are those variable region residues other than the CDR residues. The FRs of VH are also referred to herein as FR H1, FR H2, FR H3 and FR H4, respectively, wherein FR H1 corresponds to FR 1 of VH, FR H2 corresponds to FR 2 of VH, FR H3 corresponds to FR 3 of VH and FR H4 corresponds to FR 4 of VH. Likewise, the FRs of the variable region of the heavy chain are further referred to herein as HFR1, HFR2, HFR3 and HFR4, respectively, wherein HFRI corresponds to FR 1 of VH, HFR 2 corresponds to FR 2 of VH, HFR 3 corresponds to FR 3 of VH and HFR 4 corresponds to FR 4 of VH. Likewise, the FRs of VL are referred to herein as FR L1, FR L2, FR L3 and FR L4, respectively, wherein FR L1 corresponds to FR 1 of VL, FR L2 corresponds to FR 2 of VL, FR L3 corresponds to FR 3 of VL and FR L4 corresponds to FR 4 of VL. Likewise, the FRs of the variable region of the light chain are further referred to herein as LFR1, LFR2, LFR3 and LFR4, respectively, wherein LFR1 corresponds to FR 1 of VL, LFR 2 corresponds to FR 2 of VL, LFR 3 corresponds to FR 3 of VL and LFR 4 corresponds to FR 4 of VL.

In embodiments, the variable light chain (VL) domain and a constant light chain (CL) domain form part of an antibody light chain. In embodiments, the variable heavy chain (VH) domain and a constant heavy chain (CH1) domain form part of an antibody heavy chain. In embodiments, the variable heavy chain (VH) domain and one or more constant heavy chain (CH1, CH2, or CH3) domains form part of an antibody heavy chain. In embodiments, the variable light chain (VL) domain forms part of an antibody fragment. In embodiments, the variable heavy chain (VH) domain forms part of an antibody fragment. In embodiments, the variable light chain (VL) domain forms part of an antibody variant. In embodiments, the variable heavy chain (VH) domain forms part of an antibody variant. In embodiments, the variable light chain (VL) domain forms part of a Fab. In embodiments, the variable heavy chain (VH) domain forms part of a Fab. In embodiments, the variable light chain (VL) domain forms part of a scFv. In embodiments, the variable heavy chain (VH) domain forms part of a scFv.

In embodiments, the antibody light chain is bound to the growth factor protein through a first chemical linker. In embodiments, the antibody heavy chain is bound to the growth factor protein through a second chemical linker. In embodiments, the antibody light chain is bound to the N-terminus of the growth factor protein through the first chemical linker. In embodiments, the antibody heavy chain is bound to the C-terminus of the growth factor protein through the second chemical linker. In embodiments, the complex includes from the N-terminus to the C-terminus the antibody light chain, the first chemical linker, the growth factor protein, the second chemical linker and the antibody heavy chain.

In embodiments, the antibody heavy chain is bound to the growth factor protein through a first chemical linker. In embodiments, the antibody heavy chain is bound to the N-terminus of the growth factor protein through the first chemical linker. In embodiments, the antibody light chain is bound to the growth factor protein through a second chemical linker. In embodiments, the antibody light chain is bound to the C-terminus of the growth factor protein through the second chemical linker. In embodiments, the complex includes from the N-terminus to the C-terminus the antibody heavy chain, the first chemical linker, the growth factor protein, the second chemical linker and the antibody light chain.

In embodiments, the first chemical linker is bound to the N-terminus of the growth factor protein and the second chemical linker is bound to the C-terminus of the growth factor protein. In embodiments, the first chemical linker is bound to the C-terminus of the antibody light chain and the second chemical linker is bound to the N-terminus of the antibody heavy chain. In embodiments, the first chemical linker is bound to the C-terminus of the antibody heavy chain and the second chemical linker is bound to the N-terminus of the antibody light chain.

In embodiments, the antibody light chain is capable of non-covalently binding to the antibody heavy chain thereby forming the anti-CD6 antibody or fragment thereof. In embodiments, the anti-CD6 antibody is a humanized anti-CD6 antibody of fragment thereof. In embodiments, the anti-CD6 antibody is a Fab. In embodiments, the anti-CD6 antibody comprises the CDR sequences of itolizumab. In embodiments, the anti-CD6 antibody is a murine antibody. In embodiments, the anti-CD6 antibody is a humanized antibody. In embodiments, the anti-CD6 antibody is a monoclonal antibody. In embodiments, the anti-CD6 antibody binds to a CD6 extracellular domain. In embodiments, the anti-CD6 antibody binds extracellular domain 1 of CD6. In embodiments, the anti-CD6 antibody binds a CD6 membrane-distal domain. In embodiments, the anti-CD6 antibody competes for antigen-binding with, specifically binds to the same antigen or epitope as, and/or contains one, more, or all CDRs (or CDRs comprising at least at or about 75, 80, 85, 90, 91, 92, 93, 94, 95, 96, 97, 98, or 99% identity to the CDRs), e.g., including a heavy chain CDR 1, 2, and/or 3 and/or a light chain CDR1, 2, and/or 3, of itolizumab.

In embodiments, the growth factor protein is an epidermal growth factor receptor (EGFR) signaling molecule. In embodiments, the growth factor protein is an EGF protein or fragment thereof, a betacellulin protein or fragment thereof, a heparin-binding EGF-like growth factor (HBEGF) protein or fragment thereof, a TGF alpha protein or fragment thereof, an amphiregulin protein or fragment thereof, an epigen protein or fragment thereof or an epiregulin protein or fragment thereof. In embodiments, the growth factor protein is a recombinant EGF protein or fragment thereof. In embodiments, the growth factor protein is a human EGF protein or fragment thereof. In embodiments, the growth factor protein is a betacellulin protein or fragment thereof. In embodiments, the growth factor protein is a heparin-binding EGF-like growth factor (HBEGF) protein or fragment thereof. In embodiments, the growth factor protein is a TGF alpha protein or fragment thereof. In embodiments, the growth factor protein is an amphiregulin protein or fragment thereof. In embodiments, the growth factor protein is an epigen protein or fragment thereof. In embodiments, the growth factor protein is an epiregulin protein or fragment thereof. In embodiments, the growth factor protein is a glucagon-like peptide 1 (GLP1) protein or fragment thereof. In embodiments, the growth factor protein is a gastrin protein or fragment thereof.

In embodiments, the growth factor protein includes the amino acid sequence of SEQ ID NO:4. In embodiments, the growth factor protein is the amino acid sequence of SEQ ID NO:4. In embodiments, the growth factor protein includes the amino acid sequence of SEQ ID NO:68. In embodiments, the growth factor protein is the amino acid sequence of SEQ ID NO:68. In embodiments, the growth factor protein includes the amino acid sequence of SEQ ID NO:69. In embodiments, the growth factor protein is the amino acid sequence of SEQ ID NO:69.

In embodiments, the growth factor protein includes one or more copies of a growth factor protein or fragment thereof. In embodiments, the growth factor protein includes a plurality of growth factor proteins or fragments thereof. In embodiments, the growth factor protein includes one or more EGF proteins or fragments thereof.

In embodiments, the chemical linker is a covalent linker. In embodiments, the chemical linker is a bond. In embodiments, the chemical linker is a peptide linker. In embodiments, the chemical linker is a peptidyl linker. I n embodiments, the first chemical linker and the second chemical linker are independently a covalent linker. In embodiments, the first chemical linker and the second chemical linker are independently a cleavable peptide linker. In embodiments, at least one of the first chemical linker and the second chemical linker is a non-cleavable peptide linker. In embodiments, only one of the first chemical linker and the second chemical linker is a cleavable peptide linker. In embodiments, the first chemical linker or the second chemical linker is an enzymatically cleavable linker. In embodiments, the first chemical linker or the second chemical linker is a protease cleavable linker. In embodiments, the first chemical linker or the second chemical linker include a diabetic microenvironment specific protease site. In embodiments, the protease is an extracellular protease. In embodiments, the protease is a disease-associated protease. In embodiments, the protease is a pro-inflammatory protease. In embodiments, the protease is a type 1 diabetes-associated protease. In embodiments, the protease is a metalloprotease, granzyme, granuloysin or perforin.

In embodiments, the first chemical linker and the second chemical linker are independently a covalent linker or a non-covalent linker. In embodiments, the first chemical linker and the second chemical linker are independently a peptidyl linker. In embodiments, the first chemical linker and the second chemical linker are independently a cleavable peptide linker. In embodiments, the first chemical linker and the second chemical linker are independently an enzymatically cleavable linker. In embodiments, the first chemical linker and the second chemical linker are independently a protease cleavable linker.

In embodiments, the first chemical linker and the second chemical linker are independently a cleavable peptide linker, including a protease cleavage site. A "cleavage site" as used herein, refers to a recognizable site for cleavage of a portion of a linker described herein. Thus, a cleavage site may be found in the sequence of a cleavable peptide linker as described herein, including embodiments thereof. In embodiments, the cleavage site is an amino acid sequence that is recognized and cleaved by a cleaving agent (e.g., a peptidyl sequence). Exemplary cleaving agents include proteins, enzymes, DNAzymes, RNAzymes, metals, acids, and bases.

In embodiments, the protease cleavage site is a disease-associated protease cleavage site. A "disease-associated protease cleavage site" as provided herein is an amino acid sequence recognized by a protease, whose expression is specific for a disease-associated cell type or disease-associated cell environment. Likewise, a "type 1 diabetes-associated protease cleavage site" as provided herein is an amino acid sequence recognized by a protease, whose expression is specific for a type 1 diabetes-associated cell (e.g., a pancreatic cell) or type 1 diabetes-associated cell environment.

In embodiments, the protease cleavage site is a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site or a legumain protease cleavage site. In embodiments, the matrix metalloprotease (MMP) cleavage site is a MMP 9 cleavage site, a MMP 13 cleavage site or a MMP 2 cleavage site. In embodiments, the disintegrin and metalloprotease domain-containing (ADAM) metalloprotease cleavage site is a ADAM 9 metalloprotease cleavage site, a ADAM 10 metalloprotease cleavage site or a ADAM 17 metalloprotease cleavage site.

Further exemplary cleavage sites include the cleavage site of ABHD12, ADAM12, ABHD12B, ABHD13, ABHD17A, ADAM19, ADAM20, ADAM21, ADAM28, ADAM30, ADAM33, ADAM8, ABHD17A, ADAMDECI, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSLI, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTRI, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEPIA, MEPIB, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSKI, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMRI, PCSK3, PHEX, TINAG, TPSAB1, TPSD1, or TPSG1.

The chemical linkers provided herein, including embodiments thereof, may have different lengths (e.g., include varying numbers of amino acid residues). In embodiments, the first chemical linker and the second chemical linker independently have a length of about 0 to about 20 amino acid residues. In embodiments, the first chemical linker and the second chemical linker independently have a length of about 0 to about 15 amino acid residues. In embodiments, the first chemical linker and the second chemical linker independently have a length of about 0 to about 10 amino acid residues. In embodiments, the first chemical linker and the second chemical linker independently have a length of about 0 to about 9 amino acid residues. In embodiments, the first chemical linker and the second chemical linker independently have a length of about 0 to about 8 amino acid residues. In embodiments, the first chemical linker and the second chemical linker independently have a length of about 0 to about 7 amino acid residues. In embodiments, the first chemical linker and the second chemical linker independently have a length of about 0 to about 6 amino acid residues. In embodiments, the first chemical linker and the second chemical linker independently have a length of about 0 to about 5 amino acid residues. In embodiments, the first chemical linker and the second chemical linker independently have a length of about 0 to about 4 amino acid residues. In embodiments, the first chemical linker and the second chemical linker independently have a length of about 0 to about 3 amino acid residues. In embodiments, the first chemical linker and the second chemical linker independently have a length of about 0 to about 2 amino acid residues. In embodiments, the first chemical linker and the second chemical linker independently have a length of about 0 to about 1 amino acid residues.

In embodiments, the first chemical linker and the second chemical linker independently have a length of 0 to 20 amino acid residues. In embodiments, the first chemical linker and the second chemical linker independently have a length of 0 to 15 amino acid residues. In embodiments, the first chemical linker and the second chemical linker independently have a length of 0 to 10 amino acid residues. In embodiments, the first chemical linker and the second chemical linker independently have a length of 0 to 9 amino acid residues. In embodiments, the first chemical linker and the second chemical linker independently have a length of 0 to 8 amino acid residues. In embodiments, the first chemical linker and the second chemical linker independently have a length of 0 to 7 amino acid residues. In embodiments, the first chemical linker and the second chemical linker independently have a length of 0 to 6 amino acid residues. In embodiments, the first chemical linker and the second chemical linker independently have a length of 0 to 5 amino acid residues. In embodiments, the first chemical linker and the second chemical linker independently have a length of 0 to 4 amino acid residues. In embodiments, the first chemical linker and the second chemical linker independently have a length of 0 to 3 amino acid residues. In embodiments, the first chemical linker and the second chemical linker independently have a length of 0 to 2 amino acid residues. In embodiments, the first chemical linker and the second chemical linker independently have a length of 0 to 1 amino acid residues.

In embodiments, the first chemical linker and the second chemical linker independently have a length of 20 amino acid residues. In embodiments, the first chemical linker and the second chemical linker independently have a length of 19 amino acid residues. In embodiments, the first chemical linker and the second chemical linker independently have a length of 18 amino acid residues. In embodiments, the first chemical linker and the second chemical linker independently have a length of 17 amino acid residues. In embodiments, the first chemical linker and the second chemical linker independently have a length of 16 amino acid residues. In embodiments, the first chemical linker and the second chemical linker independently have a length of 15 amino acid residues. In embodiments, the first chemical linker and the second chemical linker independently independently have a length of 10 amino acid residues. In embodiments, the first chemical linker and the second chemical linker independently have a length of 9 amino acid residues. In embodiments, the first chemical linker and the second chemical linker independently have a length of 8 amino acid residues. In embodiments, the first chemical linker and the second chemical linker independently have a length of 7 amino acid residues. In embodiments, the first chemical linker and the second chemical linker independently have a length of 6 amino acid residues. In embodiments, the first chemical linker and the second chemical linker independently have a length of 5 amino acid residues. In embodiments, the first chemical linker and the second chemical linker independently have a length of 4 amino acid residues. In embodiments, the first chemical linker and the second chemical linker independently have a length of 3 amino acid residues. In embodiments, the first chemical linker and the second chemical linker independently have a length of 2 amino acid residues. In embodiments, the first chemical linker and the second chemical linker independently have a length of 1 amino acid residues. In embodiments, the first chemical linker and the second chemical linker independently have a length of 0 amino acid residues.

In embodiments, the first chemical linker and the second chemical linker independently have a length of 0, 1, 2, 3, 4, 5, 6, 7, 8, 9, 10, 11, 12, 13, 14, 15, 16, 17, 18, 19, or 20 amino acid residues. In embodiments, the first chemical linker has a length of 0, 1, 2, 3, 4, 5, 6, 7, 8, 9, 10, 11, 12, 13, 14, 15, 16, 17, 18, 19, or 20 amino acid residues. In embodiments, the second chemical linker has a length of 0, 1, 2, 3, 4, 5, 6, 7, 8, 9, 10, 11, 12, 13, 14, 15, 16, 17, 18, 19, or 20 amino acid residues.

In embodiments, the first chemical linker has a length of about 8, 9, 10, 11, or 12 amino acid residues. In embodiments, the first chemical linker has a length of about 8 amino acid residues. In embodiments, the first chemical linker has a length of about 9 amino acid residues. In embodiments, the first chemical linker has a length of about 10 amino acid residues. In embodiments, the first chemical linker has a length of about 11 amino acid residues. In embodiments, the first chemical linker has a length of about 12 amino acid residues.

In embodiments, the first chemical linker has a length of 8, 9, 10, 11, or 12 amino acid residues. In embodiments, the first chemical linker has a length of 8 amino acid residues. In embodiments, the first chemical linker has a length of 9 amino acid residues. In embodiments, the first chemical linker has a length of 10 amino acid residues. In embodiments, the first chemical linker has a length of 11 amino acid residues. In embodiments, the first chemical linker has a length of 12 amino acid residues.

In embodiments, the first chemical linker includes the sequence of SEQ ID NO:34, SEQ ID NO:43, SEQ ID NO:45, SEQ ID NO:47, SEQ ID NO:49, SEQ ID NO:51, SEQ ID NO: 53 SEQ ID NO:55, SEQ ID NO:57, or SEQ ID NO:59. In embodiments, the first chemical linker is the sequence of SEQ ID NO:34, SEQ ID NO:43, SEQ ID NO:45, SEQ ID NO:47, SEQ ID NO: 49, SEQ ID NO:51, SEQ ID NO:53 SEQ ID NO:55, SEQ ID NO:57, or SEQ ID NO:59.

In embodiments, the second chemical linker has a length of about 8, 9, 10, 11, or 12 amino acid residues. In embodiments, the second chemical linker has a length of about 8 amino acid residues. In embodiments, the second chemical linker has a length of about 9 amino acid residues. In embodiments, the second chemical linker has a length of about 10 amino acid residues. In embodiments, the second chemical linker has a length of about 11 amino acid residues. In embodiments, the second chemical linker has a length of about 12 amino acid residues.

In embodiments, the second chemical linker has a length of 8, 9, 10, 11, or 12 amino acid residues. In embodiments, the second chemical linker has a length of 8 amino acid residues. In embodiments, the second chemical linker has a length of 9 amino acid residues. In embodiments, the second chemical linker has a length of 10 amino acid residues. In embodiments, the second chemical linker has a length of 11 amino acid residues. In embodiments, the second chemical linker has a length of 12 amino acid residues.

In embodiments, the second chemical linker includes the sequence of SEQ ID NO:35, SEQ ID NO:39, SEQ ID NO:61, SEQ ID NO:63, or SEQ ID NO:65. In embodiments, the second chemical linker is the sequence of SEQ ID NO:35, SEQ ID NO:39, SEQ ID NO:61, SEQ ID NO: 63, or SEQ ID NO:65. In embodiments, the second chemical linker includes the sequence of SEQ ID NO:66. In embodiments, the second chemical linker includes the sequence of SEQ ID NO:67.

In embodiments, the second chemical linker is a protease cleavable linker. In embodiments, the second chemical linker is a granzyme cleavable linker. In further embodiments, the first chemical linker is a non-cleavable linker. A non-cleavable linker as provided herein is a chemical linker that is not cleaved by a disease-associate protease at a detectable level compared to a standard control.

In embodiments, the anti-CD6 antibody or fragment thereof is bound to an Fc domain through a third chemical linker. In embodiments, the C-terminus of the antibody heavy chain is bound to the Fc domain through the third chemical linker. In embodiments the Fc domain is an IgG1 Fc domain. In embodiments, the third linker is a covalent linker. In embodiments, the third linker is a cleavable peptide linker. In embodiments, the third linker is a bond.

In one embodiment, the anti-CD6 antibody-growth factor complex includes from the N-terminus to the C-terminus an anti-CD6 antibody light chain, a first linker, wherein the first linker is a non-cleavable linker, a EGF protein, a second linker, wherein the second linker is a granzyme cleavable linker, an anti-CD6 antibody heavy chain, a third linker, wherein the third linker is a bond and a Fc domain.

In one embodiment, the anti-CD6 antibody-growth factor complex includes from the N-terminus to the C-terminus an anti-CD6 antibody heavy chain, a first linker, wherein the first linker is a non-cleavable linker, a EGF protein, a second linker, wherein the second linker is a granzyme cleavable linker, an anti-CD6 antibody light chain, a third linker, wherein the third linker is a bond and a Fc domain.

In one embodiment, the anti-CD6 antibody-growth factor complex includes from the N-terminus to the C-terminus an anti-CD6 antibody light chain, a first linker, wherein the first linker is a non-cleavable linker, a EGF protein, a second linker, wherein the second linker is an MMP2 or MMP9 cleavable linker, an anti-CD6 antibody heavy chain, a third linker, wherein the third linker is a bond and a Fc domain.

In one embodiment, the anti-CD6 antibody-growth factor complex includes from the N-terminus to the C-terminus an anti-CD6 antibody heavy chain, a first linker, wherein the first linker is a non-cleavable linker, a EGF protein, a second linker, wherein the second linker is an MMP2 or MMP9 cleavable linker, an anti-CD6 antibody light chain, a third linker, wherein the third linker is a bond and a Fc domain.

In one embodiment, the anti-CD6 antibody-growth factor complex includes from the N-terminus to the C-terminus an anti-CD6 antibody heavy chain of SEQ ID NO:36, a first linker of SEQ ID NO:34, a EGF protein of SEQ ID NO:4, a second linker of SEQ ID NO:35, an anti-CD6 antibody light chain of SEQ ID NO:33, a third linker, wherein the third linker is a bond and a Fc domain of SEQ ID NO:37.

In one embodiment, the anti-CD6 antibody-growth factor complex includes from the N-terminus to the C-terminus an anti-CD6 antibody heavy chain of SEQ ID NO:36, a first linker of SEQ ID NO:34, a EGF protein of SEQ ID NO:4, a second linker of SEQ ID NO:67, an anti-CD6 antibody light chain of SEQ ID NO:33, a third linker, wherein the third linker is a bond and a Fc domain of SEQ ID NO:37.

In embodiments, the anti-CD6 antibody-growth factor complex includes the sequence of SEQ ID NO:32. In one embodiment, the anti-CD6 antibody-growth factor complex is the sequence of SEQ ID NO:32. In embodiments, the anti-CD6 antibody-growth factor complex includes the sequence of SEQ ID NO:38. In one embodiment, the anti-CD6 antibody-growth factor complex is the sequence of SEQ ID NO:38. In embodiments, the anti-CD6 antibody-growth factor complex includes the sequence of SEQ ID NO:42. In one embodiment, the anti-CD6 antibody-growth factor complex is the sequence of SEQ ID NO:42. In embodiments, the anti-CD6 antibody-growth factor complex includes the sequence of SEQ ID NO:44. In one embodiment, the anti-CD6 antibody-growth factor complex is the sequence of SEQ ID NO:44. In embodiments, the anti-CD6 antibody-growth factor complex includes the sequence of SEQ ID NO: 46. In one embodiment, the anti-CD6 antibody-growth factor complex is the sequence of SEQ ID NO:46. In embodiments, the anti-CD6 antibody-growth factor complex includes the sequence of SEQ ID NO:48. In one embodiment, the anti-CD6 antibody-growth factor complex is the sequence of SEQ ID NO:18. In embodiments, the anti-CD6 antibody-growth factor complex includes the sequence of SEQ ID NO:50. In one embodiment, the anti-CD6 antibody-growth factor complex is the sequence of SEQ ID NO:50. In embodiments, the anti-CD6 antibody-growth factor complex includes the sequence of SEQ ID NO:52. In one embodiment, the anti-CD6 antibody-growth factor complex is the sequence of SEQ ID NO:52. In embodiments, the anti-CD6 antibody-growth factor complex includes the sequence of SEQ ID NO: 54. In one embodiment, the anti-CD6 antibody-growth factor complex is the sequence of SEQ ID NO:54. In embodiments, the anti-CD6 antibody-growth factor complex includes the sequence of SEQ ID NO:56. In one embodiment, the anti-CD6 antibody-growth factor complex is the sequence of SEQ ID NO:56. In embodiments, the anti-CD6 antibody-growth factor complex includes the sequence of SEQ ID NO:58. In one embodiment, the anti-CD6 antibody-growth factor complex is the sequence of SEQ ID NO:58. In embodiments, the anti-CD6 antibody-growth factor complex includes the sequence of SEQ ID NO:60. In one embodiment, the anti-CD6 antibody-growth factor complex is the sequence of SEQ ID NO:60. In embodiments, the anti-CD6 antibody-growth factor complex includes the sequence of SEQ ID NO: 62. In one embodiment, the anti-CD6 antibody-growth factor complex is the sequence of SEQ ID NO:62. In embodiments, the anti-CD6 antibody-growth factor complex includes the sequence of SEQ ID NO:64. In one embodiment, the anti-CD6 antibody-growth factor complex is the sequence of SEQ ID NO:64.

In one embodiment, the anti-CD6 antibody-growth factor complex includes an anti-CD6 light chain (SEQ ID NO:33) bound to the N-terminus of an EGF protein (SEQ ID NO:4) through a first linker (SEQ ID NO:34) and an anti-CD6 heavy chain (SEQ ID NO:36) bound to the C-terminus of the EGF protein (SEQ ID NO:4) through a second linker (SEQ ID NO:35), wherein the second linker includes a matrix metalloproteinase-2/9 (MMP2/9) cleavage site of (SEQ ID NO:66), and wherein a third linker is a bond and attaches a IgG1-Fc (SEQ ID NO:37) domain to the C-terminus of the anti-CD6 heavy chain (SEQ ID NO:36).

In one embodiment, the anti-CD6 antibody-growth factor complex includes from the N-terminus to the C-terminus an anti-CD6 light chain (SEQ ID NO:33) bound to the N-terminus of an EGF protein (SEQ ID NO:4) through a first linker (SEQ ID NO:43) and an anti-CD6 heavy chain (SEQ ID NO:36) bound to the C-terminus of the EGF protein (SEQ ID NO:4) through a second linker (SEQ ID NO:39), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO:36).

In one embodiment, the anti-CD6 antibody-growth factor complex includes an anti-CD6 light chain (SEQ ID NO:33) bound to the N-terminus of an EGF protein (SEQ ID NO:4) through a first linker (SEQ ID NO:45) and an anti-CD6 heavy chain (SEQ ID NO:36) bound to the C-terminus of the EGF protein (SEQ ID NO:4) through a second linker (SEQ ID NO:39), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO:36).

In one embodiment, the anti-CD6 antibody-growth factor complex includes an anti-CD6 light chain (SEQ ID NO:33) bound to the N-terminus of an EGF protein (SEQ ID NO:4) through a first linker (SEQ ID NO:47) and an anti-CD6 heavy chain (SEQ ID NO:36) bound to the C-terminus of the EGF protein (SEQ ID NO:4) through a second linker (SEQ ID NO:39), wherein the second linker includes a granzyme cleavage site of (SEQ ID NO:67), and wherein a third linker attaches a IgGI-Fc (SEQ ID NO:37) domain to the C-terminus of the anti-CD6 heavy chain (SEQ ID NO:36) . . .

In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:49), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:51), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:53), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:55), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:57), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:59), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:61), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:63), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36). ASASAAASSASSAASS In one embodiment, the anti-CD6 antibody-growth factor complex includes an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:65), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

Pharmaceutical Compositions

Pharmaceutical compositions include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. In an aspect, a pharmaceutical composition including a complex as provided herein, including embodiments thereof, and a pharmaceutically acceptable excipient is provided. When administered in methods to treat a disease, the compositions (e.g., antibodies, complexes) described herein will be provided in an effective amount to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

In embodiments, the dosage is from about 0.01 to about 7.5 mg/kg of body weight. In embodiments, the dosage is from about 0.01 to about 7 mg/kg of body weight. In embodiments, the dosage is from about 0.01 to about 6.5 mg/kg of body weight. In embodiments, the dosage is from about 0.01 to about 6.0 mg/kg of body weight. In embodiments, the dosage is from about 0.01 to about 5.5 mg/kg of body weight. In embodiments, the dosage is from about 0.01 to about 5.0 mg/kg of body weight. In embodiments, the dosage is from about 0.01 to about 4.5 mg/kg of body weight. In embodiments, the dosage is from about 0.01 to about 4.0 mg/kg of body weight. In embodiments, the dosage is from about 0.01 to about 3.5 mg/kg of body weight. In embodiments, the dosage is from about 0.01 to about 3.0 mg/kg of body weight. In embodiments, the dosage is from about 0.01 to about 2.5 mg/kg of body weight. In embodiments, the dosage is from about 0.01 to about 2.0 mg/kg of body weight. In embodiments, the dosage is from about 0.01 to about 1.5 mg/kg of body weight. In embodiments, the dosage is from about 0.01 to about 1.0 mg/kg of body weight. In embodiments, the dosage is from about 0.01 to about 0.5 mg/kg of body weight. In embodiments, the dosage is from about 0.01 to about 0.25 mg/kg of body weight. In embodiments, the dosage is from about 0.01 to about 0.1 mg/kg of body weight. In embodiments, the dosage is from about 0.01 to about 0.05 mg/kg of body weight. In embodiments, the dosage is from about 0.01 to about 0.025 mg/kg of body weight.

In embodiments, treatment is administered weekly, every 2, 4, 8, and 12 weeks. In embodiments, treatment is administered weekly or every 2, 4, 8, and 12 weeks. In embodiments, treatment is administered weekly for 2, 4, 8, or 12 weeks. In embodiments, treatment is administered every week. In embodiments, treatment is administered every 2 weeks. In embodiments, treatment is administered every 4 weeks. In embodiments, treatment is administered every 8 weeks. In embodiments, treatment is administered every 12 weeks. In embodiments, treatment is administered for up to 2, 4, 8, or 12 weeks.

In embodiments, administration is intravenous. In embodiments, the treatment is administered as a sterile solution.

For any composition (e.g., antibody, complex) provided herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Methods of Treatment

The antibodies as described herein, including embodiments thereof, are contemplated as providing effective treatment of autoimmune disease (e.g., type I diabetes). Thus, in an aspect is provided a method of treating an autoimmune disease in a subject in need thereof, the method including administering to the subject an antibody as described herein including embodiments thereof. In an aspect is provided a method of treating an autoimmune disease in a subject in need thereof, the method including administering to the subject a therapeutically effective amount of a complex as provided herein, including embodiments thereof.

In another aspect, a method of treating an autoimmune disease in a subject in need thereof is provided. The method includes administering to a subject a therapeutically effective amount of a complex provided herein including embodiments thereof is provided, thereby treating an autoimmune disease in the subject.

In embodiments, the autoimmune disease is Type I Diabetes. In embodiments, the autoimmune disease is Multiple Sclerosis. In embodiments, the autoimmune disease is type 1 diabetes, multiple sclerosis or inflammatory bowel disease. In embodiments, the disease is a graft versus host disease.

The antibodies described herein, including embodiments thereof, are capable of targeting CD6+ lymphocytes and delivering a therapeutic agent such as EGF, gastrin, and GLP-1. Thus, in embodiments, the antibodies provided herein, including embodiments thereof, inhibit CD6+lymphocyte proliferation. In embodiments, the antibodies provided herein, including embodiments thereof, increase cell growth. In embodiments, the antibodies provided herein, including embodiments thereof, increase cellular repair. In embodiments, the antibodies provided herein, including embodiments thereof, simultaneously increase cellular repair and/or cell growth and inhibit CD6+lymphocyte proliferation. In embodiments, the antibodies provided herein, including embodiments thereof, decreases or prevents cell death.

In embodiments, the cells are pancreatic beta-cells. In embodiments, the cells are Schwann cells. In embodiments, the cells are oligodendrocytes.

In embodiments, the antibodies provided herein, including embodiments thereof, inhibit the interaction of CD6 with ALCAM. In embodiments, the antibodies provided herein, including embodiments thereof, inhibit the interaction of CD6 with CD318.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Nucleic Acid Compositions

In an aspect is provided an isolated nucleic acid encoding a peptide as described herein, including embodiments thereof. The nucleic acid provided herein, including embodiments thereof, may be loaded into an expression vector such that the nucleic acid may be delivered to cells. Thus, in an aspect, an expression vector including the nucleic acid provided herein, including embodiments thereof, is provided. It is contemplated that the nucleic acid may be loaded into any expression vector useful for delivering the nucleic acid to cells either in vivo or in vitro. It is further contemplated that viruses, for example, lentivirus and onco-retrovirus, may serve as suitable expression vectors. Accordingly, in embodiments, the expression vector is a viral vector. In embodiments, the viral vector is a lentiviral vector or an onco-retroviral vector. In embodiments, the viral vector is a lentiviral vector. In embodiments, the viral vector is an onco-retroviral vector. In embodiments, the virus is a lentivirus or an onco-retrovirus. In embodiments, the virus is a lentivirus. In embodiments, the virus is an onco-retrovirus.

In an aspect is provided an isolated nucleic acid encoding a complex provided herein including embodiments thereof. The nucleic acid provided herein, including embodiments thereof, may be loaded into an expression vector such that the nucleic acid may be delivered to cells. Thus, in an aspect is provided an expression vector including the nucleic acid provided herein including embodiments thereof. In embodiments, the expression vector is a viral vector. In embodiments, the virus is a lentivirus. In embodiments, the virus is an onco-retrovirus. In embodiments, the virus is a lentivirus or an onco-retrovirus.

In another aspect is provided a cell including the expression vector provided herein including embodiments thereof.

Methods of Detecting

The compositions provided herein, including embodiments thereof, are contemplated as diagnostic tools for monitoring treatment of autoimmune disease and detecting cells related to autoimmune disease in vivo. Thus, in an aspect is provided a method of detecting an autoreactive cell or a pancreatic cell in a subject in need thereof the method including administering to a subject in need thereof a complex as described herein, including embodiments thereof and a detecting agent. In embodiments, the detecting agent is a labeled peptide. In embodiments, the labeled peptide is bound to the antibody (anti-CD6 antibody) or growth factor protein provided herein including embodiments thereof thereby detecting a pancreatic cell in the subject.

In embodiments, the antibody (anti-CD6 antibody) or growth factor protein includes a detectable moiety. In embodiments, the detectable moiety is bound (covalently or non-covalently) to the antibody (anti-CD6 antibody) or growth factor protein. In embodiments, the s antibody (anti-CD6 antibody) or growth factor protein includes a detectable moiety.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The following examples are intended to further illustrate certain embodiments of the disclosure. The examples are put forth so as to provide one of ordinary skill in the art and are not intended to limit its scope.

Example 1. Therapeutic Targeting of the Human Islet Environment WITH ANTI-CD6/EGF MEDITOPE-ENABLED MAB Define the immunomodulatory effect of Itolizumab on the pancreatic islet autoimmunity.

It has been proposed theoretically, and experimental results suggest, that the Itolizumab binding site does not interfere with the CD6-ALCAM interaction [1]. However, solving the crystal structure of the Itolizumab-CD6 complex would help further understanding of properties of the CD6 model and eventually improve the efficacy of therapeutic molecules. Applicants will use commercially available Itolizumab for crystallography experiments. Fabs will be isolated using standard methods that are routine in the lab (e.g., papain digest followed by chromatography.) Applicants will produce the extra-cellular domain of CD6. Applicants will follow the same protocol previously described to obtain structural information. Specifically, Applicants have residues 1-364 of CD6 (UniProt: P30203), containing its natural secretion sequence, and a C-terminal histidine tag synthesized (codon optimized for CHO expression). The protein will be purified from clarified supernatant using Ni-NTA columns and further purified by size exclusion chromatography. Applicants will use mass spectrometry to verify the purified protein is intact and without post-translation modification. Models defining the Itolizumab binding epitope in the human CD6 domain 1 will be generated, and it will be determined if steric hindrance is preventing the optimal interaction of ALCAM with the CD6 domain 3. In case of the latter, different versions of the Itolizumab molecule expressed in NSO and CHO cells and de-glycosylated will be compared experimentally. Confirmed the case, modified Itolizumab molecules increasing the interfering with the CD6 adhesion to ALCAM may eventually amplify the therapeutic efficacy. The immunomodulatory effect of Itolizumab will be assessed by cell culturing of human β-cell antigen specific CD8+compared to CD4+ and Treg cell clones [2, 3]. Activation of T-cell clones will be induced using synthetic tetramers containing β-cell antigens in the context of the human MHC class I and II, and human pancreatic islet cells. The expression analyses of CD6 and other cell surface or intracellular markers will be performed by Flow cytometry. Lymphocyte proliferation and survival will be analyzed by Flow cytometry and Cell Imaging Cytometry. The cytokine production (IFNγ, TNFα, IL-6 and IL-17) evaluation will be performed by Elispot, using Itolizumab and versions with different glycosylation profiles.

Define the Modulatory Effect of the Recombinant Human EGF on the Human Insulitic Microenvironment.

Freshly isolated human islets will be provided locally by the Clinical Islet Transplantation Program, which is a member of the Integrated Islet Distribution Program at City of Hope. Expression analyses of EGFR, HLA-I and other cell surface or intracellular markers will be performed by Flow cytometry. EGFR phosphorylation/activation will be measured using specific antibodies. Applicants will perform RNA-Seq experiments on a series of model systems that compare damage/recovery phases, using isolated human islets, and single-cell RNA-Seq experiments to examine the diverse recovery responses within the islet. Human islets will be exposed to pro-inflammatory cytokine stress (IL-1β, IFNγ, TNFα and IL-17) as previously described [5] for up to 48 h (0, 8, 24, and 48 h). The cytokines will then be removed, and the islets will be allowed to recover for 24 h. Glucose-stimulated insulin secretion (GSIS, insulin measured via radioimmunoassay in buffer after 1 h at 2.5 and 16.7 mM glucose) will be assessed at the end of the stress and recovery phases on a subset of the islets. The remaining islets will be used for RNA-Seq and single-cell RNA-Seq experiments. Data generated with this work provide novel insights into the self-repair pathways engaged in human β-cells.

Demonstration of the Therapeutic Immunomodulatory Effect of Anti-CD6/EGF Meditope-Enabled mAbs on Human Insulitis.

Monoclonal antibody (mAb) production: first, Applicants will generate parental and meditope-enabled anti-CD6. To generate meditope-enabled anti-CD6, Applicants will identify the appropriate residues through a sequence alignment, generate the protein sequence, and have the resulting sequence synthesized de novo, optimizing the codons for CHO expression. Applicants will also generate the synthetic gene for the parental anti-CD6 to ensure a direct comparison between the parent and enabled-mAbs can be made. Applicants are currently producing 100 to 300 mg/L of purified meditope-enabled mAbs using transient transfection. Applicants anticipate similar levels for the anti-CD6 mAb variants. Applicants will purify each IgG1 using standard methods that are routinely applied in the lab. For SPR and crystallography experiments, Applicants isolate Fabs using standard methods that are routine in the lab (e.g., papain digest followed by chromatography.) Next, Applicants will produce the extra-cellular domain of CD6. Applicants will follow the same protocol previously describe to obtain structural information. Specifically, Applicants have residues 1-364 of CD6 (UniProt: P30203), containing its natural secretion sequence, and a C-terminal histidine tag synthesized (again, codon optimized for CHO expression). The protein will be purified from clarified supernatant using Ni-NTA columns and further purified by size exclusion chromatography. Applicants will use mass spectrometry to verify the purified protein is intact and without post-translation modification. To ascertain the binding affinity of the anti-CD6 mAb variants, Applicants will conduct SPR experiments. Applicants will chemically tether each anti-CD6 mAb variant to the SPR chip using standard amine coupling. Next, Applicants will pass the purified CD6 at increasing concentrations over each channel to determine the kinetics of binding, and thus the binding constant. Applicants will use the same chip to measure the affinity of the meditope. In addition, Applicants will obtain structural information of the meditope-enabled anti-CD6 Fab and the CD6 in the presence of a high affinity meditope. This information will be used to further improve the design of the anti-CD6 Fab. To create an EGF-meditope construct, Applicants will create a panel of Fc-fusion proteins. First, Applicants will add the meditope to the C-terminus of EFG through a glycine-serine linker. The linker will contain 3, 6, and 9 residues. Next, Applicants will alter the order, fusing EGF to the C-terminus of the meditope peptide using the same peptide linker. Because EGF contains disulfide bonds, Applicants will use CHO cells for expression. Applicants will add two different secretion leader sequences to the N-terminus. Applicants will fuse these different constructs to an Fc using a linker containing a thrombin cleavage site. This will allow purification of the protein from the clarified media and then isolation of the desired EGF-meditope fusion proteins. Applicants will verify that the EGF is folded using SPR and active using cell studies (e.g., compare EGFR phosphorylation in A431 cells by Western blots using commercial EGF and the EGF-meditope fusions). Next, Applicants will use SPR to ensure the EGF-meditope fusions bind to the meditope-enabled CD6 mAbs. Based on this information, Applicants will rank order the best EGF-meditope variants, produce these, and form the complex with the meditope-enabled CD6 mAb, and isolate each by SEC.

Example 2. Anti-Cd6 Mab Chemically Conjugated to Egf or an Anti-Cd6 MAB-EGF FUSION PROTEINS The anti-CD6 mAb chemically conjugated to EGF or as an anti-CD6 mAb-EGF fusion protein brings together the specificity and immune modulatory properties of the anti-CD6 mAb and the functional properties of the EGF.

The anti-CD6 mAb and EGF conjugation (e.g., complex) will be administered intravenously and the half-life of the EGF will be measured, concentrating the EGF in the pancreas microenvironment. In turn, the pharmacokinetics of the bifunctional conjugate (e.g., complex) and the effector functions of the anti-CD6 mAb in the pancreatic insulitis will be measured.

Attempts to use the EGF administered intravenously as a single agent to induce islets protection would require high doses of EGF with high off target effect and severe toxicity.

Furthermore, considering the possibility to exploit triggering other functional receptors in the pancreas, Gastrin and the Glucagon-like peptide-1 (GLP-1) can be combined in the anti-CD6 mAb-EGF conjugate. This extends the possibility for combining the anti-CD6 meditope-enabled mAb with these cargo molecules. In embodiments, a protective and suppressive local microenvironment in treated patients with Type 1 Diabetes is provided.

Example 3. Methods for Connecting the Antibody and the Egf Domain

A bifunctional anti-CD6 monoclonal antibody (mAb) is developed with the Epidermal Growth Factor (EGF). To generate an anti-CD6 mAb fusion protein, the EGF is genetically fused to the carboxy- or amino-terminus of the full-length or to different fragments of the mAb. Different non-antibody proteins (e.g.: EGF, Gastrin or endogenous Glucagon-like peptide-1 (GLP-1) or a GLP-1 receptor agonist) can be fused in a single or in tandem format at the ends of the mAb or mAb fragments. The EGF can be fused to the amino-terminus of the heavy or light chain and the second non-antibody protein is fused to the carboxy-terminus of the heavy chain.

Figure 1:
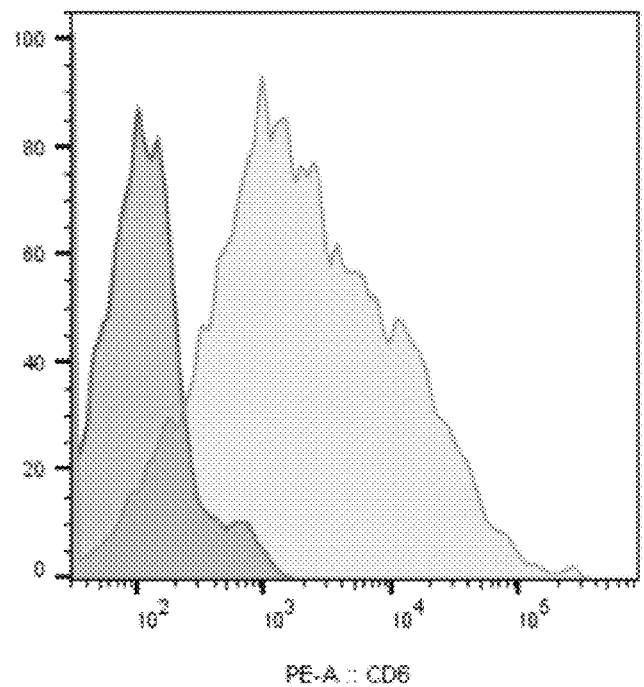
FIG. 1. PBMC recognition by meditope enabled anti-CD6 mAb by FACS.

FIG. 1 shows PBMC recognition by FACS (FIG. 1B). The anti-CD6 mAb is meditope-enabled with expression levels at ~70 mg/and the meditope-enabled mAb bound specifically to normal human peripheral blood mononuclear cells (PBMC) based on analytical flow cytometry measurements. Additional variants with higher and lower affinities are produced to maximize the therapeutic effect for this multifunctional molecule.

Cys-meditope-EGF: To link EGF to the anti-CD6 meditope-enabled mAb is used the mPACT technology. The human EGF is fused to a cysteine meditope through a glycine-serine linker. The linker will contain 6, 12, and 24 residues. In addition, it is created a cysteine meditope with tandem EGFs (e.g., meditope-linker-EGF-linker-EGF). As above, a point mutation is generated in EGF (initially using the monovalent EGF linker) to alter its affinity (also verified by SPR). These will be expressed in CHO cells as well. To create bivalent anti-CD6/EGF meditope-enabled monoclonal antibody molecules, the individual components are mixed under reducing conditions, allowing the complex to form and allowing the formation of the disulfide bond with the introduction of air. A nearly quantitative yield (e.g., 1 mole of Fab with 1 mole of cys-meditope) produces greater than 90% complex. It is ensured the conjugation does not affect either component by SPR and analytical flow cytometry.

Example 4. Effect of Egf on Human Islets

Figure 2A:
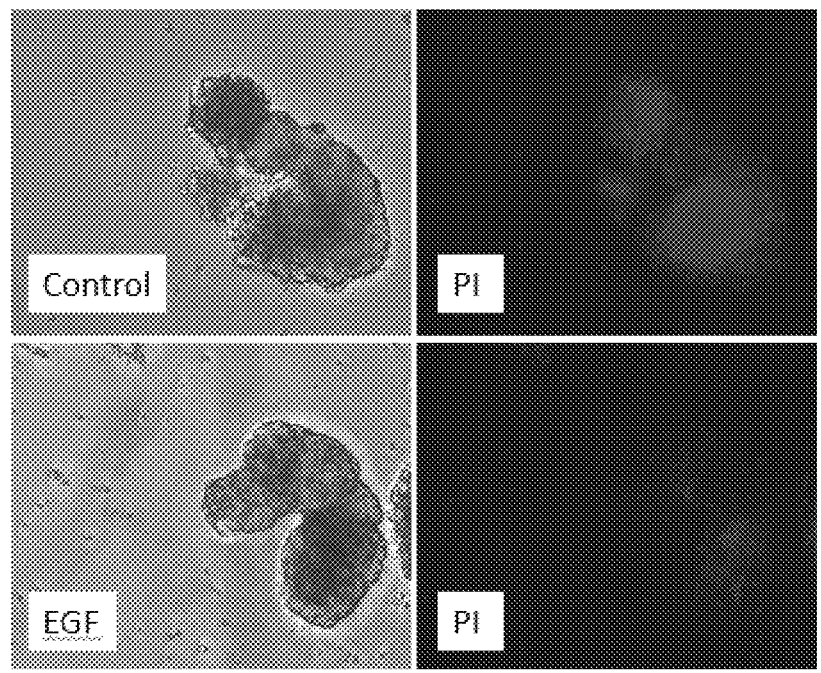
FIGS. 2A-2B. EGF effect on human islets: Freshly isolated human islets provided locally by the Clinical Islet Transplantation Program, a member of the Integrated Islet Distribution Program at City of Hope were analyzed. Human recombinant EGF was added 3 days after human pancreatic islet isolation and incubated for 24 h. Apoptosis (FIG. 2A) and Glucose-stimulated increment in oxygen consumption rate (FIG. 2B) were tested by Fluorescence Microscopy and using Seahorse Analyzers accordingly.
Figure 2B:
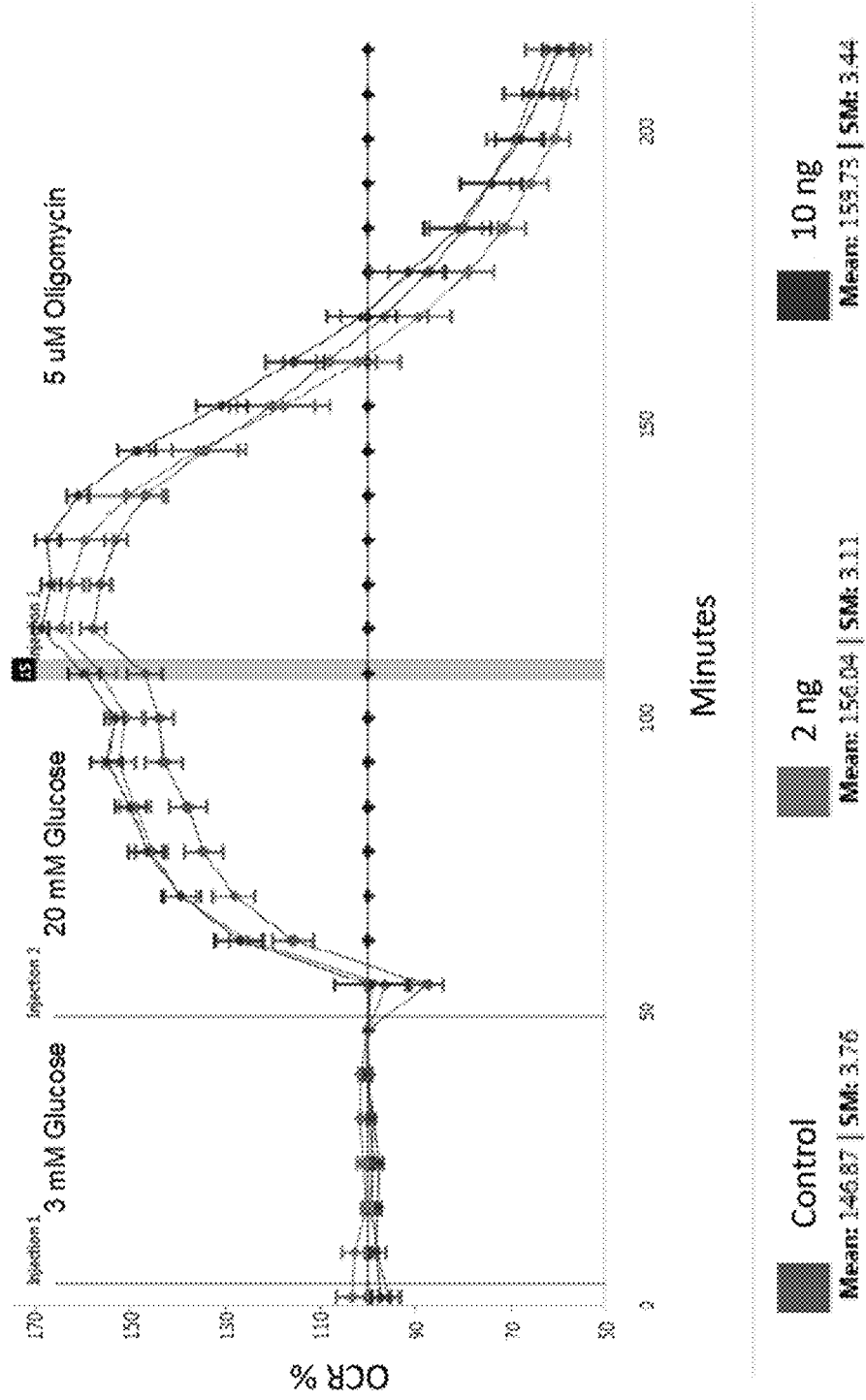

FIGS. 2A-2B show the effect of EGF on human islets: Freshly isolated human islets provided locally by the Clinical Islet Transplantation Program, a member of the Integrated Islet Distribution Program at City of Hope were analyzed. Human recombinant EGF was added 3 days after human pancreatic islet isolation and incubated for 24 h. Apoptosis (FIG. 2A) and Glucose-stimulated increment in oxygen consumption rate (FIG. 2B) were tested by Fluorescence Microscopy and using Seahorse Analyzers accordingly. The expression of an activated form of EGFR protects β-cells from destruction by cytokines or streptozotocin. These data strongly suggest that EGFR signaling can increase or preserve functional β-cell mass.

Figure 3:
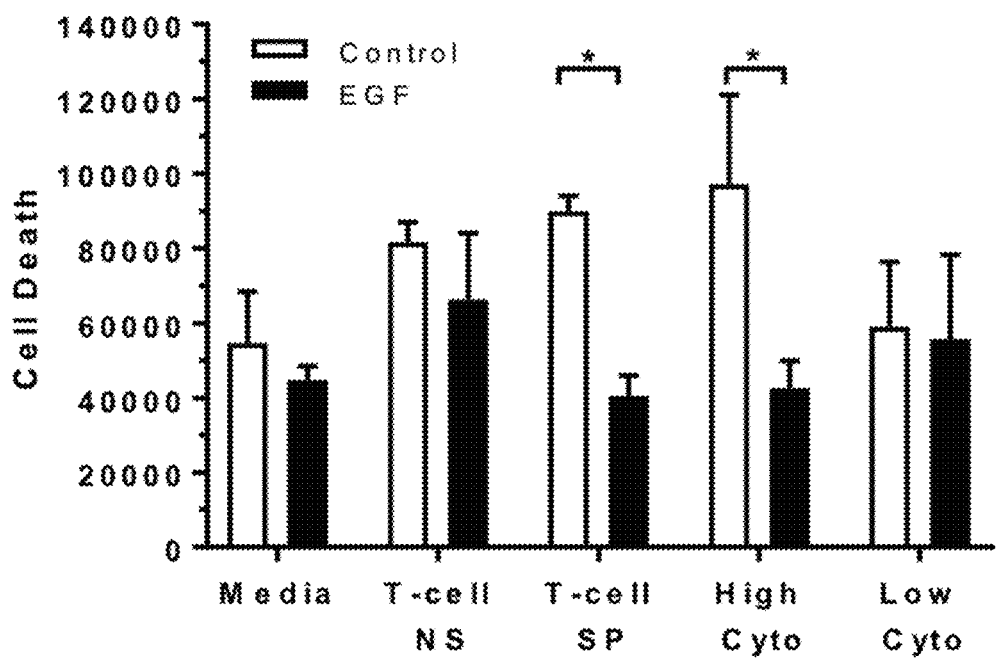
FIG. 3. EGF protects human islets cell death mediated by pro-inflammatory cytokine stress: Freshly isolated human pancreatic islets were kindly provided by the Clinical Islet Transplantation Program, a member of the Integrated Islet Distribution Program at the City of Hope. Islets Cytotoxicity Assay was analyzed using approximately 70 islets/well, isolated human pancreatic islets were cultured in Seahorse XF24 islet capture microplates at 37° C. and 5% CO2 in 200 µl of either in CMRL islet culture media with and without pro-inflammatory cytokines in triplicates, i.e.: Media (Control), high concentration (High Cyto) of human recombinant cytokines (1000 IU/ml IFN-γ, 1000 IU/ml TNF-α and 50 IU/ml IL-1β) or low concentration (Low Cyto) of human recombinant cytokines (100 IU/ml IFN-γ, 100 IU/ml TNF-α and 5 IU/ml IL-1β). Also, supernatant (100%) of a β-cell antigen (Glutamic Acid Decarboxylase, GAD) specific T-cell clone stimulated in vitro with a GAD peptide (T-cell SP) or a control peptide (T-cell NS). Islets were cultured with or without 10 ng/ml of human recombinant EGF in all culture conditions. Cell death was measured after 24 h by incubating 2 μg/ml of Propidium Iodide (PI) for 15 min at room temperature, and scanned in the Celigo Image Cytometer. Two-way ANOVA, *p<0.05, T-cell SP p=0.0231, High Cyto p=0.0137, n=3.

FIG. 3 demonstrates that EGF protects human islets cell death mediated by pro-inflammatory cytokines stress. Freshly isolated human pancreatic islets were kindly provided by the Clinical Islet Distribution Program, a member of the Integrated Islet Distribution Program at the City of Hope. Islets Cytotoxicity Assay was analyzed using approximately 70 islets/well isolated human pancreatic islets cultured in Seahorse XF24 islet capture microplates at 37° C. and 5% $CO_2$ in 200 μl of either in CMRL islet culture media with and without pro-inflammatory cytokines in triplicates, i.e.: Media (Control), high concentration (High Cyto) of human recombinant cytokines (1000 IU/ml IFN-γ, 1000 IU/ml TNF-α and 50 IU/ml IL-1ß) or low concentration (Low Cyto) of human recombinant cytokines (100 IU/ml IFN-γ, 100 IU/ml TNF-α and 5 IU/ml IL-1β). Also, supernatant (100%) of a β-cell antigen (Glutamic Acid Decarboxylase, GAD) specific T-cell clone stimulated in vitro with a GAD peptide (T-cell SP) or a control peptide (T-cell NS). Islets were cultured with or without 10 ng/ml of human recombinant EGF in all culture conditions. Cell death was measured after 24 h by incubating 2 μg/ml of Propidium Iodide (PI) for 15 min at room temperature, and scanned in the Celigo Image Cytometer (FIG. 3). Two-way ANOVA, *$p<0.05$, T-cell SP $p=0.0231$, High Cyto $p=0.0137$, $n=3$. This data supports an effect of EGF protecting human islets from destruction during the stress induced by pro-inflammatory cytokines secreted by autoreactive lymphocytes in Type 1 Diabetes.

FIGS. 4A-4D show EGFR, CD166/ALCAM and CD318/CDCP1 co-expression in human islets. We consistently obtained additional evidence for the expression of EGFR and the CD6 ligand CD166/ALCAM in human pancreatic tissues from non-diabetic and hyperglycemic donors, evaluated by immunohistochemistry using standard procedures and detection systems. Detection of both the extracellular and intracellular domains was obtained. Inter-individual variability was shown, although it does not seem to be related to the donor's medical history.

The recent finding on a new CD6 ligand (CD318/CDCP1) prompted us to evaluate also its expression in human pancreatic tissues. Interestingly it was identified in human pancreatic islets along with the CD166/ALCAM, a CD6 ligand and, the EGFR.

Figure 4A:
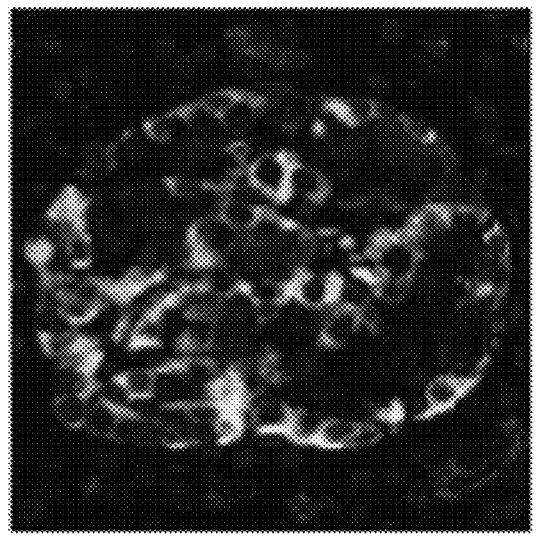
FIGS. 4A-4D. EGFR, CD166/ALCAM and CD318/CDCP1 co-expression in human islets. Representative images of paraffin-embedded pancreatic tissue sections from a diabetic donor (FIGS. 4A-4B) stained for EGFR-ECD and EGFR-ICD (FIG. 4A), CD166/ALCAM-ECD and CD166/ALCAM-ICD (FIG. 4B). Double staining of EGFR and CD166/ALCAM (FIG. 4C) and CD318/CDCP1 and CD166/ALCAM (FIG. 4D) in formalin-fixed, paraffin-embedded pancreatic tissue from a normal donor. Zoomed insets in FIGS. 4C-4D. Original magnification is 40×, taken on a Zeiss LSM 700 Confocal microscope. ECD (extracellular domain) and ICD (intracellular domain).
Figure 4B:
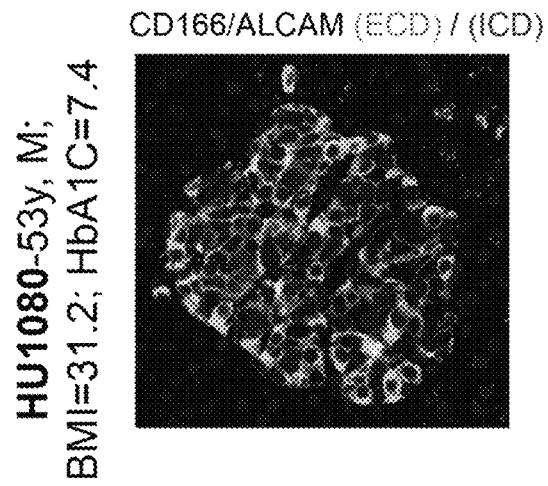
Figure 4C:
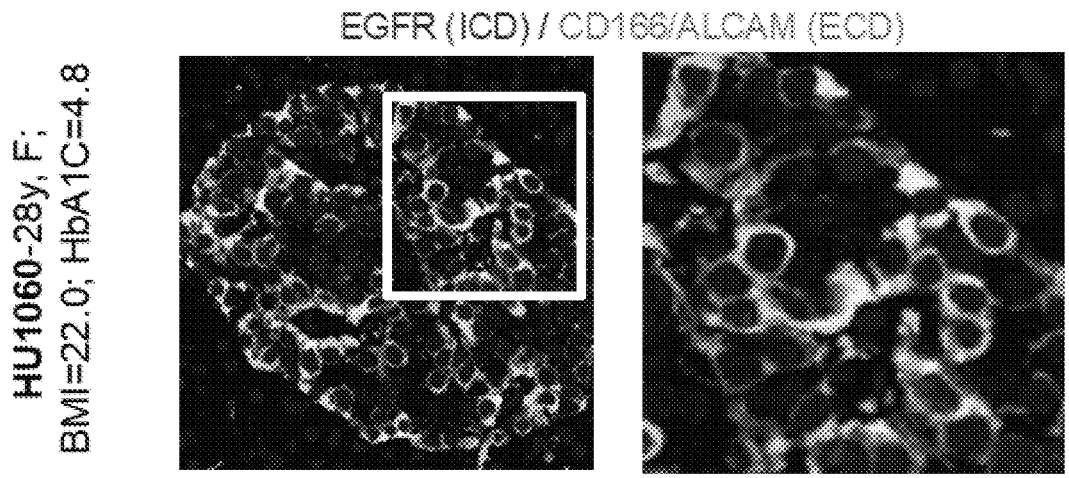
Figure 4D:
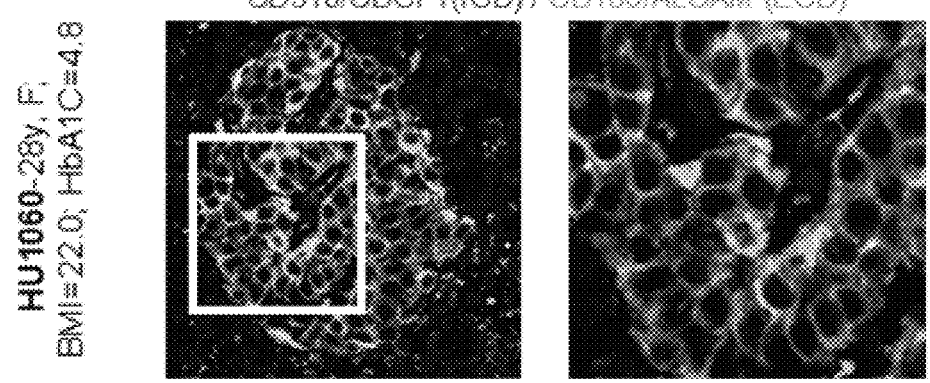

FIGS. 4A-4D show representative images of paraffin-embedded pancreatic tissue sections from a diabetic donor (FIGS. 4A-4B) stained for EGFR-ECD and EGFR-ICD (FIG. 4A), CD166/ALCAM-ECD and CD166/ALCAM-ICD (FIG. 4B). Double staining of EGFR and CD166/ALCAM (FIG. 4C) and CD318/CDCP1 and CD166/ALCAM (FIG. 4D) in formalin-fixed, paraffin-embedded pancreatic tissue from a normal donor. Zoomed inset. Original magnification is 40×, taken on a Zeiss LSM 700 Confocal microscope. ECD (extracellular domain) and ICD (intracellular domain). These results indicate that CD6/ALCAM and now CD318, drive the adhesion of CD6+ autoreactive lymphocytes to the islets, contributing to the formation of the pancreatic insulitis. The proximity of the EGFR expression on these cells favors the opportunity for therapeutic targeting of the human islet environment with anti-CD6/EGF meditope-enabled mAb.

Figure 5:
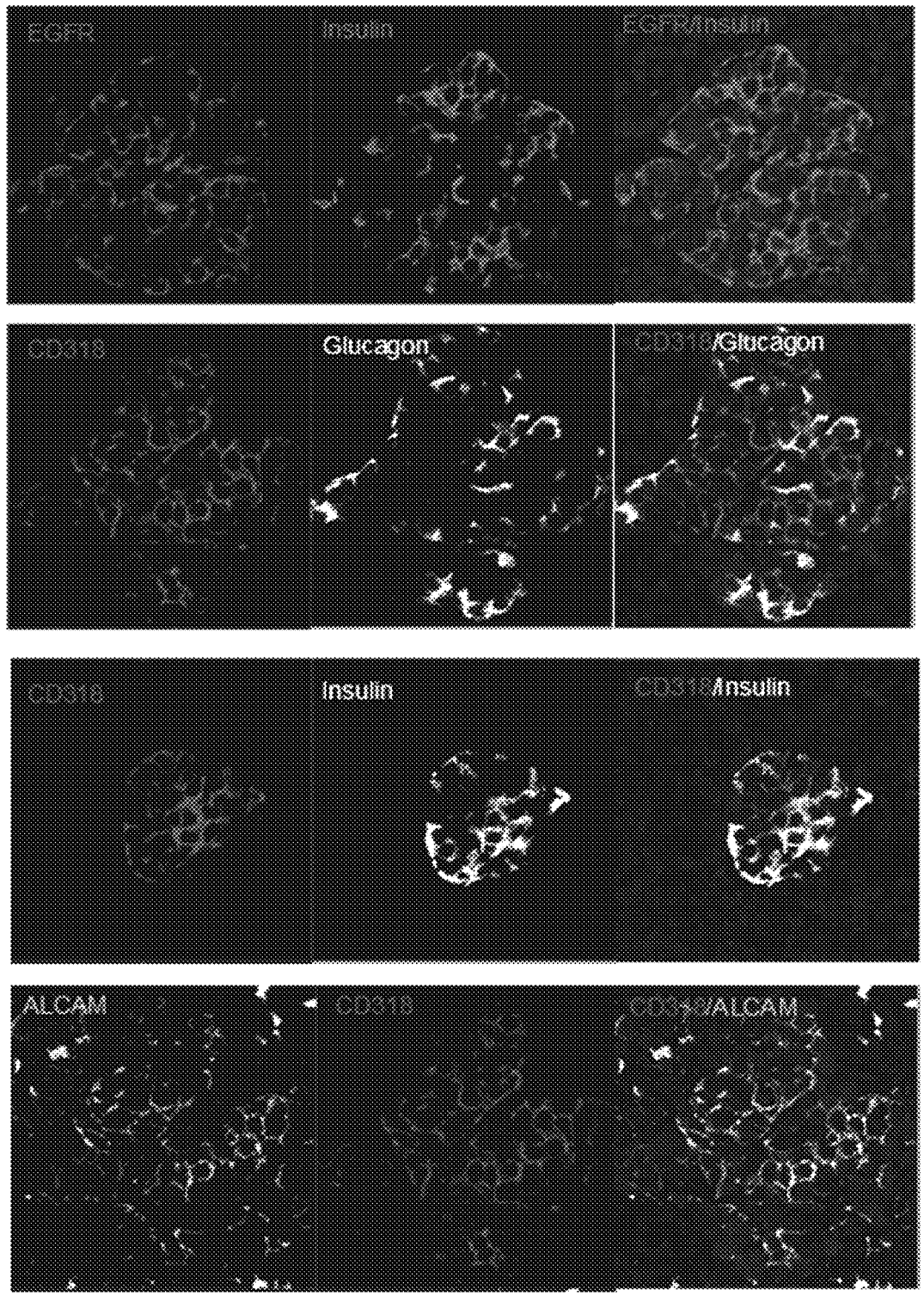
FIG. 5. EGFR, CD166/ALCAM and CD318/CDCP1 co-expression in T1D human islets. Representative images of paraffin-embedded pancreatic tissue sections from Type 1 diabetic donor stained for EGFR, ALCAM, CD318, Insulin and Glucagon. Original magnification 40× taken on Zeiss LSM 700 Confocal microscope. HU1004-44y, M; BMI-20; HbA1C=12.1

In FIG. 5 are shown representative images of paraffin-embedded pancreatic tissue sections from Type 1 diabetic donor stained for EGFR, ALCAM, CD318, Insulin and Glucagon. EGFR, CD166/ALCAM and CD318/CDCP1 are co-expressed in T1D human islets.

Figure 6:
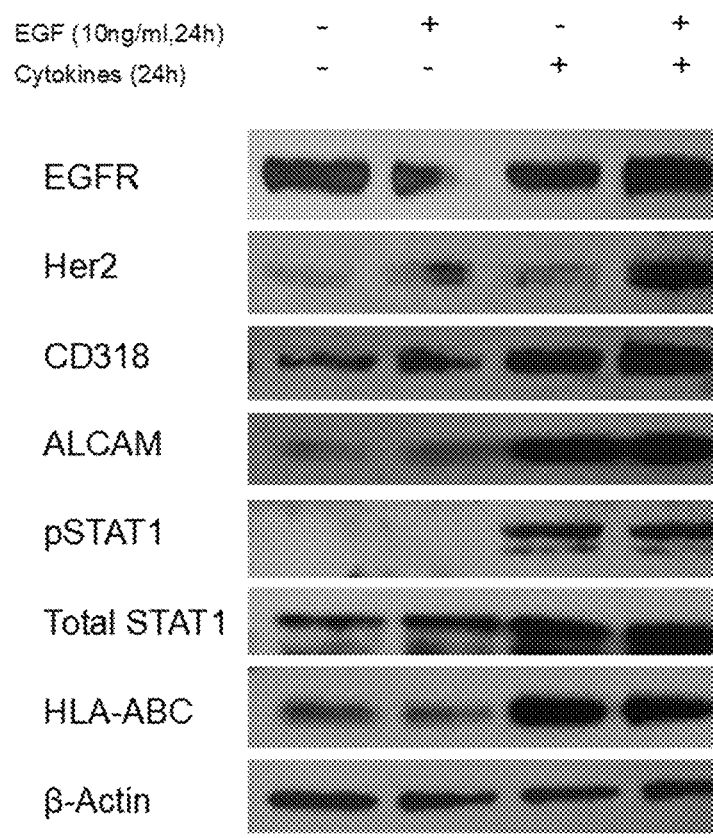
FIG. 6. EGF treatment protects human islets from pro-inflammatory cytokine stress. Pro-inflammatory cytokines enhance the expression of the CD6 ligands (CD318/CDCP1 and CD166/ALCAM) in human pancreatic tissues. EGF treatment reduces the HLA class I in human pancreatic tissues. Western blot of protein extracts from human islets (HU1114) treated with or without 10 ng/ml EGF and 50 units/mL IL-1β, 1,000 units/mL TNF-α, and 1,000 units/mL IFN-γ for 24 h.
Figure 7:
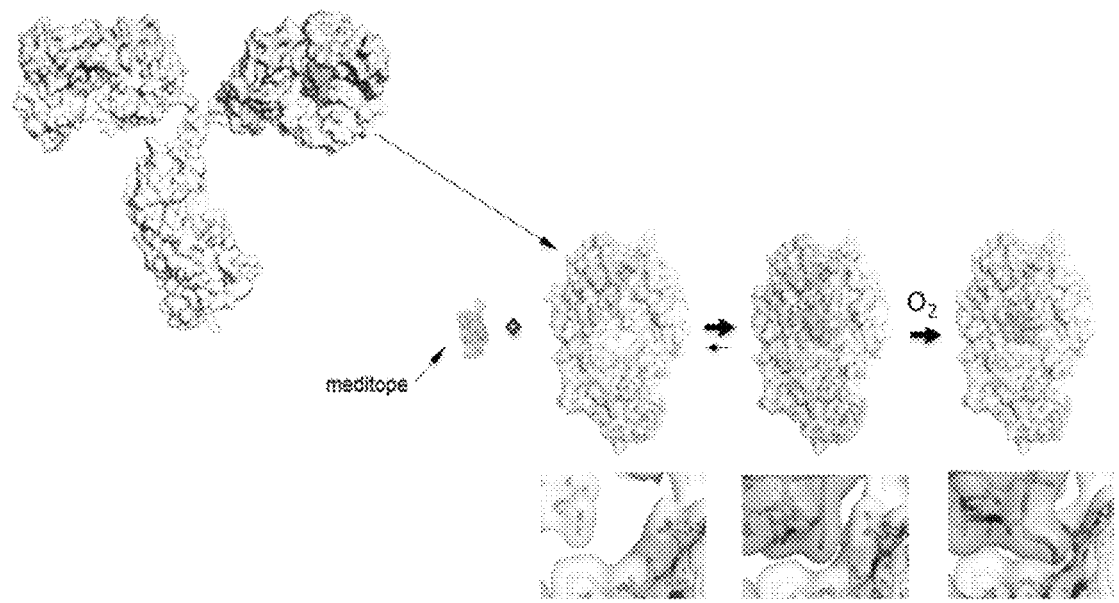
FIG. 7. Template-Catalyzed CD6 Functionalization. Meditope technology used to functionalize CD6. Shown is a meditope-enabled antibody (e.g., meditope enabled anti-CD6 antibody) and a meditope. Both the meditope-enabled antibody and the meditope have amino acid modifications allowing covalent binding of the meditope to the meditope-enabled antibody. In silico grafted, meditope-enabled anti-CD6. Produced ~100 mg/L. Using this strategy, functionalized meditopes (e.g., meditopes conjugated to proteins, peptides, or fragments) can be covalently attached to meditope-enabled antibodies. EGF, gastrin, and GLP-1 peptide or fragments may be attached to the meditope. Can use an overnight inducible system, including for example, LB. Functionalized meditopes may be mixed and matched to the meditope-enabled anti-CD6 antibody.
Figure 8A:
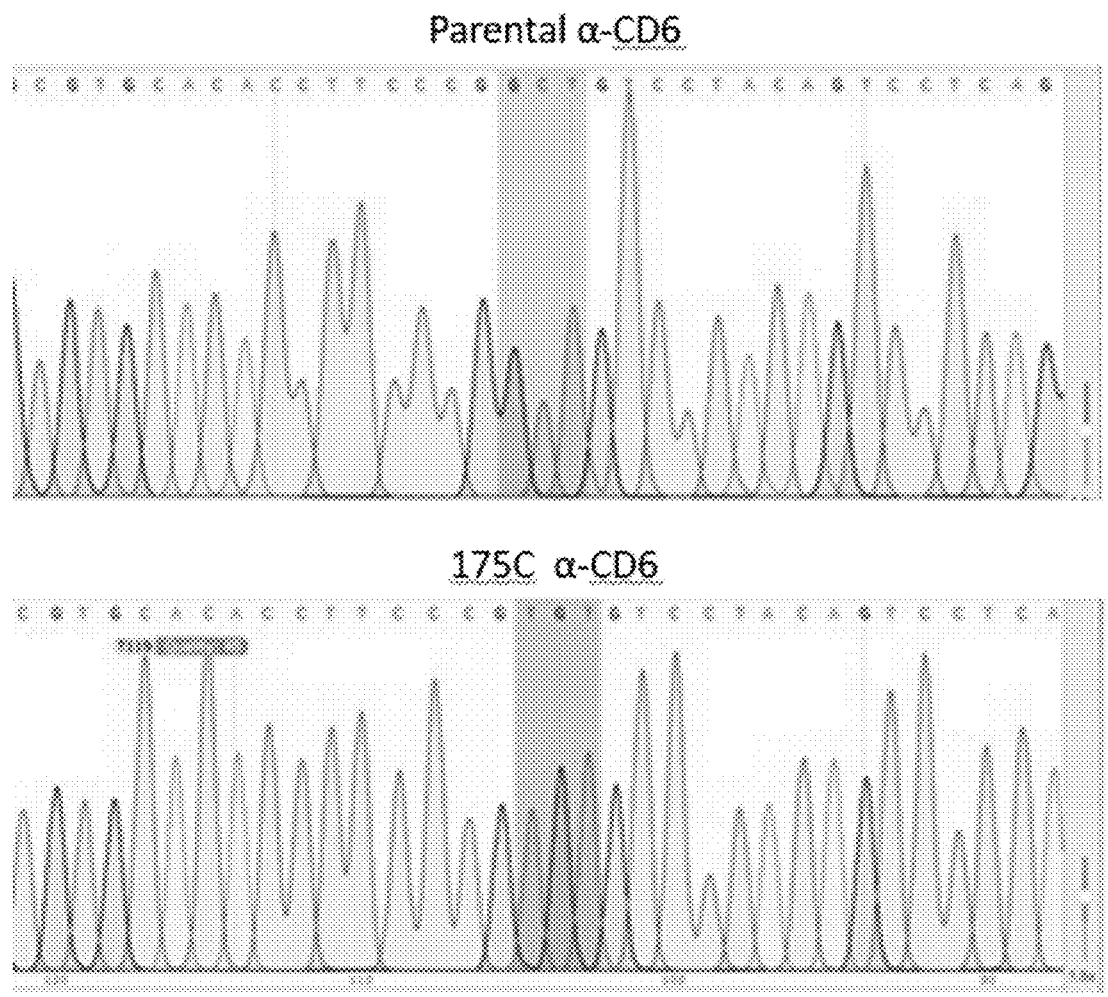
FIGS. 8A-8B. Template-Catalyzed CD6 Functionalization.
Figure 8B:
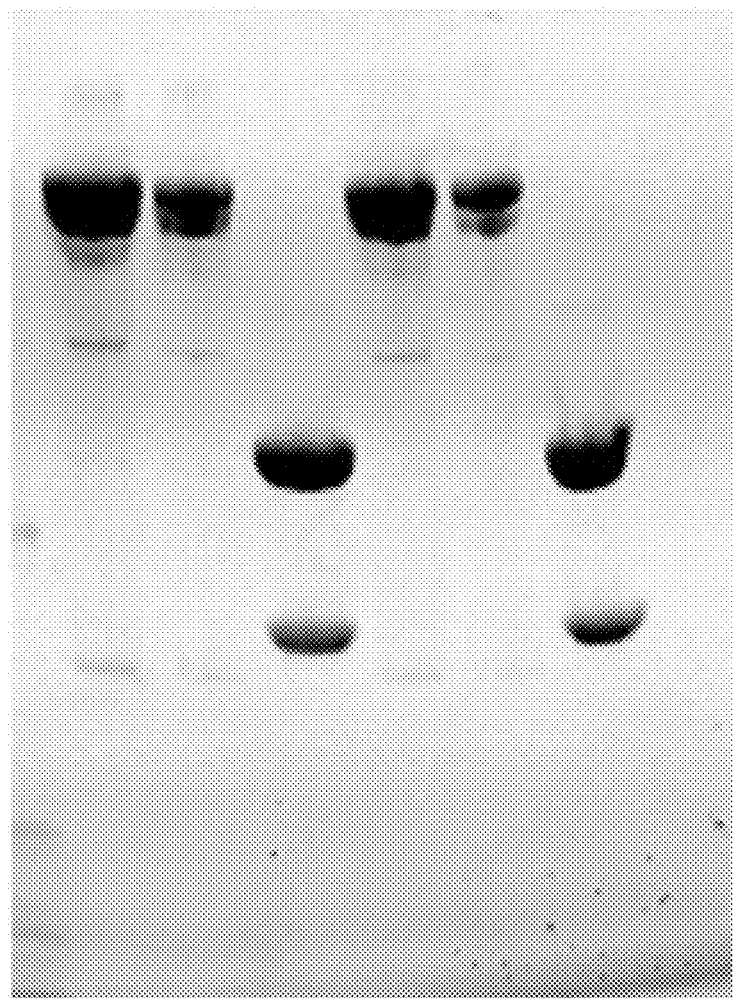

Pro-inflammatory cytokines enhance the expression of the CD6 ligands (CD318/CDCP1 and CD166/ALCAM) in human pancreatic tissues. EGF treatment reduces the HLA class I in in human pancreatic tissues. FIG. 6 shows Western blot of protein extracts from human islets (HU1114) treated with or without 10 ng/ml EGF and 50 units/mL IL-1β, 1,000 units/mL TNF-α, and 1,000 units/mL IFN-γ for 24h.

Example 5. Anti-Cd6 Mab Conjugated to Egf for Treatment in Patients WITH TYPE I DIABETES MELLITUS Type 1 Diabetes patients are treated with the anti-CD6 mAb-EGF conjugate (e.g., anti-CD6 antibody-growth factor complex). Treatment is administered at different doses ranging from 0.05 to 6.4 mg/kg of body weight. Treatment is administered weekly, every 2, 4, 8 and 12 weeks. It is inoculated by intravenous route in a sterile solution.

The efficacy outcomes include the Area under the curve (AUC) of stimulated C-peptide production, Peak of stimulated C-peptide production. Non-stimulated C-peptide. Glycosylated hemoglobin, HbAlc (%). Doses of basal, prandial and total daily insulin (IU, IU/kg). Fasting and postprandial glycemia based on laboratory blood chemistry. Glucose by self-monitoring (glucometer). The anti-CD6 mAb-EGF conjugate is safe and induces a long-term efficacy extended beyond the treatment period.

Example 6. Cd6 Antibody Targeting

Applicants will rationally design CD6 for optimal therapeutic efficacy. Applicants will use PDB to define the ecto domain of CD6. Will make use of codon optimized gene. Applicants will express in CHO cells, purify, and measure affinity of CD6. Applicants will co-crystallize with Fab. Applicants will generate and optimize zippering CD6. The therapeutic agent may be an anti-CD6 antibody-growth factor complex provided herein including embodiments thereof. The therapeutic agent may be an antibody covalently bound through a disulfide linkage to a meditope, wherein the meditope is covalently bound (conjugated) to a growth factor (e.g., EGF). In embodiments, the meditope is covalently bound (conjugated) to more than one growth factor protein or fragment thereof (e.g., more than one EGF protein or fragment thereof). Thus, the protein compound may include a plurality of (more than one) growth factor proteins and each of the plurality of growth factor protein may be independently the same or different. For example, protein compound may include 2 or 3 copies of a EGF protein or fragments thereof or the protein compound may include one copy of a EGF protein and one copy of a gastrin protein or fragment thereof.

Example 7. Therapeutic Targeting of the Human Islet Environment WITH ANTI-CD6/EGF CONJUGATED ANTIBODY The ability to locally activate potent molecules at the site of disease is expected to mitigate adverse side effects due to on-target, off-tissue toxicities. Applicants used the switchblade technology to create an anti-CD6/EGF biologic, which will be conditionally activated at the diabetic lesion. Applicants show in vitro that MMP9 cleavage of the anti-CD6-EGF frees EGF to bind to EGFR. Finally, Applicants show that the compound is stable for 17 days in PBS at 37° C.

A bionic antibody conjugate (e.g., the protein of SEQ ID NO:32) including the antigen-binding portion of a CD6 monoclonal antibody and the EGF protein was constructed to locally and conditionally activate EGFR while inhibiting immune cells for the treatment of autoimmune diseases, for example Type I diabetes. An exemplary complex of the invention provided herein and referred to as a bionic anti-CD6/EGF protein is shown in FIG. 24. The exemplary complex includes: an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:35), wherein the second linker includes a matrix metalloproteinase-2/9 (MMP2/9) cleavage site of (SEQ ID NO:66), and wherein a third linker attaches a IgG1-Fc (SEQ ID NO:37) domain to the C-terminus of the anti-CD6 heavy chain (SEQ ID NO:36). Sequences corresponding to each domain of the exemplary complex as shown in FIG. 24 are provided in Table 1.

TABLE 1

| Domain | Sequence | SEQ ID NO: |
|---|---|---|
| Anti-CD6 LC | DIQMTQSPILLSASVGDRVTITCKASRDIRSYLTWYQQRTNGSPRTLIYYATSLADGVPSRFSGSGSGQDYSLTISS LESDDIADYYCLQHGESPFTFGSGTKLEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVTKSFNRGEC | 33 |
| Linker | ASASAAASSASSAASS | 34 |
| EGF | NSDSECPLSHDGYCLHDGVCMYIEALDKYACNCVVGYIGERCQYRDLKWWELR | 4 |
| Linker with MMPS/9 Substrate Sequence | GSGVLPASLYSGS1 | 35 |
| Anti-CD6 HC | EVQLVESGGGLVKPGGSLKLSCAASGFKFSRYAMSWVRQAPGKRLEWVATISSGGSYIYYPDSVKGRFTISRDNVKN TLYLQMSSLRSEDTAIYYCARRDYDLDYFDSWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNHKPSNTKVDKKVEPKSC | 36 |
| IgG1-Fc | DKTHTCPPCPAPELLGGPSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVMHEALHNHYTQKSLSLSPGK | 37 |

The Anti-CD6 reduces autoimmune effects by targeting CD6, a key molecule in the development of autoimmunity, while EGF protects human islet cells from pro-inflammatory cytokine stress. Enzymatic cleavage of the conjugate by MMP2/9 increases EGF exposure at the site of inflammation.

Figure 13A:
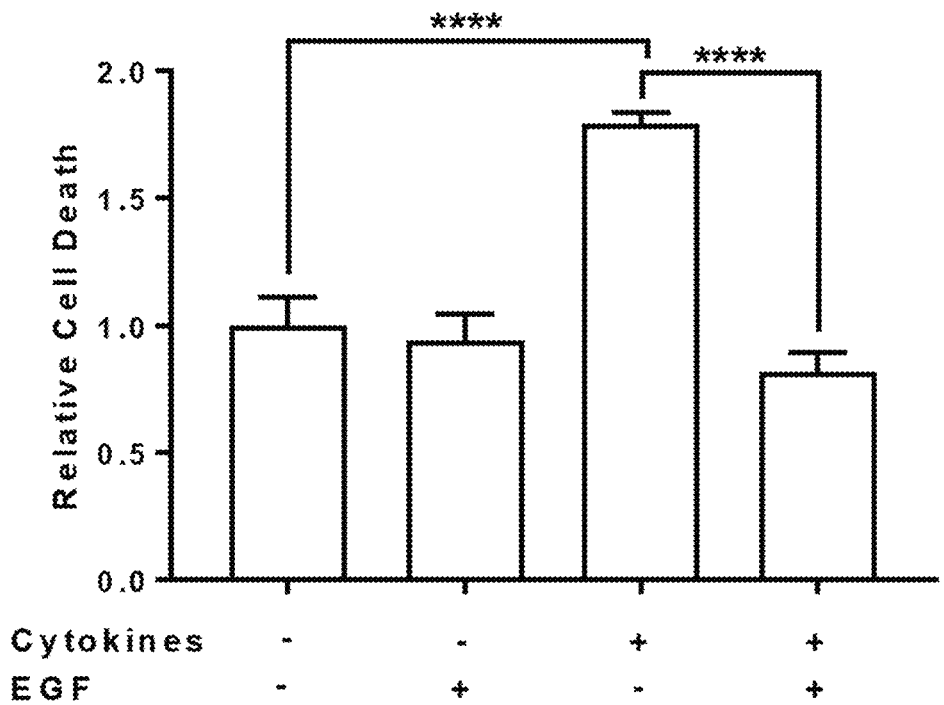
FIG. 13A-13B. EGF protects human islets from cell death mediated by pro-inflammatory cytokine stress (FIG. 13A). Isolated human islets were cultured in media in the presence of either cytokines or EGF, both cytokines and EGF, or without cytokines or EGF (FIG. 13B).
Figure 13B:
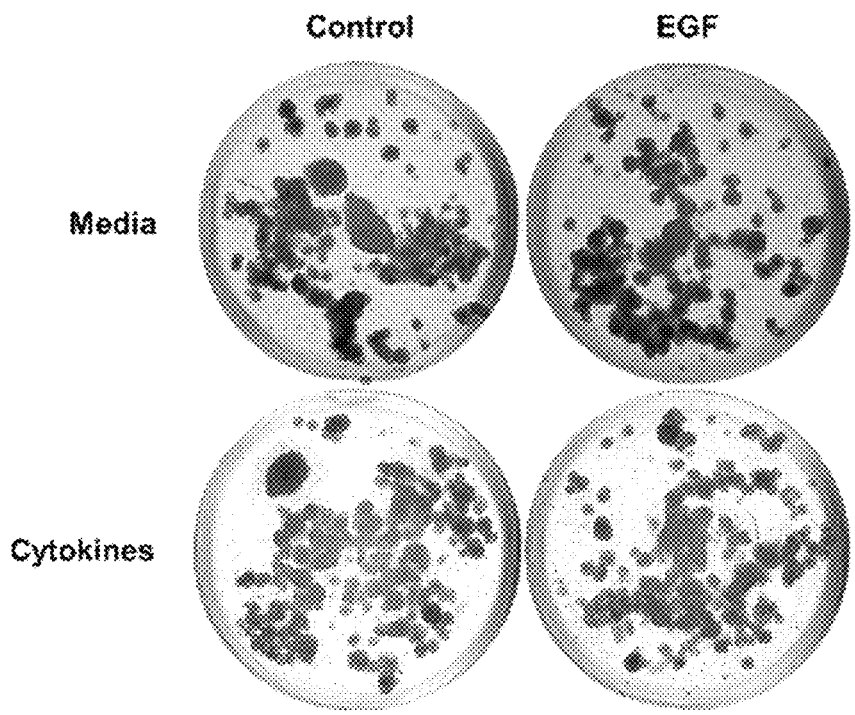
Figure 14A:
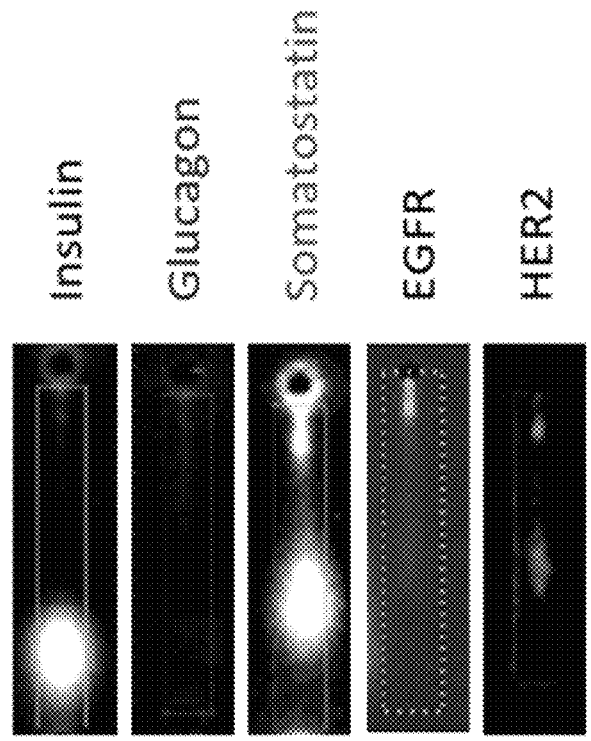
FIG. 14A-14B. EGFR and HER2 expression in dissociated human islets from a non-diabetic donor. Single-cell western blot analysis (FIG. 14A) using MILO technology show the percentage of EGFR and HER2 positive cells among glucagon, somatotatin, and insulin expressing cells, respectively (FIG. 14B).
Figure 14B:
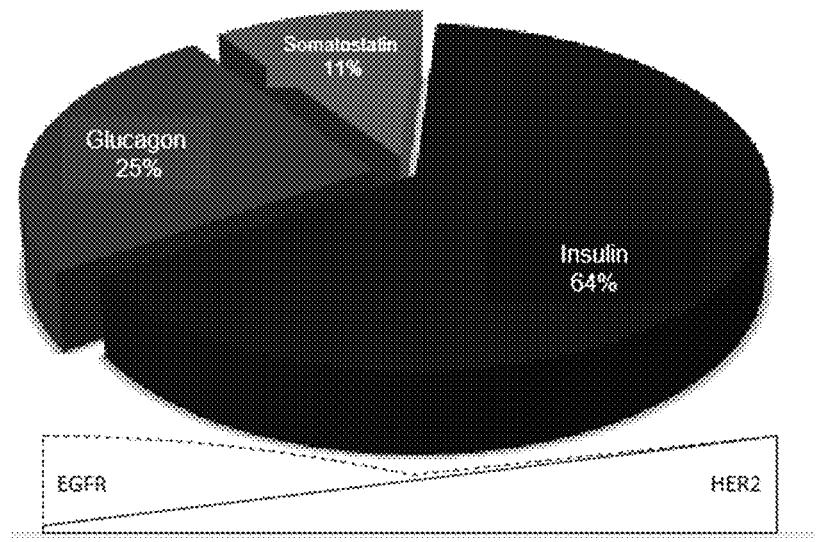
Figure 15A:
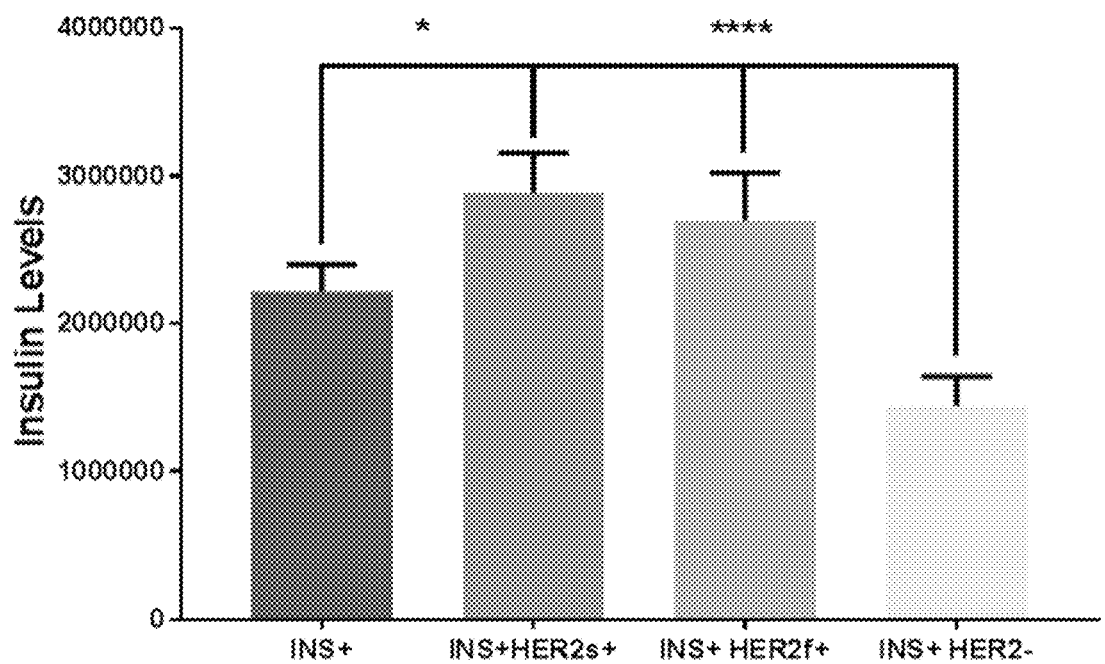
FIG. 15A-15C. Single cell analysis of dissociated islets from a non-diabetic human donor. HER2 expressed in INS producing cells. All double hormonal cells (INS+SST) are HER2+. Single SST+ cells do not express HER2. INS+HER2+ cells express 2× insultin over INS+HER2-cells. No such effect is observed with SST. Fluorescence intensity plots created from chip images allowed to identify target peaks and calculate the area under the curve, to quantify the abundance of each protein of interest (FIG. 15A-15B).
Figure 15B:
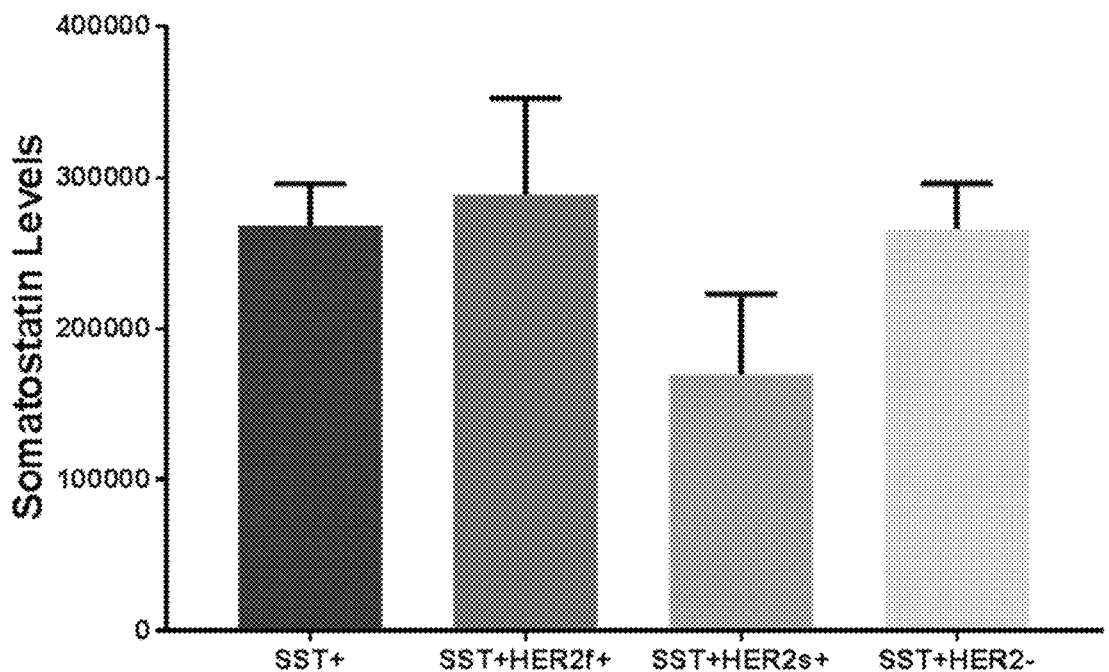
Figures 15C, 16A:
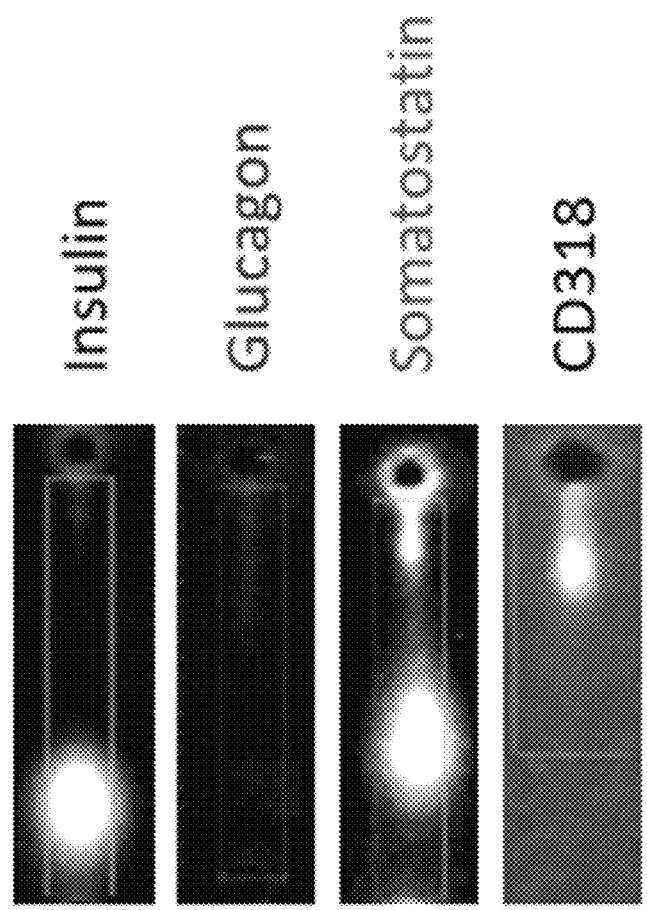
FIG. 16A-16B. Evaluation of CD6 ligands CD166/ALCAM and CD318/CDP1 in human islets from a healthy donor. Single-cell western analysis (FIG. 16A) using MILO technology show percentage of CD166 and CD318 positive cells among glucagon, somatotatin, and insulin expressing cells (FIG. 16B).
Figure 16B:
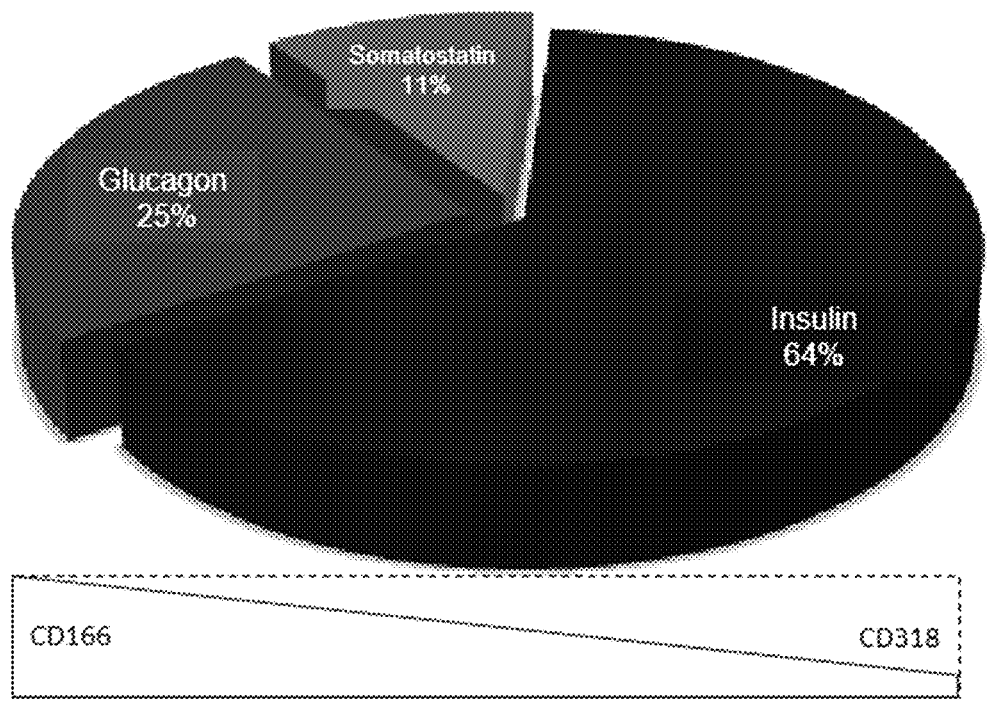
Figure 17A:
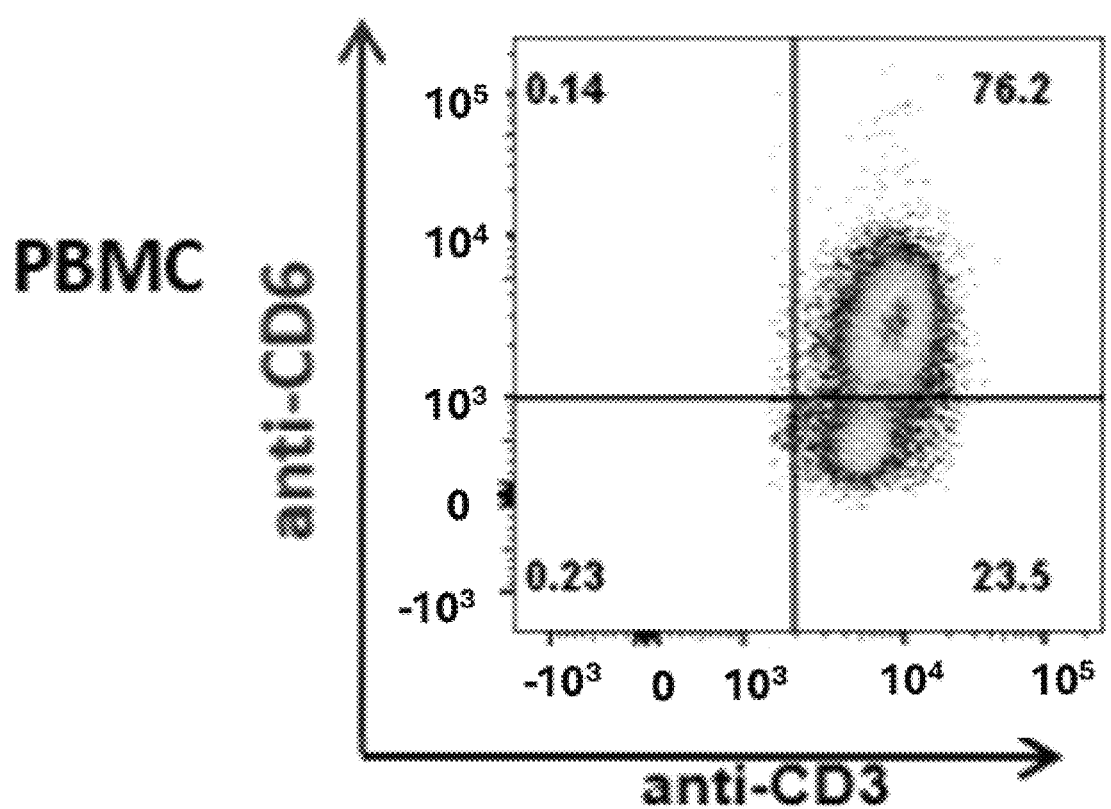
FIG. 17A-17F. Flow cytometry evaluation of therapeutic targeting of the human islet environment with an anti-CD6 antibody-growth factor complex provided herein.
Figure 17B:
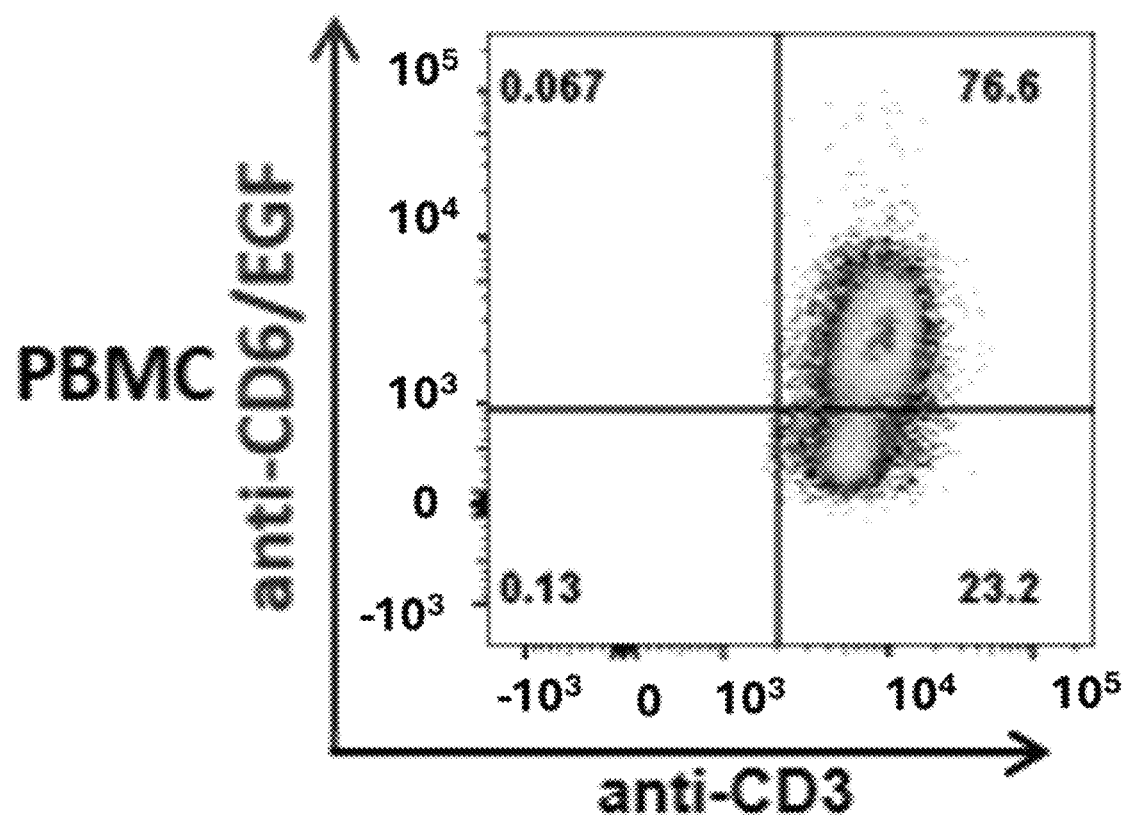
Figure 17C:
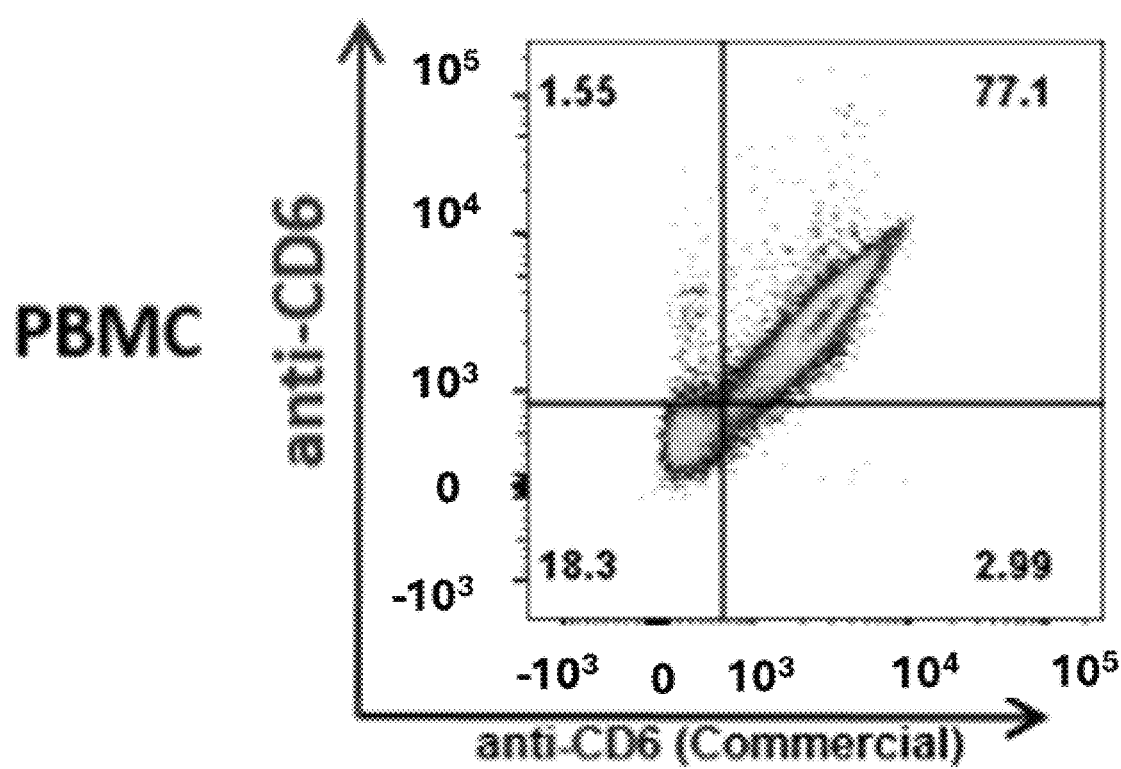
Figure 17D:
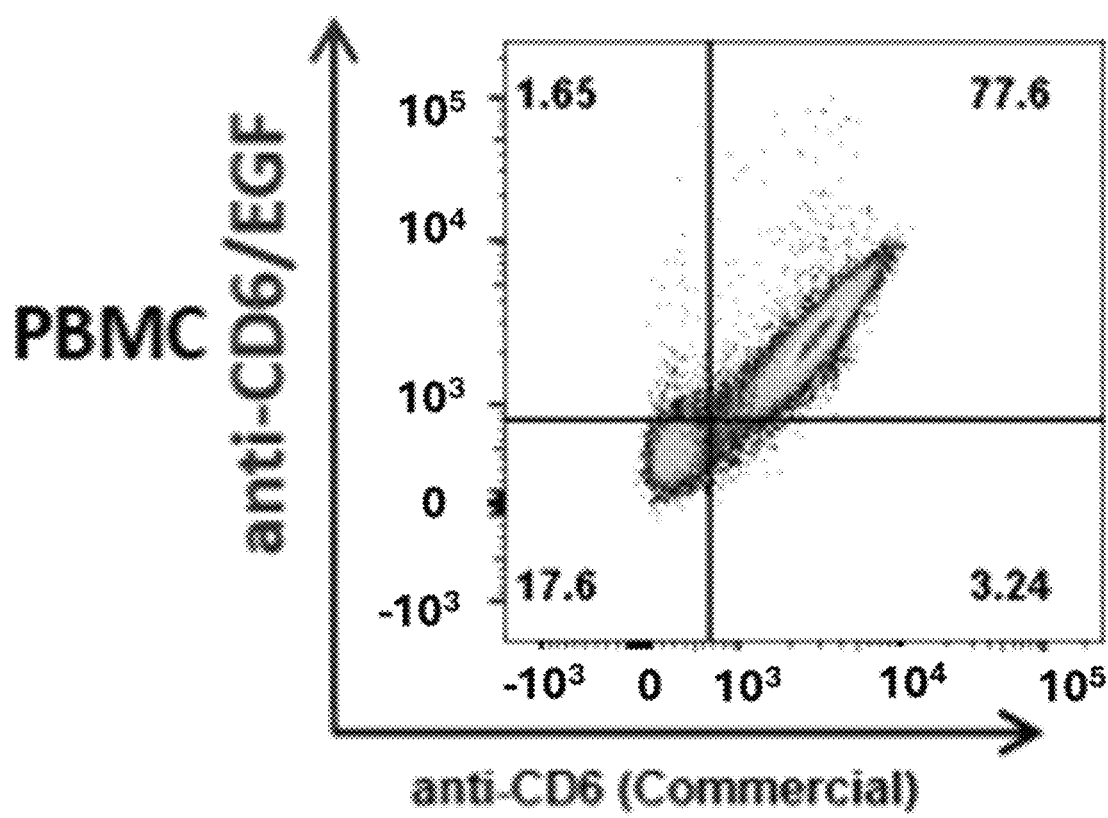
Figure 17E:
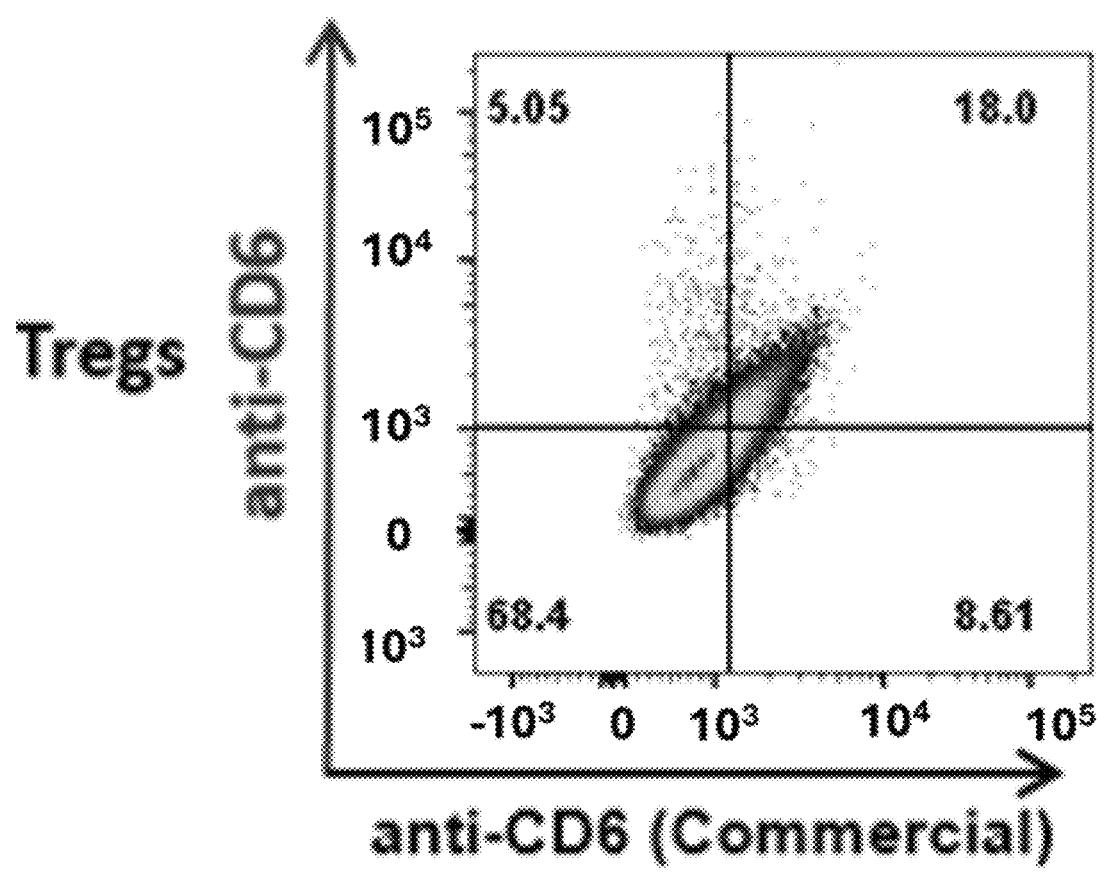
Figure 17F:
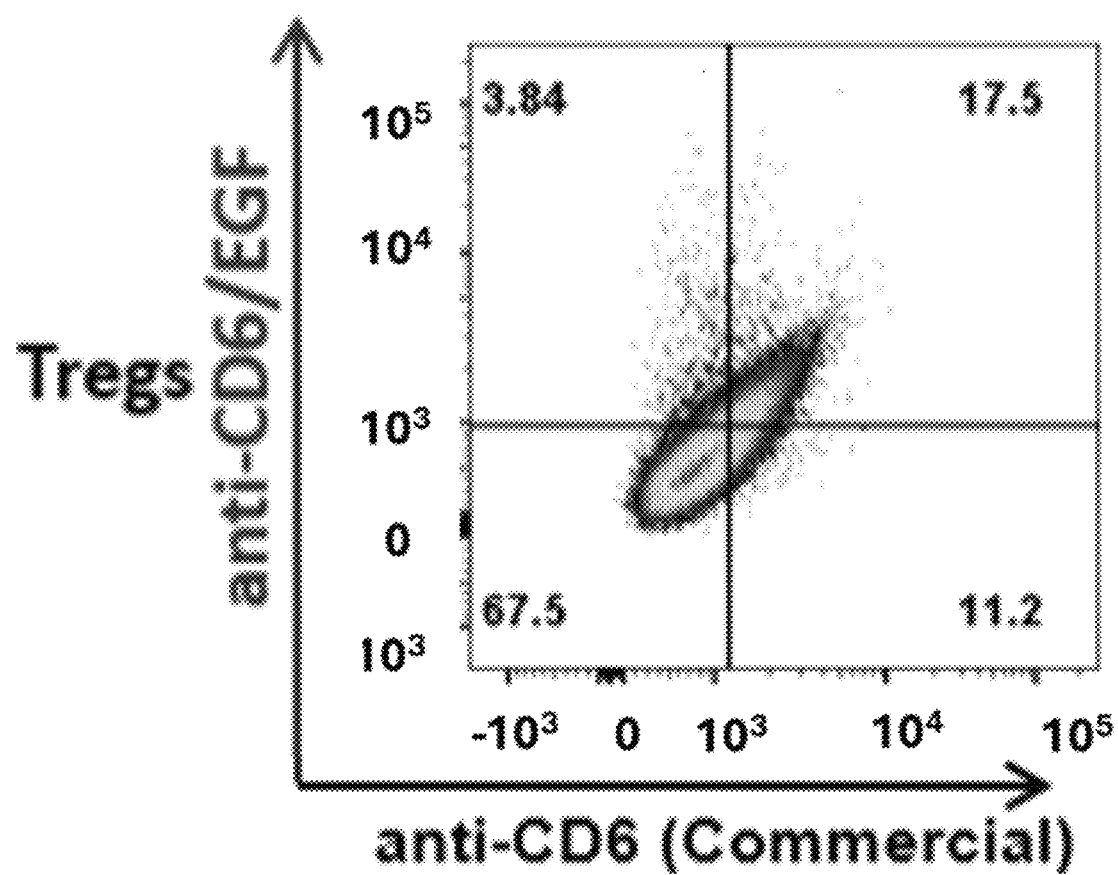
Figure 18:
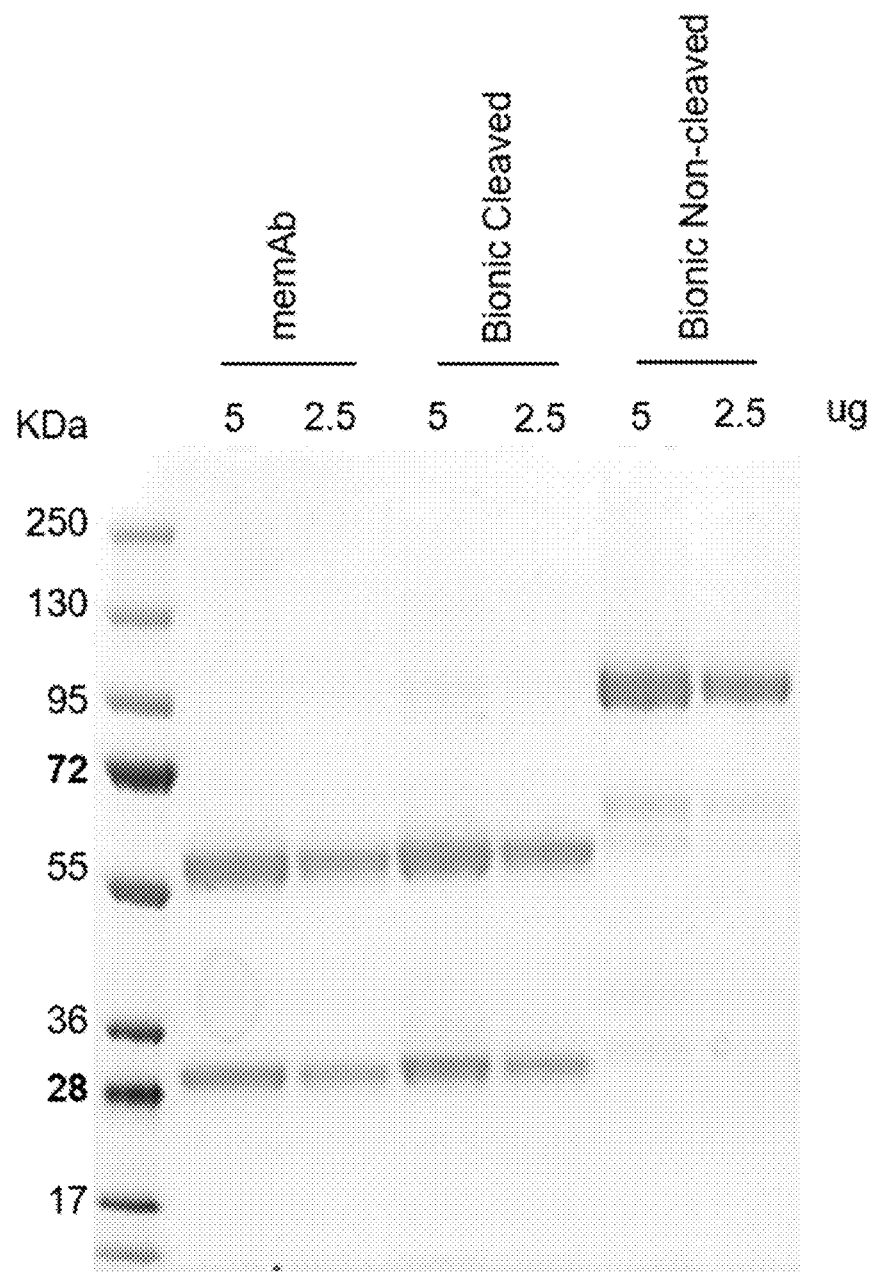
FIG. 18. Coomasie stained SDS-PAGE gel of anti-CD6 antibody-growth factor complexes provided herein, memAb refers to meditope-enabled anti-CD6 antibody. Cleaved and uncleaved bionic anti-CD6/EGF complexes are shown. From left to right: molecular weight marker in kilodaltons (KDa); 5 and 2.5 μg of anti-human CD6 meditope-enabled antibody (memAb); 5 and 2.5 μg of the cleaved bionic anti-CD6/EGF antibody conjugate (Bionic Cleaved); 5 and 2.5 μg of non-cleaved bionic anti-CD6/EGF antibody conjugate (Bionic Non-Cleaved). Protein concentrations were determined by optical density at 280 nm.
Figure 19:
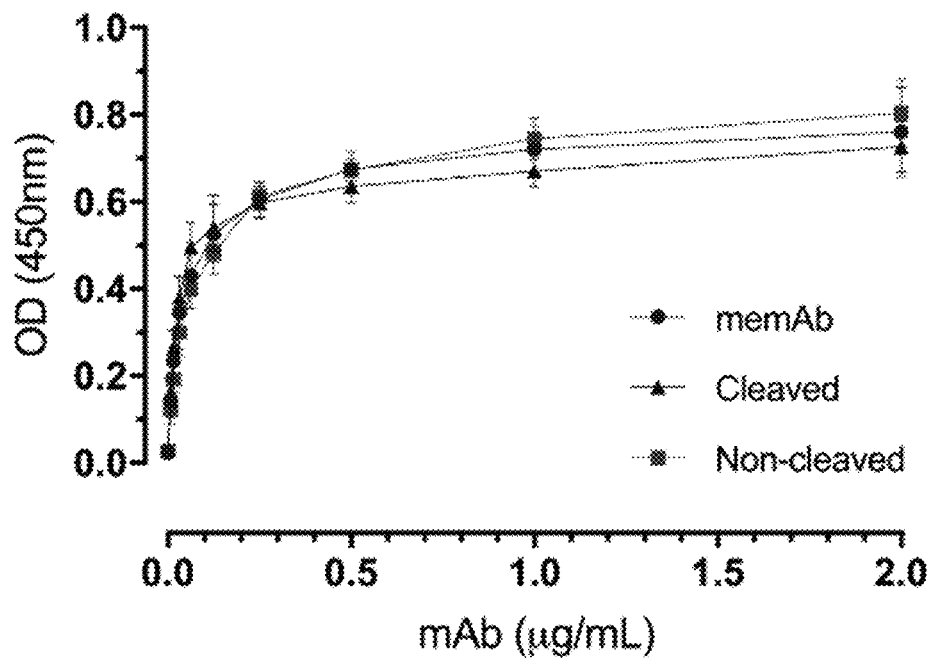
FIG. 19. Human CD6 meditope enabled antibody and bionic anti-CD6/EGF antibody conjugate provided herein binding determined with ELISA binding curves as shown. Concentrations of the anti-CD6 meditope-enabled antibody (memAb), cleaved bionic anti-CD6/EGF antibody conjugate (Cleaved), and non-cleaved bionic anti-CD6/EGF antibody conjugate were determined by the optical density at 280 nm.
Figure 20A:
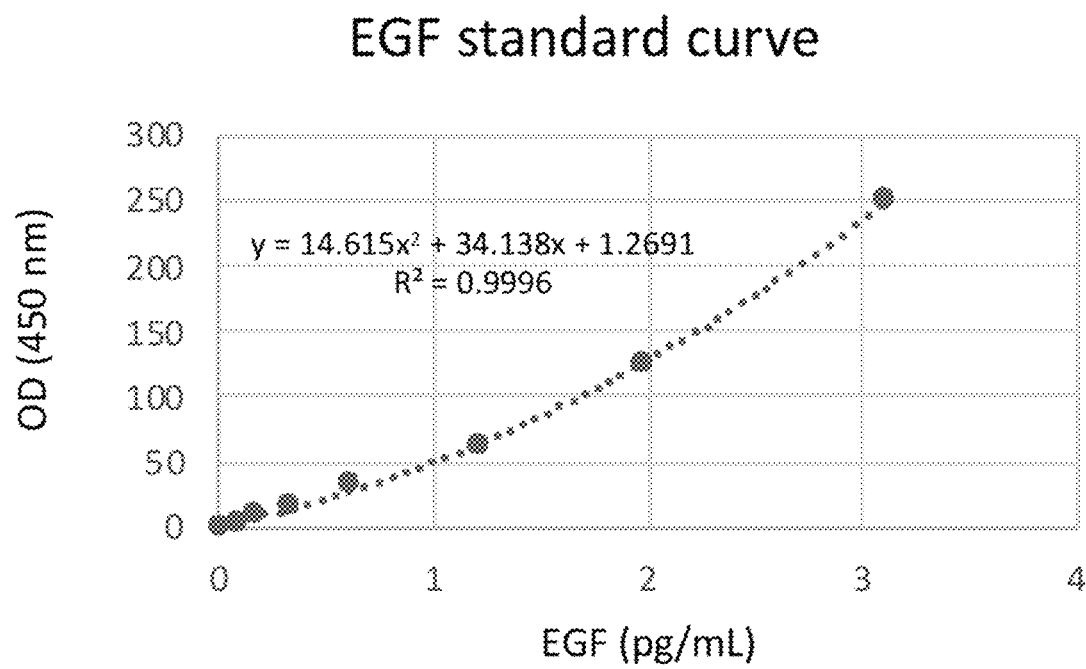
FIG. 20A-20C. The EGF content of in vitro human islets cells was determined by ELISA using a Human EGF Quantikine ELISA Kit (R&D). The bionic anti-CD6/EGF antibody conjugate was cleaved at the MMP2/9 cleavage site within the linker region of the conjugate, and EGF content was determined by an ELISA standard curve as shown (FIG. 20A). The concentrations of EGF at human islet cells for the non-cleaved and cleaved bionic anti-CD6/EGF antibody conjugate were determined to be 11.2% and 14.6% respectively (FIG. 20B), with respect to the theoretical concentration of EGF (FIG. 20C).
Figure 20B:
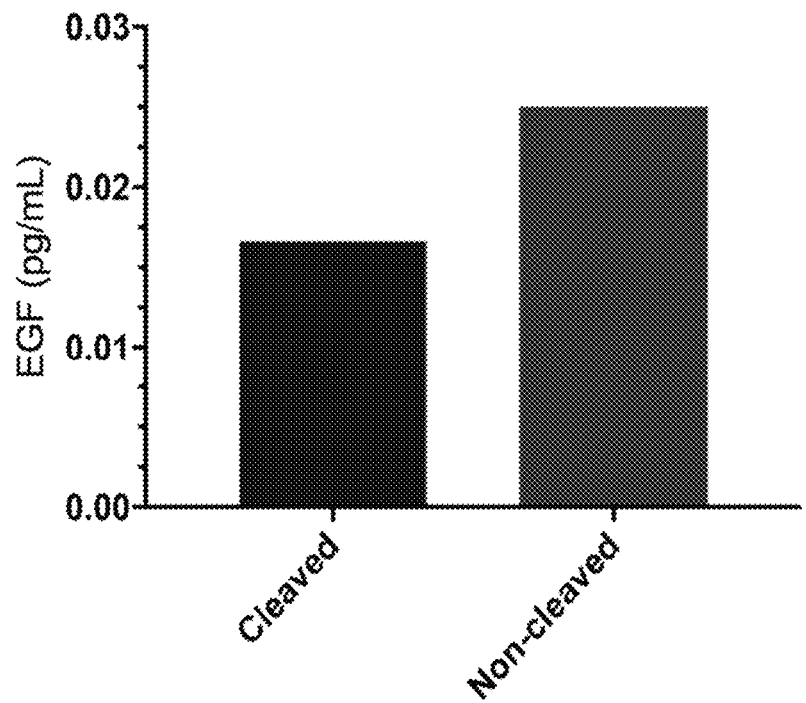
Figure 20C:
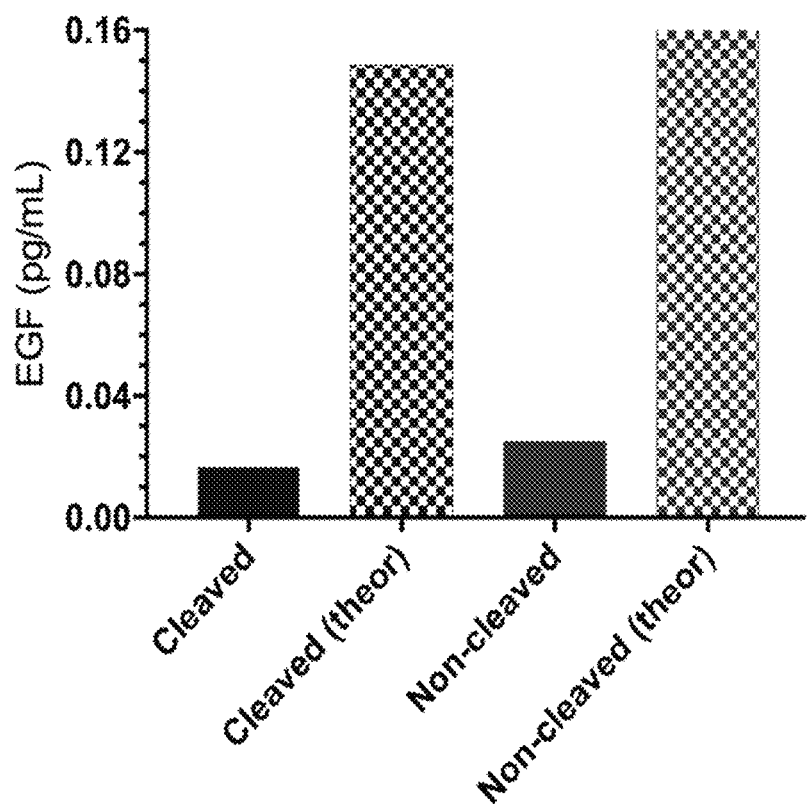
Figure 21A:
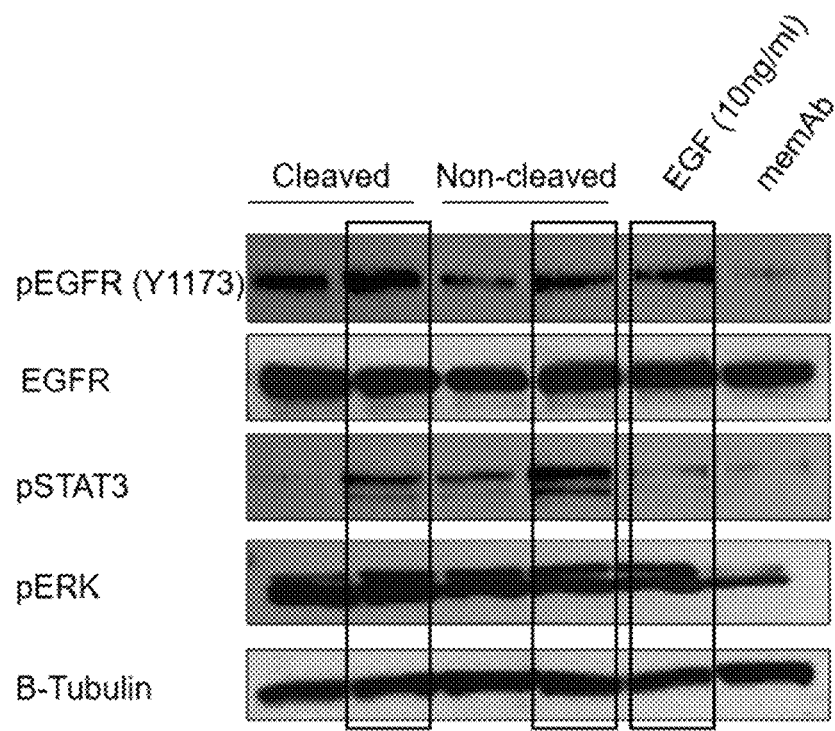
FIG. 21A-21B. EGF functionality was determined by Western blot in islets and in the 1.1B4 cell line. The 1.1B4 cell line is a hybrid cell line formed by the electrofusion of a primary culture of human pancreatic islets with PANC-1, a human pancreatic ductal carcinoma cell line (ECACC catalogue number 87092802). Serum-starved (1% FCS) cells were stimulated with cleaved bionic anti-CD6/EGF conjugated mAb (Cleaved), non-cleaved bionic anti-CD6/EGF conjugated mAb (Non-cleaved), recombinant human EGF (EGF 10 ng/mL), or meditope enabled anti-CD6 (me-mAb) for 10 min. Whole cell lysates were prepared using RIPA lysis buffer with Protease inhibitor mixture and PhosSTOP, and expression of proteins were detected by Western blot as shown (FIG. 21A). J Biol Chem. 2011 Jun. 24;286 (25): 21982-92. Int J Cancer. 1975 May 15;15 (5): 741-7. Expression of EGF receptors (EGFR and HER-2), and CD6 ligands (CD166/ALCAM and CD318) is shown (FIG. 21B).
Figure 21B:
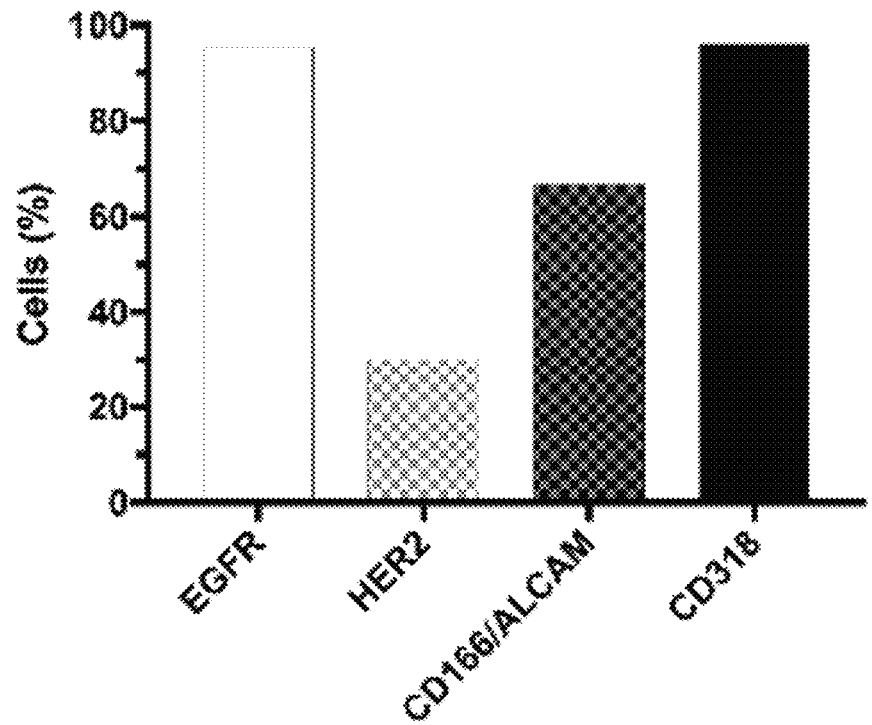
Figure 22:
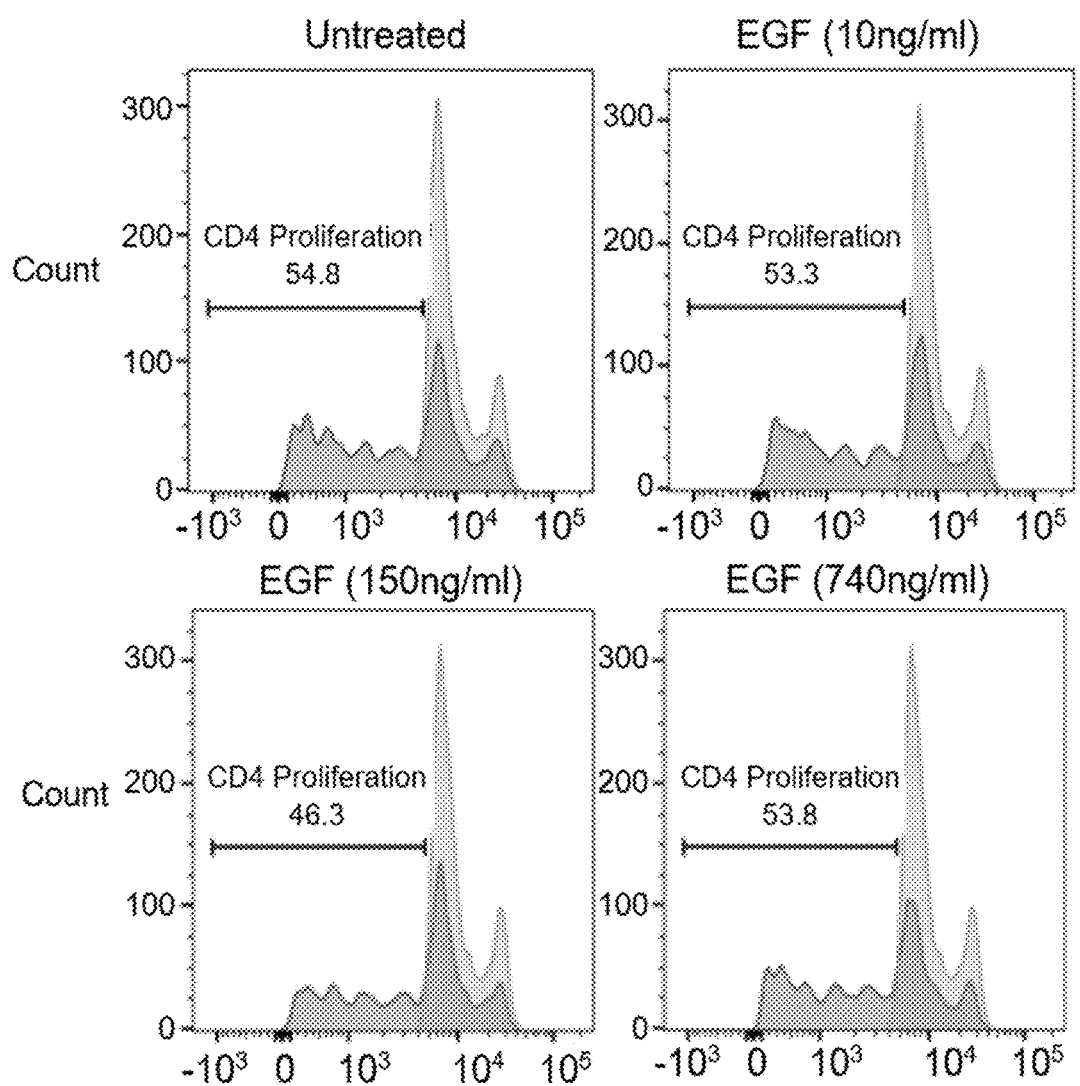
FIG. 22. Inhibition of CD4 T effector cell proliferation in vitro by anti-human CD6 mAb provided herein. Human naïve (light gray) or anti-CD3 mAb activated lymphocytes (dark gray) were evaluated using CellTrace carboxyfluorescein succinimidyl ester (CFSE) dilution by flow cytometry. Human recombinant EGF was added at different concentrations as indicated.
Figure 22:
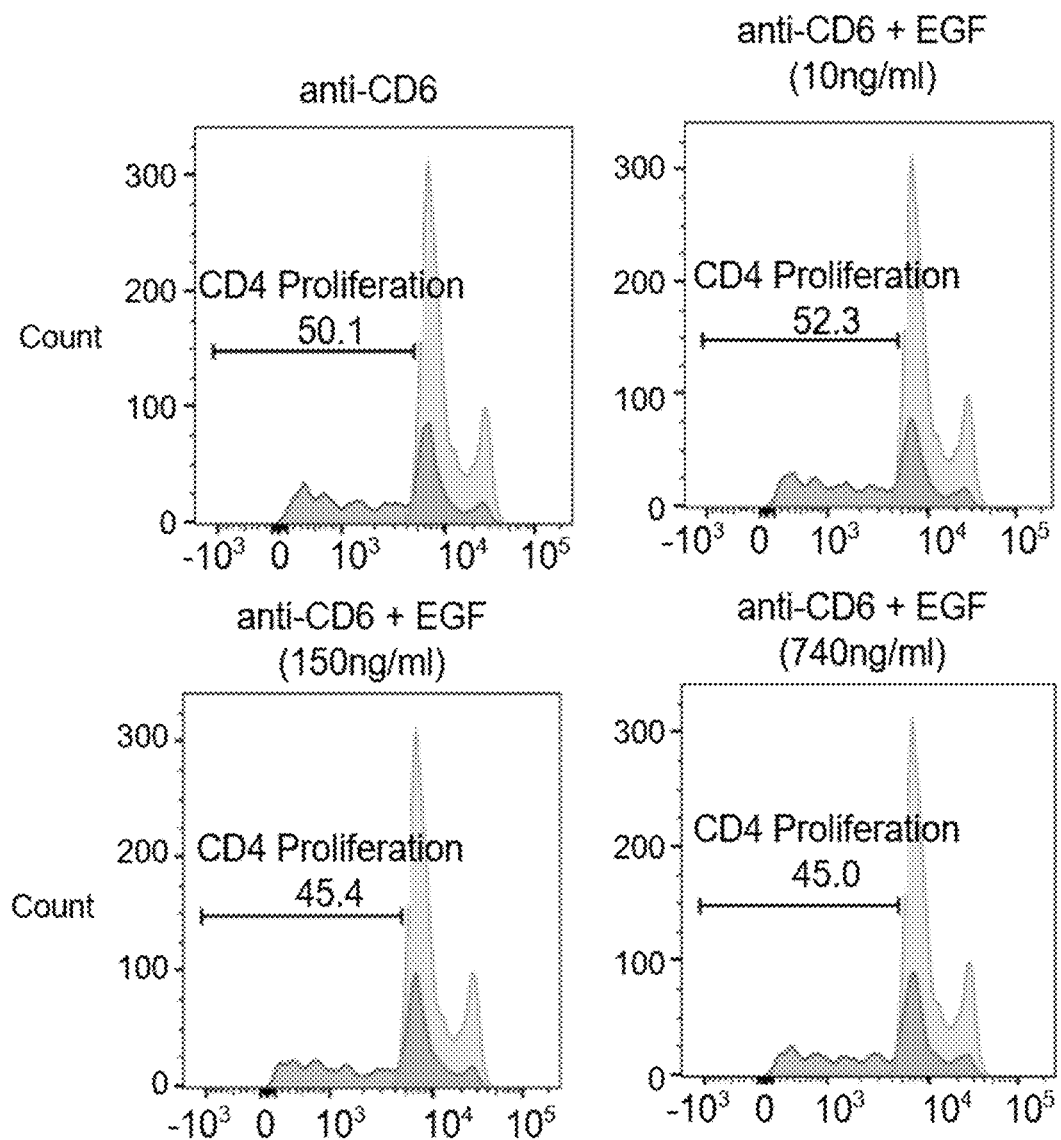
Figure 23A:
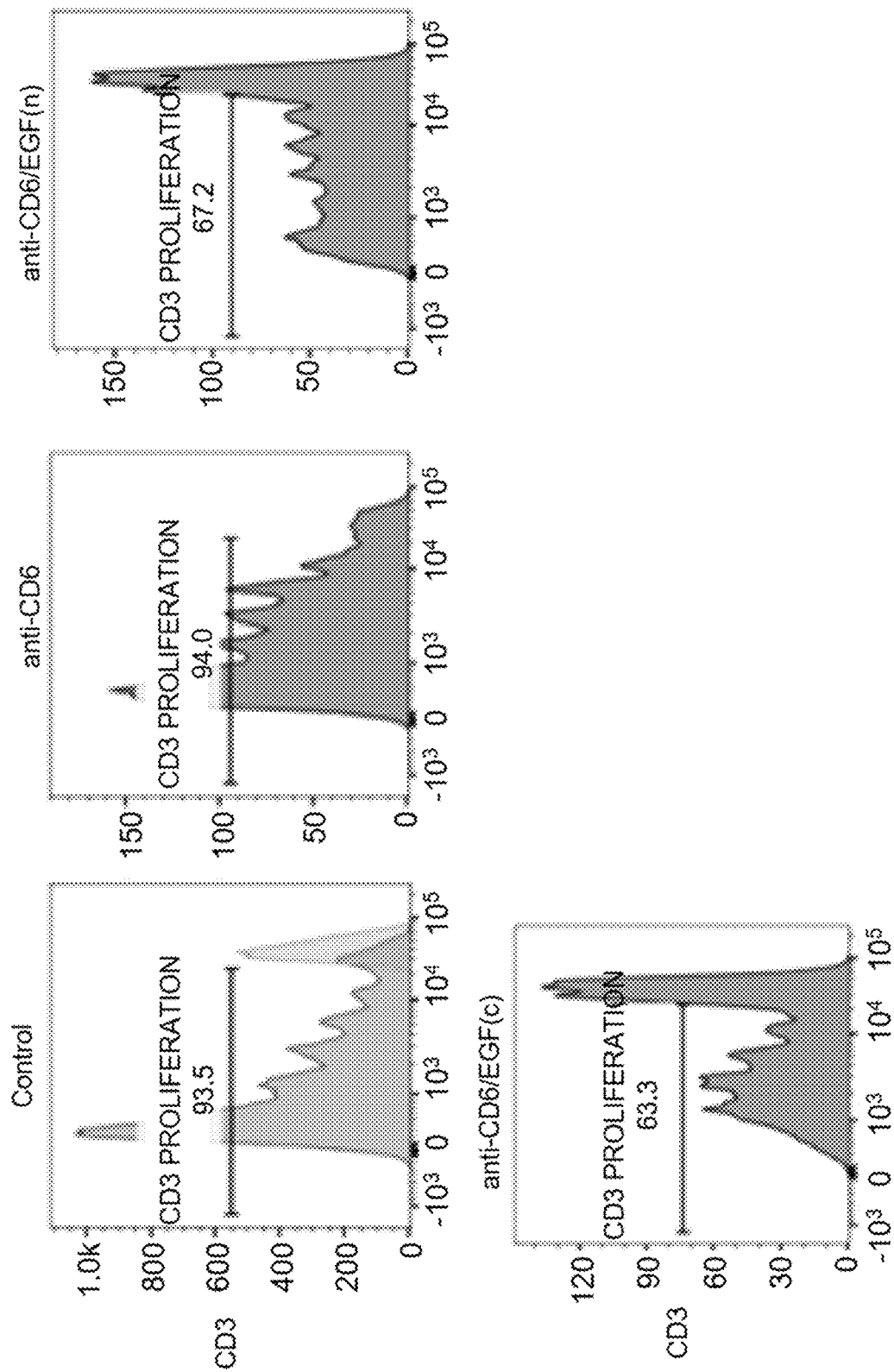
FIG. 23A-23D. Inhibition of T effector (Teff) cell proliferation in vitro using anti-CD6 antibody-growth factor complexes provided herein. Human naïve (light gray) or anti-CD3 mAb activated lymphocytes (dark gray) were evaluated using CellTrace CFSE dilution by flow cytometry (FIG. 23A-23C). CD3 (FIG. 23A), CD4 (FIG. 23B), and CD8 (FIG. 23C) Teff cell proliferation following treatment by anti-human CD6 meditope-enabled antibody, non-cleaved bionic anti-CD6/EGF antibody conjugate (anti-CD6/EGF (n)) or cleaved bionic anti-CD6/EGF antibody conjugate (anti-CD6/EGF (c)), each at 10 µg/mL, is shown. Graphs displaying CD3, CD4, and CD6 immune cell proliferation following treatment with anti-human CD6 meditope-enabled antibody (anti-CD6), uncleaved anti-CD6/EGF antibody conjugate (anti-CD6/EGF (n)), or cleaved anti-CD6/EGF antibody conjugate (anti-CD6/EGF (c)) is shown (FIG. 23D).
Figure 23B:
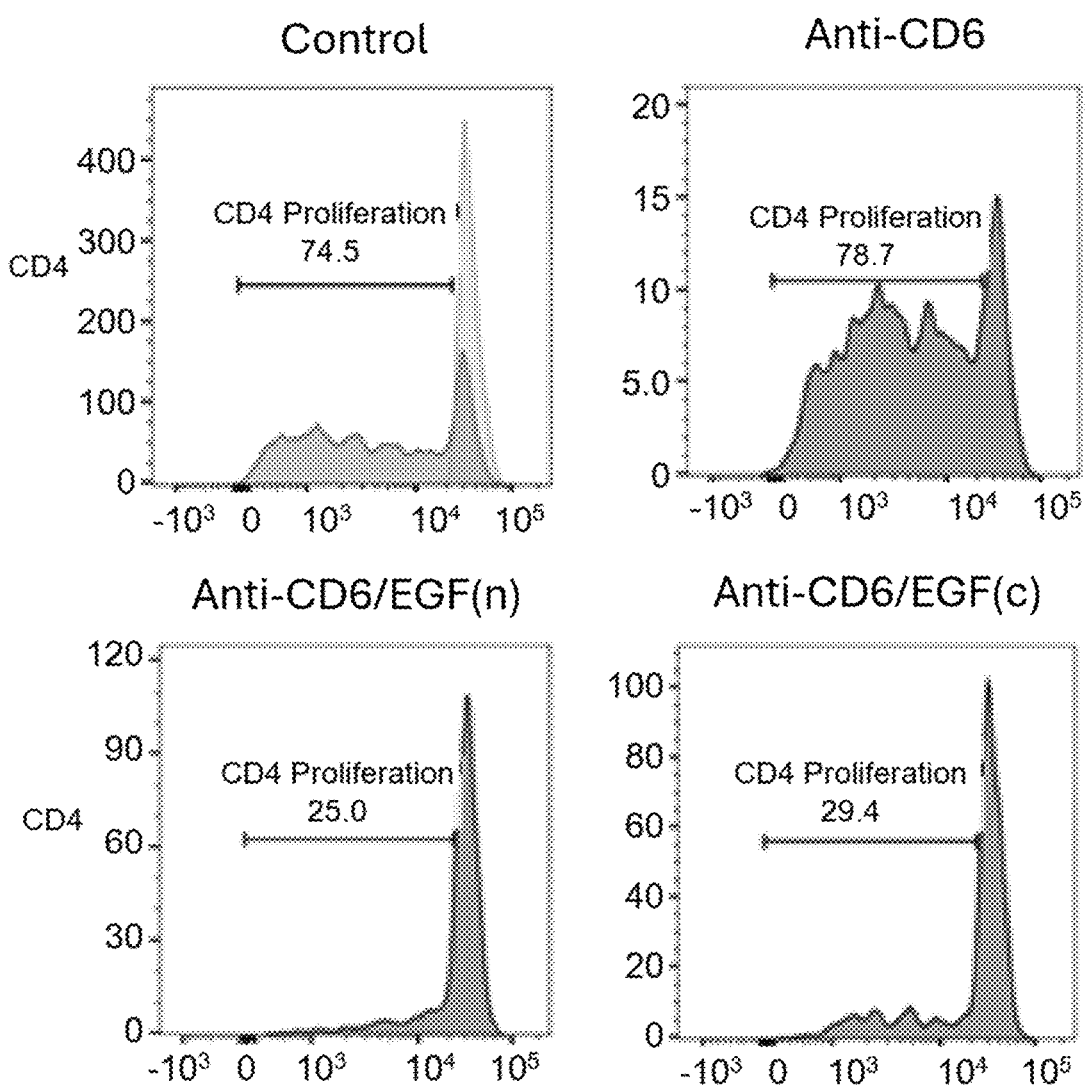
Figure 23C:
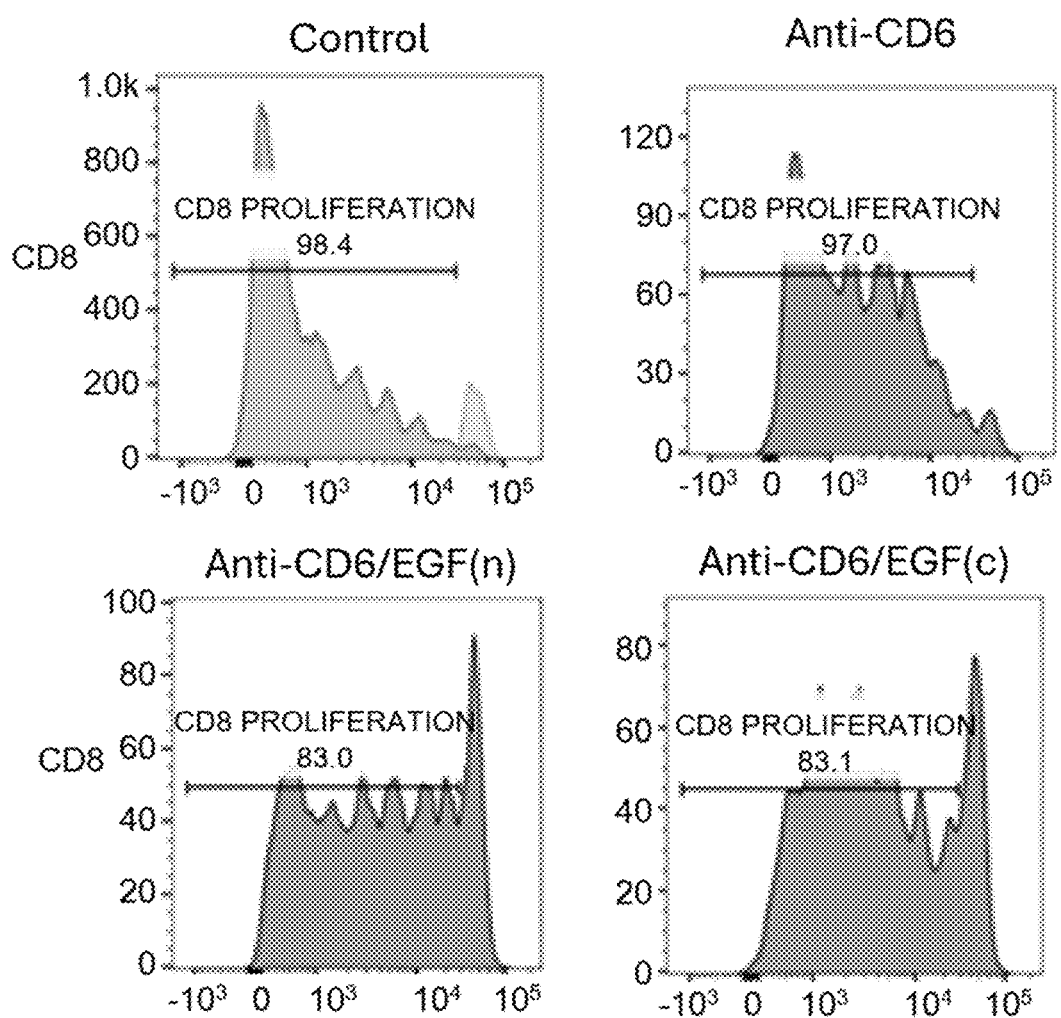
Figure 23D:
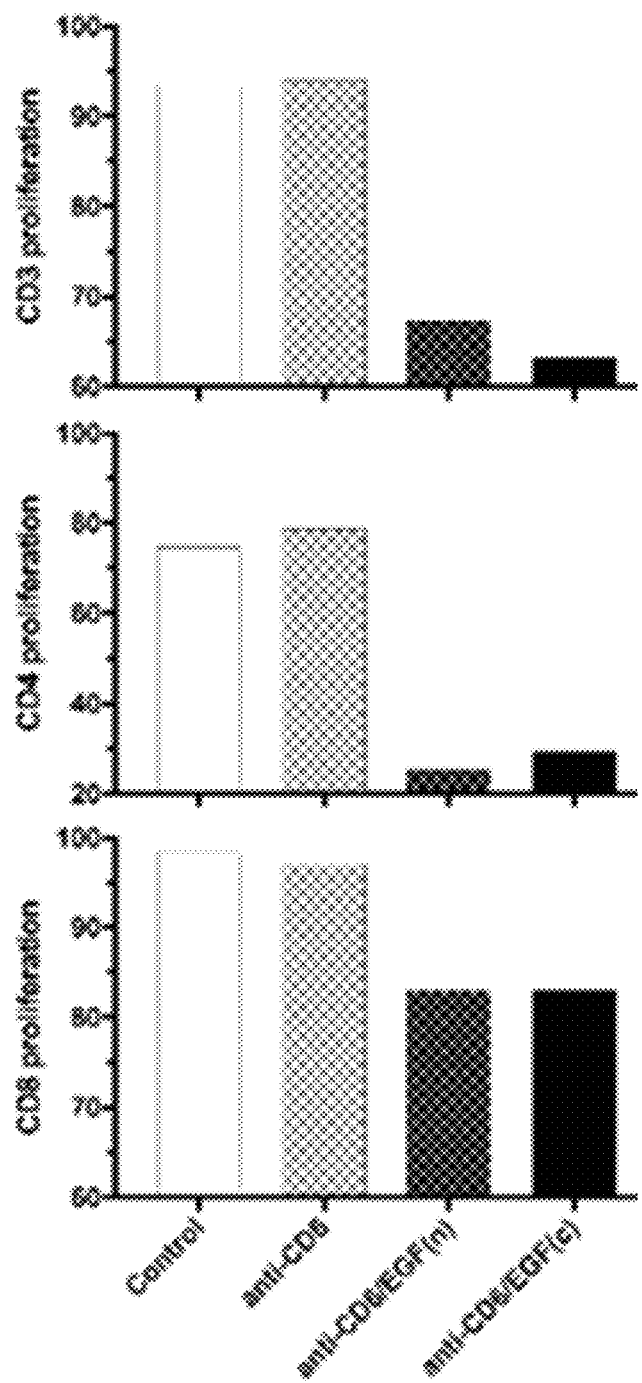

EGF from bionic anti-CD6/EGF antibody conjugate was shown to reach their cell targets and exert desired effects. FIG. 20A-20C demonstrates both cleaved and noncleaved EGF from bionic anti-CD6/EGF antibody conjugate reach islet cells. Further, islet cells from donors (Table 2) were cultured with cytokines and/or EGF (FIG. 13A-13B). Cells cultured with EGF were protected from apoptotic cell death induced by inflammatory cytokines (FIG. 13A-13B).

TABLE 2

| Gender | Race | Age | BMI | HbA1c (%) | IEQ/IPN | Purity (%) | Islet Grade |
|---|---|---|---|---|---|---|---|
| F | Caucasian | 43 | 25 | 4.9 | 2.57 | 75 | A |
| F | Hispanic | 27 | 24.7 | 5 | 0.74 | 75 | B |
| M | Caucasian | 23 | 26.5 | 6.1 | 0.84 | 78 | B |
| M | Hispanic | 51 | 36 | 5.4 | 1.07 | 78 | A |
| F | Hispanic | 29 | 24 | 4.3 | 1.81 | 80 | B |

FIG. 23A-D shows that the bionic anti-CD6/EGF antibody conjugate not only exerts a protective effect on B cells in the human islet environment, but inhibits proliferation of immune cells. Lymphocytes treated with both cleaved and un-cleaved bionic anti-CD6/EGF antibody conjugate show inhibited proliferation of CD3, CD4, and CD8 expressing immune cells compared to untreated cells.

Example 8. Modifications of Bionic Anti-Cd6/Egf Antibody Conjugate LINKER LENGTH AND COMPOSITION Applicants designed and made anti-CD6 antibody-growth factor complexes wherein the second linker or first linker includes a granzyme cleavage site to allow for specific cleavage by an active protease in the Type I diabetes environment. The exemplary complex includes: an anti-CD6 light chain (SEQ ID NO:33) bound to the N-terminus of an EGF protein (SEQ ID NO:4) through a first linker and an anti-CD6 heavy chain (SEQ ID NO:36) bound to the C-terminus of the EGF protein (SEQ ID NO:4) through a second linker (SEQ ID NO:39), wherein the second linker includes a granzyme cleavage site of (SEQ ID NO:67), and wherein a third linker attaches a IgG1-Fc (SEQ ID NO:37) domain to the C-terminus of the anti-CD6 heavy chain (SEQ ID NO: 36).

To test the effect of linker length and composition of the linker (e.g., second linker or first linker) on the anti-CD6 antibody-growth factor complex (e.g., bionic anti-CD6/EGF antibody conjugate of SEQ ID NO:38), Applicants made a series of protein complexes where the linker between the Fab light chain and EGF and EGF and the Fab heavy chain was altered. Sequences of protein complexes with altered linkers are shown in Table 3 and were characterized by SDS PAGE gel and size exclusion chromatography (FIG. 38A-38M). All antibody conjugates were attached to an IgG1 Fc. The protein complexes express well and express as a single chain. Further, Granzyme B efficiently cleaves the majority of the linker EGF-CD6 variants.

TABLE 3

| Protein ID | Protein Name | Polypeptide ID | Variable ID | Constant ID | Amino Acid Sequence | SEQ ID NO: |
|---|---|---|---|---|---|---|
| 50252.1 | CD6 | CD6 | G: 363808 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSASSAASSNSDSECPLSH DGYCLHDGVCMYIEALDKYACNCVVGYIGERCQYRDLK WWELRGSGSGIEPDSGGSEVQLVESGGGLVKPGGSLKL SCAASGFKFSRYAMSWVRQAPGKRLEWVATISSGGSYIY YPDSVKGRFTISRDNVKNTLYLQMSSLRSEDTAIYYCARR DYDLDYFDSWGQGTLVTVSSASTKGPSVFPLAPSSKSTS GGTAALGCLVKDYFPEPVTVSWNSGALTSGVHTFPAVL QSSGLYSLSSVVTVPSSSLGTQTYICNVNHKPSNTKVDKK VEPKSCDKTHTCPPCPAPELLGGPSVFLFPPKPKDTLMIS RTPEVTCVVVDVSHEDPEVKFNWYVDGVEVHNAKTKPR EEQYNSTYRVVSVLTVLHQDWLNGKEYKCKVSNKALPA PIEKTISKAKGQPREPQVYTLPPSRDELTKNQVSLTCLVKG FYPSDIAVEWESNGQPENNYKTTPPVLDSDGSFFLYSKLT VDKSRWQQGNVFSCSVMHEALHNHYTQKSLSLSPGK* | 38 |
| 50253.1 | CD6-minus2L | CD6-minus2L | G: 363809 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSASSAANSDSECPLSHDG YCLHDGVCMYIEALDKYACNCVVGYIGERCQYRDLKWW ELRGSGSGIEPDSGGSEVQLVESGGGLVKPGGSLKLSCAA SGFKFSRYAMSWVRQAPGKRLEWVATISSGGSYIYYPDS VKGRFTISRDNVKNTLYLQMSSLRSEDTAIYYCARRDYDL DYFDSWGQGTLVTVSSASTKGPSVFPLAPSSKSTSGGTA ALGCLVKDYFPEPVTVSWNSGALTSGVHTFPAVLQSSGL YSLSSVVTVPSSSLGTQTYICNVNHKPSNTKVDKKVEPKS CDKTHTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIEKTI SKAKGQPREPQVYTLPPSRDELTKNQVSLTCLVKGFYPSD IAVEWESNGQPENNYKTTPPVLDSDGSFFLYSKLTVDKS RWQQGNVFSCSVMHEALHNHYTQKSLSLSPGK* | 42 |

TABLE 3-continued

| Protein ID | Protein Name | Variable Polypeptide ID | Constant ID | Amino Acid Sequence | SEQ ID NO: |
|---|---|---|---|---|---|
| 50254.1 | CD6-minus4L | CD6-minus4L G: 363810 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSASSNSDSECPLSHDGYC LHDGVCMYIEALDKYACNCVVGYIGERCQYRDLKWWEL RGSGSGIEPDSGGSEVQLVESGGGLVKPGGSLKLSCAAS GFKFSRYAMSWVRQAPGKRLEWVATISSGGSYIYYPDSV KGRFTISRDNVKNTLYLQMSSLRSEDTAIYYCARRDYDLD YFDSWGQGTLVTVSSASTKGPSVFPLAPSSKSTSGGTAA LGCLVKDYFPEPVTVSWNSGALTSGVHTFPAVLQSSGLY SLSSVVTVPSSSLGTQTYICNVNHKPSNTKVDKKVEPKSC DKTHTCPPCPAPELLGGPSVFLFPPKPKDTLMISRTPEVT CVVVDVSHEDPEVKFNWYVDGVEVHNAKTKPREEQYN STYRVVSVLTVLHQDWLNGKEYKCKVSNKALPAPIEKTIS KAKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGK* | 44 |
| 50255.1 | CD6-minus6L | CD6-minus6L G: 363811 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSANSDSECPLSHDGYCLH DGVCMYIEALDKYACNCVVGYIGERCQYRDLKWWELR GSGSGIEPDSGGSEVQLVESGGGLVKPGGSLKLSCAASG FKFSRYAMSWVRQAPGKRLEWVATISSGGSYIYYPDSVK GRFTISRDNVKNTLYLQMSSLRSEDTAIYYCARRDYDLDY FDSWGQGTLVTVSSASTKGPSVFPLAPSSKSTSGGTAAL GCLVKDYFPEPVTVSWNSGALTSGVHTFPAVLQSSGLYS LSSVVTVPSSSLGTQTYICNVNHKPSNTKVDKKVEPKSCD KTHTCPPCPAPELLGGPSVFLFPPKPKDTLMISRTPEVTC VVVDVSHEDPEVKFNWYVDGVEVHNAKTKPREEQYNS TYRVVSVLTVLHQDWLNGKEYKCKVSNKALPAPIEKTISK AKGQPREPQVYTLPPSRDELTKNQVSLTCLVKGFYPSDIA VEWESNGQPENNYKTTPPVLDSDGSFFLYSKLTVDKSR WQQGNVFSCSVMHEALHNHYTQKSLSLSPGK* | 46 |
| 50256.1 | CD6-minus8L | CD6-minus8L G: 363812 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASNSDSECPLSHDGYCLHD GVCMYIEALDKYACNCVVGYIGERCQYRDLKWWELRGS GSGIEPDSGGSEVQLVESGGGLVKPGGSLKLSCAASGFKF SRYAMSWVRQAPGKRLEWVATISSGGSYIYYPDSVKGR FTISRDNVKNTLYLQMSSLRSEDTAIYYCARRDYDLDYFD SWGQGTLVTVSSASTKGPSVFPLAPSSKSTSGGTAALGC LVKDYFPEPVTVSWNSGALTSGVHTFPAVLQSSGLYSLSS VVTVPSSSLGTQTYICNVNHKPSNTKVDKKVEPKSCDKT HTCPPCPAPELLGGPSVFLFPPKPKDTLMISRTPEVTCVV VDVSHEDPEVKFNWYVDGVEVHNAKTKPREEQYNSTYR VVSVLTVLHQDWLNGKEYKCKVSNKALPAPIEKTISKAKG QPREPQVYTLPPSRDELTKNQVSLTCLVKGFYPSDIAVE WESNGQPENNYKTTPPVLDSDGSFFLYSKLTVDKSRWQ QGNVFSCSVMHEALHNHYTQKSLSLSPGK* | 48 |
| 50257.1 | CD6-EGF_PP | CD6-EGF_PP G: 363813 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSASSAAPPNSDSECPLSH DGYCLHDGVCMYIEALDKYACNCVVGYIGERCQYRDLK WWELRGSGSGIEPDSGGSEVQLVESGGGLVKPGGSLKL SCAASGFKFSRYAMSWVRQAPGKRLEWVATISSGGSYIY YPDSVKGRFTISRDNVKNTLYLQMSSLRSEDTAIYYCARR DYDLDYFDSWGQGTLVTVSSASTKGPSVFPLAPSSKSTS GGTAALGCLVKDYFPEPVTVSWNSGALTSGVHTFPAVL QSSGLYSLSSVVTVPSSSLGTQTYICNVNHKPSNTKVDKK VEPKSCDKTHTCPPCPAPELLGGPSVFLFPPKPKDTLMIS RTPEVTCVVVDVSHEDPEVKFNWYVDGVEVHNAKTKPR EEQYNSTYRVVSVLTVLHQDWLNGKEYKCKVSNKALPA PIEKTISKAKGQPREPQVYTLPPSRDELTKNQVSLTCLVKG | 50 |

TABLE 3-continued

| Protein ID | Protein Name | Polypeptide ID | Variable ID | Constant ID | Amino Acid Sequence | SEQ ID NO: |
|---|---|---|---|---|---|---|
| | | | | | FYPSDIAVEWESNGQPENNYKTTPPVLDSDGSFFLYSKLT VDKSRWQQGNVFSCSVMHEALHNHYTQKSLSLSPGK* | |
| 50258.1 | CD6-LC_PP | CD6-LC_PP | G: 363814 | G: 363327 | DIQMTQSPILLSASVGDRVTITCKASRDIRSYLTWYQQRT NGSPRTLIYYATSLADGVPSRFSGSGSGQDYSLTISSSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECPPASAAASSASSAASSNSDSECPLSH DGYCLHDGVCMYIEALDKYACNCVVGYIGERCQYRDLK WWELRGSGSGIEPDSGGSEVQLVESGGGLVKPGGSLKL SCAASGFKFSRYAMSWVRQAPGKRLEWVATISSGGSYIY YPDSVKGRFTISRDNVKNTLYLQMSSLRSEDTAIYYCARR DYDLDYFDSWGQGTLVTVSSASTKGPSVFPLAPSSKSTS GGTAALGCLVKDYFPEPVTVSWNSGALTSGVHTFPAVL QSSGLYSLSSVVTVPSSSLGTQTYICNVNHKPSNTKVDKK VEPKSCDKTHTCPPCPAPELLGGPSVFLFPPKPKDTLMIS RTPEVTCVVVDVSHEDPEVKFNWYVDGVEVHNAKTKPR EEQYNSTYRVVSVLTVLHQDWLNGKEYKCKVSNKALPA PIEKTISKAKGQPREPQVYTLPPSRDELTKNQVSLTCLVKG FYPSDIAVEWESNGQPENNYKTTPPVLDSDGSFFLYSKLT VDKSRWQQGNVFSCSVMHEALHNHYTQKSLSLSPGK* | 52 |
| 50259.1 | CD6-L1_4PP | CD6-L1_4PP | G: 363815 | G: 363327 | DIQMTQSPILLSASVGDRVTITCKASRDIRSYLTWYQQRT NGSPRTLIYYATSLADGVPSRFSGSGSGQDYSLTISSSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECPPASAAASSASSAAPPNSDSECPLSH DGYCLHDGVCMYIEALDKYACNCVVGYIGERCQYRDLK WWELRGSGSGIEPDSGGSEVQLVESGGGLVKPGGSLKL SCAASGFKFSRYAMSWVRQAPGKRLEWVATISSGGSYIY YPDSVKGRFTISRDNVKNTLYLQMSSLRSEDTAIYYCARR DYDLDYFDSWGQGTLVTVSSASTKGPSVFPLAPSSKSTS GGTAALGCLVKDYFPEPVTVSWNSGALTSGVHTFPAVL QSSGLYSLSSVVTVPSSSLGTQTYICNVNHKPSNTKVDKK VEPKSCDKTHTCPPCPAPELLGGPSVFLFPPKPKDTLMIS RTPEVTCVVVDVSHEDPEVKFNWYVDGVEVHNAKTKPR EEQYNSTYRVVSVLTVLHQDWLNGKEYKCKVSNKALPA PIEKTISKAKGQPREPQVYTLPPSRDELTKNQVSLTCLVKG FYPSDIAVEWESNGQPENNYKTTPPVLDSDGSFFLYSKLT VDKSRWQQGNVFSCSVMHEALHNHYTQKSLSLSPGK* | 54 |
| 50260.1 | CD6-L1_6PP | CD6-L1_6PP | G: 363816 | G: 363327 | DIQMTQSPILLSASVGDRVTITCKASRDIRSYLTWYQQRT NGSPRTLIYYATSLADGVPSRFSGSGSGQDYSLTISSSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECPPASAAAPPASSAAPPNSDSECPLSH DGYCLHDGVCMYIEALDKYACNCVVGYIGERCQYRDLK WWELRGSGSGIEPDSGGSEVQLVESGGGLVKPGGSLKL SCAASGFKFSRYAMSWVRQAPGKRLEWVATISSGGSYIY YPDSVKGRFTISRDNVKNTLYLQMSSLRSEDTAIYYCARR DYDLDYFDSWGQGTLVTVSSASTKGPSVFPLAPSSKSTS GGTAALGCLVKDYFPEPVTVSWNSGALTSGVHTFPAVL QSSGLYSLSSVVTVPSSSLGTQTYICNVNHKPSNTKVDKK VEPKSCDKTHTCPPCPAPELLGGPSVFLFPPKPKDTLMIS RTPEVTCVVVDVSHEDPEVKFNWYVDGVEVHNAKTKPR EEQYNSTYRVVSVLTVLHQDWLNGKEYKCKVSNKALPA PIEKTISKAKGQPREPQVYTLPPSRDELTKNQVSLTCLVKG FYPSDIAVEWESNGQPENNYKTTPPVLDSDGSFFLYSKLT VDKSRWQQGNVFSCSVMHEALHNHYTQKSLSLSPGK* | 56 |
| 50261.1 | CD6-N1 | CD6-N1 | G: 363817 | G: 363327 | DIQMTQSPILLSASVGDRVTITCKASRDIRSYLTWYQQRT NGSPRTLIYYATSLADGVPSRFSGSGSGQDYSLTISSSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSASSAASSNSDSECPLSH DGYCLHDGVCMYIEALDKYACNCVVGYIGERCQYRDLK WWELRSGSGIEPDSGGSEVQLVESGGGLVKPGGSLKLSC AASGFKFSRYAMSWVRQAPGKRLEWVATISSGGSYIYYP DSVKGRFTISRDNVKNTLYLQMSSLRSEDTAIYYCARRDY DLDYFDSWGQGTLVTVSSASTKGPSVFPLAPSSKSTSGG TAALGCLVKDYFPEPVTVSWNSGALTSGVHTFPAVLQSS GLYSLSSVVTVPSSSLGTQTYICNVNHKPSNTKVDKKVEP KSCDKTHTCPPCPAPELLGGPSVFLFPPKPKDTLMISRTPE | 58 |

TABLE 3-continued

| Protein ID | Protein Name | Variable Polypeptide ID | Constant ID | Amino Acid Sequence | SEQ ID NO: |
|---|---|---|---|---|---|
| | | | | VTCVVVDVSHEDPEVKFNWYVDGVEVHNAKTKPREEQ YNSTYRVVSVLTVLHQDWLNGKEYKCKVSNKALPAPIEK TISKAKGQPREPQVYTLPPSRDELTKNQVSLTCLVKGFYP SDIAVEWESNGQPENNYKTTPPVLDSDGSFFLYSKLTVD KSRWQQGNVFSCSVMHEALHNHYTQKSLSLSPGK* | |
| 50262.1 | CD6-C1 | CD6-C1 | G: 363818 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSASSAASSNSDSECPLSH DGYCLHDGVCMYIEALDKYACNCVVGYIGERCQYRDLK WWELRGSGSGIEPDSGSEVQLVESGGGLVKPGGSLKLSC AASGFKFSRYAMSWVRQAPGKRLEWVATISSGGSYIYYP DSVKGRFTISRDNVKNTLYLQMSSLRSEDTAIYYCARRDY DLDYFDSWGQGTLVTVSSASTKGPSVFPLAPSSKSTSGG TAALGCLVKDYFPEPVTVSWNSGALTSGVHTFPAVLQSS GLYSLSSVVTVPSSSLGTQTYICNVNHKPSNTKVDKKVEP KSCDKTHTCPPCPAPELLGGPSVFLFPPKPKDTLMISRTPE VTCVVVDVSHEDPEVKFNWYVDGVEVHNAKTKPREEQ YNSTYRVVSVLTVLHQDWLNGKEYKCKVSNKALPAPIEK TISKAKGQPREPQVYTLPPSRDELTKNQVSLTCLVKGFYP SDIAVEWESNGQPENNYKTTPPVLDSDGSFFLYSKLTVD KSRWQQGNVFSCSVMHEALHNHYTQKSLSLSPGK* | 60 |
| 50263.1 | CD6-N1C1 | CD6-N1C1 | G: 363819 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSASSAASSNSDSECPLSH DGYCLHDGVCMYIEALDKYACNCVVGYIGERCQYRDLK WWELRGSGIEPDSGSEVQLVESGGGLVKPGGSLKLSCA ASGFKFSRYAMSWVRQAPGKRLEWVATISSGGSYIYYPD SVKGRFTISRDNVKNTLYLQMSSLRSEDTAIYYCARRDYD LDYFDSWGQGTLVTVSSASTKGPSVFPLAPSSKSTSGGT AALGCLVKDYFPEPVTVSWNSGALTSGVHTFPAVLQSSG LYSLSSVVTVPSSSLGTQTYICNVNHKPSNTKVDKKVEPK SCDKTHTCPPCPAPELLGGPSVFLFPPKPKDTLMISRTPE VTCVVVDVSHEDPEVKFNWYVDGVEVHNAKTKPREEQ YNSTYRVVSVLTVLHQDWLNGKEYKCKVSNKALPAPIEK TISKAKGQPREPQVYTLPPSRDELTKNQVSLTCLVKGFYP SDIAVEWESNGQPENNYKTTPPVLDSDGSFFLYSKLTVD KSRWQQGNVFSCSVMHEALHNHYTQKSLSLSPGK* | 62 |
| 50264.1 | CD6-N2C2 | CD6-N2C2 | G: 363820 | G: 363327 | DIQMTQSPILLSASVGDRVTITCKASRDIRSYLTWYQQRT NGSPRTLIYYATSLADGVPSRFSGSGSGQDYSLTISSLESD DIADYYCLQHGESPFTFGSGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQG LSSPVTKSFNRGECASASAAASSASSAASSNSDSECPLSH DGYCLHDGVCMYIEALDKYACNCVVGYIGERCQYRDLK WWELRGSGIEPDSGEVQLVESGGGLVKPGGSLKLSCAA SGFKFSRYAMSWVRQAPGKRLEWVATISSGGSYIYYPDS VKGRFTISRDNVKNTLYLQMSSLRSEDTAIYYCARRDYDL DYFDSWGQGTLVTVSSASTKGPSVFPLAPSSKSTSGGTA ALGCLVKDYFPEPVTVSWNSGALTSGVHTFPAVLQSSGL YSLSSVVTVPSSSLGTQTYICNVNHKPSNTKVDKKVEPKS CDKTHTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIEKTI SKAKGQPREPQVYTLPPSRDELTKNQVSLTCLVKGFYPSD IAVEWESNGQPENNYKTTPPVLDSDGSFFLYSKLTVDKS RWQQGNVFSCSVMHEALHNHYTQKSLSLSPGK* | 64 |

Summary of expression data for the protein complexes with altered linkers are shown in Table 4.

TABLE 4

| Protein ID | Protein Name | Conc. (mg/ml) | Yield (mg) | Culture Volume (mL) | Titer (mg/L) | Aliquots | Aliquot Volume (mL) |
|---|---|---|---|---|---|---|---|
| 50252.1.o | CD6 | 0.19 | 0.12 | 10 | 11.67 | 1 | 0.60 |
| 50253.1.o | CD6-minus2L | 0.20 | 0.11 | 10 | 11.37 | 1 | 0.56 |
| 50254.1.o | CD6-minus4L | 0.18 | 0.09 | 10 | 9.06 | 1 | 0.51 |
| 50255.1.o | CD6-minus6L | 0.20 | 0.08 | 10 | 9.06 | 1 | 0.40 |
| 50256.1.o | CD6-minus8L | 0.20 | 0.08 | 10 | 7.54 | 1 | 0.37 |
| 50257.1.o | CD6-EGF_PP | 0.31 | 0.11 | 10 | 10.53 | 1 | 0.34 |
| 50258.1.o | CD6-LC_PP | 0.37 | 0.12 | 10 | 11.73 | 1 | 0.32 |
| 50259.1.o | CD6-L1_4PP | 0.23 | 0.09 | 10 | 9.10 | 1 | 0.40 |
| 50260.1.o | CD6-L1_6PP | 0.38 | 0.11 | 10 | 10.96 | 1 | 0.29 |
| 50261.1.o | CD6-N1 | 0.33 | 0.12 | 10 | 12.16 | 1 | 0.37 |
| 50262.1.o | CD6-C1 | 0.09 | 0.06 | 10 | 5.52 | 1 | 0.61 |
| 50263.1.o | CD6-N1C1 | 0.20 | 0.20 | 10 | 9.55 | 1 | 0.48 |
| 50264.1.o | CD6-N2C2 | 0.29 | 0.11 | 10 | 11.34 | 1 | 0.39 |

Summary of protein information for the protein complexes with altered linkers are shown in Table 5.

TABLE 5

| Protein Name | Molecular Weight (Da) | Extinction Coefficient | Isoelectric Point | SEQ ID NO |
|---|---|---|---|---|
| CD6 | 81340 | 122505 | 6.74 | 38 |
| CD6-minus2L | 81166 | 122505 | 6.74 | 42 |
| CD6-minus4L | 81024 | 122505 | 6.74 | 44 |
| CD6-minus6L | 80850 | 122505 | 6.74 | 46 |
| CD6-minus8L | 80692 | 122505 | 6.74 | 48 |
| CD6-EGF PP | 81360 | 122505 | 6.74 | 50 |
| CD6-LC_PP | 81376 | 122505 | 6.74 | 52 |
| CD6-L1_4PP | 81396 | 122505 | 6.74 | 54 |
| CD6-L1_6PP | 81416 | 122505 | 6.74 | 56 |
| CD6-N1 | 81283 | 122505 | 6.74 | 58 |
| CD6-C1 | 81283 | 122505 | 6.74 | 60 |
| CD6-N1C1 | 81226 | 122505 | 6.74 | 62 |
| CD6-N2C2 | 81052 | 122505 | 6.74 | 64 |

Figure 29:
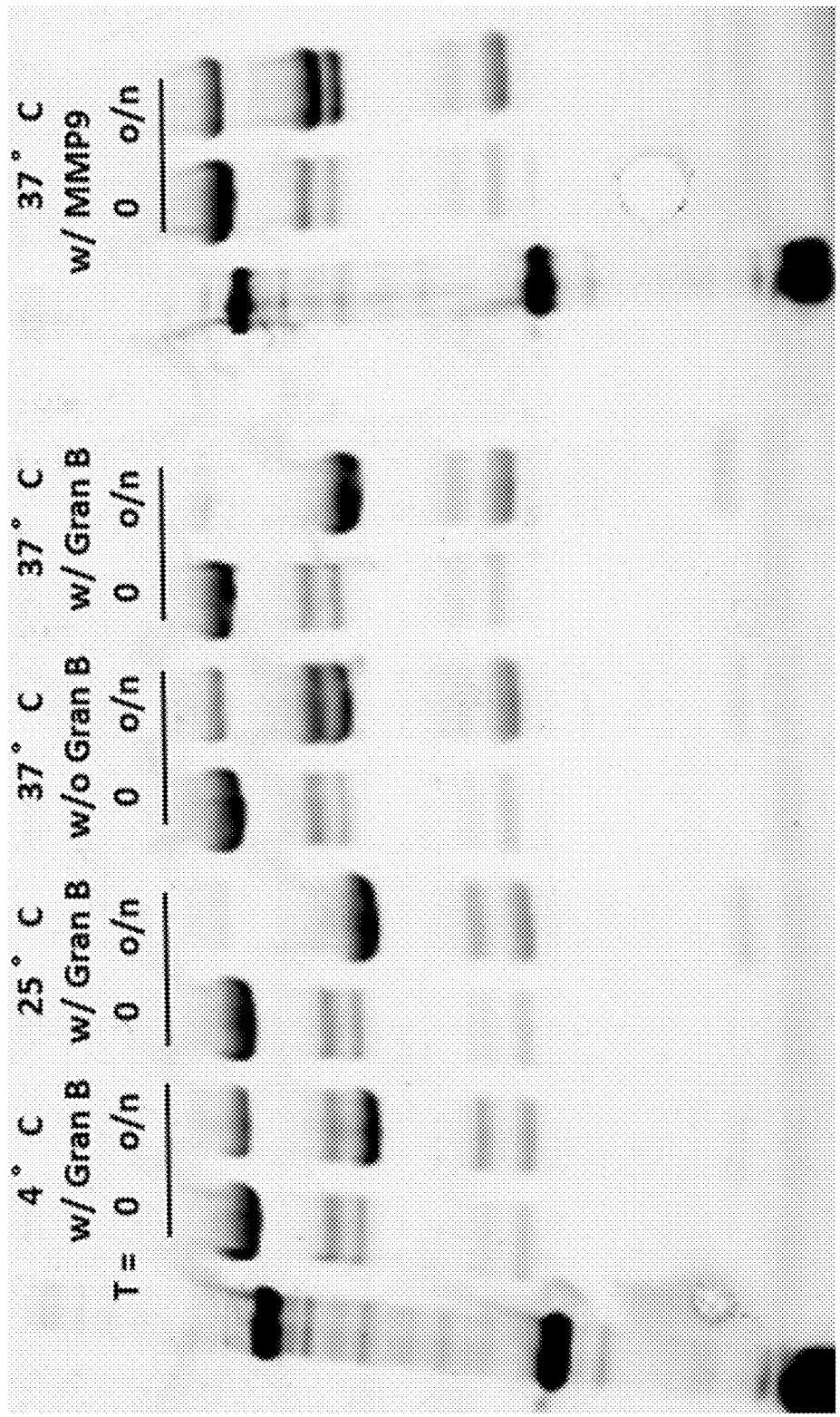
FIG. 29. SDS PAGE gel of an exemplary anti-CD6 antibody-growth factor complex provided herein. A bionic anti-CDG/EGF antibody conjugate of SEQ ID NO:38 incubated with or without Granzyme B or MMP9. Each sample contains 100 µg of protein with (w/) or without (w/o) 29.5 ng of Granzyme B or MMP9 at the designated temperature as indicated. For each temperature, two time points were run on the gel, 0 hrs (0) and overnight (o/n).
Figure 30:
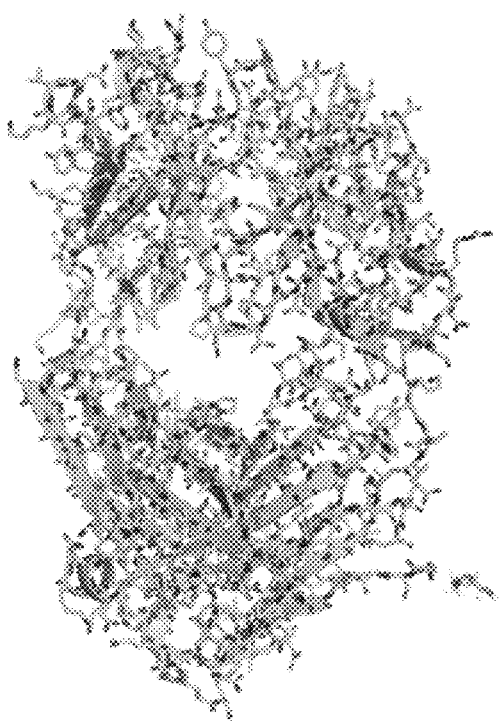
FIG. 30. Crystal structure of anti-CD6 Fab. Left panel is the anti-CD6 Fab. Top panel on the right shows Asp104 in the Fab heavy chain. Bottom panel on the right shows Asn104 in the Fab heavy chain in the D104N anti-CD6 Fab mutant.
Figure 30:
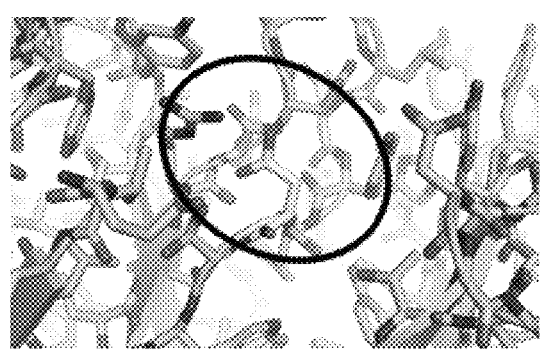
Figure 30:
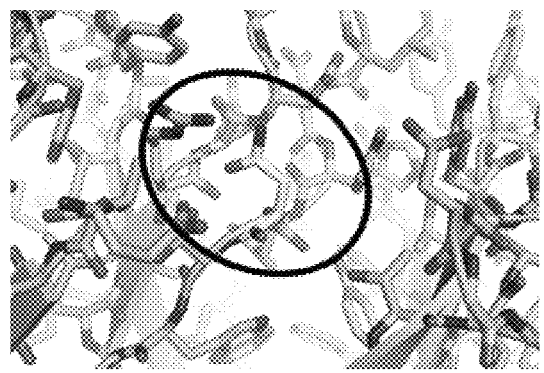
Figure 31:
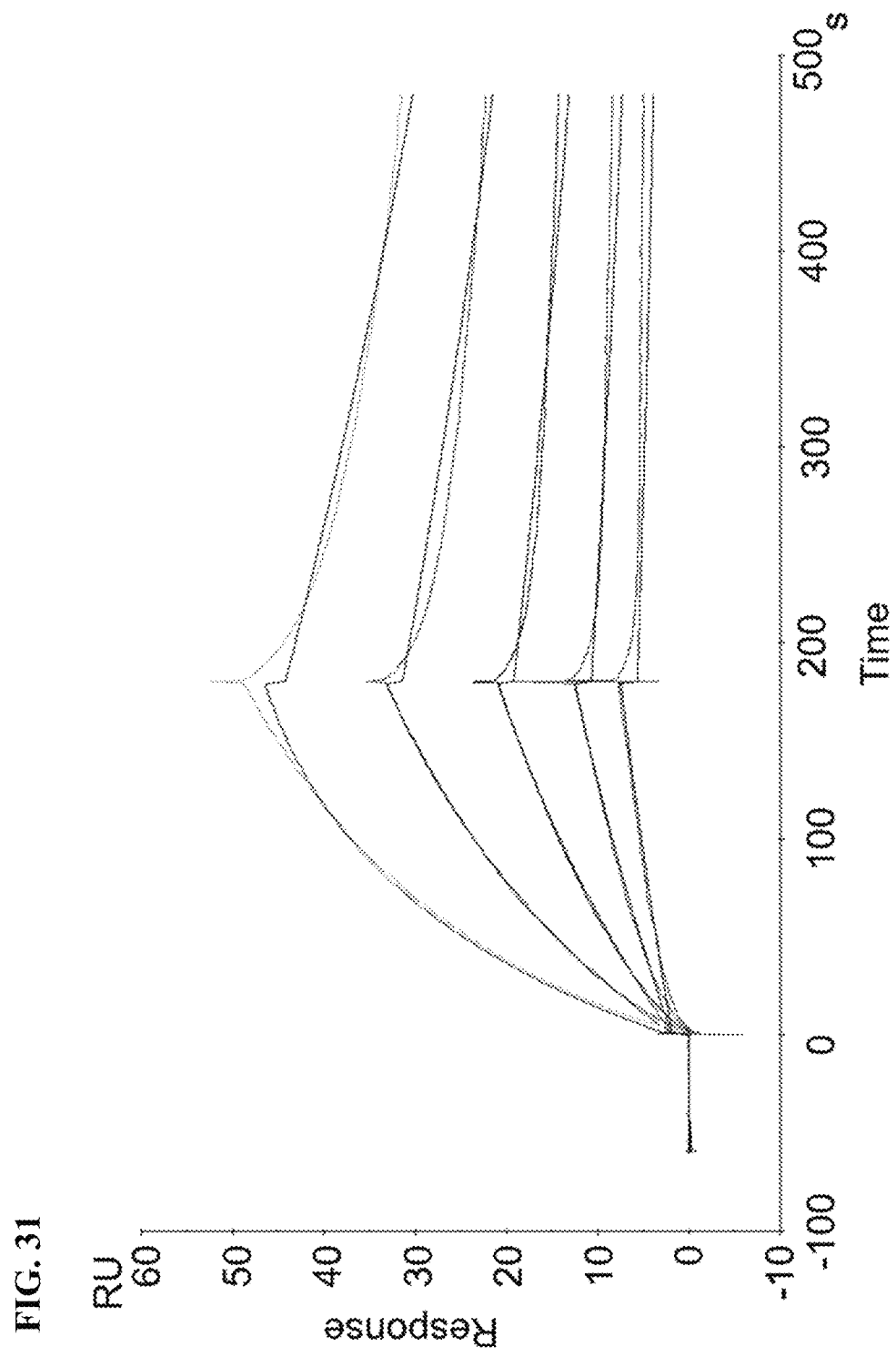
FIG. 31. SPR of an exemplary anti-CD6 antibody-growth factor complex provided herein. SPR with non-cleaved bionic anti-CD6/EGF antibody conjugate with CD6 Ecto is shown. CD6 Ecto was immobilized to a Biacore CM5 chip using NHS chemistry. Concentrations of purified bionic anti-CD6/EGF antibody conjugate ranging from 50 nM to 0.39 nM were flown over the chip at 25° C. On-rate constant $k_{on}$ is $1.69 \times 10^6$ 1/(Ms), the off-rate constant $k_{off}$ is 0.0013 (1/s), and the $K_D$ was determined to be $7.47 \times 10^{-10}$ M.
Figure 32:
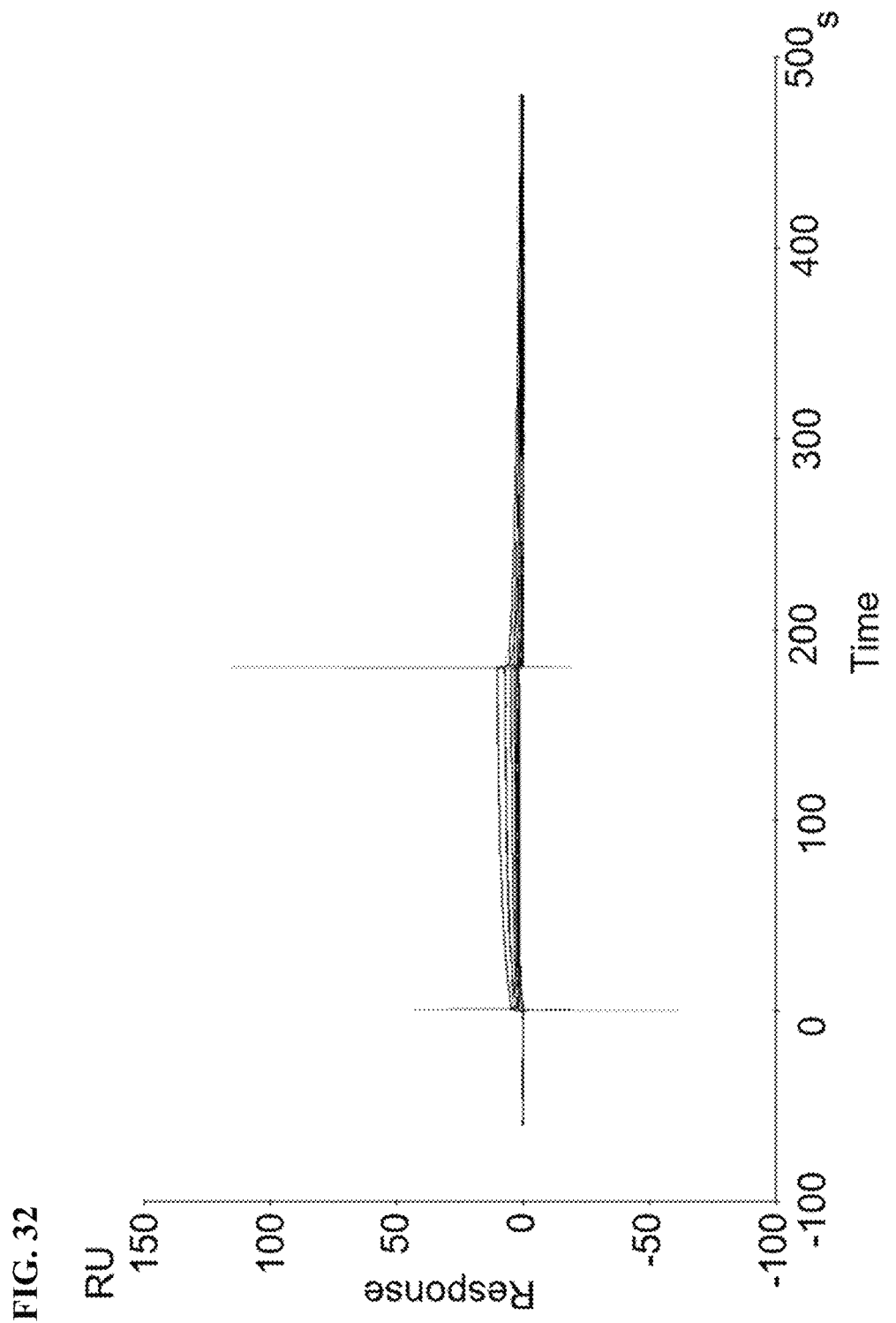
FIG. 32. SPR of an exemplary anti-CD6 antibody-growth factor complex provided herein. SPR with non-cleaved D104N mutant bionic anti-CD6/EGF antibody conjugate with CD6 Ecto is shown. CD6 Ecto was immobilized to a Biacore CM5 chip using NHS chemistry. Concentrations of purified D104N bionic anti-CD6/EGF antibody conjugate ranging from 4 µM to 0.016 µm were flown over the chip at 25° C. On-rate constant $k_{on}$ is $2.8 \times 10^3$ 1/(Ms), the off-rate constant $k_{off}$ is 0.0062 (1/s), and the Kp is determined to be $2.26 \times 10^{-6}$ M.
Figure 33:
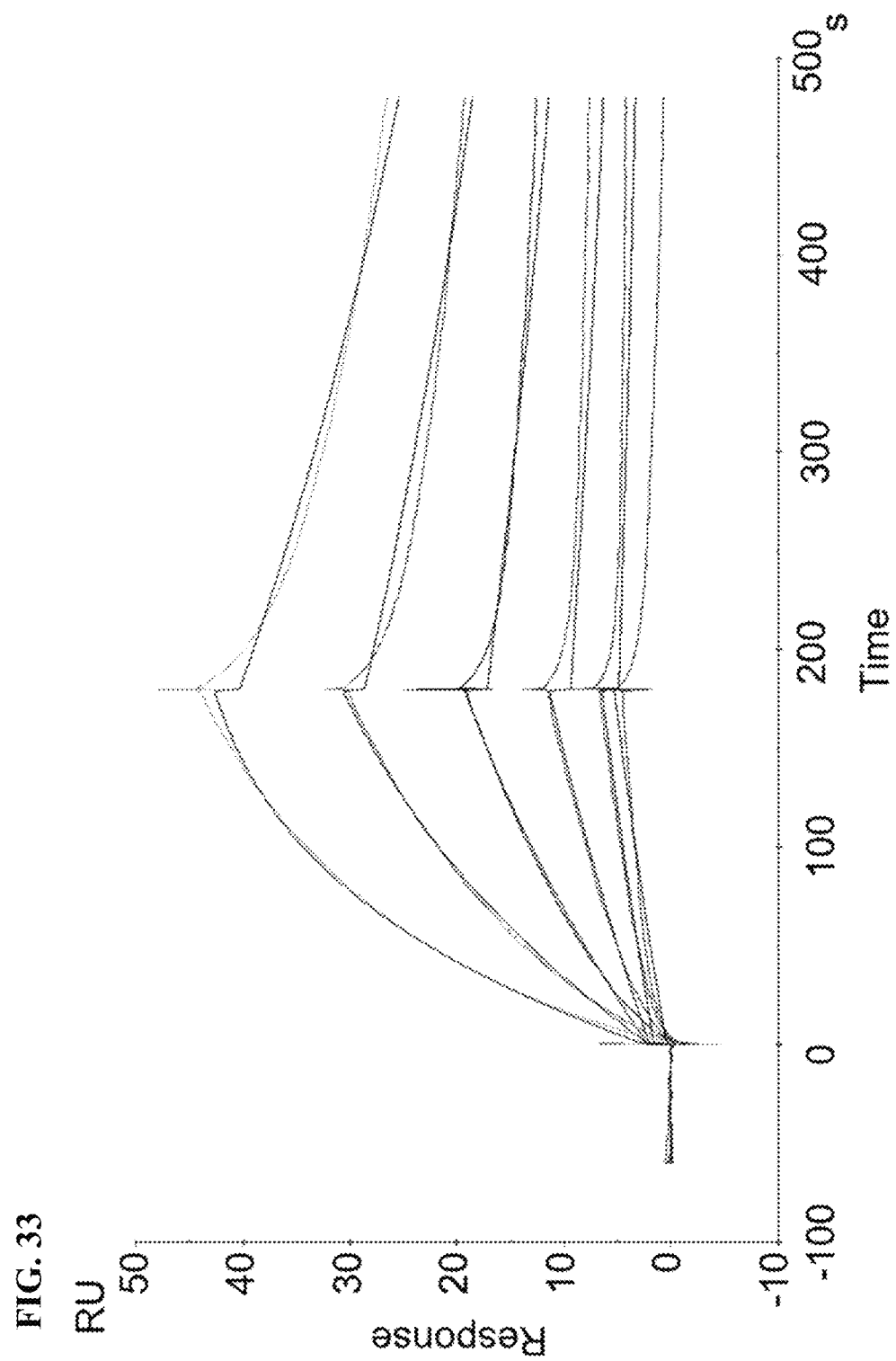
FIG. 33. SPR of an exemplary anti-CD6 antibody-growth factor complex provided herein. SPR with MMP2 cleaved bionic anti-CD6/EGF antibody conjugate with CD6 Ecto is shown. CD6 Ecto was immobilized to a Biacore CM5 chip using NHS chemistry.

The extent of activation of the anti-CD6 antibody-growth factor complex (e.g., bionic anti-CD6/EGF antibody conjugate of SEQ ID NO:38) by granzyme was assayed by SDS-PAGE, as shown in FIG. 29. The affinity of each purified protein to CD6 ecto domain and to EGFR is characterized by SPR. Finally, the activity of the cleaved material is assayed by SPR.

Example 9. Making a Single Point Mutation to Eliminate Cd6 Binding in THE BIONIC SWITCHBLADE ANTI-CDG/EGF ANTIBODY CONJUGATE To better characterize the role of CD6 binding, Applicants sought to block CD6 binding of the bionic anti-CD6/EGF antibody conjugate. Specifically, Applicants sought to introduce one or two mutations at the antigen binding site of the anti-CD6 Fab such that the bionic anti-CD6/EGF antibody conjugate would be minimally perturbed. Careful examination of the anti-CD6 Fab model (FIG. 30), obtained from producing crystals and solving the structure, indicates the mutation of Asp104 in the heavy chain to asparagine may affect an electrostatic interaction with the CD6 antigen.

Therefore, Applicants generated the D104N mutation in the heavy chain of the bionic anti-CD6/EGF antibody conjugate, both in the non-cleavable and cleavable version of the conjugate. SPR was performed with the antibody conjugates with CD6 Ecto immobilized on a CM5 chip. The wild type non-cleaved (FIG. 31) and cleaved (FIG. 33) bionic anti-CD6/EGF antibody conjugate have binding affinities of $K_D=7.47\times10^{-10}$ M and $K_D=7.62\times10^{-10}$ M, respectively. The non-cleaved (FIG. 32) and cleaved (FIG. 34) D104N bionic anti-CD6/EGF antibody conjugate mutant have binding affinities of $Kp=2.26\times10^{-6}$ M and $Kp=8.0\times10^{-7}$ M, respectively.

Example 10. Therapeutic Targeting of the Human Islet Environment WITH ANTI-CD6/EGF CONJUGATED MAB Applicants determined by ELISA binding of human CD6 by the bionic anti-CD6/EGF antibody conjugate of SEQ ID NO:38 and D104N bionic anti-CD6/EGF antibody conjugate mutant (FIG. 35). Applicants confirmed the D105N mutation interferes with CD6 recognition and binding.

EGF from both the bionic anti-CD6/EGF antibody conjugate of SEQ ID NO:38 and D104N bionic anti-CD6/EGF antibody conjugate mutant was shown to reach their cell targets (FIG. 36B). Further, both antibody conjugates demonstrated EGF functionality as shown in FIG. 37. 1.1B4 cells, stimulated with recombinant human EGF or the antibody conjugates showed expression of signaling molecules, pEGFR, pSTAT3, pERK, and pAKT.

REFERENCES

1. Alonso, R., et al., *Towards the definition of a chimpanzee and human conserved CD6 domain lepitope recognized by T1 monoclonal antibody*. Hybridoma (Larchmt), 2008. 27 (4): p. 291-301.
2. Pinkse, G. G., et al., *Autoreactive CD*8 *T cells associated with beta cell destruction in type* 1 *diabetes*. Proc Natl Acad Sci USA, 2005. 102 (51): p. 18425-30.
3. Unger, W. W., et al., Islet-specific CTL cloned from a type 1 diabetes patient cause beta-cell destruction after engraftment into HLA-A2 transgenic NOD/scid/IL2RG null mice. PLOS One, 2012. 7 (11): p. e49213.
4. Garcia Santana, C. A., J. W. Tung, and S. Gulnik, *Human treg cells are characterized by low/negative CD6 expression*. Cytometry A, 2014. 85 (10): p. 901-8.
5. Chen, Y. C., et al., *Mig6 haploinsufficiency protects mice against streptozotocin-induced diabetes*. Diabetologia, 2014.

INFORMAL SEQUENCE LISTING

SEQ ID NO:1 (Nucleic acid sequence of the meditope-enabled anti-CD6 mAb, light chain $C_6$m_lc):

GGTCTCTGGGGAGCTTGCTTGTTCTTTTTGCAGAAGCTCAGAATAAACGC

TCAACTTTGGCCGCCACCATGGACATGAGGGTCCCCGCTCAGCTCCTGGG

GCTCCTGCTGCTCTGGCTCCCAGGTGCCAAATGTGACATCCAGATGACCC

AGTCCCTATTCTGCTGAGCGCCTCCGTGGGCGACCGCGTGACCATCACT

TGCAAAGCCTCCCGGGATATCCGGTCCTACCTCACCTGGTACCAGCAGAG

GACTAACGGATCGCCCAGAACCCTGATCTACTACGCGACTAGCCTGGCCG

ATGGCGTCCCGTCCCGGTTCTCGGGGTCGGGTTCAGGACAGGACTATAGC

CTTACCATCTCATCCCTGGAGTCCGATGACATCGCCGACTACTACTGCCT

GCAACACGGCGAATCTCCCTTCACGTTCGGGTCCGGAACCAAGCTCGAGA

TTAAGCGAAGAAGAGC

SEQ ID NO:2 (Nucleic acid sequence of the meditope-enabled anti-CD6 mAb, heavy chain $C_6m\_hc$)

GCTCTTCTTCAGAGGTGCAGCTTGTGGAATCGGGTGGCGGACTGGTCAAG

CCTGGGGGATCGCTGAAACTGAGCTGTGCAGCCAGCGGTTTCAAGTTCTC

ACGCTACGCCATGTCCTGGGTCAGACAGGCGCCGGGAAAGCGCCTGGAAT

GGGTGGCTACTATCTCCTCCGGCGGATCCTACATCTACTACCCCGACTCC

GTGAAGGGCCGGTTCACCATTAGCCGCGACAACGTGAAGAACACTCTGTA

CCTCCAAATGTCAAGCCTGAGGTCTGAGGATACCGCCATCTACTATTGCG

CCCGGCGGGACTACGACTTGGATTACTTTGACTCCTGGGGCCAGGGGACC

CTCGTGACCGTGTCCTCGGCCAAGAGACC

SEQ ID NO:3 (Nucleic acid sequence of the meditope-enabled anti-CD6 mAb $C_6m\_assembly$)

GGGGAGCTTGCTTGTTCTTTTTGCAGAAGCTCAGAATAAACGCTCAACTT

TGGCCGCCACCATGGACATGAGGGTCCCCGCTCAGCTCCTGGGGCTCCTG

CTGCTCTGGCTCCCAGGTGCCAAATGTGACATCCAGATGACCCAGTCCCC

TATTCTGCTGAGCGCCTCCGTGGGCGACCGCGTGACCATCACTTGCAAAG

CCTCCCGGGATATCCGGTCCTACCTCACCTGGTACCAGCAGAGGACTAAC

GGATCGCCCAGAACCCTGATCTACTACGCGACTAGCCTGGCCGATGGCGT

CCCGTCCCGGTTCTCGGGGTCGGGTTCAGGACAGGACTATAGCCTTACCA

TCTCATCCCTGGAGTCCGATGACATCGCCGACTACTACTGCCTGCAACAC

GGCGAATCTCCCTTCACGTTCGGGTCCGGAACCAAGCTCGAGATTAAGCG

AACTGTGGCTGCACCATCTGTCTTCATCTTCCCGCCATCTGATGAGCAGT

TGAAATCTGGAACTGCCTCTGTTGTGTGCCTGCTGAATAACTTCTATCCC

AGAGAGGCCAAAGTACAGTGGAAGGTGGATAACGCCCTCCAATCGGGTAA

CTCCCAGGAGAGTGTCACAGAGCAGGACAGCAAGGACAGCACCTACAGCC

TCAGCAGCACCCTGACGCTGAGCAAAGCAGACTACGAGAAACACAAAGTC

TACGCCTGCGAAGTCACCCATCAGGGCCTGAGCTCGCCCGTCACAAAGAG

CTTCAACAGGGGAGAGTGTTAATAGCTCTTAAAAAATTCCGCCCCCCCCC

TAACGTTACTGGCCGAAGCCGCTTGGAATAAGGCCGGTGTGCGTTTGTCT

ATATGTTATTTTCCACCATATTGCCGTCTTTTGGCAATGTGAGGGCCCGG

AAACCTGGCCCTGTCTTCTTGACGAGCATTCCTAGGGGTCTTTCCCCTCT

CGCCAAAGGAATGCAAGGTCTGTTGAATGTCGTGAAGGAAGCAGTTCCTC

TGGAAGCTTCTTGAAGACAAACAACGTCTGTAGCGACCCTTTGCAGGCAG

CGGAACCCCCCACCTGGCGACAGGTGCCTCTGCGGCCAAAAGCCACGTGT

ATAAGATACACCTGCAAAGGCGGCACAACCCCAGTGCCACGTTGTGAGTT

GGATAGTTGTGGAAAGAGTCAAATGGCTCTCCTCAAGCGTATTCAACAAG

GGGCTGAAGGATGCCCAGAAGGTACCCCATTGTATGGGATCTGATCTGGG

GCCTCGGTACACATGCTTTACATGTGTTTAGTCGAGGTTAAAAAACGTCT

AGGCCCCCCGAACCACGGGGACGTGGTTTTCCTTTGAAAAACACGATGAT

AATATGGCCACAACCATGGGCTGGTCCCTGATCCTGCTGTTCCTGGTGGC

CGTGGCCACGCGTGTGCTGTCAGAGGTGCAGCTTGTGGAATCGGGTGGCG

GACTGGTCAAGCCTGGGGGATCGCTGAAACTGAGCTGTGCAGCCAGCGGT

TTCAAGTTCTCACGCTACGCCATGTCCTGGGTCAGACAGGCGCCGGGAAA

GCGCCTGGAATGGGTGGCTACTATCTCCTCCGGCGGATCCTACATCTACT

ACCCCGACTCCGTGAAGGGCCGGTTCACCATTAGCCGCGACAACGTGAAG

AACACTCTGTACCTCCAAATGTCAAGCCTGAGGTCTGAGGATACCGCCAT

CTACTATTGCGCCCGGCGGGACTACGACTTGGATTACTTTGACTCCTGGG

GCCAGGGGACCCTCGTGACCGTGTCCTCGGCCA

SEQ ID NO:4 (Human EGF)
NSDSECPLSHDGYCLHDGVCMYIEALDKY-ACNCVVGYIGERCQYRDLKWWELR

SEQ ID NO:5 (Fragment of human EGF)
DGYCLHDGVCMYIEALDKYAC

SEQ ID NO:6 (Human EGF domain, amino acids 12-32, quasi-cyclic peptide (Cys4-Cys21) with a Cys-to-Ser substitution at position 10))
DGYCLHDGVSMYIEALDKYAC SEQ ID NO:7 (Human CD6 amino acid sequence; NCBI Reference Number: NP_006716.3)

MWLFFGITGLLTAALSGHPSPAPPDQLNTSSAESELWEPGERLPVRLTNG

SSSCSGTVEVRLEASWEPACGALWDSRAAEAVCRALGCGGAEAASQLAPP

TPELPPPPAAGNTSVAANATLAGAPALLCSGAEWRLCEVVEHACRSDGRR

ARVTCAENRALRLVDGGGACAGRVEMLEHGEWGSVCDDTWDLEDAHVVCR

QLGCGWAVQALPGLHFTPGRGPIHRDQVNCSGAEAYLWDCPGLPGQHYCG

HKEDAGAVCSEHQSWRLTGGADRCEGQVEVHFRGVWNTVCDSEWYPSEAK

VLCQSLGCGTAVERPKGLPHSLSGRMYYSCNGEELTLSNCSWRFNNSNLC

SQSLAARVLCSASRSLHNLSTPEVPASVQTVTIESSVTVKIENKESRELM

LLIPSIVLGILLLGSLIFIAFILLRIKGKYALPVMVNHQHLPTTIPAGSN

SYQPVPITIPKEVFMLPIQVQAPPPEDSDSGSDSDYEHYDFSAQPPVALT

TFYNSQRHRVTDEEVQQSRFQMPPLEEGLEELHASHIPTANPGHCITDPP

SLGPQYHPRSNSESSTSSGEDYCNSPKSKLPPWNPQVFSSERSSFLEQPP

NLELAGTQPAFSAGPPADDSSSTSSGEWYQNFQPPPQPPSEEQFGCPGSP

SPQPDSTDNDDYDDISAA

SEQ ID NO:8 (Human CD6 amino acid sequence; NCBI Reference Number: NP_001241679.1)

MWLFFGITGLLTAALSGHPSPAPPDQLNTSSAESELWEPGERLPVRLTNG
SSSCSGTVEVRLEASWEPACGALWDSRAAEAVCRALGCGGAEAASQLAPP
TPELPPPPAAGNTSVAANATLAGAPALLCSGAEWRLCEVVEHACRSDGRR
ARVTCAENRALRLVDGGGACAGRVEMLEHGEWGSVCDDTWDLEDAHVVCR
QLGCGWAVQALPGLHFTPGRGPIHRDQVNCSGAEAYLWDCPGLPGQHYCG
HKEDAGAVCSEHQSWRLTGGADRCEGQVEVHFRGVWNTVCDSEWYPSEAK
VLCQSLGCGTAVERPKGLPHSLSGRMYYSCNGEELTLSNCSWRFNNSNLC
SQSLAARVLCSASRSLHNLSTPEVPASVQTVTIESSVTVKIENKESRELM
LLIPSIVLGILLLGSLIFIAFILLRIKGKYVFMLPIQVQAPPPEDSDSGS
DSDYEHYDFSAQPPVALTTFYNSQRHRVTDEEVQQSRFQMPPLEEGLEEL
HASHIPTANPGHCITDPPSLGPQYHPRSNSESSTSSGEDYCNSPKSKLPP
WNPQVFSSERSSFLEQPPNLELAGTQPAFSGSPSPQPDSTDNDDYDDISA
A

SEQ ID NO:9 (human CD6 amino acid sequence; NCBI Reference Number: NP_001241680.1)

MWLFFGITGLLTAALSGHPSPAPPDQLNTSSAESELWEPGERLPVRLTNG
SSSCSGTVEVRLEASWEPACGALWDSRAAEAVCRALGCGGAEAASQLAPP
TPELPPPPAAGNTSVAANATLAGAPALLCSGAEWRLCEVVEHACRSDGRR
ARVTCAENRALRLVDGGGACAGRVEMLEHGEWGSVCDDTWDLEDAHVVCR
QLGCGWAVQALPGLHFTPGRGPIHRDQVNCSGAEAYLWDCPGLPGQHYCG
HKEDAGAVCSEHQSWRLTGGADRCEGQVEVHFRGVWNTVCDSEWYPSEAK
VLCQSLGCGTAVERPKGLPHSLSGRMYYSCNGEELTLSNCSWRFNNSNLC
SQSLAARVLCSASRSLHNLSTPEVPASVQTVTIESSVTVKIENKESRELM
LLIPSIVLGILLLGSLIFIAFILLRIKGKYALPVMVNHQHLPTTIPAGSN
SYQPVPITIPKEDSQRHRVTDEEVQQSRFQMPPLEEGLEELHASHIPTAN
PGHCITDPPSLGPQYHPRSNSESSTSSGEDYCNSPKSKLPPWNPQVFSSE
RSSFLEQPPNLELAGTQPAFSGSPSPQPDSTDNDDYDDISAA

SEQ IDO NO: 10 (Anti-CD6 antibody light chain)

DIQMTQSPSSLSASVGDRVTITCKASRDIRSYLTWYQQKPGKAPKTLIYY
ATSLADGVPSRFSGSGSGQDYSLTISSLESDDTATYYCLQHGESPFTFGS
GTKLEIKRA

SEQ ID NO:11 (Anti-CD6 antibody heavy chain)

EVQLVESGGGLVKPGGSLKLSCAASGFKFSRYAMSWVRQAPGKRLEWVAT
ISSGGSYIYYPDSVKGRFTISRDNVKNTLYLQMSSLRSEDTAMYYCARRD
YDLDYFDSWGQGTLVTVSS

SEQ ID NO:12 (EGF protein) MNSDSECPLSHDGY-CLHDGVCMYIEALDKYACNCVVGYIGER-CQYRDLKWWELR SEQ ID NO:13 (Anti-CD6 mAb meditope enabled with IgG1 Fc)

ACTTACGGTAAATGGCCCGCCTGGCTGACCGCCCAACGACCCCCGCCCATTGACGTC
AATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCC
AAGTCCGCCCCCTATTGACGTCAATGACGGTAAATGGCCCGCCTGGCATTATGCCCA
GTACATGACCTTACGGGACTTTCCTACTTGGCAGTACATCTACGTATTAGTCATCGCT
ATTACCATGGTGATGCGGTTTTGGCAGTACACCAATGGGCGTGGATAGCGGTTTGAC
TCACGGGGATTTCCAAGTCTCCACCCCATTGACGTCAATGGGAGTTTGTTTTGGCAC
CAAAATCAACGGGACTTTCCAAAATGTCGTAATAACCCCGCCCCGTTGACGCAAAT
GGGCGGTAGGCGTGTACGGTGGGAGGTCTATATAAGCAGAGCTCGTTTAGTGAACC
GTCAGATCCTCACTCTCTTCCGCATCGCTGTCTGCGAGGGCCAGCTGTTGGGCTCGC
GGTTGAGGACAAACTCTTCGCGGTCTTTCCAGTACTCTTGGATCGGAAACCCGTCGG
CCTCCGAACGGTACTCCGCCACCGAGGGACCTGAGCGAGTCCGCATCGACCGGATC
GGAAAACCTCTCGAGAAAGGCGTCTAACCAGTCACAGTCGCAAGGTAGGCTGAGCA
CCGTGGCGGGCGGCAGCGGGTGGCGGTCGGGGTTGTTTCTGGCGGAGGTGCTGCTG
ATGATGTAATTAAAGTAGGCGGTCTTGAGACGGCGGATGGTCGAGGTGAGGTGTGG
CAGGCTTGAGATCCAGCTGTTGGGGTGAGTACTCCCTCTCAAAAGCGGGCATTACTT
CTGCGCTAAGATTGTCAGTTTCCAAAAACGAGGAGGATTTGATATTCACCTGGCCCG
ATCTGGCCATACACTTGAGTGACAATGACATCCACTTTGCCTTTCTCTCCACAGGTGT

-continued

CCACTCCCAGGGGAGCTTGCTTGTTCTTTTTGCAGAAGCTCAGAATAAACGCTCAAC

TTTGGCCGCCACCATGGACATGAGGGTCCCCGCTCAGCTCCTGGGGCTCCTGCTGCT

CTGGCTCCCAGGTGCCAAATGTGACATCCAGATGACCCAGTCCCCTATTCTGCTGAG

CGCCTCCGTGGGCGACCGCGTGACCATCACTTGCAAAGCCTCCCGGGATATCCGGTC

CTACCTCACCTGGTACCAGCAGAGGACTAACGGATCGCCCAGAACCCTGATCTACTA

CGCGACTAGCCTGGCCGATGGCGTCCCGTCCCGGTTCTCGGGGTCGGGTTCAGGACA

GGACTATAGCCTTACCATCTCATCCCTGGAGTCCGATGACATCGCCGACTACTACTG

CCTGCAACACGGCGAATCTCCCTTCACGTTGGGGTCCGGAACCAAGCTCGAGATTAA

GCGAACTGTGGCTGCACCATCTGTCTTCATCTTCCCGCCATCTGATGAGCAGTTGAA

ATCTGGAACTGCCTCTGTTGTGTGCCTGCTGAATAACTTCTATCCCAGAGAGGCCAA

AGTACAGTGGAAGGTGGATAACGCCCTCCAATCGGGTAACTCCCAGGAGAGTGTCA

CAGAGCAGGACAGCAAGGACAGCACCTACAGCCTCAGCAGCACCCTGACGCTGAGC

AAAGCAGACTACGAGAAACACAAAGTCTACGCCTGCGAAGTCACCCATCAGGGCCT

GAGCTCGCCCGTCACAAAGAGCTTCAACAGGGGAGAGTGTTAATAGCTCTTAAAAA

ATTCCGCCCCCCCCCTAACGTTACTGGCCGAAGCCGCTTGGAATAAGGCCGGTGTGC

GTTTGTCTATATGTTATTTTCCACCATATTGCCGTCTTTTGGCAATGTGAGGGCCCGG

AAACCTGGCCCTGTCTTCTTGACGAGCATTCCTAGGGGTCTTTCCCCTCTCGCCAAA

GGAATGCAAGGTCTGTTGAATGTCGTGAAGGAAGCAGTTCCTCTGGAAGCTTCTTGA

AGACAAACAACGTCTGTAGCGACCCTTTGCAGGCAGCGGAACCCCCCACCTGGCGA

CAGGTGCCTCTGCGGCCAAAAGCCACGTGTATAAGATACACCTGCAAAGGCGGCAC

AACCCCAGTGCCACGTTGTGAGTTGGATAGTTGTGGAAAGAGTCAAATGGCTCTCCT

CAAGCGTATTCAACAAGGGGCTGAAGGATGCCCAGAAGGTACCCCATTGTATGGGA

TCTGATCTGGGGCCTCGGTACACATGCTTTACATGTGTTTAGTCGAGGTTAAAAAAC

GTCTAGGCCCCCCGAACCACGGGGACGTGGTTTTCCTTTGAAAAACACGATGATAAT

ATGGCCACAACCATGGGCTGGTCCCTGATCCTGCTGTTCCTGGTGGCCGTGGCCACG

CGTGTGCTGTCAGAGGTGCAGCTTGTGGAATCGGGTGGCGGACTGGTCAAGCCTGG

GGGATCGCTGAAACTGAGCTGTGCAGCCAGCGGTTTCAAGTTCTCACGCTACGCCAT

GTCCTGGGTCAGACAGGCGCCGGGAAAGCGCCTGGAATGGGTGGCTACTATCTCCT

CCGGCGGATCCTACATCTACTACCCCGACTCCGTGAAGGGCCGGTTCACCATTAGCC

GCGACAACGTGAAGAACACTCTGTACCTCCAAATGTCAAGCCTGAGGTCTGAGGAT

ACCGCCATCTACTATTGCGCCCGGCGGGACTACGACTTGGATTACTTTGACTCCTGG

GGCCAGGGGACCCTCGTGACCGTGTCCTCGGCCAGCACCAAGGGCCCATCGGTCTTC

CCCCTGGCACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGCCCTGAC

CAGCGGCGTGCACACCTTCCCGGCTGTCCTACAGTCCTCAGGACTCTACTCCCTCAG

CAGCGTGGTGACCGTGCCCTCCAGCAGCTTGGGCACCCAGACCTACATCTGCAACGT

GAATCACAAGCCCAGCAACACCAAGGTGGACAAGAAAGTTGAGCCCAAATCTTGTG

ACAAAACTCACACATGCCCACCGTGCCCAGCACCTGAACTCCTGGGGGGACCGTCA

GTCTTCCTCTTCCCCCCAAAACCCAAGGACACCCTCATGATCTCCCGGACCCCTGAG

GTCACATGCGTGGTGGTGGACGTGAGCCACGAAGACCCTGAGGTCAAGTTCAACTG

GTACGTGGACGGCGTGGAGGTGCATAATGCCAAGACAAAGCCGCGGGAGGAGCAG

-continued

```
TACAACAGCACGTACCGGGTGGTCAGCGTCCTCACCGTCCTGCACCAGGACTGGCTG

AATGGCAAGGAGTACAAGTGCAAGGTCAGCAACAAAGCCCTCCCAGCCCCCATCGA

GAAAACCATCTCCAAAGCCAAAGGGCAGCCCCGAGAACCACAGGTGTACACCCTGC

CCCCATCCCGGGATGAGCTGACCAAGAACCAGGTCAGCCTGACCTGCCTGGTCAAA

GGCTTCTATCCCAGCGACATCGCCGTGGAGTGGGAGAGCAATGGGCAGCCGGAGAA

CAACTACAAGACCACGCCTCCCGTGCTGGACTCCGACGGCTCCTTCTTCCTCTACAG

CAAGCTCACCGTGGACAAGAGCAGGTGGCAGCAGGGGAACGTCTTCTCATGCTCCG

TGATGCATGAGGCTCTGCACAACCACTACACGCAGAAGTCCCTCTCCCTGTCTCCGG

GTAAATAGGCGGCCGCTAAAAGCGGCCGCTCGAGGCCGGCAAGGCCGGATCCCCCG

ACCTCTGGCTAATAAAGGAAATTTATTTTCATTGCAATAGTGTGTTGGAATTTTTTGT

GTCTCTCACTCGGAAGGACATATGGGAGGGCAAATCATTTAAAACATCAGAATGAG

TATTTGGTTTAGAGTTTGGCAACATATGCCCATATGCTGGCTGCCATGAACAAAGGT

TGGCTATAAAGAGGTCATCAGTATATGAAACAGCCCCCTGCTGTCCATTCCTTATTC

CATAGAAAAGCCTTGACTTGAGGTTAGATTTTTTTTATATTTTGTTTTGTGTTATTTTT

TTCTTTAACATCCCTAAAATTTTCCTTACATGTTTTACTAGCCAGATTTTTCCTCCTCT

CCTGACTACTCCCAGTCATAGCTGTCCCTCTTCTCTTATGGAGATCTCAGCCTTGAGC

GGTATCAGCTCACTCAAAGGCGGTAATACGGTTATCCACAGAATCAGGGGATAACG

CAGGAAAGAACATGTGAGCAAAAGGCCAGCAAAAGGCCAGGAACCGTAAAAAGGC

CGCGTTGCTGGCGTTTTTCCATAGGCTCCGCCCCCCTGACGAGCATCACAAAAATCG

ACGCTCAAGTCAGAGGTGGCGAAACCCGACAGGACTATAAAGATACCAGGCGTTTC

CCCCTGGAAGCTCCCTCGTGCGCTCTCCTGTTCCGACCCTGCCGCTTACCGGATACCT

GTCCGCCTTTCTCCCTTCGGGAAGCGTGGCGCTTTCTCATAGCTCACGCTGTAGGTAT

CTCAGTTCGGTGTAGGTCGTTCGCTCCAAGCTGGGCTGTGTGCACGAACCCCCCGTT

CAGCCCGACCGCTGCGCCTTATCCGGTAACTATCGTCTTGAGTCCAACCCGGTAAGA

CACGACTTATCGCCACTGGCAGCAGCCACTGGTAACAGGATTAGCAGAGCGAGGTA

TGTAGGCGGTGCTACAGAGTTCTTGAAGTGGTGGGCTAACTACGGCTACACTAGAA

GAACAGTATTTGGTATCTGCGCTCTGCTGAAGCCAGTTACCTTCGGAAAAAGAGTTG

GTAGCTCTTGATCCGGCAAACAAACCACCGCTGGTAGCGGTGGTTTTTTTGTTTGCA

AGCAGCAGATTACGCGCAGAAAAAAAGGATCTCAAGAAGATCCTTTGATCTTTTCT

ACGGGGTCTGACGCTCAGTGGAACGACGCGCGCGTAACTCACGTTAAGGGATTTTG

GTCATGAGTTAGAAAAACTCATCGAGCATCAAATGAAACTGCAATTTATTCATATCA

GGATTATCAATACCATATTTTTGAAAAAGCCGTTTCTGTAATGAAGGAGAAAACTCA

CCGAGGCAGTTCCATAGGATGGCAAGATCCTGGTATCGGTCTGCGATTCCGACTCGT

CCAACATCAATACAACCTATTAATTTCCCCTCGTCAAAAATAAGGTTATCAAGTGAG

AAATCACCATGAGTGACGACTGAATCCGGTGAGAATGGCAAAAGTTTATGCATTTCT

TTCCAGACTTGTTCAACAGGCCAGCCATTACGCTCGTCATCAAAATCACTCGCATCA

ACCAAACCGTTATTCATTCGTGATTGCGCCTGAGCGAGGCGAAATACGCGATCGCTG

TTAAAAGGACAATTACAAACAGGAATCGAGTGCAACCGGCGCAGGAACACTGCCAG

CGCATCAACAATATTTTCACCTGAATCAGGATATTCTTCTAATACCTGGAACGCTGT

TTTTCCGGGGATCGCAGTGGTGAGTAACCATGCATCATCAGGAGTACGGATAAAAT
```

-continued
```
GCTTGATGGTCGGAAGTGGCATAAATTCCGTCAGCCAGTTTAGTCTGACCATCTCAT

CTGTAACATCATTGGCAACGCTACCTTTGCCATGTTTCAGAAACAACTCTGGCGCAT

CGGGCTTCCCATACAAGCGATAGATTGTCGCACCTGATTGCCCGACATTATCGCGAG

CCCATTTATACCCATATAAATCAGCATCCATGTTGGAATTTAATCGCGGCCTCGACG

TTTCCCGTTGGATATGGCTCATTTTTTACTTCCTCACCTTGTCGTATTATACTATGCCG

ATATACTATGCCGATGATTAATTGTCGACACTGCGGGGGCTCTATATATGGAGTTCC

GCGTTACATA
```

SEQ ID NO:14 (Human CD6 Domain 1 amino acid sequence 45-156, being positions R61 and E63 critical for binding of the anti-CD6 mAb)

```
VRLTNGSSSCSGTVEVRLEASWEPACGALWDSRAAEAVCRALGCGGAEAA
SQLAPPTPELPPPPAAGNTSVAANATLAGAPALLCSGAEWRLCEVVEHAC
RSDGRRARVTCA
```

SEQ ID NO:15 (Anti-CD6 heavy chain, HCDRI NA) GTCCAACTTGTTGAATCAGGTGGGGGCTGGT-CAAACCCGGGGGCTCTCTGAAACT AAGT SEQ ID NO: 16 (Anti-CD6 heavy chain, HCDR2 NA) TTCTCTCGGTACGCTATGTCGTGGGTCA-GACAAGCGCCCGGCAAA SEQ ID NO:17 (Anti-CD6 heavy chain, HCDR3 NA) CGTGATTATGATCTAGACTACTTTGACTCCTGGGGT-CAAGGTACGCTCGTGACGGTT SEQ ID NO:18 (Anti-CD6 heavy chain, HCDR1 AA) VQLVESGGGLVKPGGSLKLS SEQ ID NO:19 (Anti-CD6 heavy chain, HCDR2 AA) FSRYAMSWVRQAPGK SEQ ID NO:20 (Anti-CD6 heavy chain, HCDR3 AA) RDYDLDYFDSWGQGTLVTV

SEQ ID NO:21

```
MGWSLILLFLVAVATRVLSHPSPAPPDQLNTSSAESELWEPGERLPVRLI
NGSSSCSGTVEVRLEASWEPACGALWDSRAAEAVCRALGCGGAEAASQLA
PPTPELPPPPAAGNTSVAANATLAGAPALLCSGAEWRLCEVVEHACRSDG
RRARVTCAENRALRLVDGGGACAGRVEMLEHGEWGSVCDDTWDLEDAHVV
CRQLGCGWAVQALPGLHFTPGRGPIHRDQVNCSGAEAYLWDCPGLPGQHY
CGHKEDAGVVCSEHQSWRLTGGADRCEGQVEVHFRGVWNTVCDSEWYPSE
AKVLCQSLGCGTAVERPKGLPHSLSGRMYYSCNGEELTLSNCSWRFNNSN
LCSQSLAARVLCSASRGHHHHHH
```

SEQ ID NO:22 (CQFD, Meditope) CQFDLSTRRLKC

SEQ ID NO:23 (cQYN, Meditope) CQYNLSSRALKC

SEQ ID NO:24 (VL of anti-CD6)

```
IQMTQSPSSLSASVGDRVTITCKASRDIRSYLTWYQQKPGKAPKTLIYYA
TSLADGVPSRFSGSGSGQ
```

SEQ ID NO:25 (Fragment of VL of anti-CD6) DIQMTQSPSSLSASVGDRVTITCKASRDIRSY

SEQ ID NO:26 (VL of anti-CD6)

```
LTWYQQKPGKAPKTLIYYATSLADGVPSRFSGSGSGQDYSLTISSLESDD
TATYYCLQHGESPFT
```

SEQ ID NO:27 (Fragment of VL of anti-CD6) FGSGTKLEIKRA

SEQ ID NO:28 (Fragment of VH of anti-CD6) EVOLVESGGGLVKPGGSLKLSCAASGFKFSRYAMS

SEQ ID NO:29 (Fragment of VH of anti-CD6) WVRQAPGKRLEWVATISSGG

SEQ ID NO:30 (Fragment of VH of anti-CD6) SYIYYPDSVKGRFTISRDNVKNTLYLQMSSLRSED-TAMYYCARRDYDLDYFDS SEQ ID NO:31 (Fragment of VH of anti-CD6) WGQGTLVTVSS SEQ ID NO:32 (Bionic anti-human CD6 antibody conjugate with MMP2/9 cleavage site)

```
DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECASASAAASSASSAASSNSDSECPLSHDGYCLHDGVC
MYIEALDKYACNCVVGYIGERCQYRDLKWWELRGSGVLPASLYSGSEVQL
VESGGGLVKPGGSLKLSCAASGFKFSRYAMSWVRQAPGKRLEWVATISSG
GSYIYYPDSVKGRFTISRDNVKNTLYLQMSSLRSEDTAIYYCARRDYDLD
YFDSWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK
```

SEQ ID NO:33 (Anti-CD6 LC of the bionic anti-human CD6 antibody conjugate of SEQ ID NO:32)

DIQMTQSPILLSASVGDRVTITCKASRDIRSYLTWYQQRINGSPRTLIYY

ATSLADGVPSRFSGSGSGQDYSLTISSLESDDIADYYCLQHGESPFTFGS

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO:34 (Linker of the bionic antibody conjugate of SEQ ID NO:32) ASASAAASSASSAASS SEQ ID NO:35 (Linker MMP2/9 cleavage site of the bionic anti-human CD6 antibody conjugate of SEQ ID NO:32) GSGVLPASLYSGS SEQ ID NO:36 (Anti-CD6 HC of the bionic anti-human CD6 antibody conjugate of SEQ ID NO:32)

EVQLVESGGGLVKPGGSLKLSCAASGFKFSRYAMSWVRQAPGKRLEWVAT

ISSGGSYIYYPDSVKGRFTISRDNVKNTLYLQMSSLRSEDTAIYYCARRD

YDLDYFDSWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSC

SEQ ID NO:37 (IgG1-Fc of the bionic anti-human CD6 antibody conjugate of SEQ ID NO: 32)

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK

SEQ ID NO:38 (Base bionic CD6-EGF antibody conjugate with granzyme cleavage site)

DIQMTQSPILLSASVGDRVTITCKASRDIRSYLTWYQQRINGSPRTLIYY

ATSLADGVPSRFSGSGSGQDYSLTISSLESDDIADYYCLQHGESPFTFGS

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECASASAAASSASSAASSNSDSECPLSHDGYCLHDGVC

MYIEALDKYACNCVVGYIGERCQYRDLKWWELRGSGSGIEPDSGGSEVQL

VESGGGLVKPGGSLKLSCAASGFKFSRYAMSWVRQAPGKRLEWVATISSG

GSYIYYPDSVKGRFTISRDNVKNTLYLQMSSLRSEDTAIYYCARRDYDLD

YFDSWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

SEQ ID NO:39 (Linker with granzyme cleavage site of the bionic anti-CD6-EGF antibody conjugate of SEQ ID NO:38)
GSGSGIEPDSGGS SEQ ID NO:40 (Anti-CD6 HC of the bionic anti-CD6-EGF antibody conjugate of SEQ ID NO: 38)

EVQLVESGGGLVKPGGSLKLSCAASGFKFSRYAMSWVRQAPGKRLEWVAT

ISSGGSYIYYPDSVKGRFTISRDNVKNTLYLQMSSLRSEDTAIYYCARRD

YDLDYFDSWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHT

SEQ ID NO:41 (IgG1-Fc of the bionic anti-CD6-EGF antibody conjugate of SEQ ID NO: 38)

CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK

SEQ ID NO:42 (CD6-minus2L bionic CD6-EGF antibody conjugate with granzyme cleavage site)

DIQMTQSPILLSASVGDRVTITCKASRDIRSYLTWYQQRTNGSPRTLIYY

ATSLADGVPSRFSGSGSGQDYSLTISSLESDDIADYYCLQHGESPFTFGS

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECASASAAASSASSAANSDSECPLSHDGYCLHDGVCMY

IEALDKYACNCVVGYIGERCQYRDLKWWELRGSGSGIEPDSGGSEVQLVE

SGGGLVKPGGSLKLSCAASGFKFSRYAMSWVRQAPGKRLEWVATISSGGS

YIYYPDSVKGRFTISRDNVKNTLYLQMSSLRSEDTAIYYCARRDYDLDYF

DSWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPGK

SEQ ID NO:43 (Linker of the CD6-minus2L bionic CD6-EGF antibody conjugate of SEQ ID NO:42)
ASASAAASSASSAA SEQ ID NO:44 (CD6-minus4L bionic CD6-EGF antibody conjugate with granzyme cleavage site)

DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECASASAAASSASSNSDSECPLSHDGYCLHDGVCMYIE
ALDKYACNCVVGYIGERCQYRDLKWWELRGSGSGIEPDSGGSEVQLVESG
GGLVKPGGSLKLSCAASGFKFSRYAMSWVRQAPGKRLEWVATISSGGSYI
YYPDSVKGRFTISRDNVKNTLYLQMSSLRSEDTAIYYCARRDYDLDYFDS
WGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFL
YSKLTVDKSRWQQGNVFSCSVMHEALHNHYTQKSLSLSPGK

SEQ ID NO:45 (Linker of the CD6-minus4L bionic CD6-EGF antibody conjugate of SEQ ID NO:44)
ASASAAASSASS SEQ ID NO:46 (CD6-minus6L bionic CD6-EGF antibody conjugate with granzyme cleavage site)

DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECASASAAASSANSDSECPLSHDGYCLHDGVCMYIEAL
DKYACNCVVGYIGERCQYRDLKWWELRGSGSGIEPDSGGSEVQLVESGGG
LVKPGGSLKLSCAASGFKFSRYAMSWVRQAPGKRLEWVATISSGGSYIYY
PDSVKGRFTISRDNVKNTLYLQMSSLRSEDTAIYYCARRDYDLDYFDSWG
QGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYS
KLTVDKSRWQQGNVFSCSVMHEALHNHYTQKSLSLSPGK

SEQ ID NO:47 (Linker of the CD6-minus6L bionic CD6-EGF antibody conjugate of SEQ ID NO:46)
ASASAAASSA SEQ ID NO:48 (CD6-minus8L bionic CD6-EGF antibody conjugate with granzyme cleavage site)

DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECASASAAASNSDSECPLSHDGYCLHDGVCMYIEALDK
YACNCVVGYIGERCQYRDLKWWELRGSGSGIEPDSGGSEVQLVESGGGLV
KPGGSLKLSCAASGFKFSRYAMSWVRQAPGKRLEWVATISSGGSYIYYPD
SVKGRFTISRDNVKNTLYLQMSSLRSEDTAIYYCARRDYDLDYFDSWGQG
TLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKL
TVDKSRWQQGNVFSCSVMHEALHNHYTQKSLSLSPGK

SEQ ID NO:49 (Linker of the CD6-minus8L bionic CD6-EGF antibody conjugate of SEQ ID NO:48)
ASASAAAS SEQ ID NO:50 (CD6-EGF_PP bionic CD6-EGF antibody conjugate with granzyme cleavage site)

DIQMTQSPILLSASVGDRVTITCKASRDIRSYLTWYQQRTNGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECASASAAASSASSAAPPNSDSECPLSHDGYCLHDGVC
MYIEALDKYACNCVVGYIGERCQYRDLKWWELRGSGSGIEPDSGGSEVQL
VESGGGLVKPGGSLKLSCAASGFKFSRYAMSWVRQAPGKRLEWVATISSG
GSYIYYPDSVKGRFTISRDNVKNTLYLQMSSLRSEDTAIYYCARRDYDLD
YFDSWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

SEQ ID NO:51 (Linker of the CD6-EGF_PP bionic CD6-EGF antibody conjugate of SEQ ID NO:50)
ASASAAASSASSAAPP SEQ ID NO:52 (CD6-LC_PP bionic CD6-EGF antibody conjugate with granzyme cleavage site)

DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECPPASAAASSASSAASSNSDSECPLSHDGYCLHDGVC
MYIEALDKYACNCVVGYIGERCQYRDLKWWELRGSGSGIEPDSGGSEVQL
VESGGGLVKPGGSLKLSCAASGFKFSRYAMSWVRQAPGKRLEWVATISSG
GSYIYYPDSVKGRFTISRDNVKNTLYLQMSSLRSEDTAIYYCARRDYDLD
YFDSWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

SEQ ID NO:53 (Linker of the CD6-LC_PP bionic CD6-EGF antibody conjugate of SEQ ID NO:52)
PPASAAASSASSAASS SEQ ID NO:54 (CD6-L1_4PP bionic CD6-EGF antibody conjugate with granzyme cleavage site)

DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECPPASAAASSASSAAPPNSDSECPLSHDGYCLHDGVC
MYIEALDKYACNCVVGYIGERCQYRDLKWWELRGSGSGIEPDSGGSEVQL
VESGGGLVKPGGSLKLSCAASGFKFSRYAMSWVRQAPGKRLEWVATISSG
GSYIYYPDSVKGRFTISRDNVKNTLYLQMSSLRSEDTAIYYCARRDYDLD
YFDSWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

SEQ ID NO:55 (Linker of the CD6-L1_4PP bionic CD6-EGF antibody conjugate of SEQ ID NO:54)
PPASAAASSASSAAPP SEQ ID NO:56 (CD6-L1_6PP bionic CD6-EGF antibody conjugate with granzyme cleavage site)

DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECPPASAAAPPASSAAPPNSDSECPLSHDGYCLHDGVC
MYIEALDKYACNCVVGYIGERCQYRDLKWWELRGSGSGIEPDSGGSEVQL
VESGGGLVKPGGSLKLSCAASGFKFSRYAMSWVRQAPGKRLEWVATISSG
GSYIYYPDSVKGRFTISRDNVKNTLYLQMSSLRSEDTAIYYCARRDYDLD
YFDSWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

SEQ ID NO:57 (Linker of CD6-L1_6PP bionic CD6-EGF antibody conjugate of SEQ ID NO: 56)
PPASAAAPPASSAAPP SEQ ID NO:58 (CD6-N1 bionic CD6-EGF antibody conjugate with granzyme cleavage site)

DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECASASAAASSASSAASSNSDSECPLSHDGYCLHDGVC
MYIEALDKYACNCVVGYIGERCQYRDLKWWELRGSGSGIEPDSGGSEVQLV
ESGGGLVKPGGSLKLSCAASGFKFSRYAMSWVRQAPGKRLEWVATISSGG
SYIYYPDSVKGRFTISRDNVKNTLYLQMSSLRSEDTAIYYCARRDYDLDY
FDSWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMI
SRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGS
FFLYSKLTVDKSRWQQGNVFSCSVMHEALHNHYTQKSLSLSPGK

SEQ ID NO:59 (Linker with granzyme cleavage site of the CD6-N$_1$ bionic CD6-EGF antibody conjugate of SEQ ID NO:58)
SGSGIEPDSGGS SEQ ID NO:60 (CD6-C1 bionic CD6-EGF antibody conjugate with granzyme cleavage site)

DIQMTQSPILLSASVGDRVTITCKASRDIRSYLTWYQQRINGSPRTLIYY
ATSLADGVPSRFSGSGSGQDYSLTISSLESDDIADYYCLQHGESPFTFGS

-continued

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECASASAAASSASSAASSNSDSECPLSHDGYCLHDGVC

MYIEALDKYACNCVVGYIGERCQYRDLKWWELRGSGSGIEPDSGSEVQLV

ESGGGLVKPGGSLKLSCAASGFKFSRYAMSWVRQAPGKRLEWVATISSGG

SYIYYPDSVKGRFTISRDNVKNTLYLQMSSLRSEDTAIYYCARRDYDLDY

FDSWGQGTLVTVSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK

SEQ ID NO:61 (Linker with granzyme cleavage site of the CD6-C1 bionic CD6-EGF antibody conjugate of SEQ ID NO:60)
GSGSGIEPDSGS SEQ ID NO:62 (CD6-NIC1 bionic CD6-EGF antibody conjugate with granzyme cleavage site)

DIQMTQSPILLSASVGDRVTITCKASRDIRSYLTWYQQRINGSPRTLIYY

ATSLADGVPSRFSGSGSGQDYSLTISSLESDDIADYYCLQHGESPFTFGS

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECASASAAASSASSAASSNSDSECPLSHDGYCLHDGVC

MYIEALDKYACNCVVGYIGERCQYRDLKWWELRGSGSIEPDSGSEVQLVE

SGGGLVKPGGSLKLSCAASGFKFSRYAMSWVRQAPGKRLEWVATISSGGS

YIYYPDSVKGRFTISRDNVKNTLYLQMSSLRSEDTAIYYCARRDYDLDYF

DSWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPGK

SEQ ID NO:63 (Linker with granzyme cleavage site of the CD6-NIC1 bionic CD6-EGF antibody conjugate of SEQ ID NO:62)
SGSGIEPDSGS SEQ ID NO:64 (CD6-N₂C2 bionic CD6-EGF antibody conjugate with granzyme cleavage site)

DIQMTQSPILLSASVGDRVTITCKASRDIRSYLTWYQQRINGSPRTLIYY

ATSLADGVPSRFSGSGSGQDYSLTISSLESDDIADYYCLQHGESPFTFGS

-continued

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECASASAAASSASSAASSNSDSECPLSHDGYCLHDGVC

MYIEALDKYACNCVVGYIGERCQYRDLKWWELRGSGIEPDSGEVQLVESG

GGLVKPGGSLKLSCAASGFKFSRYAMSWVRQAPGKRLEWVATISSGGSYI

YYPDSVKGRFTISRDNVKNTLYLQMSSLRSEDTAIYYCARRDYDLDYFDS

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO:65 (Linker with granzyme cleavage site of the CD6-N₂C2 bionic CD6-EGF antibody conjugate of SEQ ID NO:64)
GSGIEPDSG SEQ ID NO:66 (MMP2/9 cleavage site)
VLPASLYS SEQ ID NO:67 (Granzyme cleavage site)
GSGIEPDSG SEQ ID NO:68 (Betacellulin)
TTQSKRKGHFSRCPKQYKHYCIKGRCRFVVAEQTP-SCVCDEGYIGARCERVDLFY

SEQ ID NO:69 (HBEGF)
KGKGLGKKRDPCLRKYKDFCIHGECKYVKELRAP-SCICHPGYHGERCHGLSLPV

P EMBODIMENTS

Embodiment P1. An anti-CD6 antibody-growth factor complex comprising:
  (i) an anti-CD6 antibody or fragment thereof; and
  (ii) a growth factor protein or fragment thereof, wherein said growth factor protein is bound to said anti-CD6 antibody through a chemical linker.

Embodiment P2. The complex of embodiment P1, wherein said chemical linker is a non-covalent linker.

Embodiment P3. The complex of embodiment P2, wherein said non-covalent linker comprises a peptide non-covalently bound to a non-CDR peptide binding region of said anti-CD6 antibody.

Embodiment P4. The complex of embodiment P3, wherein said peptide is covalently bound to said growth factor protein.

Embodiment P5. The complex of embodiment P1, wherein said chemical linker is a covalent linker.

Embodiment P6. The complex of embodiment P5, wherein said chemical linker is a bond.

Embodiment P7. The complex of embodiment P1, wherein said growth factor protein is bound to the N-terminus of the light chain of said anti-CD6 antibody.

Embodiment P8. The complex of embodiment P1, wherein said growth factor protein is bound to the C-terminus of the light chain of said anti-CD6 antibody.

Embodiment P9. The complex of embodiment P1, wherein said growth factor protein is bound to the N-terminus of the heavy chain of said anti-CD6 antibody.

Embodiment P10. The complex of embodiment P1, wherein said growth factor protein is bound to the C-terminus of the heavy chain of said anti-CD6 antibody.

Embodiment P11. The complex of embodiment P5, wherein said covalent linker comprises a peptide covalently bound to said anti-CD6 antibody through a disulfide bond.

Embodiment P12. The complex of embodiment P11, wherein said peptide is covalently bound to said growth factor protein.

Embodiment P13. The complex of one of embodiments P1-P12, wherein said anti-CD6 antibody comprises the CDR sequences of itolizumab.

Embodiment P14. The complex of one of embodiments P1-P13, wherein said anti-CD6 antibody comprises the variable light chain of itolizumab.

Embodiment P15. The complex of one of embodiments P1-P14, wherein said anti-CD6 antibody comprises the variable heavy chain of itolizumab.

Embodiment P16. The complex of one of embodiments P1-P15, wherein said growth factor protein is epidermal growth factor (EGF) or a fragment thereof.

Embodiment P17. The complex of embodiment P16, wherein said EGF is recombinant EGF.

Embodiment P18. The complex of embodiment P16, wherein the EGF is human EGF.

Embodiment P19. The complex of embodiment P16, wherein the EGF comprises the amino acid sequence of SEQ ID NO: 4.

Embodiment P20. The complex of embodiment P16, wherein the EGF fragment comprises the amino acid sequence of SEQ ID NO: 5 or 6.

Embodiment P21. The complex of one of embodiments P1-P15, wherein said growth factor protein is glucagon-like peptide-1 (GLP-1) or a fragment thereof.

Embodiment P22. The complex of one of embodiments P1-P15, wherein said growth factor protein is gastrin or a fragment thereof.

Embodiment P23. A pharmaceutical composition comprising a complex of any one of embodiments P1-P22 and a pharmaceutically acceptable excipient.

Embodiment P24. A method of treating an autoimmune disease in a subject in need thereof, said method comprising administering to said subject a therapeutically effective amount of a complex of any one of embodiments P1-P22.

Embodiment P25. The method of embodiment P24, wherein said autoimmune disease is type 1 diabetes.

Embodiment P26. An antibody, comprising:
(1) a central hole enclosed by the heavy chain variable (VH) region, the light chain variable (VL) region, the heavy chain constant (CH1) region and the light chain constant (CL) region of said antibody between a first cavity and a second cavity; and
(2) a non-CDR peptide binding region comprising:
(a) said first cavity lined by a first set of amino acid residues of the VH, VL, CH1, and CL regions of said antibody;
(b) said second cavity lined by a second set of amino acid residues of the VH, VL, CHI, and CL regions of said antibody; and
(c) a hole region enclosing said hole between said first cavity and said second cavity, said hole region lined by a third set of amino acid residues of the VH, VL, CHI, and CL regions of said antibody;
wherein said antibody is an anti-CD6 antibody.

Embodiment P27. The antibody of Embodiment P26, wherein said non-CDR peptide binding region is bound to a peptide.

Embodiment P28. The antibody of Embodiment P27, wherein said peptide comprises an epidermal growth factor receptor (EGFR)-binding domain.

Embodiment P29. The antibody of Embodiment P27, wherein said peptide comprises epidermal growth factor (EGF).

Embodiment P30. The antibody of Embodiment P29, wherein said EGF is human EGF.

Embodiment P31. The antibody of Embodiment P27, wherein said peptide is non covalently bound to said non-CDR peptide binding region.

Embodiment P32. The antibody of Embodiment P26, wherein said anti-CD6 antibody comprises the CDR sequences of itolizumab.

Embodiment P33. A method of treating an autoimmune disease in a subject in need thereof, comprising administering to said subject an antibody according to any one of Embodiments P26-P32.

Embodiments

Embodiment 1. An anti-CD6 antibody-growth factor complex comprising:
(i) an anti-CD6 antibody or fragment thereof; and
(ii) a growth factor protein or fragment thereof, wherein said growth factor protein is bound to said anti-CD6 antibody through a chemical linker.

Embodiment 2. The complex of embodiment 1, wherein said chemical linker is a covalent linker.

Embodiment 3. The complex of embodiment 1 or 2, wherein said chemical linker is a bond.

Embodiment 4. The complex of any one of embodiments 1-3, wherein said chemical linker is a peptide linker.

Embodiment 5. The complex of any one of embodiments 1-4, wherein said complex forms a single chain polypeptide.

Embodiment 6. The complex of any one of embodiments 1-5, wherein said anti-CD6 antibody comprises a variable light chain domain.

Embodiment 7. The complex of any one of embodiments 1-6, wherein said anti-CD6 antibody comprises a constant light chain domain.

Embodiment 8. The complex of any one of embodiments 1-7, wherein said anti-CD6 antibody comprises an antibody light chain.

Embodiment 9. The complex of any one of embodiments 1-8, wherein said anti-CD6 antibody comprises a variable heavy chain domain.

Embodiment 10. The complex of any one of embodiments 1-9, wherein said anti-CD6 antibody comprises a constant heavy chain domain.

Embodiment 11. The complex of any one of embodiments 1-10, wherein said anti-CD6 antibody comprises an antibody heavy chain.

Embodiment 12. The complex of any one of embodiments 8-11, wherein said antibody light chain is bound to said growth factor protein through a first chemical linker.

Embodiment 13. The complex of embodiment 11 or 12, wherein said antibody heavy chain is bound to said growth factor protein through a second chemical linker.

Embodiment 14. The complex of embodiment 13, wherein said antibody light chain is bound to the N-terminus of said growth factor protein through said first chemical linker.

Embodiment 15. The complex of embodiment 14, wherein said antibody heavy chain is bound to the C-terminus of said growth factor protein through said second chemical linker.

Embodiment 16. The complex of embodiment 15, comprising from the N-terminus to the C-terminus said antibody light chain, said first chemical linker, said growth factor protein, said second chemical linker and said antibody heavy chain.

Embodiment 17. The complex of embodiment 11 or 12, wherein said antibody heavy chain is bound to said growth factor protein through a first chemical linker.

Embodiment 18. The complex of embodiment 17, wherein said antibody heavy chain is bound to the N-terminus of said growth factor protein through said first chemical linker.

Embodiment 19. The complex of any one of embodiments 8-11, wherein said antibody light chain is bound to said growth factor protein through a second chemical linker.

Embodiment 20. The complex of embodiment 19, wherein said antibody light chain is bound to the C-terminus of said growth factor protein through said second chemical linker.

Embodiment 21. The complex of embodiment 20, comprising from the N-terminus to the C-terminus said antibody heavy chain, said first chemical linker, said growth factor protein, said second chemical linker and said antibody light chain.

Embodiment 22. The complex of any one of embodiments 1-13, wherein said first chemical linker is bound to the N-terminus of said growth factor protein and said second chemical linker is bound to the C-terminus of said growth factor protein.

Embodiment 23. The complex of any one of embodiments 1-13, wherein said first chemical linker is bound to the C-terminus of said antibody light chain and said second chemical linker is bound to the N-terminus of said antibody heavy chain.

Embodiment 24. The complex of any one of embodiments 1-13, wherein said first chemical linker is bound to the C-terminus of said antibody heavy chain and said second chemical linker is bound to the N-terminus of said antibody light chain.

Embodiment 25. The complex of any one of embodiments 13-24, wherein said antibody light chain is capable of non-covalently binding to said antibody heavy chain thereby forming said anti-CD6 antibody or fragment thereof.

Embodiment 26. The complex of any one of embodiments 1-25, wherein said anti-CD6 antibody is a humanized anti-CD6 antibody of fragment thereof.

Embodiment 27. The complex of any one of embodiments 1-26, wherein said anti-CD6 antibody is a Fab.

Embodiment 28. The complex of any one of embodiments 1-27, wherein said anti-CD6 antibody comprises the CDR sequences of itolizumab.

Embodiment 29. The complex of any one of embodiments 1-28, wherein said growth factor protein is an epidermal growth factor receptor (EGFR) signaling molecule.

Embodiment 30. The complex of any one of embodiments 1-29, wherein said growth factor protein is an EGF protein or fragment thereof, a betacellulin protein or fragment thereof, a heparin-binding EGF-like growth factor (HBEGF) protein or fragment thereof, a TGF alpha protein or fragment thereof, an amphiregulin protein or fragment thereof, an epigen protein or fragment thereof or an epiregulin protein or fragment thereof.

Embodiment 31. The complex of any one of embodiments 1-30, wherein said growth factor protein is a recombinant EGF protein or fragment thereof.

Embodiment 32. The complex of any one of embodiments 1-30, wherein said growth factor protein is a human EGF protein or fragment thereof.

Embodiment 33. The complex of any one of embodiments 13-32, wherein said first chemical linker and said second chemical linker are independently a covalent linker.

Embodiment 34. The complex of any one of embodiments 13-33, wherein said first chemical linker and said second chemical linker are independently a cleavable peptide linker.

Embodiment 35. The complex of any one of embodiments 13-33, wherein at least one of said first chemical linker and said second chemical linker is a non-cleavable peptide linker.

Embodiment 36. The complex of any one of embodiments 13-33, wherein only one of said first chemical linker and said second chemical linker is a cleavable peptide linker.

Embodiment 37. The complex of any one of embodiments 13-36, wherein said first chemical linker or said second chemical linker is an enzymatically cleavable linker.

Embodiment 38. The complex of any one of embodiments 13-37, wherein said first chemical linker or said second chemical linker is a protease cleavable linker.

Embodiment 39. The complex of embodiment 38, wherein said protease is an extracellular protease.

Embodiment 40. The complex of embodiment 38, wherein said protease is a disease-associated protease.

Embodiment 41. The complex of embodiment 38, wherein said protease is a pro-inflammatory protease.

Embodiment 42. The complex of embodiment 38, wherein said protease is a type 1 diabetes-associated protease.

Embodiment 43. The complex of any one of embodiments 38-42, wherein said protease is a metalloprotease, granzyme, granuloysin or perforin.

Embodiment 44. The complex of any one of embodiments 13-43, wherein said first chemical linker and said second chemical linker independently have a length of about 0 to about 20 amino acid residues.

Embodiment 45. The complex of any one of embodiments 13-44, wherein said first chemical linker has a length of about 8, 10, 12, 14 or 16 amino acid residues.

Embodiment 46. The complex of any one of embodiments 13-45, wherein said second chemical linker has a length of about 8, 9, 10, 11, or 12 amino acid residues.

Embodiment 47. The complex of any one of embodiments 13-46, wherein said second chemical linker is a protease cleavable linker.

Embodiment 48. The complex of any one of embodiments 13-47, wherein said second chemical linker is a granzyme cleavable linker.

Embodiment 49. The complex of any one of embodiments 1-46, wherein said anti-CD6 antibody or fragment thereof is bound to an Fc domain through a third chemical linker.

Embodiment 50. The complex of embodiment 49, wherein the C-terminus of said antibody heavy chain is bound to said Fc domain through said third chemical linker.

Embodiment 51. The complex of embodiment 49-50, wherein said Fc domain is an IgG1 Fc domain.

Embodiment 52. The complex of any one of embodiments 49-51, wherein said third linker is a covalent linker.

Embodiment 53. The complex of any one of embodiments 49-52, wherein said third linker is a cleavable peptide linker.

Embodiment 54. The complex of embodiment 2, wherein said covalent linker comprises a peptide compound covalently bound to said anti-CD6 antibody through a disulfide linkage.

Embodiment 55. The complex of embodiment 54, wherein said peptide compound is covalently bound to said growth factor protein.

Embodiment 56. The complex of embodiment 54 or 55, wherein said anti-CD6 antibody comprises:
(1) a central hole enclosed by the heavy chain variable (VH) domain, the light chain variable (VL) domain, the heavy chain constant (CH1) domain and the light chain constant (CL) domain of said anti-CD6 antibody between a first cavity and a second cavity; and
(2) a non-CDR peptide binding region comprising:
(a) said first cavity lined by a first set of amino acid residues of the VH, VL, CH1, and CL domains of said anti-CD6 antibody;
(b) said second cavity lined by a second set of amino acid residues of the VH, VL, CHI, and CL domains of said anti-CD6 antibody; and
(c) a hole region enclosing said hole between said first cavity and said second cavity, said hole region lined by a third set of amino acid residues of the VH, VL, CHI, and CL domains of said anti-CD6 antibody;
wherein said non-CDR peptide binding region comprises a first cysteine; and
wherein said peptide compound comprises a thiol side chain amino acid covalently bound to said anti-CD6 antiody through a disulfide linkage between said first cysteine and said thiol side chain amino acid.

Embodiment 57. The complex of any one of embodiments 54-56, wherein said peptide compound is a meditope.

Embodiment 58. The complex of embodiment 56, wherein said second set of amino acid residues comprises said first cysteine at a position corresponding to Kabat position 158 of said VH domain.

Embodiment 59. The complex of embodiment 1, wherein said chemical linker is a non-covalent linker.

Embodiment 60. The complex of embodiment 59, wherein said non-covalent linker comprises a peptide compound non-covalently bound to a non-CDR peptide binding region of said anti-CD6 antibody.

Embodiment 61. The complex of embodiment 60, wherein said peptide compound is covalently bound to said growth factor protein.

Embodiment 62. The complex of any one of embodiments 60-61, wherein said peptide compound is a meditope.

Embodiment 63. The isolated nucleic acid encoding a complex of any one of embodiments 1-53.

Embodiment 64. The expression vector comprising the nucleic acid of embodiment 63.

Embodiment 65. The expression vector of embodiment 64, wherein said expression vector is a viral vector.

Embodiment 66. The expression vector of embodiment 65, wherein said virus is a lentivirus or onco-retrovirus Embodiment 67. The cell comprising the expression vector of any one of embodiments 64-66.

Embodiment 68. The method of treating an autoimmune disease in a subject in need thereof, said method comprising administering to a subject a therapeutically effective amount of a complex of any one of embodiments 1-53, thereby treating an autoimmune disease in said subject.

Embodiment 69. The method of embodiment 68, wherein said autoimmune disease is type 1 diabetes, multiple sclerosis or inflammatory bowel disease.

Embodiment 70. A pharmaceutical composition comprising a therapeutically effective amount of a complex of any one of embodiments 1-53 and a pharmaceutically acceptable excipient.

What is claimed is:

1. An anti-CD6 antibody-growth factor complex comprising:
   (i) an anti-CD6 antibody or antigen-binding fragment thereof; and
   (ii) a growth factor protein or fragment thereof, wherein said growth factor protein is bound to said anti-CD6 antibody or antigen-binding fragment thereof through a chemical linker,
   wherein said growth factor protein is an epidermal growth factor receptor (EGFR) signaling molecule; and
   wherein said anti-CD6 antibody or antigen-binding fragment thereof comprises the complementary-determining region (CDR) H1, CDR H2, CDR H3, CDR L1, CDR L2, and CDR L3 sequences of itolizumab.

2. The complex of claim 1, wherein said chemical linker is a peptide linker.

3. The complex of claim 1, wherein said complex forms a single chain polypeptide.

4. The complex of claim 3, wherein said anti-CD6 antibody comprises an antibody light chain, wherein said chemical linker is a first chemical linker, and wherein said complex further comprises a second chemical linker.

5. The complex of claim 4, wherein said anti-CD6 antibody comprises an antibody heavy chain.

6. The complex of claim 5, wherein said antibody light chain or said antibody heavy chain is bound to said growth factor protein through said first chemical linker.

7. The complex of claim 6, wherein said antibody heavy chain or said antibody light chain is bound to said growth factor protein through said second chemical linker.

8. The complex of claim 7, wherein said antibody light chain is capable of non-covalently binding to said antibody heavy chain thereby forming said anti-CD6 antibody or fragment thereof.

9. The complex of claim 7, further comprising a third chemical linker and wherein said anti-CD6 antibody or fragment thereof is bound to an Fc domain through said third chemical linker.

10. The complex of claim 9, comprising from the N-terminus to the C-terminus:
   said antibody light chain, wherein said antibody light chain comprises the sequence of SEQ ID NO:33;
   said first chemical linker, wherein said first chemical linker is a non-cleavable linker;
   said EGFR signaling molecule, wherein said EGFR signaling molecule is EGF, betacellulin, or HBEFG;
   said second chemical linker, wherein said second chemical linker is a matrix metalloprotease-2 (MMP2), matrix metalloprotease-9 (MMP9), or granzyme cleavable linker;
   said antibody heavy chain, wherein said antibody heavy chain comprises the sequence of SEQ ID NO:36;
   said third chemical linker, and
   said Fc domain.

11. The complex of claim 7, wherein said EGFR signaling molecule is epidermal growth factor (EGF), betacellulin, heparin-binding EGF-like growth factor (HBEFG), transforming growth factor α (TGFα), amphiregulin, epigen, or epiregulin.

12. The complex of claim 4, wherein said first chemical linker or said second chemical linker is a protease cleavable linker.

13. The complex of claim 12, wherein said protease is a disease-associated protease.

14. The complex of claim 4, wherein said first chemical linker and said second chemical linker are protease cleavable linkers.

15. The complex of claim 1, wherein said anti-CD6 antibody is a Fab.

16. A pharmaceutical composition comprising a therapeutically effective amount of a complex of claim 1 and a pharmaceutically acceptable excipient.

17. A method of treating an autoimmune disease in a subject in need thereof, said method comprising administering to a subject a therapeutically effective amount of a complex of claim 1, thereby treating an autoimmune disease in said subject.

18. An isolated nucleic acid encoding a complex of claim 1.

19. An expression vector comprising the nucleic acid of claim 18.

20. A cell comprising the expression vector of claim 19.

* * * * *

SEQUENCE LISTING

```
<160> NUMBER OF SEQ ID NOS: 67

<210> SEQ ID NO 1
<211> LENGTH: 466
<212> TYPE: DNA
<213> ORGANISM: Artificial Sequence
<220> FEATURE:
<223> OTHER INFORMATION: Synthetic construct

<400> SEQUENCE: 1
ggtctctggg gagcttgctt gttctttttg cagaagctca gaataaacgc tcaactttgg      60
ccgccaccat ggacatgagg gtccccgctc agctcctggg gctcctgctg ctctggctcc     120
caggtgccaa atgtgacatc cagatgaccc agtccctat tctgctgagc gcctccgtgg     180
gcgaccgcgt gaccatcact tgcaaagcct cccgggatat ccggtcctac ctcacctggt     240
accagcagag gactaacgga tcgcccagaa ccctgatcta ctacgcgact agcctggccg     300
atggcgtccc gtcccggttc tcggggtcgg gttcaggaca ggactatagc cttaccatct     360
catccctgga gtccgatgac atcgccgact actactgcct gcaacacggc gaatctccct     420
tcacgttcgg gtccggaacc aagctcgaga ttaagcgaag aagagc                   466

<210> SEQ ID NO 2
<211> LENGTH: 379
<212> TYPE: DNA
<213> ORGANISM: Artificial Sequence
<220> FEATURE:
<223> OTHER INFORMATION: Synthetic construct

<400> SEQUENCE: 2
```

```
gctcttcttc agaggtgcag cttgtggaat cgggtggcgg actggtcaag cctgggggat      60
cgctgaaact gagctgtgca gccagcggtt tcaagttctc acgctacgcc atgtcctggg     120
tcagacaggc gccgggaaag cgcctggaat gggtggctac tatctcctcc ggcggatcct     180
acatctacta ccccgactcc gtgaaggggcc ggttcaccat tagccgcgac aacgtgaaga    240
acactctgta cctccaaatg tcaagcctga ggtctgagga taccgccatc tactattgcg     300
cccggcggga ctacgacttg gattactttg actcctgggg ccaggggacc ctcgtgaccg     360
tgtcctcggc caagagacc                                                  379

<210> SEQ ID NO 3
<211> LENGTH: 1783
<212> TYPE: DNA
<213> ORGANISM: Artificial Sequence
<220> FEATURE:
<223> OTHER INFORMATION: Synthetic construct

<400> SEQUENCE: 3
ggggagcttg cttgttcttt ttgcagaagc tcagaataaa cgctcaactt tggccgccac      60
catggacatg agggtccccg ctcagctcct ggggctcctg ctgctctggc tcccaggtgc     120
caaatgtgac atccagatga cccagtcccc tattctgctg agcgcctccg tgggcgaccg     180
cgtgaccatc acttgcaaag cctcccggga tatccggtcc tacctcacct ggtaccagca     240
gaggactaac ggatcgccca gaaccctgat ctactacgcg actagcctgg ccgatggcgt     300
cccgtcccgg ttctcggggt cgggttcagg acaggactat agccttacca tctcatccct     360
ggagtccgat gacatcgccg actactactg cctgcaacac ggcgaatctc ccttcacgtt     420
cgggtccgga accaagctcg agattaagcg aactgtggct gcaccatctg tcttcatctt     480
cccgccatct gatgagcagt tgaaatctgg aactgcctct gttgtgtgcc tgctgaataa     540
cttctatccc agagaggcca agtacagtg gaaggtggaa aacgcccctcc aatcgggtaa     600 ctcccaggag agtgtcacag agcaggacag caaggacagc acctacagcc tcagcagcac     660
cctgacgctg agcaaagcag actacgagaa acacaaagtc tacgcctgcg aagtcaccca     720
tcagggcctg agctcgcccg tcacaaagag cttcaacagg ggagagtgtt aatagctctt     780
aaaaaattcc gccccccccc taacgttact ggccgaagcc gcttggaata aggccggtgt     840
gcgtttgtct atatgttatt ttccaccata ttgccgtctt ttggcaatgt gagggcccgg     900
aaacctggcc ctgtcttctt gacgagcatt cctaggggtc tttcccctct cgccaaagga    960
atgcaaggtc tgttgaatgt cgtgaaggaa gcagttcctc tggaagcttc ttgaagacaa    1020
acaacgtctg tagcgaccct ttgcaggcag cggaaccccc cacctggcga caggtgcctc    1080
tgcggccaaa agccacgtgt ataagataca cctgcaaagg cggcacaacc ccagtgccac    1140
gttgtgagtt ggatagttgt ggaaagagtc aaatggctct cctcaagcgt attcaacaag    1200
gggctgaagg atgcccagaa ggtaccccat tgtatgggat ctgatctggg gcctcggtac    1260
acatgcttta catgtgttta gtcgaggtta aaaaacgtct aggccccccg aaccacgggg    1320
acgtggtttt cctttgaaaa acacgatgat aatatggcca caaccatggg ctggtccctg    1380
atcctgctgt tcctggtggc cgtggccacg cgtgtgctgt cagaggtgca gcttgtggaa    1440
tcgggtggcg gactggtcaa gcctggggga tcgctgaaac tgagctgtgc agccagcggt    1500
ttcaagttct cacgctacgc catgtcctgg gtcagacagg cgccgggaaa gcgcctggaa    1560
tgggtggcta ctatctcctc cggcggatcc tacatctact accccgactc cgtgaagggc    1620
```

```
cggttcacca ttagccgcga caacgtgaag aacactctgt acctccaaat gtcaagcctg    1680
aggtctgagg ataccgccat ctactattgc gcccggcggg actacgactt ggattacttt    1740
gactcctggg gccaggggac cctcgtgacc gtgtcctcgg cca                      1783
```

<210> SEQ ID NO 4
<211> LENGTH: 53
<212> TYPE: PRT
<213> ORGANISM: Homo sapiens

<400> SEQUENCE: 4

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 5
<211> LENGTH: 21
<212> TYPE: PRT
<213> ORGANISM: Homo sapiens

<400> SEQUENCE: 5

```
Asp Gly Tyr Cys Leu His Asp Gly Val Cys Met Tyr Ile Glu Ala Leu
1               5                   10                  15

Asp Lys Tyr Ala Cys
            20
```

<210> SEQ ID NO 6
<211> LENGTH: 21
<212> TYPE: PRT
<213> ORGANISM: Artificial Sequence
<220> FEATURE:
<223> OTHER INFORMATION: Synthetic construct

<400> SEQUENCE: 6

```
Asp Gly Tyr Cys Leu His Asp Gly Val Ser Met Tyr Ile Glu Ala Leu
1               5                   10                  15

Asp Lys Tyr Ala Cys
            20
```

<210> SEQ ID NO 7
<211> LENGTH: 668
<212> TYPE: PRT
<213> ORGANISM: Homo sapiens

<400> SEQUENCE: 7

```
Met Trp Leu Phe Phe Gly Ile Thr Gly Leu Leu Thr Ala Ala Leu Ser
1               5                   10                  15

Gly His Pro Ser Pro Ala Pro Pro Asp Gln Leu Asn Thr Ser Ser Ala
            20                  25                  30

Glu Ser Glu Leu Trp Glu Pro Gly Glu Arg Leu Pro Val Arg Leu Thr
        35                  40                  45

Asn Gly Ser Ser Ser Cys Ser Gly Thr Val Glu Val Arg Leu Glu Ala
    50                  55                  60

Ser Trp Glu Pro Ala Cys Gly Ala Leu Trp Asp Ser Arg Ala Ala Glu
65                  70                  75                  80
```

```
Ala Val Cys Arg Ala Leu Gly Cys Gly Gly Ala Glu Ala Ala Ser Gln
                85                  90                  95

Leu Ala Pro Pro Thr Pro Glu Leu Pro Pro Pro Ala Ala Gly Asn
            100                 105                 110

Thr Ser Val Ala Ala Asn Ala Thr Leu Ala Gly Ala Pro Ala Leu Leu
            115                 120                 125

Cys Ser Gly Ala Glu Trp Arg Leu Cys Glu Val Val Glu His Ala Cys
            130                 135                 140

Arg Ser Asp Gly Arg Arg Ala Arg Val Thr Cys Ala Glu Asn Arg Ala
145                 150                 155                 160

Leu Arg Leu Val Asp Gly Gly Ala Cys Ala Gly Arg Val Glu Met
                165                 170                 175

Leu Glu His Gly Glu Trp Gly Ser Val Cys Asp Asp Thr Trp Asp Leu
                180                 185                 190

Glu Asp Ala His Val Val Cys Arg Gln Leu Gly Cys Gly Trp Ala Val
            195                 200                 205

Gln Ala Leu Pro Gly Leu His Phe Thr Pro Gly Arg Gly Pro Ile His
    210                 215                 220

Arg Asp Gln Val Asn Cys Ser Gly Ala Glu Ala Tyr Leu Trp Asp Cys
225                 230                 235                 240

Pro Gly Leu Pro Gly Gln His Tyr Cys Gly His Lys Glu Asp Ala Gly
                245                 250                 255

Ala Val Cys Ser Glu His Gln Ser Trp Arg Leu Thr Gly Gly Ala Asp
            260                 265                 270

Arg Cys Glu Gly Gln Val Glu Val His Phe Arg Gly Val Trp Asn Thr
            275                 280                 285

Val Cys Asp Ser Glu Trp Tyr Pro Ser Glu Ala Lys Val Leu Cys Gln
    290                 295                 300

Ser Leu Gly Cys Gly Thr Ala Val Glu Arg Pro Lys Gly Leu Pro His
305                 310                 315                 320

Ser Leu Ser Gly Arg Met Tyr Tyr Ser Cys Asn Gly Glu Glu Leu Thr
                325                 330                 335

Leu Ser Asn Cys Ser Trp Arg Phe Asn Asn Ser Asn Leu Cys Ser Gln
            340                 345                 350

Ser Leu Ala Ala Arg Val Leu Cys Ser Ala Ser Arg Ser Leu His Asn
            355                 360                 365

Leu Ser Thr Pro Glu Val Pro Ala Ser Val Gln Thr Val Thr Ile Glu
    370                 375                 380

Ser Ser Val Thr Val Lys Ile Glu Asn Lys Glu Ser Arg Glu Leu Met
385                 390                 395                 400

Leu Leu Ile Pro Ser Ile Val Leu Gly Ile Leu Leu Gly Ser Leu
                405                 410                 415

Ile Phe Ile Ala Phe Ile Leu Leu Arg Ile Lys Gly Lys Tyr Ala Leu
            420                 425                 430

Pro Val Met Val Asn His Gln His Leu Pro Thr Thr Ile Pro Ala Gly
            435                 440                 445

Ser Asn Ser Tyr Gln Pro Val Pro Ile Thr Ile Pro Lys Glu Val Phe
    450                 455                 460

Met Leu Pro Ile Gln Val Gln Ala Pro Pro Glu Asp Ser Asp Ser
465                 470                 475                 480

Gly Ser Asp Ser Asp Tyr Glu His Tyr Asp Phe Ser Ala Gln Pro Pro
                485                 490                 495

Val Ala Leu Thr Thr Phe Tyr Asn Ser Gln Arg His Arg Val Thr Asp
```

```
                    500                 505                 510
Glu Glu Val Gln Gln Ser Arg Phe Gln Met Pro Pro Leu Glu Glu Gly
                515                 520                 525

Leu Glu Glu Leu His Ala Ser His Ile Pro Thr Ala Asn Pro Gly His
            530                 535                 540

Cys Ile Thr Asp Pro Pro Ser Leu Gly Pro Gln Tyr His Pro Arg Ser
545                 550                 555                 560

Asn Ser Glu Ser Ser Thr Ser Ser Gly Glu Asp Tyr Cys Asn Ser Pro
                565                 570                 575

Lys Ser Lys Leu Pro Pro Trp Asn Pro Gln Val Phe Ser Ser Glu Arg
            580                 585                 590

Ser Ser Phe Leu Glu Gln Pro Pro Asn Leu Glu Leu Ala Gly Thr Gln
        595                 600                 605

Pro Ala Phe Ser Ala Gly Pro Pro Ala Asp Asp Ser Ser Ser Thr Ser
        610                 615                 620

Ser Gly Glu Trp Tyr Gln Asn Phe Gln Pro Pro Gln Pro Pro Ser
625                 630                 635                 640

Glu Glu Gln Phe Gly Cys Pro Gly Ser Pro Ser Gln Pro Asp Ser
                645                 650                 655

Thr Asp Asn Asp Asp Tyr Asp Asp Ile Ser Ala Ala
                660                 665
```

<210> SEQ ID NO 8
<211> LENGTH: 601
<212> TYPE: PRT
<213> ORGANISM: Homo sapiens

<400> SEQUENCE: 8

```
Met Trp Leu Phe Phe Gly Ile Thr Gly Leu Leu Thr Ala Ala Leu Ser
1               5                   10                  15

Gly His Pro Ser Pro Ala Pro Pro Asp Gln Leu Asn Thr Ser Ser Ala
            20                  25                  30

Glu Ser Glu Leu Trp Glu Pro Gly Glu Arg Leu Pro Val Arg Leu Thr
        35                  40                  45

Asn Gly Ser Ser Ser Cys Ser Gly Thr Val Glu Val Arg Leu Glu Ala
    50                  55                  60

Ser Trp Glu Pro Ala Cys Gly Ala Leu Trp Asp Ser Arg Ala Ala Glu
65                  70                  75                  80

Ala Val Cys Arg Ala Leu Gly Cys Gly Gly Ala Glu Ala Ala Ser Gln
                85                  90                  95

Leu Ala Pro Pro Thr Pro Glu Leu Pro Pro Pro Ala Ala Gly Asn
            100                 105                 110

Thr Ser Val Ala Ala Asn Ala Thr Leu Ala Gly Ala Pro Ala Leu Leu
        115                 120                 125

Cys Ser Gly Ala Glu Trp Arg Leu Cys Glu Val Val Glu His Ala Cys
    130                 135                 140

Arg Ser Asp Gly Arg Arg Ala Arg Val Thr Cys Ala Glu Asn Arg Ala
145                 150                 155                 160

Leu Arg Leu Val Asp Gly Gly Gly Ala Cys Ala Gly Arg Val Glu Met
                165                 170                 175

Leu Glu His Gly Glu Trp Gly Ser Val Cys Asp Asp Thr Trp Asp Leu
            180                 185                 190

Glu Asp Ala His Val Val Cys Arg Gln Leu Gly Cys Gly Trp Ala Val
        195                 200                 205
```

Gln Ala Leu Pro Gly Leu His Phe Thr Pro Gly Arg Gly Pro Ile His
    210                 215                 220

Arg Asp Gln Val Asn Cys Ser Gly Ala Glu Ala Tyr Leu Trp Asp Cys
225                 230                 235                 240

Pro Gly Leu Pro Gly Gln His Tyr Cys Gly His Lys Glu Asp Ala Gly
                245                 250                 255

Ala Val Cys Ser Glu His Gln Ser Trp Arg Leu Thr Gly Gly Ala Asp
            260                 265                 270

Arg Cys Glu Gly Gln Val Glu Val His Phe Arg Gly Val Trp Asn Thr
        275                 280                 285

Val Cys Asp Ser Glu Trp Tyr Pro Ser Glu Ala Lys Val Leu Cys Gln
    290                 295                 300

Ser Leu Gly Cys Gly Thr Ala Val Glu Arg Pro Lys Gly Leu Pro His
305                 310                 315                 320

Ser Leu Ser Gly Arg Met Tyr Tyr Ser Cys Asn Gly Glu Glu Leu Thr
                325                 330                 335

Leu Ser Asn Cys Ser Trp Arg Phe Asn Asn Ser Asn Leu Cys Ser Gln
            340                 345                 350

Ser Leu Ala Ala Arg Val Leu Cys Ser Ala Ser Arg Ser Leu His Asn
        355                 360                 365

Leu Ser Thr Pro Glu Val Pro Ala Ser Val Gln Thr Val Thr Ile Glu
    370                 375                 380

Ser Ser Val Thr Val Lys Ile Glu Asn Lys Glu Ser Arg Glu Leu Met
385                 390                 395                 400

Leu Leu Ile Pro Ser Ile Val Leu Gly Ile Leu Leu Gly Ser Leu
                405                 410                 415

Ile Phe Ile Ala Phe Ile Leu Leu Arg Ile Lys Gly Lys Tyr Val Phe
            420                 425                 430

Met Leu Pro Ile Gln Val Gln Ala Pro Pro Glu Asp Ser Asp Ser
        435                 440                 445

Gly Ser Asp Ser Asp Tyr Glu His Tyr Asp Phe Ser Ala Gln Pro Pro
    450                 455                 460

Val Ala Leu Thr Thr Phe Tyr Asn Ser Gln Arg His Arg Val Thr Asp
465                 470                 475                 480

Glu Glu Val Gln Gln Ser Arg Phe Gln Met Pro Pro Leu Glu Glu Gly
                485                 490                 495

Leu Glu Glu Leu His Ala Ser His Ile Pro Thr Ala Asn Pro Gly His
            500                 505                 510

Cys Ile Thr Asp Pro Pro Ser Leu Gly Pro Gln Tyr His Pro Arg Ser
        515                 520                 525

Asn Ser Glu Ser Ser Thr Ser Ser Gly Glu Asp Tyr Cys Asn Ser Pro
    530                 535                 540

Lys Ser Lys Leu Pro Pro Trp Asn Pro Gln Val Phe Ser Ser Glu Arg
545                 550                 555                 560

Ser Ser Phe Leu Glu Gln Pro Pro Asn Leu Glu Leu Ala Gly Thr Gln
                565                 570                 575

Pro Ala Phe Ser Gly Ser Pro Ser Pro Gln Pro Asp Ser Thr Asp Asn
            580                 585                 590

Asp Asp Tyr Asp Asp Ile Ser Ala Ala
        595                 600

<210> SEQ ID NO 9
<211> LENGTH: 592
<212> TYPE: PRT

<213> ORGANISM: Homo sapiens

<400> SEQUENCE: 9

Met Trp Leu Phe Phe Gly Ile Thr Gly Leu Leu Thr Ala Ala Leu Ser
1               5                   10                  15

Gly His Pro Ser Pro Ala Pro Pro Asp Gln Leu Asn Thr Ser Ser Ala
            20                  25                  30

Glu Ser Glu Leu Trp Glu Pro Gly Glu Arg Leu Pro Val Arg Leu Thr
        35                  40                  45

Asn Gly Ser Ser Ser Cys Ser Gly Thr Val Glu Val Arg Leu Glu Ala
    50                  55                  60

Ser Trp Glu Pro Ala Cys Gly Ala Leu Trp Asp Ser Arg Ala Ala Glu
65                  70                  75                  80

Ala Val Cys Arg Ala Leu Gly Cys Gly Gly Ala Glu Ala Ala Ser Gln
                85                  90                  95

Leu Ala Pro Pro Thr Pro Glu Leu Pro Pro Pro Ala Ala Gly Asn
            100                 105                 110

Thr Ser Val Ala Ala Asn Ala Thr Leu Ala Gly Ala Pro Ala Leu Leu
            115                 120                 125

Cys Ser Gly Ala Glu Trp Arg Leu Cys Glu Val Val Glu His Ala Cys
130                 135                 140

Arg Ser Asp Gly Arg Arg Ala Arg Val Thr Cys Ala Glu Asn Arg Ala
145                 150                 155                 160

Leu Arg Leu Val Asp Gly Gly Ala Cys Ala Gly Arg Val Glu Met
                165                 170                 175

Leu Glu His Gly Glu Trp Gly Ser Val Cys Asp Asp Thr Trp Asp Leu
            180                 185                 190

Glu Asp Ala His Val Val Cys Arg Gln Leu Gly Cys Gly Trp Ala Val
            195                 200                 205

Gln Ala Leu Pro Gly Leu His Phe Thr Pro Gly Arg Gly Pro Ile His
210                 215                 220

Arg Asp Gln Val Asn Cys Ser Gly Ala Glu Ala Tyr Leu Trp Asp Cys
225                 230                 235                 240

Pro Gly Leu Pro Gly Gln His Tyr Cys Gly His Lys Glu Asp Ala Gly
                245                 250                 255

Ala Val Cys Ser Glu His Gln Ser Trp Arg Leu Thr Gly Gly Ala Asp
            260                 265                 270

Arg Cys Glu Gly Gln Val Glu Val His Phe Arg Gly Val Trp Asn Thr
            275                 280                 285

Val Cys Asp Ser Glu Trp Tyr Pro Ser Glu Ala Lys Val Leu Cys Gln
            290                 295                 300

Ser Leu Gly Cys Gly Thr Ala Val Glu Arg Pro Lys Gly Leu Pro His
305                 310                 315                 320

Ser Leu Ser Gly Arg Met Tyr Tyr Ser Cys Asn Gly Glu Glu Leu Thr
                325                 330                 335

Leu Ser Asn Cys Ser Trp Arg Phe Asn Asn Ser Asn Leu Cys Ser Gln
            340                 345                 350

Ser Leu Ala Ala Arg Val Leu Cys Ser Ala Ser Arg Ser Leu His Asn
            355                 360                 365

Leu Ser Thr Pro Glu Val Pro Ala Ser Val Gln Thr Val Thr Ile Glu
370                 375                 380

Ser Ser Val Thr Val Lys Ile Glu Asn Lys Glu Ser Arg Glu Leu Met
385                 390                 395                 400

```
Leu Leu Ile Pro Ser Ile Val Leu Gly Ile Leu Leu Gly Ser Leu
                405                 410                 415

Ile Phe Ile Ala Phe Ile Leu Leu Arg Ile Lys Gly Lys Tyr Ala Leu
            420                 425                 430

Pro Val Met Val Asn His Gln His Leu Pro Thr Thr Ile Pro Ala Gly
            435                 440                 445

Ser Asn Ser Tyr Gln Pro Val Pro Ile Thr Ile Pro Lys Glu Asp Ser
        450                 455                 460

Gln Arg His Arg Val Thr Asp Glu Glu Val Gln Ser Arg Phe Gln
465                 470                 475                 480

Met Pro Pro Leu Glu Glu Gly Leu Glu Leu His Ala Ser His Ile
                485                 490                 495

Pro Thr Ala Asn Pro Gly His Cys Ile Thr Asp Pro Ser Leu Gly
            500                 505                 510

Pro Gln Tyr His Pro Arg Ser Asn Ser Glu Ser Ser Thr Ser Ser Gly
        515                 520                 525

Glu Asp Tyr Cys Asn Ser Pro Lys Ser Lys Leu Pro Pro Trp Asn Pro
            530                 535                 540

Gln Val Phe Ser Ser Glu Arg Ser Ser Phe Leu Glu Gln Pro Pro Asn
545                 550                 555                 560

Leu Glu Leu Ala Gly Thr Gln Pro Ala Phe Ser Gly Ser Pro Ser Pro
                565                 570                 575

Gln Pro Asp Ser Thr Asp Asn Asp Asp Tyr Asp Asp Ile Ser Ala Ala
            580                 585                 590

<210> SEQ ID NO 10
<211> LENGTH: 109
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg Ala
            100                 105

<210> SEQ ID NO 11
<211> LENGTH: 119
<212> TYPE: PRT
<213> ORGANISM: Homo sapiens

<400> SEQUENCE: 11

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30
```

Ala Met Ser Trp Val Arg Gln Ala Pro Gly Lys Arg Leu Glu Trp Val
            35                  40                  45

Ala Thr Ile Ser Ser Gly Gly Ser Tyr Ile Tyr Tyr Pro Asp Ser Val
 50                  55                  60

Lys Gly Arg Phe Thr Ile Ser Arg Asp Asn Val Lys Asn Thr Leu Tyr
 65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser
        115

<210> SEQ ID NO 12
<211> LENGTH: 54
<212> TYPE: PRT
<213> ORGANISM: Homo sapiens

<400> SEQUENCE: 12

Met Asn Ser Asp Ser Glu Cys Pro Leu Ser His Asp Gly Tyr Cys Leu
 1               5                  10                  15

His Asp Gly Val Cys Met Tyr Ile Glu Ala Leu Asp Lys Tyr Ala Cys
            20                  25                  30

Asn Cys Val Val Gly Tyr Ile Gly Glu Arg Cys Gln Tyr Arg Asp Leu
        35                  40                  45

Lys Trp Trp Glu Leu Arg
    50

<210> SEQ ID NO 13
<211> LENGTH: 5969
<212> TYPE: DNA
<213> ORGANISM: Artificial Sequence
<220> FEATURE:
<223> OTHER INFORMATION: Synthetic construct

<400> SEQUENCE: 13
acttacggta atggcccgc ctggctgacc gcccaacgac ccccgcccat tgacgtcaat      60
aatgacgtat gttcccatag taacgccaat agggactttc cattgacgtc aatgggtgga    120
gtatttacgg taaactgccc acttggcagt acatcaagtg tatcatatgc caagtccgcc    180
ccctattgac gtcaatgacg gtaaatggcc cgcctggcat tatgcccagt acatgacctt    240
acgggacttt cctacttggc agtacatcta cgtattagtc atcgctatta ccatggtgat    300
gcggttttgg cagtacacca tgggcgtgg atagcggttt gactcacggg gatttccaag    360
tctccacccc attgacgtca atgggagttt gttttggcac caaaatcaac gggactttcc    420
aaaatgtcgt aataaccccg ccccgttgac gcaaatgggc ggtaggcgtg tacggtggga    480
ggtctatata agcagagctc gtttagtgaa ccgtcagatc ctcactctct tccgcatcgc    540
tgtctgcgag ggccagctgt tgggctcgcg gttgaggaca aactcttcgc ggtctttcca    600
gtactcttgg atcggaaacc cgtcggcctc cgaacggtac tccgccaccg agggacctga    660
gcgagtccgc atcgaccgga tcggaaaacc tctcgagaaa ggcgtctaac cagtcacagt    720
cgcaaggtag gctgagcacc gtggcgggcg gcagcgggtg gcggtcgggg ttgtttctgg    780
cggaggtgct gctgatgatg taattaaagt aggcggtctt gagacggcgg atggtcgagg    840
tgaggtgtgg caggcttgag atccagctgt tgggtgagt actccctctc aaaagcgggc    900
attacttctg cgctaagatt gtcagtttcc aaaaacgagg aggatttgat attcacctgg    960

-continued

```
cccgatctgg ccatacactt gagtgacaat gacatccact ttgcctttct ctccacaggt  1020
gtccactccc aggggagctt gcttgttctt tttgcagaag ctcagaataa acgctcaact  1080
ttggccgcca ccatggacat gagggtcccc gctcagctcc tggggctcct gctgctctgg  1140
ctcccaggtg ccaaatgtga catccagatg acccagtccc ctattctgct gagcgcctcc  1200
gtgggcgacc gcgtgaccat cacttgcaaa gcctcccggg atatccggtc ctacctcacc  1260
tggtaccagc agaggactaa cggatcgccc agaaccctga tctactacgc gactagcctg  1320
gccgatggcg tcccgtcccg gttctcgggg tcggttcag acaggacta tagccttacc  1380 atctcatccc tggagtccga tgacatcgcc gactactact gcctgcaaca cggcgaatct  1440
cccttcacgt tggggtccgg aaccaagctc gagattaagc gaactgtggc tgcaccatct  1500
gtcttcatct cccgccatc tgatgagcag ttgaaatctg gaactgcctc tgttgtgtgc  1560
ctgctgaata acttctatcc cagagaggcc aaagtacagt ggaaggtgga taacgccctc  1620
caatcgggta actcccagga gagtgtcaca gagcaggaca gcaaggacag cacctacagc  1680
ctcagcagca ccctgacgct gagcaaagca gactacgaga acacaaaagt ctacgcctgc  1740
gaagtcaccc atcagggcct gagctcgccc gtcacaaaga gcttcaacag gggagagtgt  1800
taatagctct taaaaaattc cgccccccc ctaacgttac tggccgaagc cgcttggaat  1860
aaggccggtg tgcgtttgtc tatatgttat tttccaccat attgccgtct tttggcaatg  1920
tgagggcccg gaaacctggc cctgtcttct tgacgagcat tcctaggggt ctttcccctc  1980
tcgccaaagg aatgcaaggt ctgttgaatg tcgtgaagga agcagttcct ctggaagctt  2040
cttgaagaca acaacgtct gtagcgaccc tttgcaggca gcggaacccc ccacctggcg  2100
acaggtgcct ctgcggccaa aagccacgtg tataagatac acctgcaaag gcggcacaac  2160
cccagtgcca cgttgtgagt tggatagttg tggaaagagt caaatggctc tcctcaagcg  2220
tattcaacaa ggggctgaag gatgcccaga aggtacccca ttgtatggga tctgatctgg  2280
ggcctcggta cacatgcttt acatgtgttt agtcgaggtt aaaaaacgtc taggccccc  2340 gaaccacggg gacgtggttt tcctttgaaa aacacgatga taatatgccc acaaccatgg  2400
gctggtccct gatcctgctg ttcctggtgg ccgtggccac gcgtgtgctg tcagaggtgc  2460
agcttgtgga atcgggtggc ggactggtca gcctggggg atcgctgaaa ctgagctgtg  2520
cagccagcgg tttcaagttc tcacgctacg ccatgtcctg ggtcagacag gcgccgggaa  2580
agcgcctgga atgggtggct actatctcct ccggcggatc ctacatctac taccccgact  2640
ccgtgaaggg ccggttcacc attagccgcg acaacgtgaa gaacactctg tacctccaaa  2700
tgtcaagcct gaggtctgag gataccgcca tctactattg cgcccggcgg gactacgact  2760
tggattactt tgactcctgg ggccagggga ccctcgtgac cgtgtcctcg gccagcacca  2820
agggcccatc ggtcttcccc ctggcaccct cctccaagag cacctctggg ggcacagcgg  2880
ccctgggctg cctggtcaag gactacttcc ccgaaccggt gacggtgtcg tggaactcag  2940
gcgccctgac cagcggcgtg cacaccttcc cggctgtcct acagtcctca ggactctact  3000
ccctcagcag cgtggtgacc gtgccctcca gcagcttggg cacccagacc tacatctgca  3060
acgtgaatca caagcccagc aacaccaagg tggacaagaa agttgagccc aaatcttgtg  3120
acaaaactca cacatgccca ccgtgcccag cacctgaact cctgggggga ccgtcagtct  3180
tcctcttccc cccaaaaccc aaggacaccc tcatgatctc ccggacccct gaggtcacat  3240
gcgtggtggt ggacgtgagc cacgaagacc ctgaggtcaa gttcaactgg tacgtggacg  3300
```

```
gcgtggaggt gcataatgcc aagacaaagc cgcgggagga gcagtacaac agcacgtacc    3360
gggtggtcag cgtcctcacc gtcctgcacc aggactggct gaatggcaag gagtacaagt    3420
gcaaggtcag caacaaagcc ctcccagccc ccatcgagaa aaccatctcc aaagccaaag    3480
ggcagccccg agaaccacag gtgtacaccc tgcccccatc ccgggatgag ctgaccaaga    3540
accaggtcag cctgacctgc ctggtcaaag gcttctatcc cagcgacatc gccgtggagt    3600
gggagagcaa tgggcagccg gagaacaact acaagaccac gcctcccgtg ctggactccg    3660
acggctcctt cttcctctac agcaagctca ccgtggacaa gagcaggtgg cagcagggga    3720
acgtcttctc atgctccgtg atgcatgagg ctctgcacaa ccactacacg cagaagtccc    3780
tctccctgtc tccgggtaaa taggcggccg ctaaaagcgg ccgctcgagg ccggcaaggc    3840
cggatccccc gacctctggc taataaagga aatttatttt cattgcaata gtgtgttgga    3900
atttttgtg tctctcactc ggaaggacat atgggagggc aaatcattta aaacatcaga    3960
atgagtattt ggtttagagt ttggcaacat atgcccatat gctggctgcc atgaacaaag    4020
gttggctata aagaggtcat cagtatatga acagccccc tgctgtccat tccttattcc    4080
atagaaaagc cttgacttga ggttagattt ttttatatt ttgttttgtg ttatttttt    4140
ctttaacatc cctaaaattt tccttacatg ttttactagc cagattttc ctcctctcct    4200
gactactccc agtcatagct gtccctcttc tcttatggag atctcagcct tgagcggtat    4260
cagctcactc aaaggcggta atacggttat ccacagaatc aggggataac gcaggaaaga    4320
acatgtgagc aaaaggccag caaaaggcca ggaaccgtaa aaaggccgcg ttgctggcgt    4380
ttttccatag gctccgcccc cctgacgagc atcacaaaaa tcgacgctca agtcagaggt    4440
ggcgaaaccc gacaggacta taaagatacc aggcgtttcc ccctggaagc tccctcgtgc    4500
gctctcctgt tccgaccctg ccgcttaccg gatacctgtc cgcctttctc ccttcgggaa    4560
gcgtggcgct ttctcatagc tcacgctgta ggtatctcag ttcggtgtag gtcgttcgct    4620
ccaagctggg ctgtgtgcac gaaccccccg ttcagcccga ccgctgcgcc ttatccggta    4680
actatcgtct gagtccaac ccggtaagac acgacttatc gccactggca gcagccactg    4740
gtaacaggat tagcagagcg aggtatgtag gcggtgctac agagttcttg aagtggtggg    4800
ctaactacgg ctacactaga agaacagtat ttggtatctg cgctctgctg aagccagtta    4860
ccttcggaaa aagagttggt agctcttgat ccggcaaaca aaccaccgct ggtagcggtg    4920
gttttttgt ttgcaagcag cagattacgc gcagaaaaaa aggatctcaa gaagatcctt    4980
tgatcttttc tacggggtct gacgctcagt ggaacgacgc gcgcgtaact cacgttaagg    5040
gattttggtc atgagttaga aaaactcatc gagcatcaaa tgaaactgca atttattcat    5100
atcaggatta tcaataccat attttttgaaa aagccgtttc tgtaatgaag gagaaaactc    5160
accgaggcag ttccatagga tggcaagatc ctggtatcgg tctgcgattc cgactcgtcc    5220
aacatcaata caacctatta atttcccctc gtcaaaaata aggttatcaa gtgagaaatc    5280
accatgagtg acgactgaat ccggtgagaa tggcaaaagt ttatgcattt ctttccagac    5340
ttgttcaaca ggccagccat tacgctcgtc atcaaaatca ctcgcatcaa ccaaaccgtt    5400
attcattcgt gattgcgcct gagcgaggcg aaatacgcga tcgctgttaa aaggacaatt    5460
acaaacagga atcgagtgca accggcgcag gaacactgcc agcgcatcaa caatatttc    5520
acctgaatca ggatattctt ctaatacctg gaacgctgtt tttccgggga tcgcagtggt    5580
gagtaaccat gcatcatcag gagtacggat aaaatgcttg atggtcggaa gtggcataaa    5640
ttccgtcagc cagtttagtc tgaccatctc atctgtaaca tcattggcaa cgctacctt    5700
```

```
gccatgtttc agaaacaact ctggcgcatc gggcttccca tacaagcgat agattgtcgc    5760
acctgattgc ccgacattat cgcgagccca tttataccca tataaatcag catccatgtt    5820
ggaatttaat cgcggcctcg acgtttcccg ttggatatgg ctcatttttt acttcctcac    5880
cttgtcgtat tatactatgc cgatatacta tgccgatgat taattgtcga cactgcgggg    5940
gctctatata tggagttccg cgttacata                                      5969
```

```
<210> SEQ ID NO 14
<211> LENGTH: 112
<212> TYPE: PRT
<213> ORGANISM: Homo sapiens

<400> SEQUENCE: 14
```

Val Arg Leu Thr Asn Gly Ser Ser Cys Ser Gly Thr Val Glu Val
1               5                   10                  15

Arg Leu Glu Ala Ser Trp Glu Pro Ala Cys Gly Ala Leu Trp Asp Ser
            20                  25                  30

Arg Ala Glu Ala Val Cys Arg Ala Leu Gly Cys Gly Gly Ala Glu
        35                  40                  45

Ala Ala Ser Gln Leu Ala Pro Pro Thr Pro Glu Leu Pro Pro Pro Pro
50                  55                  60

Ala Ala Gly Asn Thr Ser Val Ala Ala Asn Ala Thr Leu Ala Gly Ala
65                  70                  75                  80

Pro Ala Leu Leu Cys Ser Gly Ala Glu Trp Arg Leu Cys Glu Val Val
                85                  90                  95

Glu His Ala Cys Arg Ser Asp Gly Arg Arg Ala Arg Val Thr Cys Ala
            100                 105                 110

```
<210> SEQ ID NO 15
<211> LENGTH: 60
<212> TYPE: DNA
<213> ORGANISM: Homo sapiens

<400> SEQUENCE: 15
gtccaacttg ttgaatcagg tggggggctg gtcaaacccg ggggctctct gaaactaagt    60

<210> SEQ ID NO 16
<211> LENGTH: 45
<212> TYPE: DNA
<213> ORGANISM: Homo sapiens

<400> SEQUENCE: 16
ttctctcggt acgctatgtc gtgggtcaga caagcgcccg gcaaa                    45

<210> SEQ ID NO 17
<211> LENGTH: 57
<212> TYPE: DNA
<213> ORGANISM: Homo sapiens

<400> SEQUENCE: 17
cgtgattatg atctagacta ctttgactcc tggggtcaag gtacgctcgt gacggtt       57

<210> SEQ ID NO 18
<211> LENGTH: 20
<212> TYPE: PRT
<213> ORGANISM: Homo sapiens

<400> SEQUENCE: 18
```

Val Gln Leu Val Glu Ser Gly Gly Gly Leu Val Lys Pro Gly Gly Ser

-continued

```
    1               5                   10                  15

Leu Lys Leu Ser
            20

<210> SEQ ID NO 19
<211> LENGTH: 15
<212> TYPE: PRT
<213> ORGANISM: Homo sapiens

<400> SEQUENCE: 19

Phe Ser Arg Tyr Ala Met Ser Trp Val Arg Gln Ala Pro Gly Lys
1               5                   10                  15

<210> SEQ ID NO 20
<211> LENGTH: 19
<212> TYPE: PRT
<213> ORGANISM: Homo sapiens

<400> SEQUENCE: 20

Arg Asp Tyr Asp Leu Asp Tyr Phe Asp Ser Trp Gly Gln Gly Thr Leu
1               5                   10                  15

Val Thr Val

<210> SEQ ID NO 21
<211> LENGTH: 373
<212> TYPE: PRT
<213> ORGANISM: Homo sapiens

<400> SEQUENCE: 21

Met Gly Trp Ser Leu Ile Leu Leu Phe Leu Val Ala Val Ala Thr Arg
1               5                   10                  15

Val Leu Ser His Pro Ser Pro Ala Pro Pro Asp Gln Leu Asn Thr Ser
            20                  25                  30

Ser Ala Glu Ser Glu Leu Trp Glu Pro Gly Glu Arg Leu Pro Val Arg
        35                  40                  45

Leu Thr Asn Gly Ser Ser Ser Cys Ser Gly Thr Val Glu Val Arg Leu
    50                  55                  60

Glu Ala Ser Trp Glu Pro Ala Cys Gly Ala Leu Trp Asp Ser Arg Ala
65                  70                  75                  80

Ala Glu Ala Val Cys Arg Ala Leu Gly Cys Gly Gly Ala Glu Ala Ala
                85                  90                  95

Ser Gln Leu Ala Pro Pro Thr Pro Glu Leu Pro Pro Pro Ala Ala
            100                 105                 110

Gly Asn Thr Ser Val Ala Ala Asn Ala Thr Leu Ala Gly Ala Pro Ala
            115                 120                 125

Leu Leu Cys Ser Gly Ala Glu Trp Arg Leu Cys Glu Val Val Glu His
    130                 135                 140

Ala Cys Arg Ser Asp Gly Arg Ala Arg Val Thr Cys Ala Glu Asn
145                 150                 155                 160

Arg Ala Leu Arg Leu Val Asp Gly Gly Ala Cys Ala Gly Arg Val
                165                 170                 175

Glu Met Leu Glu His Gly Glu Trp Gly Ser Val Cys Asp Asp Thr Trp
            180                 185                 190

Asp Leu Glu Asp Ala His Val Val Cys Arg Gln Leu Gly Cys Gly Trp
            195                 200                 205

Ala Val Gln Ala Leu Pro Gly Leu His Phe Thr Pro Gly Arg Gly Pro
    210                 215                 220
```

```
Ile His Arg Asp Gln Val Asn Cys Ser Gly Ala Glu Ala Tyr Leu Trp
225                 230                 235                 240

Asp Cys Pro Gly Leu Pro Gly Gln His Tyr Cys Gly His Lys Glu Asp
            245                 250                 255

Ala Gly Val Val Cys Ser Glu His Gln Ser Trp Arg Leu Thr Gly Gly
        260                 265                 270

Ala Asp Arg Cys Glu Gly Gln Val Glu Val His Phe Arg Gly Val Trp
    275                 280                 285

Asn Thr Val Cys Asp Ser Glu Trp Tyr Pro Ser Glu Ala Lys Val Leu
290                 295                 300

Cys Gln Ser Leu Gly Cys Gly Thr Ala Val Glu Arg Pro Lys Gly Leu
305                 310                 315                 320

Pro His Ser Leu Ser Gly Arg Met Tyr Tyr Ser Cys Asn Gly Glu Glu
                325                 330                 335

Leu Thr Leu Ser Asn Cys Ser Trp Arg Phe Asn Asn Ser Asn Leu Cys
            340                 345                 350

Ser Gln Ser Leu Ala Ala Arg Val Leu Cys Ser Ala Ser Arg Gly His
        355                 360                 365

His His His His His
    370

<210> SEQ ID NO 22
<211> LENGTH: 12
<212> TYPE: PRT
<213> ORGANISM: Artificial Sequence
<220> FEATURE:
<223> OTHER INFORMATION: Synthetic construct

<400> SEQUENCE: 22

Cys Gln Phe Asp Leu Ser Thr Arg Arg Leu Lys Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic construct

<400> SEQUENCE: 23

Cys Gln Tyr Asn Leu Ser Ser Arg Ala Leu Lys Cys
1               5                   10

<210> SEQ ID NO 24
<211> LENGTH: 68
<212> TYPE: PRT
<213> ORGANISM: Homo sapiens

<400> SEQUENCE: 24

Ile Gln Met Thr Gln Ser Pro Ser Ser Leu Ser Ala Ser Val Gly Asp
1               5                   10                  15

Arg Val Thr Ile Thr Cys Lys Ala Ser Arg Asp Ile Arg Ser Tyr Leu
            20                  25                  30

Thr Trp Tyr Gln Gln Lys Pro Gly Lys Ala Pro Lys Thr Leu Ile Tyr
        35                  40                  45

Tyr Ala Thr Ser Leu Ala Asp Gly Val Pro Ser Arg Phe Ser Gly Ser
    50                  55                  60

Gly Ser Gly Gln
65
```

```
<210> SEQ ID NO 25
<211> LENGTH: 32
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

<210> SEQ ID NO 26
<211> LENGTH: 65
<212> TYPE: PRT
<213> ORGANISM: Homo sapiens

<400> SEQUENCE: 26

Leu Thr Trp Tyr Gln Gln Lys Pro Gly Lys Ala Pro Lys Thr Leu Ile
1               5                   10                  15

Tyr Tyr Ala Thr Ser Leu Ala Asp Gly Val Pro Ser Arg Phe Ser Gly
            20                  25                  30

Ser Gly Ser Gly Gln Asp Tyr Ser Leu Thr Ile Ser Ser Leu Glu Ser
        35                  40                  45

Asp Asp Thr Ala Thr Tyr Tyr Cys Leu Gln His Gly Glu Ser Pro Phe
    50                  55                  60

Thr
65

<210> SEQ ID NO 27
<211> LENGTH: 12
<212> TYPE: PRT
<213> ORGANISM: Homo sapiens

<400> SEQUENCE: 27

Phe Gly Ser Gly Thr Lys Leu Glu Ile Lys Arg Ala
1               5                   10

<210> SEQ ID NO 28
<211> LENGTH: 35
<212> TYPE: PRT
<213> ORGANISM: Homo sapiens

<400> SEQUENCE: 28

Glu Val Gln Leu Val Glu Ser Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser
        35

<210> SEQ ID NO 29
<211> LENGTH: 20
<212> TYPE: PRT
<213> ORGANISM: Homo sapiens

<400> SEQUENCE: 29

Trp Val Arg Gln Ala Pro Gly Lys Arg Leu Glu Trp Val Ala Thr Ile
1               5                   10                  15

Ser Ser Gly Gly
            20
```

<210> SEQ ID NO 30
<211> LENGTH: 53
<212> TYPE: PRT
<213> ORGANISM: Homo sapiens

<400> SEQUENCE: 30

Ser Tyr Ile Tyr Tyr Pro Asp Ser Val Lys Gly Arg Phe Thr Ile Ser
1               5                   10                  15

Arg Asp Asn Val Lys Asn Thr Leu Tyr Leu Gln Met Ser Ser Leu Arg
            20                  25                  30

Ser Glu Asp Thr Ala Met Tyr Tyr Cys Ala Arg Arg Asp Tyr Asp Leu
        35                  40                  45

Asp Tyr Phe Asp Ser
    50

<210> SEQ ID NO 31
<211> LENGTH: 11
<212> TYPE: PRT
<213> ORGANISM: Homo sapiens

<400> SEQUENCE: 31

Trp Gly Gln Gly Thr Leu Val Thr Val Ser Ser
1               5                   10

<210> SEQ ID NO 32
<211> LENGTH: 745
<212> TYPE: PRT
<213> ORGANISM: Artificial Sequence
<220> FEATURE:
<223> OTHER INFORMATION: Synthetic construct

<400> SEQUENCE: 32

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

```
Phe Asn Arg Gly Glu Cys Ala Ser Ala Ser Ala Ala Ser Ser Ala
    210                 215                 220
Ser Ser Ala Ala Ser Ser Asn Ser Asp Ser Glu Cys Pro Leu Ser His
225                 230                 235                 240
Asp Gly Tyr Cys Leu His Asp Gly Val Cys Met Tyr Ile Glu Ala Leu
                245                 250                 255
Asp Lys Tyr Ala Cys Asn Cys Val Val Gly Tyr Ile Gly Glu Arg Cys
            260                 265                 270
Gln Tyr Arg Asp Leu Lys Trp Trp Glu Leu Arg Gly Ser Gly Val Leu
        275                 280                 285
Pro Ala Ser Leu Tyr Ser Ser Glu Val Gln Leu Val Glu Ser Gly
    290                 295                 300
Gly Gly Leu Val Lys Pro Gly Gly Ser Leu Lys Leu Ser Cys Ala Ala
305                 310                 315                 320
Ser Gly Phe Lys Phe Ser Arg Tyr Ala Met Ser Trp Val Arg Gln Ala
                325                 330                 335
Pro Gly Lys Arg Leu Glu Trp Val Ala Thr Ile Ser Ser Gly Gly Ser
            340                 345                 350
Tyr Ile Tyr Tyr Pro Asp Ser Val Lys Gly Arg Phe Thr Ile Ser Arg
        355                 360                 365
Asp Asn Val Lys Asn Thr Leu Tyr Leu Gln Met Ser Ser Leu Arg Ser
370                 375                 380
Glu Asp Thr Ala Ile Tyr Tyr Cys Ala Arg Arg Asp Tyr Asp Leu Asp
385                 390                 395                 400
Tyr Phe Asp Ser Trp Gly Gln Gly Thr Leu Val Thr Val Ser Ser Ala
                405                 410                 415
Ser Thr Lys Gly Pro Ser Val Phe Pro Leu Ala Pro Ser Ser Lys Ser
            420                 425                 430
Thr Ser Gly Gly Thr Ala Ala Leu Gly Cys Leu Val Lys Asp Tyr Phe
        435                 440                 445
Pro Glu Pro Val Thr Val Ser Trp Asn Ser Gly Ala Leu Thr Ser Gly
    450                 455                 460
Val His Thr Phe Pro Ala Val Leu Gln Ser Ser Gly Leu Tyr Ser Leu
465                 470                 475                 480
Ser Ser Val Val Thr Val Pro Ser Ser Ser Leu Gly Thr Gln Thr Tyr
                485                 490                 495
Ile Cys Asn Val Asn His Lys Pro Ser Asn Thr Lys Val Asp Lys Lys
            500                 505                 510
Val Glu Pro Lys Ser Cys Asp Lys Thr His Thr Cys Pro Pro Cys Pro
        515                 520                 525
Ala Pro Glu Leu Leu Gly Gly Pro Ser Val Phe Leu Phe Pro Pro Lys
530                 535                 540
Pro Lys Asp Thr Leu Met Ile Ser Arg Thr Pro Glu Val Thr Cys Val
545                 550                 555                 560
Val Val Asp Val Ser His Glu Asp Pro Glu Val Lys Phe Asn Trp Tyr
                565                 570                 575
Val Asp Gly Val Glu Val His Asn Ala Lys Thr Lys Pro Arg Glu Glu
            580                 585                 590
Gln Tyr Asn Ser Thr Tyr Arg Val Val Ser Val Leu Thr Val Leu His
        595                 600                 605
Gln Asp Trp Leu Asn Gly Lys Glu Tyr Lys Cys Lys Val Ser Asn Lys
610                 615                 620
```

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Asp Glu Leu
            645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
        690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
                740                 745

<210> SEQ ID NO 33
<211> LENGTH: 214
<212> TYPE: PRT
<213> ORGANISM: Artificial Sequence
<220> FEATURE:
<223> OTHER INFORMATION: Synthetic construct

<400> SEQUENCE: 33

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 16

```
<212> TYPE: PRT
<213> ORGANISM: Artificial Sequence
<220> FEATURE:
<223> OTHER INFORMATION: Synthetic construct

<400> SEQUENCE: 34

Ala Ser Ala Ser Ala Ala Ser Ser Ala Ser Ser Ala Ala Ser Ser
1               5                   10                  15

<210> SEQ ID NO 35
<211> LENGTH: 13
<212> TYPE: PRT
<213> ORGANISM: Artificial Sequence
<220> FEATURE:
<223> OTHER INFORMATION: Synthetic construct

<400> SEQUENCE: 35

Gly Ser Gly Val Leu Pro Ala Ser Leu Tyr Ser Gly Ser
1               5                   10

<210> SEQ ID NO 36
<211> LENGTH: 227
<212> TYPE: PRT
<213> ORGANISM: Artificial Sequence
<220> FEATURE:
<223> OTHER INFORMATION: Synthetic construct

<400> SEQUENCE: 36

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Ile Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225
```

```
<210> SEQ ID NO 37
<211> LENGTH: 222
<212> TYPE: PRT
<213> ORGANISM: Artificial Sequence
<220> FEATURE:
<223> OTHER INFORMATION: Synthetic construct

<400> SEQUENCE: 37

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 38
<211> LENGTH: 745
<212> TYPE: PRT
<213> ORGANISM: Artificial Sequence
<220> FEATURE:
<223> OTHER INFORMATION: Synthetic construct

<400> SEQUENCE: 38

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95
```

-continued

```
Thr Phe Gly Ser Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Ala Ser Ala Ser Ala Ala Ser Ser Ala
    210                 215                 220
Ser Ser Ala Ala Ser Ser Asn Ser Asp Ser Glu Cys Pro Leu Ser His
225                 230                 235                 240
Asp Gly Tyr Cys Leu His Asp Gly Val Cys Met Tyr Ile Glu Ala Leu
                245                 250                 255
Asp Lys Tyr Ala Cys Asn Cys Val Val Gly Tyr Ile Gly Glu Arg Cys
            260                 265                 270
Gln Tyr Arg Asp Leu Lys Trp Trp Glu Leu Arg Gly Ser Gly Ser Gly
        275                 280                 285
Ile Glu Pro Asp Ser Gly Gly Ser Glu Val Gln Leu Val Glu Ser Gly
    290                 295                 300
Gly Gly Leu Val Lys Pro Gly Gly Ser Leu Lys Leu Ser Cys Ala Ala
305                 310                 315                 320
Ser Gly Phe Lys Phe Ser Arg Tyr Ala Met Ser Trp Val Arg Gln Ala
                325                 330                 335
Pro Gly Lys Arg Leu Glu Trp Val Ala Thr Ile Ser Ser Gly Gly Ser
            340                 345                 350
Tyr Ile Tyr Tyr Pro Asp Ser Val Lys Gly Arg Phe Thr Ile Ser Arg
        355                 360                 365
Asp Asn Val Lys Asn Thr Leu Tyr Leu Gln Met Ser Ser Leu Arg Ser
    370                 375                 380
Glu Asp Thr Ala Ile Tyr Tyr Cys Ala Arg Arg Asp Tyr Asp Leu Asp
385                 390                 395                 400
Tyr Phe Asp Ser Trp Gly Gln Gly Thr Leu Val Thr Val Ser Ser Ala
                405                 410                 415
Ser Thr Lys Gly Pro Ser Val Phe Pro Leu Ala Pro Ser Ser Lys Ser
            420                 425                 430
Thr Ser Gly Gly Thr Ala Ala Leu Gly Cys Leu Val Lys Asp Tyr Phe
        435                 440                 445
Pro Glu Pro Val Thr Val Ser Trp Asn Ser Gly Ala Leu Thr Ser Gly
    450                 455                 460
Val His Thr Phe Pro Ala Val Leu Gln Ser Ser Gly Leu Tyr Ser Leu
465                 470                 475                 480
Ser Ser Val Val Thr Val Pro Ser Ser Ser Leu Gly Thr Gln Thr Tyr
                485                 490                 495
Ile Cys Asn Val Asn His Lys Pro Ser Asn Thr Lys Val Asp Lys Lys
            500                 505                 510
Val Glu Pro Lys Ser Cys Asp Lys Thr His Thr Cys Pro Pro Cys Pro
```

```
            515                 520                 525
Ala Pro Glu Leu Leu Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
    690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 39
<211> LENGTH: 13
<212> TYPE: PRT
<213> ORGANISM: Artificial Sequence
<220> FEATURE:
<223> OTHER INFORMATION: Synthetic construct

<400> SEQUENCE: 39

Gly Ser Gly Ser Gly Ile Glu Pro Asp Ser Gly Gly Ser
1               5                   10

<210> SEQ ID NO 40
<211> LENGTH: 227
<212> TYPE: PRT
<213> ORGANISM: Homo sapiens

<400> SEQUENCE: 40

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80
```

```
Leu Gln Met Ser Ser Leu Arg Ser Glu Asp Thr Ala Ile Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 41
<211> LENGTH: 222
<212> TYPE: PRT
<213> ORGANISM: Homo sapiens

<400> SEQUENCE: 41

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
```

-continued

<210> SEQ ID NO 42
<211> LENGTH: 743
<212> TYPE: PRT
<213> ORGANISM: Artificial Sequence
<220> FEATURE:
<223> OTHER INFORMATION: Synthetic construct

<400> SEQUENCE: 42

```
Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Ser Ala Ser Ala Ala Ser Ser Ala
    210                 215                 220

Ser Ser Ala Ala Asn Ser Asp Ser Glu Cys Pro Leu Ser His Asp Gly
225                 230                 235                 240

Tyr Cys Leu His Asp Gly Val Cys Met Tyr Ile Glu Ala Leu Asp Lys
                245                 250                 255

Tyr Ala Cys Asn Cys Val Val Gly Tyr Ile Gly Glu Arg Cys Gln Tyr
            260                 265                 270

Arg Asp Leu Lys Trp Trp Glu Leu Arg Gly Ser Gly Ser Gly Ile Glu
        275                 280                 285

Pro Asp Ser Gly Gly Ser Glu Val Gln Leu Val Glu Ser Gly Gly Gly
    290                 295                 300

Leu Val Lys Pro Gly Gly Ser Leu Lys Leu Ser Cys Ala Ala Ser Gly
305                 310                 315                 320

Phe Lys Phe Ser Arg Tyr Ala Met Ser Trp Val Arg Gln Ala Pro Gly
                325                 330                 335

Lys Arg Leu Glu Trp Val Ala Thr Ile Ser Ser Gly Gly Ser Tyr Ile
            340                 345                 350

Tyr Tyr Pro Asp Ser Val Lys Gly Arg Phe Thr Ile Ser Arg Asp Asn
```

```
                355                 360                 365
Val Lys Asn Thr Leu Tyr Leu Gln Met Ser Ser Leu Arg Ser Glu Asp
370                 375                 380
Thr Ala Ile Tyr Tyr Cys Ala Arg Arg Asp Tyr Asp Leu Asp Tyr Phe
385                 390                 395                 400
Asp Ser Trp Gly Gln Gly Thr Leu Val Thr Val Ser Ser Ala Ser Thr
                405                 410                 415
Lys Gly Pro Ser Val Phe Pro Leu Ala Pro Ser Ser Lys Ser Thr Ser
            420                 425                 430
Gly Gly Thr Ala Ala Leu Gly Cys Leu Val Lys Asp Tyr Phe Pro Glu
        435                 440                 445
Pro Val Thr Val Ser Trp Asn Ser Gly Ala Leu Thr Ser Gly Val His
450                 455                 460
Thr Phe Pro Ala Val Leu Gln Ser Ser Gly Leu Tyr Ser Leu Ser Ser
465                 470                 475                 480
Val Val Thr Val Pro Ser Ser Ser Leu Gly Thr Gln Thr Tyr Ile Cys
                485                 490                 495
Asn Val Asn His Lys Pro Ser Asn Thr Lys Val Asp Lys Lys Val Glu
            500                 505                 510
Pro Lys Ser Cys Asp Lys Thr His Thr Cys Pro Pro Cys Pro Ala Pro
        515                 520                 525
Glu Leu Leu Gly Gly Pro Ser Val Phe Leu Phe Pro Pro Lys Pro Lys
530                 535                 540
Asp Thr Leu Met Ile Ser Arg Thr Pro Glu Val Thr Cys Val Val Val
545                 550                 555                 560
Asp Val Ser His Glu Asp Pro Glu Val Lys Phe Asn Trp Tyr Val Asp
                565                 570                 575
Gly Val Glu Val His Asn Ala Lys Thr Lys Pro Arg Glu Glu Gln Tyr
            580                 585                 590
Asn Ser Thr Tyr Arg Val Val Ser Val Leu Thr Val Leu His Gln Asp
        595                 600                 605
Trp Leu Asn Gly Lys Glu Tyr Lys Cys Lys Val Ser Asn Lys Ala Leu
610                 615                 620
Pro Ala Pro Ile Glu Lys Thr Ile Ser Lys Ala Lys Gly Gln Pro Arg
625                 630                 635                 640
Glu Pro Gln Val Tyr Thr Leu Pro Pro Ser Arg Asp Glu Leu Thr Lys
                645                 650                 655
Asn Gln Val Ser Leu Thr Cys Leu Val Lys Gly Phe Tyr Pro Ser Asp
            660                 665                 670
Ile Ala Val Glu Trp Glu Ser Asn Gly Gln Pro Glu Asn Asn Tyr Lys
        675                 680                 685
Thr Thr Pro Pro Val Leu Asp Ser Asp Gly Ser Phe Phe Leu Tyr Ser
690                 695                 700
Lys Leu Thr Val Asp Lys Ser Arg Trp Gln Gln Gly Asn Val Phe Ser
705                 710                 715                 720
Cys Ser Val Met His Glu Ala Leu His Asn His Tyr Thr Gln Lys Ser
                725                 730                 735
Leu Ser Leu Ser Pro Gly Lys
            740

<210> SEQ ID NO 43
<211> LENGTH: 14
<212> TYPE: PRT
<213> ORGANISM: Artificial Sequence
```

```
<220> FEATURE:
<223> OTHER INFORMATION: Synthetic construct

<400> SEQUENCE: 43

Ala Ser Ala Ser Ala Ala Ala Ser Ser Ala Ser Ser Ala Ala
1               5                   10

<210> SEQ ID NO 44
<211> LENGTH: 741
<212> TYPE: PRT
<213> ORGANISM: Artificial Sequence
<220> FEATURE:
<223> OTHER INFORMATION: Synthetic construct

<400> SEQUENCE: 44

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Ser Ala Ser Ala Ala Ser Ser Ala
    210                 215                 220

Ser Ser Asn Ser Asp Ser Glu Cys Pro Leu Ser His Asp Gly Tyr Cys
225                 230                 235                 240

Leu His Asp Gly Val Cys Met Tyr Ile Glu Ala Leu Asp Lys Tyr Ala
                245                 250                 255

Cys Asn Cys Val Val Gly Tyr Ile Gly Glu Arg Cys Gln Tyr Arg Asp
            260                 265                 270

Leu Lys Trp Trp Glu Leu Arg Gly Ser Gly Ser Gly Ile Glu Pro Asp
        275                 280                 285

Ser Gly Gly Ser Glu Val Gln Leu Val Glu Ser Gly Gly Gly Leu Val
    290                 295                 300

Lys Pro Gly Gly Ser Leu Lys Leu Ser Cys Ala Ala Ser Gly Phe Lys
305                 310                 315                 320

Phe Ser Arg Tyr Ala Met Ser Trp Val Arg Gln Ala Pro Gly Lys Arg
```

```
                325                 330                 335
Leu Glu Trp Val Ala Thr Ile Ser Ser Gly Gly Ser Tyr Ile Tyr Tyr
            340                 345                 350

Pro Asp Ser Val Lys Gly Arg Phe Thr Ile Ser Arg Asp Asn Val Lys
            355                 360                 365

Asn Thr Leu Tyr Leu Gln Met Ser Ser Leu Arg Ser Glu Asp Thr Ala
            370                 375                 380

Ile Tyr Tyr Cys Ala Arg Arg Asp Tyr Asp Leu Asp Tyr Phe Asp Ser
385                 390                 395                 400

Trp Gly Gln Gly Thr Leu Val Thr Val Ser Ser Ala Ser Thr Lys Gly
                405                 410                 415

Pro Ser Val Phe Pro Leu Ala Pro Ser Ser Lys Ser Thr Ser Gly Gly
                420                 425                 430

Thr Ala Ala Leu Gly Cys Leu Val Lys Asp Tyr Phe Pro Glu Pro Val
                435                 440                 445

Thr Val Ser Trp Asn Ser Gly Ala Leu Thr Ser Gly Val His Thr Phe
            450                 455                 460

Pro Ala Val Leu Gln Ser Ser Gly Leu Tyr Ser Leu Ser Ser Val Val
465                 470                 475                 480

Thr Val Pro Ser Ser Ser Leu Gly Thr Gln Thr Tyr Ile Cys Asn Val
                485                 490                 495

Asn His Lys Pro Ser Asn Thr Lys Val Asp Lys Lys Val Glu Pro Lys
                500                 505                 510

Ser Cys Asp Lys Thr His Thr Cys Pro Pro Cys Pro Ala Pro Glu Leu
                515                 520                 525

Leu Gly Gly Pro Ser Val Phe Leu Phe Pro Pro Lys Pro Lys Asp Thr
            530                 535                 540

Leu Met Ile Ser Arg Thr Pro Glu Val Thr Cys Val Val Val Asp Val
545                 550                 555                 560

Ser His Glu Asp Pro Glu Val Lys Phe Asn Trp Tyr Val Asp Gly Val
                565                 570                 575

Glu Val His Asn Ala Lys Thr Lys Pro Arg Glu Glu Gln Tyr Asn Ser
                580                 585                 590

Thr Tyr Arg Val Val Ser Val Leu Thr Val Leu His Gln Asp Trp Leu
            595                 600                 605

Asn Gly Lys Glu Tyr Lys Cys Lys Val Ser Asn Lys Ala Leu Pro Ala
            610                 615                 620

Pro Ile Glu Lys Thr Ile Ser Lys Ala Lys Gly Gln Pro Arg Glu Pro
625                 630                 635                 640

Gln Val Tyr Thr Leu Pro Pro Ser Arg Asp Glu Leu Thr Lys Asn Gln
                645                 650                 655

Val Ser Leu Thr Cys Leu Val Lys Gly Phe Tyr Pro Ser Asp Ile Ala
                660                 665                 670

Val Glu Trp Glu Ser Asn Gly Gln Pro Glu Asn Asn Tyr Lys Thr Thr
                675                 680                 685

Pro Pro Val Leu Asp Ser Asp Gly Ser Phe Phe Leu Tyr Ser Lys Leu
            690                 695                 700

Thr Val Asp Lys Ser Arg Trp Gln Gln Gly Asn Val Phe Ser Cys Ser
705                 710                 715                 720

Val Met His Glu Ala Leu His Asn His Tyr Thr Gln Lys Ser Leu Ser
                725                 730                 735

Leu Ser Pro Gly Lys
            740
```

<210> SEQ ID NO 45
<211> LENGTH: 12
<212> TYPE: PRT
<213> ORGANISM: Artificial Sequence
<220> FEATURE:
<223> OTHER INFORMATION: Synthetic construct

<400> SEQUENCE: 45

```
Ala Ser Ala Ser Ala Ala Ala Ser Ser Ala Ser Ser
1               5                   10
```

<210> SEQ ID NO 46
<211> LENGTH: 739
<212> TYPE: PRT
<213> ORGANISM: Artificial Sequence
<220> FEATURE:
<223> OTHER INFORMATION: Synthetic construct

<400> SEQUENCE: 46

```
Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Ser Ala Ser Ala Ala Ala Ser Ser Ala
    210                 215                 220

Asn Ser Asp Ser Glu Cys Pro Leu Ser His Asp Gly Tyr Cys Leu His
225                 230                 235                 240

Asp Gly Val Cys Met Tyr Ile Glu Ala Leu Asp Lys Tyr Ala Cys Asn
                245                 250                 255

Cys Val Val Gly Tyr Ile Gly Glu Arg Cys Gln Tyr Arg Asp Leu Lys
            260                 265                 270

Trp Trp Glu Leu Arg Gly Ser Gly Ser Gly Ile Glu Pro Asp Ser Gly
        275                 280                 285

Gly Ser Glu Val Gln Leu Val Glu Ser Gly Gly Gly Leu Val Lys Pro
```

-continued

```
              290                 295                 300
Gly Gly Ser Leu Lys Leu Ser Cys Ala Ala Ser Gly Phe Lys Phe Ser
305                 310                 315                 320

Arg Tyr Ala Met Ser Trp Val Arg Gln Ala Pro Gly Lys Arg Leu Glu
                    325                 330                 335

Trp Val Ala Thr Ile Ser Ser Gly Gly Ser Tyr Ile Tyr Tyr Pro Asp
                340                 345                 350

Ser Val Lys Gly Arg Phe Thr Ile Ser Arg Asp Asn Val Lys Asn Thr
            355                 360                 365

Leu Tyr Leu Gln Met Ser Ser Leu Arg Ser Glu Asp Thr Ala Ile Tyr
        370                 375                 380

Tyr Cys Ala Arg Arg Asp Tyr Asp Leu Asp Tyr Phe Asp Ser Trp Gly
385                 390                 395                 400

Gln Gly Thr Leu Val Thr Val Ser Ser Ala Ser Thr Lys Gly Pro Ser
                405                 410                 415

Val Phe Pro Leu Ala Pro Ser Ser Lys Ser Thr Ser Gly Gly Thr Ala
                420                 425                 430

Ala Leu Gly Cys Leu Val Lys Asp Tyr Phe Pro Glu Pro Val Thr Val
            435                 440                 445

Ser Trp Asn Ser Gly Ala Leu Thr Ser Gly Val His Thr Phe Pro Ala
        450                 455                 460

Val Leu Gln Ser Ser Gly Leu Tyr Ser Leu Ser Ser Val Val Thr Val
465                 470                 475                 480

Pro Ser Ser Ser Leu Gly Thr Gln Thr Tyr Ile Cys Asn Val Asn His
                485                 490                 495

Lys Pro Ser Asn Thr Lys Val Asp Lys Lys Val Glu Pro Lys Ser Cys
                500                 505                 510

Asp Lys Thr His Thr Cys Pro Pro Cys Pro Ala Pro Glu Leu Leu Gly
            515                 520                 525

Gly Pro Ser Val Phe Leu Phe Pro Pro Lys Pro Lys Asp Thr Leu Met
        530                 535                 540

Ile Ser Arg Thr Pro Glu Val Thr Cys Val Val Val Asp Val Ser His
545                 550                 555                 560

Glu Asp Pro Glu Val Lys Phe Asn Trp Tyr Val Asp Gly Val Glu Val
                565                 570                 575

His Asn Ala Lys Thr Lys Pro Arg Glu Glu Gln Tyr Asn Ser Thr Tyr
                580                 585                 590

Arg Val Val Ser Val Leu Thr Val Leu His Gln Asp Trp Leu Asn Gly
            595                 600                 605

Lys Glu Tyr Lys Cys Lys Val Ser Asn Lys Ala Leu Pro Ala Pro Ile
        610                 615                 620

Glu Lys Thr Ile Ser Lys Ala Lys Gly Gln Pro Arg Glu Pro Gln Val
625                 630                 635                 640

Tyr Thr Leu Pro Pro Ser Arg Asp Glu Leu Thr Lys Asn Gln Val Ser
                645                 650                 655

Leu Thr Cys Leu Val Lys Gly Phe Tyr Pro Ser Asp Ile Ala Val Glu
                660                 665                 670

Trp Glu Ser Asn Gly Gln Pro Glu Asn Tyr Lys Thr Thr Pro Pro
            675                 680                 685

Val Leu Asp Ser Asp Gly Ser Phe Phe Leu Tyr Ser Lys Leu Thr Val
        690                 695                 700

Asp Lys Ser Arg Trp Gln Gln Gly Asn Val Phe Ser Cys Ser Val Met
705                 710                 715                 720
```

His Glu Ala Leu His Asn His Tyr Thr Gln Lys Ser Leu Ser Leu Ser
            725                 730                 735

Pro Gly Lys

<210> SEQ ID NO 47
<211> LENGTH: 10
<212> TYPE: PRT
<213> ORGANISM: Artificial Sequence
<220> FEATURE:
<223> OTHER INFORMATION: Synthetic construct

<400> SEQUENCE: 47

Ala Ser Ala Ser Ala Ala Ala Ser Ser Ala
1               5                   10

<210> SEQ ID NO 48
<211> LENGTH: 737
<212> TYPE: PRT
<213> ORGANISM: Artificial Sequence
<220> FEATURE:
<223> OTHER INFORMATION: Synthetic construct

<400> SEQUENCE: 48

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Ser Ala Ser Ala Ala Ala Ser Asn Ser
    210                 215                 220

Asp Ser Glu Cys Pro Leu Ser His Asp Gly Tyr Cys Leu His Asp Gly
225                 230                 235                 240

Val Cys Met Tyr Ile Glu Ala Leu Asp Lys Tyr Ala Cys Asn Cys Val
                245                 250                 255

Val Gly Tyr Ile Gly Glu Arg Cys Gln Tyr Arg Asp Leu Lys Trp Trp
            260                 265                 270

-continued

```
Glu Leu Arg Gly Ser Gly Ser Gly Ile Glu Pro Asp Ser Gly Gly Ser
            275                 280                 285

Glu Val Gln Leu Val Glu Ser Gly Gly Gly Leu Val Lys Pro Gly Gly
290                 295                 300

Ser Leu Lys Leu Ser Cys Ala Ala Ser Gly Phe Lys Phe Ser Arg Tyr
305                 310                 315                 320

Ala Met Ser Trp Val Arg Gln Ala Pro Gly Lys Arg Leu Glu Trp Val
                325                 330                 335

Ala Thr Ile Ser Ser Gly Gly Ser Tyr Ile Tyr Tyr Pro Asp Ser Val
            340                 345                 350

Lys Gly Arg Phe Thr Ile Ser Arg Asp Asn Val Lys Asn Thr Leu Tyr
                355                 360                 365

Leu Gln Met Ser Ser Leu Arg Ser Glu Asp Thr Ala Ile Tyr Tyr Cys
370                 375                 380

Ala Arg Arg Asp Tyr Asp Leu Asp Tyr Phe Asp Ser Trp Gly Gln Gly
385                 390                 395                 400

Thr Leu Val Thr Val Ser Ser Ala Ser Thr Lys Gly Pro Ser Val Phe
            405                 410                 415

Pro Leu Ala Pro Ser Ser Lys Ser Thr Ser Gly Gly Thr Ala Ala Leu
                420                 425                 430

Gly Cys Leu Val Lys Asp Tyr Phe Pro Glu Pro Val Thr Val Ser Trp
            435                 440                 445

Asn Ser Gly Ala Leu Thr Ser Gly Val His Thr Phe Pro Ala Val Leu
450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
            485                 490                 495

Ser Asn Thr Lys Val Asp Lys Lys Val Glu Pro Lys Ser Cys Asp Lys
                500                 505                 510

Thr His Thr Cys Pro Pro Cys Pro Ala Pro Glu Leu Leu Gly Gly Pro
            515                 520                 525

Ser Val Phe Leu Phe Pro Pro Lys Pro Lys Asp Thr Leu Met Ile Ser
530                 535                 540

Arg Thr Pro Glu Val Thr Cys Val Val Val Asp Val Ser His Glu Asp
545                 550                 555                 560

Pro Glu Val Lys Phe Asn Trp Tyr Val Asp Gly Val Glu Val His Asn
                565                 570                 575

Ala Lys Thr Lys Pro Arg Glu Glu Gln Tyr Asn Ser Thr Tyr Arg Val
            580                 585                 590

Val Ser Val Leu Thr Val Leu His Gln Asp Trp Leu Asn Gly Lys Glu
                595                 600                 605

Tyr Lys Cys Lys Val Ser Asn Lys Ala Leu Pro Ala Pro Ile Glu Lys
610                 615                 620

Thr Ile Ser Lys Ala Lys Gly Gln Pro Arg Glu Pro Gln Val Tyr Thr
625                 630                 635                 640

Leu Pro Pro Ser Arg Asp Glu Leu Thr Lys Asn Gln Val Ser Leu Thr
            645                 650                 655

Cys Leu Val Lys Gly Phe Tyr Pro Ser Asp Ile Ala Val Glu Trp Glu
                660                 665                 670

Ser Asn Gly Gln Pro Glu Asn Asn Tyr Lys Thr Thr Pro Pro Val Leu
            675                 680                 685
```

```
Asp Ser Asp Gly Ser Phe Phe Leu Tyr Ser Lys Leu Thr Val Asp Lys
            690                 695                 700

Ser Arg Trp Gln Gln Gly Asn Val Phe Ser Cys Ser Val Met His Glu
705                 710                 715                 720

Ala Leu His Asn His Tyr Thr Gln Lys Ser Leu Ser Leu Ser Pro Gly
                725                 730                 735

Lys

<210> SEQ ID NO 49
<211> LENGTH: 8
<212> TYPE: PRT
<213> ORGANISM: Artificial Sequence
<220> FEATURE:
<223> OTHER INFORMATION: Synthetic construct

<400> SEQUENCE: 49

Ala Ser Ala Ser Ala Ala Ala Ser
1               5

<210> SEQ ID NO 50
<211> LENGTH: 745
<212> TYPE: PRT
<213> ORGANISM: Artificial Sequence
<220> FEATURE:
<223> OTHER INFORMATION: Synthetic construct

<400> SEQUENCE: 50

Asp Ile Gln Met Thr Gln Ser Pro Ile Leu Ser Ala Ser Val Gly
1               5                   10                  15

Asp Arg Val Thr Ile Thr Cys Lys Ala Ser Arg Asp Ile Arg Ser Tyr
                20                  25                  30

Leu Thr Trp Tyr Gln Gln Arg Thr Asn Gly Ser Pro Arg Thr Leu Ile
                35                  40                  45

Tyr Tyr Ala Thr Ser Leu Ala Asp Gly Val Pro Ser Arg Phe Ser Gly
            50                  55                  60

Ser Gly Ser Gly Gln Asp Tyr Ser Leu Thr Ile Ser Ser Leu Glu Ser
65              70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Ala Ser Ala Ser Ala Ala Ala Ser Ser Ala
        210                 215                 220

Ser Ser Ala Ala Pro Pro Asn Ser Asp Ser Glu Cys Pro Leu Ser His
225                 230                 235                 240
```

-continued

Asp Gly Tyr Cys Leu His Asp Gly Val Cys Met Tyr Ile Glu Ala Leu
            245                 250                 255

Asp Lys Tyr Ala Cys Asn Cys Val Val Gly Tyr Ile Gly Glu Arg Cys
        260                 265                 270

Gln Tyr Arg Asp Leu Lys Trp Trp Glu Leu Arg Gly Ser Gly Ser Gly
    275                 280                 285

Ile Glu Pro Asp Ser Gly Ser Glu Val Gln Leu Val Glu Ser Gly
290                 295                 300

Gly Gly Leu Val Lys Pro Gly Ser Leu Lys Leu Ser Cys Ala Ala
305                 310                 315                 320

Ser Gly Phe Lys Phe Ser Arg Tyr Ala Met Ser Trp Val Arg Gln Ala
        325                 330                 335

Pro Gly Lys Arg Leu Glu Trp Val Ala Thr Ile Ser Ser Gly Gly Ser
            340                 345                 350

Tyr Ile Tyr Tyr Pro Asp Ser Val Lys Gly Arg Phe Thr Ile Ser Arg
        355                 360                 365

Asp Asn Val Lys Asn Thr Leu Tyr Leu Gln Met Ser Ser Leu Arg Ser
    370                 375                 380

Glu Asp Thr Ala Ile Tyr Tyr Cys Ala Arg Arg Asp Tyr Asp Leu Asp
385                 390                 395                 400

Tyr Phe Asp Ser Trp Gly Gln Gly Thr Leu Val Thr Val Ser Ser Ala
            405                 410                 415

Ser Thr Lys Gly Pro Ser Val Phe Pro Leu Ala Pro Ser Ser Lys Ser
        420                 425                 430

Thr Ser Gly Gly Thr Ala Ala Leu Gly Cys Leu Val Lys Asp Tyr Phe
            435                 440                 445

Pro Glu Pro Val Thr Val Ser Trp Asn Ser Gly Ala Leu Thr Ser Gly
    450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
            485                 490                 495

Ile Cys Asn Val Asn His Lys Pro Ser Asn Thr Lys Val Asp Lys Lys
        500                 505                 510

Val Glu Pro Lys Ser Cys Asp Lys Thr His Thr Cys Pro Pro Cys Pro
    515                 520                 525

Ala Pro Glu Leu Leu Gly Gly Pro Ser Val Phe Leu Phe Pro Pro Lys
        530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
            565                 570                 575

Val Asp Gly Val Glu Val His Asn Ala Lys Thr Lys Pro Arg Glu Glu
        580                 585                 590

Gln Tyr Asn Ser Thr Tyr Arg Val Val Ser Val Leu Thr Val Leu His
    595                 600                 605

Gln Asp Trp Leu Asn Gly Lys Glu Tyr Lys Cys Lys Val Ser Asn Lys
610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Asp Glu Leu
            645                 650                 655

Thr Lys Asn Gln Val Ser Leu Thr Cys Leu Val Lys Gly Phe Tyr Pro

```
            660                 665                 670
Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Ser Phe Phe Leu
            690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 51
<211> LENGTH: 16
<212> TYPE: PRT
<213> ORGANISM: Artificial Sequence
<220> FEATURE:
<223> OTHER INFORMATION: Synthetic construct

<400> SEQUENCE: 51

Ala Ser Ala Ser Ala Ala Ala Ser Ser Ala Ser Ser Ala Ala Pro Pro
1               5                   10                  15

<210> SEQ ID NO 52
<211> LENGTH: 745
<212> TYPE: PRT
<213> ORGANISM: Artificial Sequence
<220> FEATURE:
<223> OTHER INFORMATION: Synthetic construct

<400> SEQUENCE: 52

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys Pro Ala Ser Ala Ala Ser Ser Ala
    210             215                 220

Ser Ser Ala Ala Ser Ser Asn Ser Asp Ser Glu Cys Pro Leu Ser His
225             230             235                 240

Asp Gly Tyr Cys Leu His Asp Gly Val Cys Met Tyr Ile Glu Ala Leu
                245             250                 255

Asp Lys Tyr Ala Cys Asn Cys Val Val Gly Tyr Ile Gly Glu Arg Cys
            260             265                 270

Gln Tyr Arg Asp Leu Lys Trp Trp Glu Leu Arg Gly Ser Gly Ser Gly
        275             280             285

Ile Glu Pro Asp Ser Gly Ser Glu Val Gln Leu Val Glu Ser Gly
290             295                 300

Gly Gly Leu Val Lys Pro Gly Gly Ser Leu Lys Leu Ser Cys Ala Ala
305             310             315                 320

Ser Gly Phe Lys Phe Ser Arg Tyr Ala Met Ser Trp Val Arg Gln Ala
            325             330                 335

Pro Gly Lys Arg Leu Glu Trp Val Ala Thr Ile Ser Ser Gly Gly Ser
        340             345                 350

Tyr Ile Tyr Tyr Pro Asp Ser Val Lys Gly Arg Phe Thr Ile Ser Arg
        355             360             365

Asp Asn Val Lys Asn Thr Leu Tyr Leu Gln Met Ser Ser Leu Arg Ser
370             375             380

Glu Asp Thr Ala Ile Tyr Tyr Cys Ala Arg Arg Asp Tyr Asp Leu Asp
385             390             395                 400

Tyr Phe Asp Ser Trp Gly Gln Gly Thr Leu Val Thr Val Ser Ser Ala
            405             410                 415

Ser Thr Lys Gly Pro Ser Val Phe Pro Leu Ala Pro Ser Ser Lys Ser
        420             425                 430

Thr Ser Gly Gly Thr Ala Ala Leu Gly Cys Leu Val Lys Asp Tyr Phe
        435             440             445

Pro Glu Pro Val Thr Val Ser Trp Asn Ser Gly Ala Leu Thr Ser Gly
        450             455             460

Val His Thr Phe Pro Ala Val Leu Gln Ser Ser Gly Leu Tyr Ser Leu
465             470             475                 480

Ser Ser Val Val Thr Val Pro Ser Ser Ser Leu Gly Thr Gln Thr Tyr
            485             490             495

Ile Cys Asn Val Asn His Lys Pro Ser Asn Thr Lys Val Asp Lys Lys
            500             505             510

Val Glu Pro Lys Ser Cys Asp Lys Thr His Thr Cys Pro Pro Cys Pro
        515             520             525

Ala Pro Glu Leu Leu Gly Gly Pro Ser Val Phe Leu Phe Pro Pro Lys
530             535             540

Pro Lys Asp Thr Leu Met Ile Ser Arg Thr Pro Glu Val Thr Cys Val
545             550             555                 560

Val Val Asp Val Ser His Glu Asp Pro Glu Val Lys Phe Asn Trp Tyr
            565             570             575

Val Asp Gly Val Glu Val His Asn Ala Lys Thr Lys Pro Arg Glu Glu
            580             585             590

Gln Tyr Asn Ser Thr Tyr Arg Val Val Ser Val Leu Thr Val Leu His
        595             600             605

Gln Asp Trp Leu Asn Gly Lys Glu Tyr Lys Cys Lys Val Ser Asn Lys
610             615             620

Ala Leu Pro Ala Pro Ile Glu Lys Thr Ile Ser Lys Ala Lys Gly Gln
```

```
                625                 630                 635                 640
Pro Arg Glu Pro Gln Val Tyr Thr Leu Pro Pro Ser Arg Asp Glu Leu
                    645                 650                 655

Thr Lys Asn Gln Val Ser Leu Thr Cys Leu Val Lys Gly Phe Tyr Pro
                    660                 665                 670

Ser Asp Ile Ala Val Glu Trp Glu Ser Asn Gly Gln Pro Glu Asn Asn
                675                 680                 685

Tyr Lys Thr Thr Pro Pro Val Leu Asp Ser Asp Gly Ser Phe Phe Leu
                690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                    725                 730                 735

Lys Ser Leu Ser Leu Ser Pro Gly Lys
                    740                 745

<210> SEQ ID NO 53
<211> LENGTH: 16
<212> TYPE: PRT
<213> ORGANISM: Artificial Sequence
<220> FEATURE:
<223> OTHER INFORMATION: Synthetic construct

<400> SEQUENCE: 53

Pro Pro Ala Ser Ala Ala Ala Ser Ser Ala Ser Ser Ala Ala Ser Ser
1               5                   10                  15

<210> SEQ ID NO 54
<211> LENGTH: 745
<212> TYPE: PRT
<213> ORGANISM: Artificial Sequence
<220> FEATURE:
<223> OTHER INFORMATION: Synthetic construct

<400> SEQUENCE: 54

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
                20                  25                  30

Leu Thr Trp Tyr Gln Gln Arg Thr Asn Gly Ser Pro Arg Thr Leu Ile
            35                  40                  45

Tyr Tyr Ala Thr Ser Leu Ala Asp Gly Val Pro Ser Arg Phe Ser Gly
        50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Pro Pro Ala Ser Ala Ala Ala Ser Ser Ala
    210                 215                 220

Ser Ser Ala Ala Pro Pro Asn Ser Asp Ser Glu Cys Pro Leu Ser His
225                 230                 235                 240

Asp Gly Tyr Cys Leu His Asp Gly Val Cys Met Tyr Ile Glu Ala Leu
                245                 250                 255

Asp Lys Tyr Ala Cys Asn Cys Val Val Gly Tyr Ile Gly Glu Arg Cys
            260                 265                 270

Gln Tyr Arg Asp Leu Lys Trp Trp Glu Leu Arg Gly Ser Gly Ser Gly
        275                 280                 285

Ile Glu Pro Asp Ser Gly Gly Ser Glu Val Gln Leu Val Glu Ser Gly
    290                 295                 300

Gly Gly Leu Val Lys Pro Gly Gly Ser Leu Lys Leu Ser Cys Ala Ala
305                 310                 315                 320

Ser Gly Phe Lys Phe Ser Arg Tyr Ala Met Ser Trp Val Arg Gln Ala
                325                 330                 335

Pro Gly Lys Arg Leu Glu Trp Val Ala Thr Ile Ser Ser Gly Gly Ser
            340                 345                 350

Tyr Ile Tyr Tyr Pro Asp Ser Val Lys Gly Arg Phe Thr Ile Ser Arg
        355                 360                 365

Asp Asn Val Lys Asn Thr Leu Tyr Leu Gln Met Ser Ser Leu Arg Ser
    370                 375                 380

Glu Asp Thr Ala Ile Tyr Tyr Cys Ala Arg Arg Asp Tyr Asp Leu Asp
385                 390                 395                 400

Tyr Phe Asp Ser Trp Gly Gln Gly Thr Leu Val Thr Val Ser Ser Ala
                405                 410                 415

Ser Thr Lys Gly Pro Ser Val Phe Pro Leu Ala Pro Ser Ser Lys Ser
            420                 425                 430

Thr Ser Gly Gly Thr Ala Ala Leu Gly Cys Leu Val Lys Asp Tyr Phe
        435                 440                 445

Pro Glu Pro Val Thr Val Ser Trp Asn Ser Gly Ala Leu Thr Ser Gly
    450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
                485                 490                 495

Ile Cys Asn Val Asn His Lys Pro Ser Asn Thr Lys Val Asp Lys Lys
            500                 505                 510

Val Glu Pro Lys Ser Cys Asp Lys Thr His Thr Cys Pro Pro Cys Pro
        515                 520                 525

Ala Pro Glu Leu Leu Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
```

```
                    595                 600                 605
Gln Asp Trp Leu Asn Gly Lys Glu Tyr Lys Cys Lys Val Ser Asn Lys
        610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Asp Glu Leu
            645                 650                 655

Thr Lys Asn Gln Val Ser Leu Thr Cys Leu Val Lys Gly Phe Tyr Pro
        660                 665                 670

Ser Asp Ile Ala Val Glu Trp Glu Ser Asn Gly Gln Pro Glu Asn Asn
    675                 680                 685

Tyr Lys Thr Thr Pro Pro Val Leu Asp Ser Asp Gly Ser Phe Phe Leu
690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
            725                 730                 735

Lys Ser Leu Ser Leu Ser Pro Gly Lys
        740                 745

<210> SEQ ID NO 55
<211> LENGTH: 16
<212> TYPE: PRT
<213> ORGANISM: Artificial Sequence
<220> FEATURE:
<223> OTHER INFORMATION: Synthetic construct

<400> SEQUENCE: 55

Pro Pro Ala Ser Ala Ala Ala Ser Ser Ala Ser Ser Ala Ala Pro Pro
1               5                   10                  15

<210> SEQ ID NO 56
<211> LENGTH: 745
<212> TYPE: PRT
<213> ORGANISM: Artificial Sequence
<220> FEATURE:
<223> OTHER INFORMATION: Synthetic construct

<400> SEQUENCE: 56

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

```
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Pro Ala Ser Ala Ala Pro Pro Ala
    210                 215                 220
Ser Ser Ala Ala Pro Pro Asn Ser Asp Ser Glu Cys Pro Leu Ser His
225                 230                 235                 240
Asp Gly Tyr Cys Leu His Asp Gly Val Cys Met Tyr Ile Glu Ala Leu
                245                 250                 255
Asp Lys Tyr Ala Cys Asn Cys Val Val Gly Tyr Ile Gly Glu Arg Cys
                260                 265                 270
Gln Tyr Arg Asp Leu Lys Trp Trp Glu Leu Arg Gly Ser Gly Ser Gly
            275                 280                 285
Ile Glu Pro Asp Ser Gly Gly Ser Glu Val Gln Leu Val Glu Ser Gly
290                 295                 300
Gly Gly Leu Val Lys Pro Gly Gly Ser Leu Lys Leu Ser Cys Ala Ala
305                 310                 315                 320
Ser Gly Phe Lys Phe Ser Arg Tyr Ala Met Ser Trp Val Arg Gln Ala
                325                 330                 335
Pro Gly Lys Arg Leu Glu Trp Val Ala Thr Ile Ser Gly Gly Ser
            340                 345                 350
Tyr Ile Tyr Tyr Pro Asp Ser Val Lys Gly Arg Phe Thr Ile Ser Arg
                355                 360                 365
Asp Asn Val Lys Asn Thr Leu Tyr Leu Gln Met Ser Ser Leu Arg Ser
370                 375                 380
Glu Asp Thr Ala Ile Tyr Tyr Cys Ala Arg Arg Asp Tyr Asp Leu Asp
385                 390                 395                 400
Tyr Phe Asp Ser Trp Gly Gln Gly Thr Leu Val Thr Val Ser Ser Ala
                405                 410                 415
Ser Thr Lys Gly Pro Ser Val Phe Pro Leu Ala Pro Ser Ser Lys Ser
                420                 425                 430
Thr Ser Gly Gly Thr Ala Ala Leu Gly Cys Leu Val Lys Asp Tyr Phe
            435                 440                 445
Pro Glu Pro Val Thr Val Ser Trp Asn Ser Gly Ala Leu Thr Ser Gly
450                 455                 460
Val His Thr Phe Pro Ala Val Leu Gln Ser Ser Gly Leu Tyr Ser Leu
465                 470                 475                 480
Ser Ser Val Val Thr Val Pro Ser Ser Ser Leu Gly Thr Gln Thr Tyr
                485                 490                 495
Ile Cys Asn Val Asn His Lys Pro Ser Asn Thr Lys Val Asp Lys Lys
                500                 505                 510
Val Glu Pro Lys Ser Cys Asp Lys Thr His Thr Cys Pro Pro Cys Pro
            515                 520                 525
Ala Pro Glu Leu Leu Gly Gly Pro Ser Val Phe Leu Phe Pro Pro Lys
            530                 535                 540
Pro Lys Asp Thr Leu Met Ile Ser Arg Thr Pro Glu Val Thr Cys Val
545                 550                 555                 560
Val Val Asp Val Ser His Glu Asp Pro Glu Val Lys Phe Asn Trp Tyr
```

```
                    565                 570                 575
Val Asp Gly Val Glu Val His Asn Ala Lys Thr Lys Pro Arg Glu Glu
                580                 585                 590

Gln Tyr Asn Ser Thr Tyr Arg Val Ser Val Leu Thr Val Leu His
            595                 600                 605

Gln Asp Trp Leu Asn Gly Lys Glu Tyr Lys Cys Lys Val Ser Asn Lys
610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Ser Phe Phe Leu
690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
                740                 745

<210> SEQ ID NO 57
<211> LENGTH: 16
<212> TYPE: PRT
<213> ORGANISM: Artificial Sequence
<220> FEATURE:
<223> OTHER INFORMATION: Synthetic construct

<400> SEQUENCE: 57

Pro Pro Ala Ser Ala Ala Ala Pro Pro Ala Ser Ser Ala Ala Pro Pro
1               5                   10                  15

<210> SEQ ID NO 58
<211> LENGTH: 744
<212> TYPE: PRT
<213> ORGANISM: Artificial Sequence
<220> FEATURE:
<223> OTHER INFORMATION: Synthetic construct

<400> SEQUENCE: 58

Asp Ile Gln Met Thr Gln Ser Pro Ile Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Arg Thr Asn Gly Ser Pro Arg Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Ile Ala Asp Tyr Tyr Cys Leu Gln His Gly Glu Ser Pro Phe
                85                  90                  95

Thr Phe Gly Ser Gly Thr Lys Leu Glu Ile Lys Arg Thr Val Ala Ala
            100                 105                 110
```

-continued

```
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Ala Ser Ala Ser Ala Ala Ser Ser Ala
210                 215                 220
Ser Ser Ala Ala Ser Ser Asn Ser Asp Ser Glu Cys Pro Leu Ser His
225                 230                 235                 240
Asp Gly Tyr Cys Leu His Asp Gly Val Cys Met Tyr Ile Glu Ala Leu
                245                 250                 255
Asp Lys Tyr Ala Cys Asn Cys Val Val Gly Tyr Ile Gly Glu Arg Cys
            260                 265                 270
Gln Tyr Arg Asp Leu Lys Trp Trp Glu Leu Arg Ser Gly Ser Gly Ile
        275                 280                 285
Glu Pro Asp Ser Gly Gly Ser Glu Val Gln Leu Val Glu Ser Gly Gly
    290                 295                 300
Gly Leu Val Lys Pro Gly Gly Ser Leu Lys Leu Ser Cys Ala Ala Ser
305                 310                 315                 320
Gly Phe Lys Phe Ser Arg Tyr Ala Met Ser Trp Val Arg Gln Ala Pro
                325                 330                 335
Gly Lys Arg Leu Glu Trp Val Ala Thr Ile Ser Ser Gly Gly Ser Tyr
            340                 345                 350
Ile Tyr Tyr Pro Asp Ser Val Lys Gly Arg Phe Thr Ile Ser Arg Asp
        355                 360                 365
Asn Val Lys Asn Thr Leu Tyr Leu Gln Met Ser Ser Leu Arg Ser Glu
    370                 375                 380
Asp Thr Ala Ile Tyr Tyr Cys Ala Arg Arg Asp Tyr Asp Leu Asp Tyr
385                 390                 395                 400
Phe Asp Ser Trp Gly Gln Gly Thr Leu Val Thr Val Ser Ser Ala Ser
                405                 410                 415
Thr Lys Gly Pro Ser Val Phe Pro Leu Ala Pro Ser Ser Lys Ser Thr
            420                 425                 430
Ser Gly Gly Thr Ala Ala Leu Gly Cys Leu Val Lys Asp Tyr Phe Pro
        435                 440                 445
Glu Pro Val Thr Val Ser Trp Asn Ser Gly Ala Leu Thr Ser Gly Val
    450                 455                 460
His Thr Phe Pro Ala Val Leu Gln Ser Ser Gly Leu Tyr Ser Leu Ser
465                 470                 475                 480
Ser Val Val Thr Val Pro Ser Ser Ser Leu Gly Thr Gln Thr Tyr Ile
                485                 490                 495
Cys Asn Val Asn His Lys Pro Ser Asn Thr Lys Val Asp Lys Lys Val
            500                 505                 510
Glu Pro Lys Ser Cys Asp Lys Thr His Thr Cys Pro Pro Cys Pro Ala
        515                 520                 525
Pro Glu Leu Leu Gly Gly Pro Ser Val Phe Leu Phe Pro Pro Lys Pro
```

```
                        530                 535                 540
Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
                580                 585                 590

Tyr Asn Ser Thr Tyr Arg Val Val Ser Val Leu Thr Val Leu His Gln
                595                 600                 605

Asp Trp Leu Asn Gly Lys Glu Tyr Lys Cys Lys Val Ser Asn Lys Ala
                610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Asp Glu Leu Thr
                645                 650                 655

Lys Asn Gln Val Ser Leu Thr Cys Leu Val Lys Gly Phe Tyr Pro Ser
                660                 665                 670

Asp Ile Ala Val Glu Trp Glu Ser Asn Gly Gln Pro Glu Asn Asn Tyr
                675                 680                 685

Lys Thr Thr Pro Pro Val Leu Asp Ser Asp Gly Ser Phe Phe Leu Tyr
                690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys
                740

<210> SEQ ID NO 59
<211> LENGTH: 12
<212> TYPE: PRT
<213> ORGANISM: Artificial Sequence
<220> FEATURE:
<223> OTHER INFORMATION: Synthetic construct

<400> SEQUENCE: 59

Ser Gly Ser Gly Ile Glu Pro Asp Ser Gly Gly Ser
1               5                   10

<210> SEQ ID NO 60
<211> LENGTH: 744
<212> TYPE: PRT
<213> ORGANISM: Artificial Sequence
<220> FEATURE:
<223> OTHER INFORMATION: Synthetic construct

<400> SEQUENCE: 60

Asp Ile Gln Met Thr Gln Ser Pro Ile Leu Leu Ser Ala Ser Val Gly
1               5                   10                  15

Asp Arg Val Thr Ile Thr Cys Lys Ala Ser Arg Asp Ile Arg Ser Tyr
                20                  25                  30

Leu Thr Trp Tyr Gln Gln Arg Thr Asn Gly Ser Pro Arg Thr Leu Ile
                35                  40                  45

Tyr Tyr Ala Thr Ser Leu Ala Asp Gly Val Pro Ser Arg Phe Ser Gly
            50                  55                  60

Ser Gly Ser Gly Gln Asp Tyr Ser Leu Thr Ile Ser Ser Leu Glu Ser
65              70                  75                  80
```

-continued

```
Asp Asp Ile Ala Asp Tyr Tyr Cys Leu Gln His Gly Glu Ser Pro Phe
                 85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Ala Ser Ala Ser Ala Ala Ser Ser Ala
            210                 215                 220

Ser Ser Ala Ala Ser Ser Asn Ser Asp Ser Glu Cys Pro Leu Ser His
225                 230                 235                 240

Asp Gly Tyr Cys Leu His Asp Gly Val Cys Met Tyr Ile Glu Ala Leu
            245                 250                 255

Asp Lys Tyr Ala Cys Asn Cys Val Val Gly Tyr Ile Gly Glu Arg Cys
            260                 265                 270

Gln Tyr Arg Asp Leu Lys Trp Trp Glu Leu Arg Gly Ser Gly Ser Gly
            275                 280                 285

Ile Glu Pro Asp Ser Gly Ser Glu Val Gln Leu Val Glu Ser Gly Gly
            290                 295                 300

Gly Leu Val Lys Pro Gly Gly Ser Leu Lys Leu Ser Cys Ala Ala Ser
305                 310                 315                 320

Gly Phe Lys Phe Ser Arg Tyr Ala Met Ser Trp Val Arg Gln Ala Pro
            325                 330                 335

Gly Lys Arg Leu Glu Trp Val Ala Thr Ile Ser Ser Gly Gly Ser Tyr
            340                 345                 350

Ile Tyr Tyr Pro Asp Ser Val Lys Gly Arg Phe Thr Ile Ser Arg Asp
            355                 360                 365

Asn Val Lys Asn Thr Leu Tyr Leu Gln Met Ser Ser Leu Arg Ser Glu
            370                 375                 380

Asp Thr Ala Ile Tyr Tyr Cys Ala Arg Arg Asp Tyr Asp Leu Asp Tyr
385                 390                 395                 400

Phe Asp Ser Trp Gly Gln Gly Thr Leu Val Thr Val Ser Ser Ala Ser
            405                 410                 415

Thr Lys Gly Pro Ser Val Phe Pro Leu Ala Pro Ser Ser Lys Ser Thr
            420                 425                 430

Ser Gly Gly Thr Ala Ala Leu Gly Cys Leu Val Lys Asp Tyr Phe Pro
            435                 440                 445

Glu Pro Val Thr Val Ser Trp Asn Ser Gly Ala Leu Thr Ser Gly Val
            450                 455                 460

His Thr Phe Pro Ala Val Leu Gln Ser Ser Gly Leu Tyr Ser Leu Ser
465                 470                 475                 480

Ser Val Val Thr Val Pro Ser Ser Ser Leu Gly Thr Gln Thr Tyr Ile
            485                 490                 495

Cys Asn Val Asn His Lys Pro Ser Asn Thr Lys Val Asp Lys Lys Val
```

-continued

```
                500                 505                 510
Glu Pro Lys Ser Cys Asp Lys Thr His Thr Cys Pro Pro Cys Pro Ala
            515                 520                 525
Pro Glu Leu Leu Gly Gly Pro Ser Val Phe Leu Phe Pro Pro Lys Pro
        530                 535                 540
Lys Asp Thr Leu Met Ile Ser Arg Thr Pro Glu Val Thr Cys Val Val
545                 550                 555                 560
Val Asp Val Ser His Glu Asp Pro Glu Val Lys Phe Asn Trp Tyr Val
                565                 570                 575
Asp Gly Val Glu Val His Asn Ala Lys Thr Lys Pro Arg Glu Glu Gln
            580                 585                 590
Tyr Asn Ser Thr Tyr Arg Val Val Ser Val Leu Thr Val Leu His Gln
        595                 600                 605
Asp Trp Leu Asn Gly Lys Glu Tyr Lys Cys Lys Val Ser Asn Lys Ala
    610                 615                 620
Leu Pro Ala Pro Ile Glu Lys Thr Ile Ser Lys Ala Lys Gly Gln Pro
625                 630                 635                 640
Arg Glu Pro Gln Val Tyr Thr Leu Pro Pro Ser Arg Asp Glu Leu Thr
                645                 650                 655
Lys Asn Gln Val Ser Leu Thr Cys Leu Val Lys Gly Phe Tyr Pro Ser
            660                 665                 670
Asp Ile Ala Val Glu Trp Glu Ser Asn Gly Gln Pro Glu Asn Asn Tyr
        675                 680                 685
Lys Thr Thr Pro Pro Val Leu Asp Ser Asp Gly Ser Phe Phe Leu Tyr
    690                 695                 700
Ser Lys Leu Thr Val Asp Lys Ser Arg Trp Gln Gln Gly Asn Val Phe
705                 710                 715                 720
Ser Cys Ser Val Met His Glu Ala Leu His Asn His Tyr Thr Gln Lys
                725                 730                 735
Ser Leu Ser Leu Ser Pro Gly Lys
            740
```

<210> SEQ ID NO 61
<211> LENGTH: 12
<212> TYPE: PRT
<213> ORGANISM: Artificial Sequence
<220> FEATURE:
<223> OTHER INFORMATION: Synthetic construct

<400> SEQUENCE: 61

```
Gly Ser Gly Ser Gly Ile Glu Pro Asp Ser Gly Ser
1               5                   10
```

<210> SEQ ID NO 62
<211> LENGTH: 743
<212> TYPE: PRT
<213> ORGANISM: Artificial Sequence
<220> FEATURE:
<223> OTHER INFORMATION: Synthetic construct

<400> SEQUENCE: 62

```
Asp Ile Gln Met Thr Gln Ser Pro Ile Leu Leu Ser Ala Ser Val Gly
1               5                   10                  15
Asp Arg Val Thr Ile Thr Cys Lys Ala Ser Arg Asp Ile Arg Ser Tyr
            20                  25                  30
Leu Thr Trp Tyr Gln Gln Arg Thr Asn Gly Ser Pro Arg Thr Leu Ile
        35                  40                  45
```

```
Tyr Tyr Ala Thr Ser Leu Ala Asp Gly Val Pro Ser Arg Phe Ser Gly
    50              55                  60
Ser Gly Ser Gly Gln Asp Tyr Ser Leu Thr Ile Ser Ser Leu Glu Ser
65              70                  75                  80
Asp Asp Ile Ala Asp Tyr Tyr Cys Leu Gln His Gly Glu Ser Pro Phe
                85                  90                  95
Thr Phe Gly Ser Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145             150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
    195                 200                 205
Phe Asn Arg Gly Glu Cys Ala Ser Ala Ser Ala Ala Ser Ser Ala
    210                 215                 220
Ser Ser Ala Ala Ser Ser Asn Ser Asp Ser Glu Cys Pro Leu Ser His
225             230                 235                 240
Asp Gly Tyr Cys Leu His Asp Gly Val Cys Met Tyr Ile Glu Ala Leu
                245                 250                 255
Asp Lys Tyr Ala Cys Asn Cys Val Val Gly Tyr Ile Gly Glu Arg Cys
            260                 265                 270
Gln Tyr Arg Asp Leu Lys Trp Trp Glu Leu Arg Ser Gly Ser Gly Ile
    275                 280                 285
Glu Pro Asp Ser Gly Ser Glu Val Gln Leu Val Glu Ser Gly Gly Gly
    290                 295                 300
Leu Val Lys Pro Gly Gly Ser Leu Lys Leu Ser Cys Ala Ala Ser Gly
305             310                 315                 320
Phe Lys Phe Ser Arg Tyr Ala Met Ser Trp Val Arg Gln Ala Pro Gly
                325                 330                 335
Lys Arg Leu Glu Trp Val Ala Thr Ile Ser Ser Gly Gly Ser Tyr Ile
            340                 345                 350
Tyr Tyr Pro Asp Ser Val Lys Gly Arg Phe Thr Ile Ser Arg Asp Asn
    355                 360                 365
Val Lys Asn Thr Leu Tyr Leu Gln Met Ser Ser Leu Arg Ser Glu Asp
    370                 375                 380
Thr Ala Ile Tyr Tyr Cys Ala Arg Arg Asp Tyr Asp Leu Asp Tyr Phe
385                 390                 395                 400
Asp Ser Trp Gly Gln Gly Thr Leu Val Thr Val Ser Ser Ala Ser Thr
                405                 410                 415
Lys Gly Pro Ser Val Phe Pro Leu Ala Pro Ser Ser Lys Ser Thr Ser
                420                 425                 430
Gly Gly Thr Ala Ala Leu Gly Cys Leu Val Lys Asp Tyr Phe Pro Glu
            435                 440                 445
Pro Val Thr Val Ser Trp Asn Ser Gly Ala Leu Thr Ser Gly Val His
    450                 455                 460
Thr Phe Pro Ala Val Leu Gln Ser Ser Gly Leu Tyr Ser Leu Ser Ser
```

```
                465                 470                 475                 480
Val Val Thr Val Pro Ser Ser Leu Gly Thr Gln Thr Tyr Ile Cys
                485                 490                 495

Asn Val Asn His Lys Pro Ser Asn Thr Lys Val Asp Lys Lys Val Glu
                500                 505                 510

Pro Lys Ser Cys Asp Lys Thr His Thr Cys Pro Pro Cys Pro Ala Pro
            515                 520                 525

Glu Leu Leu Gly Gly Pro Ser Val Phe Leu Phe Pro Pro Lys Pro Lys
        530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                565                 570                 575

Gly Val Glu Val His Asn Ala Lys Thr Lys Pro Arg Glu Glu Gln Tyr
                580                 585                 590

Asn Ser Thr Tyr Arg Val Val Ser Val Leu Thr Val Leu His Gln Asp
            595                 600                 605

Trp Leu Asn Gly Lys Glu Tyr Lys Cys Lys Val Ser Asn Lys Ala Leu
        610                 615                 620

Pro Ala Pro Ile Glu Lys Thr Ile Ser Lys Ala Lys Gly Gln Pro Arg
625                 630                 635                 640

Glu Pro Gln Val Tyr Thr Leu Pro Pro Ser Arg Asp Glu Leu Thr Lys
                645                 650                 655

Asn Gln Val Ser Leu Thr Cys Leu Val Lys Gly Phe Tyr Pro Ser Asp
                660                 665                 670

Ile Ala Val Glu Trp Glu Ser Asn Gly Gln Pro Glu Asn Asn Tyr Lys
            675                 680                 685

Thr Thr Pro Pro Val Leu Asp Ser Asp Gly Ser Phe Phe Leu Tyr Ser
        690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 63
<211> LENGTH: 11
<212> TYPE: PRT
<213> ORGANISM: Artificial Sequence
<220> FEATURE:
<223> OTHER INFORMATION: Synthetic construct

<400> SEQUENCE: 63

Ser Gly Ser Gly Ile Glu Pro Asp Ser Gly Ser
1               5                   10

<210> SEQ ID NO 64
<211> LENGTH: 741
<212> TYPE: PRT
<213> ORGANISM: Artificial Sequence
<220> FEATURE:
<223> OTHER INFORMATION: Synthetic construct

<400> SEQUENCE: 64

Asp Ile Gln Met Thr Gln Ser Pro Ile Leu Leu Ser Ala Ser Val Gly
1               5                   10                  15
```

-continued

```
Asp Arg Val Thr Ile Thr Cys Lys Ala Ser Arg Asp Ile Arg Ser Tyr
             20                  25                  30
Leu Thr Trp Tyr Gln Gln Arg Thr Asn Gly Ser Pro Arg Thr Leu Ile
         35                  40                  45
Tyr Tyr Ala Thr Ser Leu Ala Asp Gly Val Pro Ser Arg Phe Ser Gly
 50                  55                  60
Ser Gly Ser Gly Gln Asp Tyr Ser Leu Thr Ile Ser Ser Leu Glu Ser
 65                  70                  75                  80
Asp Asp Ile Ala Asp Tyr Tyr Cys Leu Gln His Gly Glu Ser Pro Phe
                 85                  90                  95
Thr Phe Gly Ser Gly Thr Lys Leu Glu Ile Lys Arg Thr Val Ala Ala
             100                 105                 110
Pro Ser Val Phe Ile Phe Pro Pro Ser Asp Glu Gln Leu Lys Ser Gly
         115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Ala Ser Ala Ser Ala Ala Ser Ser Ala
210                 215                 220
Ser Ser Ala Ala Ser Ser Asn Ser Asp Ser Glu Cys Pro Leu Ser His
225                 230                 235                 240
Asp Gly Tyr Cys Leu His Asp Gly Val Cys Met Tyr Ile Glu Ala Leu
                245                 250                 255
Asp Lys Tyr Ala Cys Asn Cys Val Val Gly Tyr Ile Gly Glu Arg Cys
            260                 265                 270
Gln Tyr Arg Asp Leu Lys Trp Trp Glu Leu Arg Gly Ser Gly Ile Glu
        275                 280                 285
Pro Asp Ser Gly Glu Val Gln Leu Val Glu Ser Gly Gly Gly Leu Val
290                 295                 300
Lys Pro Gly Gly Ser Leu Lys Leu Ser Cys Ala Ala Ser Gly Phe Lys
305                 310                 315                 320
Phe Ser Arg Tyr Ala Met Ser Trp Val Arg Gln Ala Pro Gly Lys Arg
                325                 330                 335
Leu Glu Trp Val Ala Thr Ile Ser Ser Gly Gly Ser Tyr Ile Tyr Tyr
            340                 345                 350
Pro Asp Ser Val Lys Gly Arg Phe Thr Ile Ser Arg Asp Asn Val Lys
        355                 360                 365
Asn Thr Leu Tyr Leu Gln Met Ser Ser Leu Arg Ser Glu Asp Thr Ala
370                 375                 380
Ile Tyr Tyr Cys Ala Arg Arg Asp Tyr Asp Leu Asp Tyr Phe Asp Ser
385                 390                 395                 400
Trp Gly Gln Gly Thr Leu Val Thr Val Ser Ser Ala Ser Thr Lys Gly
                405                 410                 415
Pro Ser Val Phe Pro Leu Ala Pro Ser Ser Lys Ser Thr Ser Gly Gly
            420                 425                 430
Thr Ala Ala Leu Gly Cys Leu Val Lys Asp Tyr Phe Pro Glu Pro Val
```

```
                    435                 440                 445
Thr Val Ser Trp Asn Ser Gly Ala Leu Thr Ser Gly Val His Thr Phe
    450                 455                 460
Pro Ala Val Leu Gln Ser Ser Gly Leu Tyr Ser Leu Ser Val Val
465                 470                 475                 480
Thr Val Pro Ser Ser Ser Leu Gly Thr Gln Thr Tyr Ile Cys Asn Val
                485                 490                 495
Asn His Lys Pro Ser Asn Thr Lys Val Asp Lys Lys Val Glu Pro Lys
                500                 505                 510
Ser Cys Asp Lys Thr His Thr Cys Pro Pro Cys Pro Ala Pro Glu Leu
            515                 520                 525
Leu Gly Gly Pro Ser Val Phe Leu Phe Pro Pro Lys Pro Lys Asp Thr
        530                 535                 540
Leu Met Ile Ser Arg Thr Pro Glu Val Thr Cys Val Val Val Asp Val
545                 550                 555                 560
Ser His Glu Asp Pro Glu Val Lys Phe Asn Trp Tyr Val Asp Gly Val
                565                 570                 575
Glu Val His Asn Ala Lys Thr Lys Pro Arg Glu Glu Gln Tyr Asn Ser
            580                 585                 590
Thr Tyr Arg Val Val Ser Val Leu Thr Val Leu His Gln Asp Trp Leu
        595                 600                 605
Asn Gly Lys Glu Tyr Lys Cys Lys Val Ser Asn Lys Ala Leu Pro Ala
    610                 615                 620
Pro Ile Glu Lys Thr Ile Ser Lys Ala Lys Gly Gln Pro Arg Glu Pro
625                 630                 635                 640
Gln Val Tyr Thr Leu Pro Pro Ser Arg Asp Glu Leu Thr Lys Asn Gln
                645                 650                 655
Val Ser Leu Thr Cys Leu Val Lys Gly Phe Tyr Pro Ser Asp Ile Ala
            660                 665                 670
Val Glu Trp Glu Ser Asn Gly Gln Pro Glu Asn Asn Tyr Lys Thr Thr
        675                 680                 685
Pro Pro Val Leu Asp Ser Asp Gly Ser Phe Phe Leu Tyr Ser Lys Leu
    690                 695                 700
Thr Val Asp Lys Ser Arg Trp Gln Gln Gly Asn Val Phe Ser Cys Ser
705                 710                 715                 720
Val Met His Glu Ala Leu His Asn His Tyr Thr Gln Lys Ser Leu Ser
                725                 730                 735
Leu Ser Pro Gly Lys
            740

<210> SEQ ID NO 65
<211> LENGTH: 9
<212> TYPE: PRT
<213> ORGANISM: Artificial Sequence
<220> FEATURE:
<223> OTHER INFORMATION: Synthetic construct

<400> SEQUENCE: 65

Gly Ser Gly Ile Glu Pro Asp Ser Gly
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 66

Val Leu Pro Ala Ser Leu Tyr Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic construct

<400> SEQUENCE: 67

Gly Ser Gly Ile Glu Pro Asp Ser Gly
1               5
```